(12) United States Patent
Bourke, Jr. et al.

(10) Patent No.: US 12,702,861 B2
(45) Date of Patent: Aug. 11, 2026

(54) ENERGY AUGMENTATION STRUCTURES FOR USE WITH ENERGY EMITTERS AND COLLECTORS

(71) Applicant: IMMUNOLIGHT, LLC, Detroit, MI (US)

(72) Inventors: Frederic A. Bourke, Jr., Aspen, CO (US); Harold Walder, Oak Island, NC (US); Zakaryae Fathi, Raleigh, NC (US); Wayne F. Beyer, Jr., Ivanhoe, VA (US); Ronald A. Rudder, Clarksville, VA (US); Joseph H. Simmons, Tucson, AZ (US)

(73) Assignee: IMMUNOLIGHT, LLC, Detroit, MI (US)

( * ) Notice: Subject to any disclaimer, the term of this patent is extended or adjusted under 35 U.S.C. 154(b) by 175 days.

(21) Appl. No.: 18/435,235

(22) Filed: Feb. 7, 2024

(65) Prior Publication Data

US 2024/0216713 A1 Jul. 4, 2024

Related U.S. Application Data

(63) Continuation of application No. 17/433,748, filed as application No. PCT/US2020/015790 on Jan. 30, 2020, now Pat. No. 11,964,167.

(Continued)

(51) Int. Cl.
*A61N 5/06* (2006.01)
*A61K 35/12* (2015.01)
(Continued)

(52) U.S. Cl.
CPC .............. *A61N 5/062* (2013.01); *A61K 35/12* (2013.01); *A61K 41/00* (2013.01);
(Continued)

(58) Field of Classification Search
CPC ............ A61N 5/062; A61N 5/067; F21V 9/40
See application file for complete search history.

(56) References Cited

U.S. PATENT DOCUMENTS 7,538,641 B2 5/2009 Puente Baliarda et al.
8,376,013 B2 2/2013 Bourke
(Continued)

FOREIGN PATENT DOCUMENTS

EP 1 917 556 B1 5/2008
EP 2 028 225 A1 2/2009
(Continued)

OTHER PUBLICATIONS

P. Jung, et al., "Progress in Superconducting Metamaterials", Superconductor Science and Technology, 27, 2014, 13pp.
(Continued)

*Primary Examiner* — Hugh Maupin
(74) *Attorney, Agent, or Firm* — TUCKER ELLIS LLP; J. Derek Mason

(57) ABSTRACT

An emission enhancement structure having at least one energy augmentation structure; and an energy converter capable of receiving energy from an energy source, converting the energy and emitting therefrom a light of a different energy than the received energy. The energy converter is disposed in a vicinity of the at least one energy augmentation structure such that the emitted light is emitted with an intensity larger than if the converter were remote from the at least one energy augmentation structure. Also described are various uses for the energy emitters, energy augmentation structures and energy collectors in a wide array of fields, such as color enhancement, and color enhancement structures containing the same.

19 Claims, 58 Drawing Sheets

Related U.S. Application Data

(60) Provisional application No. 62/955,533, filed on Dec. 31, 2019, provisional application No. 62/946,648, filed on Dec. 11, 2019, provisional application No. 62/897,677, filed on Sep. 9, 2019, provisional application No. 62/855,508, filed on May 31, 2019, provisional application No. 62/813,390, filed on Mar. 4, 2019.

(51) Int. Cl.

| | |
|---|---|
| ***A61K 41/00*** | (2020.01) |
| ***A61N 5/067*** | (2006.01) |
| ***C09J 133/08*** | (2006.01) |
| ***C09K 11/02*** | (2006.01) |
| ***C12N 15/01*** | (2006.01) |
| ***F21K 2/00*** | (2006.01) |
| ***F21S 11/00*** | (2006.01) |
| ***F21V 9/40*** | (2018.01) |
| ***H10F 10/10*** | (2025.01) |
| ***H10F 77/14*** | (2025.01) |
| ***H10F 77/42*** | (2025.01) |
| *A23B 2/50* | (2025.01) |
| *H10F 77/45* | (2025.01) |

(52) U.S. Cl.

CPC ........ *A61K 41/0057* (2013.01); *A61N 5/0601* (2013.01); *A61N 5/067* (2021.08); *C09J 133/08* (2013.01); *C09K 11/025* (2013.01); *C12N 15/01* (2013.01); *F21K 2/00* (2013.01); *F21S 11/007* (2013.01); *F21V 9/40* (2018.02); *H10F 10/10* (2025.01); *H10F 77/14* (2025.01); *H10F 77/147* (2025.01); *H10F 77/42* (2025.01); *A23B 2/50* (2025.01); *A61N 2005/0661* (2013.01); *A61N 2005/0662* (2013.01); *A61N 2005/0663* (2013.01); *H10F 77/45* (2025.01)

(56) References Cited

U.S. PATENT DOCUMENTS

| | | | | |
|---|---|---|---|---|
| 8,389,958 | B2 | 3/2013 | Vo-Dinh | |
| 8,618,509 | B2 | 12/2013 | Vo-Dinh | |
| 8,658,086 | B2 | 2/2014 | Bourke | |
| 8,927,615 | B2 | 1/2015 | Bourke | |
| 9,004,131 | B2 | 4/2015 | Bourke | |
| 9,005,406 | B2 | 4/2015 | Bourke | |
| 9,023,249 | B2 | 5/2015 | Fathi | |
| 9,174,190 | B2 | 11/2015 | Bourke | |
| 9,232,618 | B2 | 1/2016 | Bourke | |
| 9,278,331 | B2 | 3/2016 | Bourke | |
| 9,488,916 | B2 | 11/2016 | Bourke | |
| 9,526,914 | B2 | 12/2016 | Vo-Dinh | |
| 9,579,523 | B2 | 2/2017 | Bourke | |
| 9,630,022 | B2 | 4/2017 | Bourke | |
| 9,649,832 | B2 | 5/2017 | Fathi | |
| 9,662,389 | B2 | 5/2017 | Vo-Dinh | |
| 9,676,918 | B2 | 6/2017 | Fathi | |
| 9,701,102 | B2 | 7/2017 | Fathi | |
| 9,715,159 | B1 | 7/2017 | Akselrod et al. | |
| 9,907,976 | B2 | 3/2018 | Bourke | |
| 9,937,695 | B2 | 4/2018 | Fathi | |
| 10,026,711 | B2 | 7/2018 | Fathi | |
| 10,029,117 | B2 | 7/2018 | Bourke | |
| 10,054,839 | B1 * | 8/2018 | Brener | G02F 1/3526 |
| 10,074,627 | B2 | 9/2018 | Fathi | |
| 10,080,275 | B2 | 9/2018 | Bourke | |
| 10,087,343 | B2 | 10/2018 | Fathi | |
| 10,093,784 | B2 | 10/2018 | Fathi | |
| 10,201,796 | B2 | 2/2019 | Bourke | |
| 10,213,763 | B2 | 2/2019 | Bourke | |
| 10,283,476 | B2 | 5/2019 | Fathi | |
| 10,363,541 | B2 | 7/2019 | Bourke | |
| 10,410,991 | B2 | 9/2019 | Fathi | |
| 10,494,500 | B2 | 12/2019 | Fathi | |
| 10,575,541 | B2 | 3/2020 | Bourke | |
| 10,593,642 | B2 | 3/2020 | Fathi | |
| 10,682,624 | B2 | 6/2020 | Bourke | |
| 10,717,062 | B2 | 7/2020 | Bourke | |
| 10,734,353 | B2 | 8/2020 | Fathi | |
| 10,748,868 | B2 | 8/2020 | Fathi | |
| 10,847,666 | B2 | 11/2020 | Bourke | |
| 10,874,123 | B2 | 12/2020 | Bourke | |
| 10,899,907 | B2 | 1/2021 | Fathi | |
| 10,974,493 | B2 | 4/2021 | Fathi | |
| 11,173,467 | B2 | 11/2021 | Bourke | |
| 11,270,973 | B2 | 3/2022 | Fathi | |
| 11,278,861 | B2 | 3/2022 | Bourke | |
| 11,345,833 | B2 | 5/2022 | Fathi | |
| 11,476,222 | B2 | 10/2022 | Fathi | |
| 11,589,432 | B2 | 2/2023 | Bourke | |
| 11,648,750 | B2 | 5/2023 | Fathi | |
| 11,678,682 | B2 | 6/2023 | Bourke | |
| 2004/0233512 | A1 | 11/2004 | Fujioka | |
| 2007/0067058 | A1 * | 3/2007 | Miyamoto | B33Y 80/00 700/120 |
| 2007/0210956 | A1 * | 9/2007 | Hillis | H01Q 3/2676 342/179 |
| 2008/0011509 | A1 | 1/2008 | Baliarda | |
| 2008/0057000 | A1 | 3/2008 | Loveridge | |
| 2008/0231517 | A1 | 9/2008 | Zheng | |
| 2009/0159510 | A1 | 6/2009 | Haushalter | |
| 2009/0212696 | A1 | 8/2009 | Terao | |
| 2009/0314333 | A1 | 12/2009 | Shepard | |
| 2010/0016783 | A1 | 1/2010 | Bourke | |
| 2010/0188171 | A1 | 7/2010 | Mohajer-Iravani et al. | |
| 2010/0261263 | A1 | 10/2010 | Vo-Dinh et al. | |
| 2011/0126889 | A1 | 6/2011 | Bourke, Jr. et al. | |
| 2011/0263920 | A1 * | 10/2011 | Bourke, Jr. | A61K 31/4427 514/561 |
| 2012/0064134 | A1 | 3/2012 | Bourke | |
| 2013/0171060 | A1 | 7/2013 | Vo-Dinh | |
| 2013/0214986 | A1 * | 8/2013 | Zhu | H01Q 1/243 343/866 |
| 2014/0269806 | A1 | 9/2014 | Bora et al. | |
| 2014/0323946 | A1 | 10/2014 | Bourke | |
| 2014/0354411 | A1 * | 12/2014 | Pudenz | H01Q 9/0407 343/700 MS |
| 2015/0014022 | A1 | 1/2015 | Young | |
| 2015/0141268 | A1 * | 5/2015 | Rothberg | G01N 21/64 438/22 |
| 2016/0027949 | A1 | 1/2016 | Cooke | |
| 2017/0154866 | A1 | 6/2017 | Fathi et al. | |
| 2017/0167977 | A1 | 6/2017 | Rivera | |
| 2017/0239489 | A1 | 8/2017 | Bourke | |
| 2017/0256849 | A1 * | 9/2017 | Cohen | H01Q 17/008 |
| 2018/0205134 | A1 * | 7/2018 | Khan | H01Q 5/314 |
| 2018/0269174 | A1 | 9/2018 | Fathi et al. | |
| 2018/0271121 | A1 | 9/2018 | Bourke, Jr. et al. | |
| 2018/0317307 | A1 | 11/2018 | Bourke, Jr. et al. | |
| 2018/0358327 | A1 | 12/2018 | Fathi et al. | |
| 2020/0044352 | A1 * | 2/2020 | Cohen | H01Q 19/10 |
| 2020/0323711 | A1 | 10/2020 | Bourke | |
| 2020/0357943 | A1 * | 11/2020 | Rotschild | H10F 77/315 |
| 2021/0353954 | A1 | 11/2021 | Bourke | |
| 2022/0146076 | A1 | 5/2022 | Bourke | |
| 2022/0148997 | A1 | 5/2022 | Bourke | |
| 2022/0181292 | A1 | 6/2022 | Fathi | |
| 2022/0275914 | A1 | 9/2022 | Bourke | |
| 2022/0315809 | A1 | 10/2022 | Bourke | |
| 2023/0191747 | A1 | 6/2023 | Fathi | |

FOREIGN PATENT DOCUMENTS

| | | | |
|---|---|---|---|
| EP | 3 273 278 | A1 | 1/2018 |
| EP | 3 594 557 | A1 | 1/2020 |
| JP | 2009-205928 | | 9/2009 |
| JP | 2017-62902 | | 3/2017 |
| JP | 2017-62902 | A | 3/2017 |
| JP | 2017-138558 | | 8/2017 |

(56) References Cited

FOREIGN PATENT DOCUMENTS

| | | | |
|---|---|---|---|
| JP | 2018-13688 | | 1/2018 |
| JP | 2018-147725 | | 9/2018 |
| KR | 10-1928757 | | 1/2014 |
| WO | WO 99/11727 | | 3/1999 |
| WO | WO 2010/107720 | A2 | 9/2010 |
| WO | WO 2017/189506 | A1 | 11/2017 |

OTHER PUBLICATIONS

P. Cai, et al., "Synthesis and Realization of Novel Ultra-Wideband Bandpass Filters Using ¾ Wavelength Parallel-Coupled Line Resonators", Proceedings of Asia-Pacific Microwave Conference, 2006, 4pp.

Search Report issued Mar. 14, 2023, in European Patent Application No. 20766537.3.

Search Report issued Mar. 24, 2023, in European Patent Application No. 20766868.2.

Search Report issued Feb. 17, 2023, in European Patent Application No. 20765906.1.

Search Report issued Feb. 21, 2023, in European Patent Application No. 20767183.5.

K. Watanabe, et al., "A Microstrip UWB Bandpass Filter Using a Stub-Loaded Dual-Mode Ring Resonator and a Step Impedance Two-Mode Resonator", Microwave Conference, 2008, 4pp. XP031636965.

L. Snehalatha, et al., "A Compact Half-Wave Folded Waveguide Resonator for Dual-Band Applications", National Conference on Recent Advances in Electronics & Computer Engineering, 2015, 4pp., XP032923138.

Office Action issued Nov. 6, 2023, in Japanese Patent Application 2021-552649 w/English translation.

International Search Report and Written Opinion issued Jun. 19, 2020 in PCT/US2020/015790 filed Jan. 30, 2020, 4 pages.

Karpov, S., et al., "Spectroscopic Studies of Fractal Aggregates of Silver Nanospheres Undergoing Local Restructuring", Physics Optics, 2006, 4 total pages.

Supplementary European Search Report issued Mar. 27, 2023 in European Patent Application No. 20765910.3.

Office Action issued Nov. 6, 2023, in Japanese Patent Application No. 2021-552649, filed Jan. 30, 2020 w/English translation.

Office Action issued Apr. 8, 2024, in Japanese Patent Application No. 2021-552649, filed Jan. 30, 2020 w/English translation.

Examination Report issued Apr. 30, 2024, in Australian Patent Application No. 2020233571, filed Jan. 30, 2020.

M. Humar, et al., "Whispering-Gallery-Mode Emission From Biological Luminescent Protein Microcavity Assemblies", Optica, 2017, vol. 4, No. 2, pp. 222-228.

W. Kim, et al., "Fractal-Microcavity Composites: Giant Optical Responses", V.M. Shalaev (Ed.): Optical Properties of Nanostructured Random Media, Topics Appl. Phys., 2002, vol. 82, pp. 149-168.

Examination Report issued Mar. 28, 2025, in European Patent Application No. 20 765 910, filed Feb. 28, 2020.

* cited by examiner

λ/16
λ/32
λ/64
λ/128

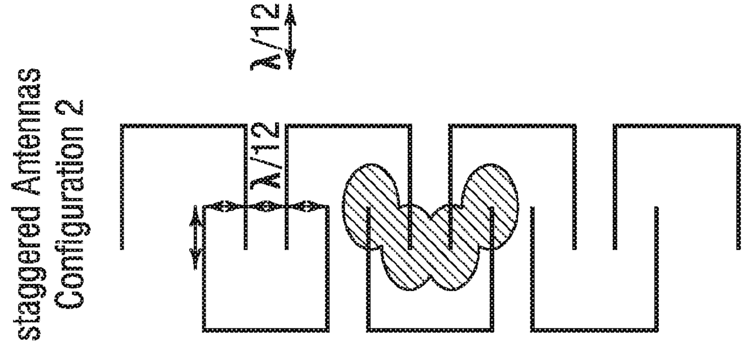
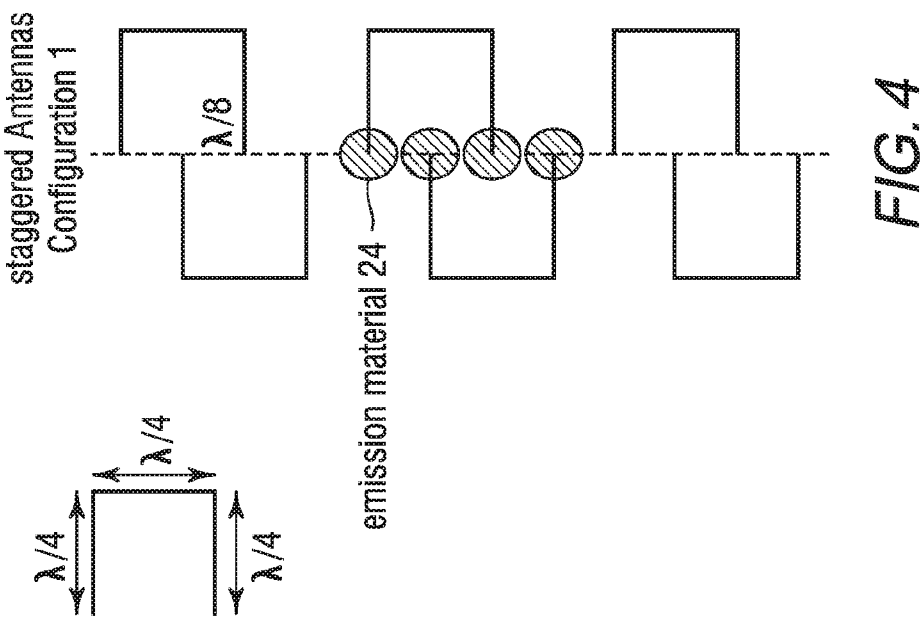
FIG. 4

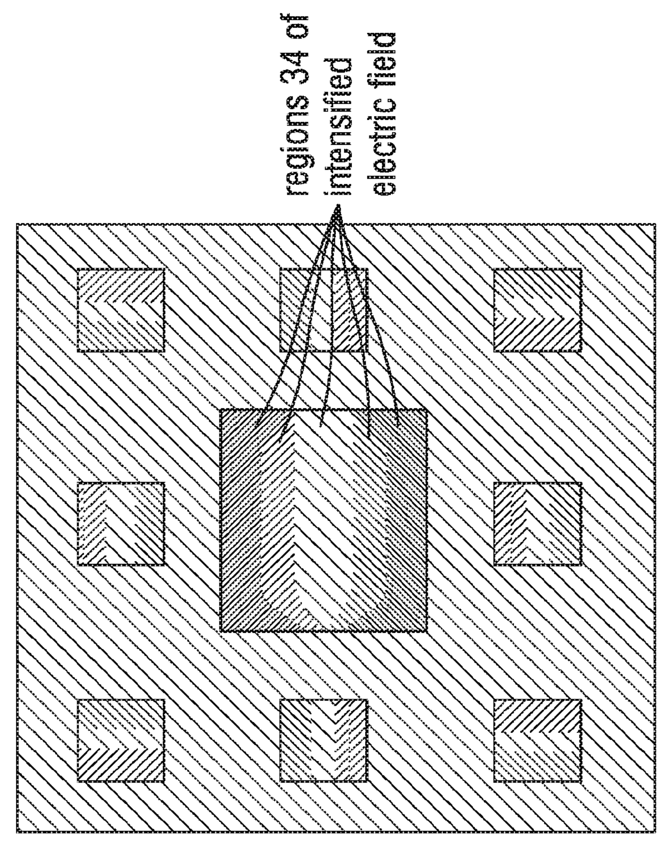
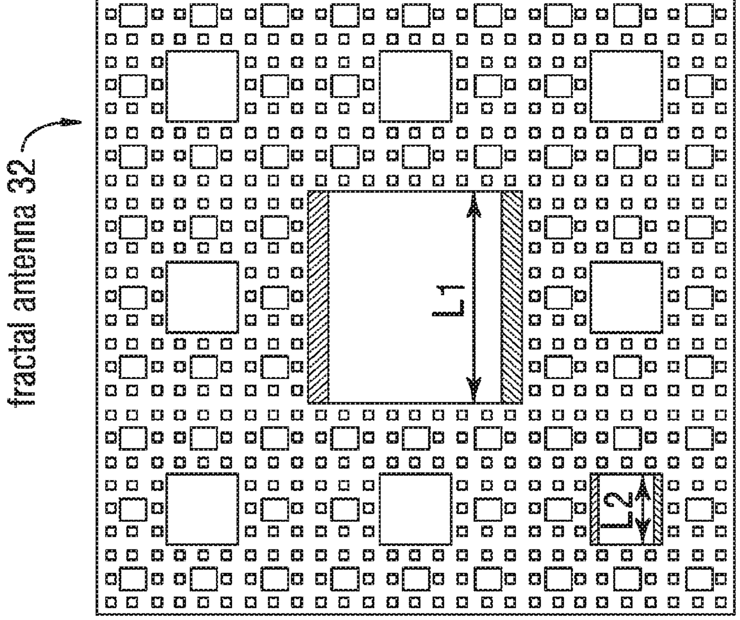
FIG. 13

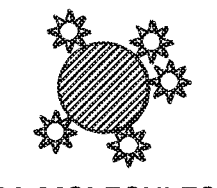

PA MOLECULES BOUND TO METAL NANOPARTICLE

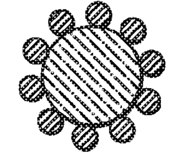

PA-CONTAINING NANOPARTICLE COVERED WITH METAL NANOPARTICLES

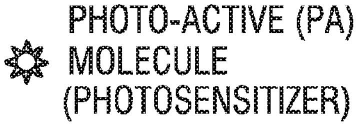

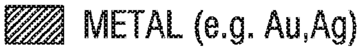

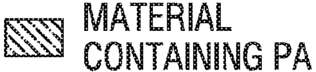

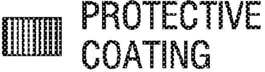

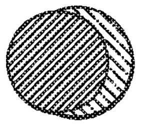

METAL NANOPARTICLE COVERED WITH PA NANOCAP

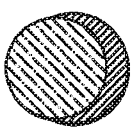

PA-CONTAINING NANO-PARTICLE COVERED WITH METAL NANOCAP

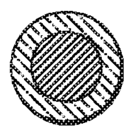

METAL NANOPARTICLE COVERED WITH PA NANOSHELL

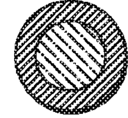

PA-CONTAINING NANOPARTICLE COVERED WITH METAL NANOSHELL

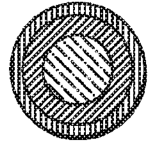

PA-CONTAINING NANO-PARTICLE COVERED WITH METAL NANOSHELL WITH PROTECTIVE COATING LAYER

*FIG. 26*

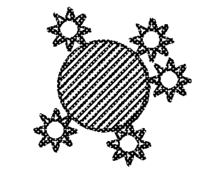

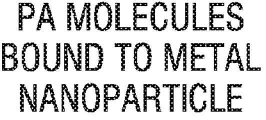

PA MOLECULES BOUND TO METAL NANOPARTICLE

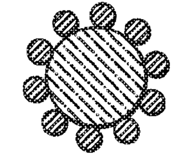

PA-CONTAINING NANOPARTICLE COVERED WITH METAL NANOPARTICLES

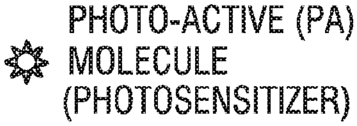

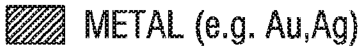

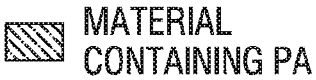

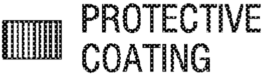

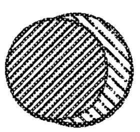

METAL NANOPARTICLE COVERED WITH PA NANOCAP

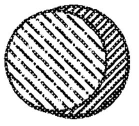

PA-CONTAINING NANO-PARTICLE COVERED WITH METAL NANOCAP

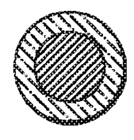

METAL NANOPARTICLE COVERED WITH PA NANOSHELL

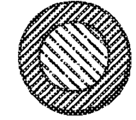

PA-CONTAINING NANOPARTICLE COVERED WITH METAL NANOSHELL

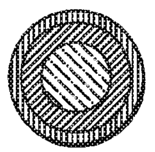

PA-CONTAINING NANO-PARTICLE COVERED WITH METAL NANOSHELL WITH PROTECTIVE COATING LAYER

*FIG. 28A*

PLASMONICS PHOTO-ACTIVE PROBE WITH ENERGY UPCONVERTING MATERIALS

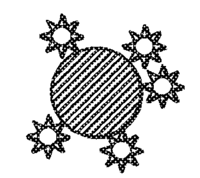

PA MOLECULES BOUND TO METAL NANOPARTICLE

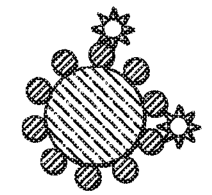

UCn-CONTAINING NANOPARTICLE COVERED WITH METAL NANOPARTICLES

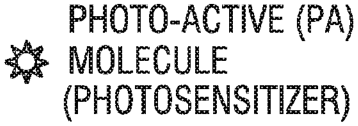

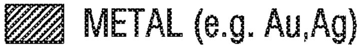

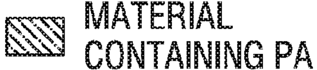

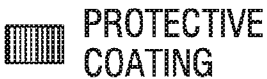

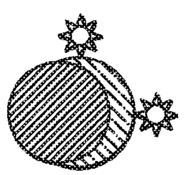

METAL NANOPARTICLE COVERED WITH UCn NANOCAP

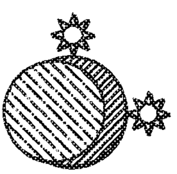

UCN-CONTAINING NANO-PARTICLE COVERED WITH METAL NANOCAP

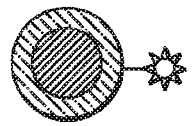

METAL NANOPARTICLE COVERED WITH DIELECTRIC LAYER AND UCm NANOSHELL

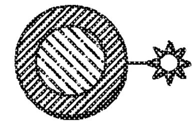

METAL NANOPARTICLE COVERED WITH DIELECTRIC LAYER AND METAL NANOSHELL

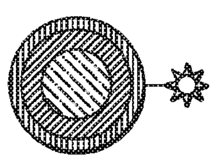

METAL NANO-PARTICLE COVERED WITH DIELECTRIC LAYER AND METAL NANOSHELL WITH PROTECTIVE COATING LAYER

*FIG. 28B*

PLASMONICS-ACTIVE METAL STRUCTURES

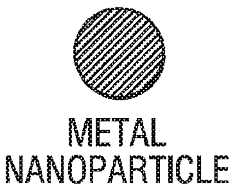
METAL NANOPARTICLE

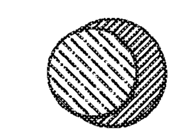
DIELECTRIC NANOPARTICLE CORE COVERED WITH METAL NANOCAP

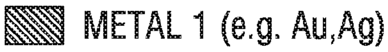
METAL 1 (e.g. Au,Ag)

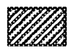
METAL 2 (e.g. Au,Ag)

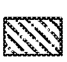
MATERIAL CONTAINING PA

PROTECTIVE COATING

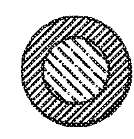
SPHERICAL METAL NANOSHELL COVERING UCn SPHEROID CORE

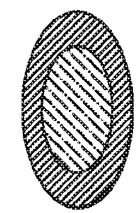
OBLATE METAL NANO-SHELL COVERING UCn SPHEROID CORE

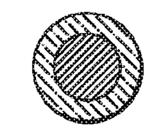
METAL NANOPARTICLE CORE COVERED WITH UCn NANOSHELL

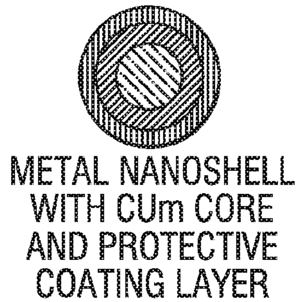
METAL NANOSHELL WITH CUm CORE AND PROTECTIVE COATING LAYER

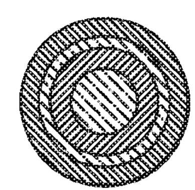
MULTI-LAYER METAL NANOSHELLS COVERING UCm CORE AND NANOSHELL

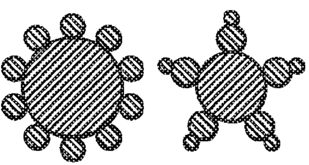
MULTI-NANO-PARTICLE

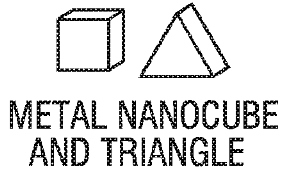
METAL NANOCUBE AND TRIANGLE

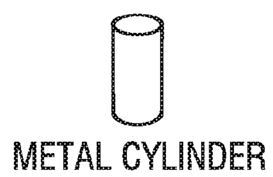
METAL CYLINDER

*FIG. 28C*

Plasmonics Photo-active Probes With Energy Upconverting Materials

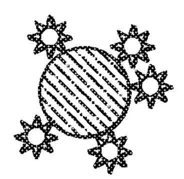

PA molecules bound to UC anaoparticle

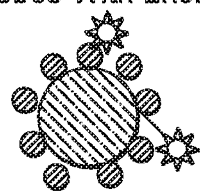

UCm-containing nanoparticle covered with metal nanoparticles

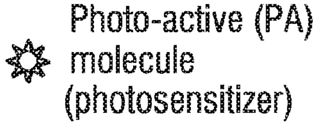

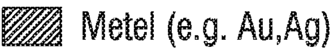

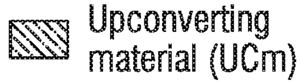

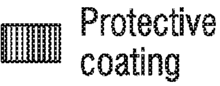

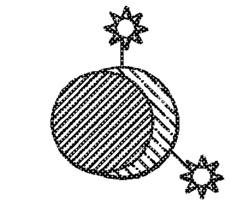

Metal nanoparticle covered with UCm nanocap

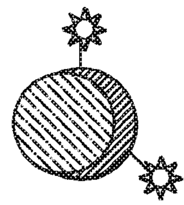

UCm-containing nanoparticle covered with metal nanocap

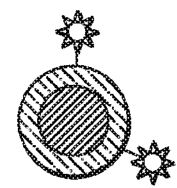

Metal nanoparticle covered with UCm nanoshell

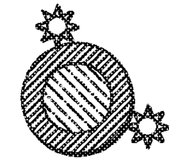

UCm-containing nanoparticle covered with metal nanoshell

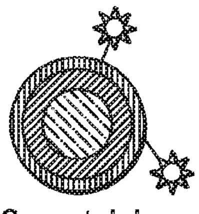

UC-containing nanoparticle covered with metal nanoshell with protective coating layer

*FIG. 28D*

ENERGY AUGMENTATION STRUCTURES FOR USE WITH ENERGY EMITTERS AND COLLECTORS

CROSS REFERENCE TO RELATED APPLICATIONS

This application is a Continuation of U.S. Ser. No. 17/433,748, filed Aug. 25, 2021, now allowed, which is a 371 of PCT application PCT/US2020/015790, filed Jan. 30, 2020, now expired, the entire contents of each of which are incorporated herein by reference. This application is also related to, and claims priority to, provisional application U.S. Ser. No. 62/955,533, filed Dec. 31, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/946,648, filed Dec. 11, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/897,677, filed Sep. 9, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/855,508, filed May 31, 2019, entitled ENERGY AUGMENTATION STRUCTURE; ENERGY COLLECTOR CONTAINING THE SAME; AND COLOR ENHANCEMENT UTILIZING AT LEAST ONE ENERGY AUGMENTATION STRUCTURE, the entire disclosure of which is hereby incorporated by reference. This application is related to, and claims priority to, provisional application U.S. Ser. No. 62/813,390, filed Mar. 4, 2019, entitled COLOR ENHANCEMENT UTILIZING AT LEAST ONE ENERGY AUGMENTATION STRUCTURE, the entire disclosure of which is hereby incorporated by reference.

This application is related to U.S. application Ser. No. 16/599,732, filed Oct. 11, 2019, pending, which claims priority to provisional application U.S. Ser. No. 62/745,057, filed Oct. 12, 2018, the entire contents of each of which are hereby incorporated by reference. This application is related to U.S. Ser. No. 13/204,355 filed Aug. 5, 2011, the entire disclosures of which are hereby incorporated by reference. This application is related to U.S. provisional patent application 61/371,549, filed Aug. 6, 2010. This application is related to U.S. provisional patent application 61/161,328, filed Mar. 18, 2009 and to U.S. provisional patent application 61/259,940, filed Nov. 10, 2009, the entire disclosures of which are hereby incorporated by reference. This application is related to U.S. Ser. No. 12/725,108, the entire disclosures of which are hereby incorporated by reference.

This application is related to Provisional Application Ser. No. 60/954,263, filed Aug. 6, 2007, and 61/030,437, filed Feb. 21, 2008, and U.S. application Ser. No. 12/059,484, filed Mar. 31, 2008, the contents of which are hereby incorporated herein by reference. This application is also related to U.S. application Ser. No. 11/935,655, filed Nov. 6, 2007; and Provisional Application Ser. No. 61/042,561, filed Apr. 4, 2008; 61/035,559, filed Mar. 11, 2008, and 61/080,140, filed Jul. 11, 2008, the entire contents of which are hereby incorporated herein by reference. This application is related to U.S. patent application Ser. No. 12/401,478 filed Mar. 10, 2009, the entire contents of which are hereby incorporated herein by reference. This application is related to U.S. patent application Ser. No. 11/935,655, filed Nov. 6, 2007, and Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009, the entire disclosures of which are hereby incorporated by reference.

BACKGROUND OF THE INVENTION

Field of the Invention

The invention relates to methods, systems, and devices for energy augmentation, with and without an energy modulation agent/energy conversion agent present, and uses particularly for generating or enhancing photon or electron emission and/or for enhancing light or photon collection.

Discussion of the Background

Presently, light (i.e., electromagnetic radiation from the radio frequency through the visible to the X-ray wavelength range) is used in a number of industrial, communication, electronic, and pharmaceutical processes. Light in the infrared and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occur with the emission of light. There are also semiconductor based light sources (as in light emitting diodes and semiconducting lasers) where electrons/holes in a material recombine to produce light emission.

Visible light is defined as the electromagnetic radiation with wavelengths between 380 nm and 750 nm. In general, electromagnetic radiation including light is generated by the acceleration and deceleration or changes in movement (vibration) of electrically charged particles, such as parts of molecules (or adjacent atoms) with high thermal energy, or electrons in atoms (or molecules).

For reference purposes, infra-red (IR) radiation just beyond the red end of the visible region; and, ultra-violet (UV) radiation has a shorter wavelength than violet light. The UV portion of the spectrum is divided into three regions: UVA (315-400 nm), UVB (280-315 nm) and UVC (100-280 nm).

Industrial lamps used in lighting applications cover the visible range of wavelengths for proper white perception. Thermal sources like heated filaments can be made of different type conductors, including W-filaments, halogen-protected W-filaments, and electrically induced high temperature plasmas (arc lamps).

The power (energy emitted per second) of a radiant source is frequently expressed in watts (W), but light can also be expressed in lumens (lm) to account for the varying sensitivity of the eye to different wavelengths of light. The derived relevant units are the radiance (luminance) of a source in $W/m^2$ ($lm/m^2$) in a certain direction per steradian (unit of solid angle) and the irradiance (illuminance) of a surface in W/$m^2$ (lm/$m^2$ or lux).

With the development of ultraviolet sources, ultraviolet radiation is being increasingly utilized for industrial, chemical, and pharmaceutical purposes. For example, UV light is known to sterilize media and is known to drive a number of photo-activated chemical processes such as the cross-linking of polymers in adhesives or coatings. Typically, ultraviolet sources use gas discharge lamps to generate emitted light in the ultraviolet range. The emitted light is then optically filtered to remove many of not all of the non-ultraviolet frequencies. Ultraviolet light can also be produced in semiconductor phosphors from the excitation of these phosphors from high energy sources such as, for example, X-ray irradiation.

With the development of infrared radiation sources, infrared radiation is being increasingly utilized for communications and signaling purposes. Typically, infrared sources use broad spectrum light sources referred to as glowbars to generate a broad spectrum of light centered in the infrared range or use lasers to emit very specific infrared wavelengths. For the broad band sources, the emitted light is optically filtered to remove many, if not all, of the non-infrared frequencies.

It is generally desirable to have devices, materials, and capabilities to convert light from one frequency range to another. Down conversion has been one way to convert higher energy light to lower energy, as used in the phosphors noted above. Up conversion has also been shown where lower energy light is converted to higher energy light. Typically, this process is a multi-photon absorption process where two or more photons are used to promote an excited electronic state in a host medium which in turn radiates at a wavelength of light that has a higher energy than the energy of the incident light which promoted the multi-photon absorption process. Both down conversion and up conversion have been studied and documented in the past.

Indeed, workers have studied the phenomenon of photoluminescence and fluorescence, which is the ability of certain solids to emit light when driven or charged by an external energy source. Many well-known phosphors and fluorescors are triggered by high-energy electrons or photons and emit photons of lower energy. It has been recognized that certain infrared phosphors can convert infrared light to light in the visible range (violet through red).

The properties of light such as its radiance is particularly important in reading or display applications where the human eye has to perceive and discern temporary images or permanent images (as for example shown by road and highway signs) formed with visible light. Televisions, computer monitors, displays, and signs use a cathode ray technology (CRT) technology where high energy electrons impinge on phosphors that emit visible light. Televisions, computer monitors, displays, and signs more recently have used liquid crystal display or plasma display technology to generate visible images discernable to the human eye.

In these and other reading or display applications, attempts have been made to develop displays with relatively high contrast images while minimizing the amount of broadband light emitted or reflected from a display, which may detract from the contrast of the image displayed.

In general, the up conversion and the down conversion discussed above have been used in a number of fields to in effect convert an incident wavelength of light to a different wavelength. In one example, high energy photons such as X-rays are converted by absorption in phosphors of the x-ray energy, and luminescence from the phosphors in the ultraviolet, visible, and/or near infrared spectrum has been used for driving photoactive reactions. In other examples, infrared or near infrared light has been up converted by absorption in phosphors of the infrared or near infrared light, and luminescence from the phosphors in the visible and/or ultraviolet spectrum. In other examples, light within the visible region can be down converted or up converted (depending on the phosphors chosen) to a different band within the visible wavelengths. This shifting (energy conversion) can be for color enhancement and can be used in solar cells to convert one part of the solar spectrum to another part more favorable for a photovoltaic device to generate power.

In many of these prior applications, metallic structures have been placed on the phosphors or in a vicinity of the phosphors to generate a plasmonics effect which essentially is an amplification of the local field very nearby the outside of the metallic structures. Plasmonic effects can enhance coupling of incident light into the phosphors and/or enhance the reactivity of the converted light tons nearby receptor. While the plasmons in the metal can propagate along the metal, the plasmons decay evanescently in the z direction normal to the metal/dielectric interface with 1/e decay length of the order of half the wavelength (~200 nm for wavelengths in the visible range).

In some prior applications, photonic band gap structures have been used. In a photonics band gap structure, the materials thereof consist or photonic crystals (PhCs) are materials with a periodic dielectric profile, which can prevent light of certain frequencies or wavelengths from propagating in one, two or any number of directions within the materials. In this way, light not suitable or detrimental to a process can be rejected while light more suitable for a process can be confined within the photonic band gap structure or better confined within the photovoltaic converter.

In the field of solar cells, the addition of plasmonics, photonics band gap, and up and down conversion is known in the literature. Additionally, antireflection coatings and concentrators are well known in the literature.

The problem with the plasmonics effect is that, as noted above, the plasmons and the electric field enhancement decays rapidly with distance away from the metal structure meaning that the effect is only useful for a small volume of interaction.

The problem with antireflection coatings is that, although sun light is not scattered away as much as if there were no coatings, the light transmitted is still predominantly that of wavelengths that are not optimum for power generation.

The problem with concentrators is that, besides concentrating light which can be converted to power, a concentrator also concentrates light which does not generate power, which in general makes for waste heat.

While photonic band gap structures can serve to reflect or confine light, they have no effective way to gain power from the discarded light.

SUMMARY OF THE INVENTION

In one embodiment, there is provided an energy augmentation structure capable of capturing one or more wavelengths of electromagnetic energy, and augmenting the one or more wavelengths of electromagnetic energy in at least one property.

In one embodiment, the energy augmentation structure may be one or more of an electromagnetic resonator structure, a folded resonator structure, and a fractal structure having a region of an intensified electromagnetic field within the structure.

In a further embodiment, there is provided an energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

In one embodiment, the energy converter noted above is disposed with an energy augmentation structure comprising one or more of an electromagnetic resonator structure, a folded resonator structure, and a fractal structure, any of which having a region of an intensified electromagnetic field within the resonating structures.

In one embodiment, the energy converter noted above includes one or more luminescing materials. As described herein, there are uses of the energy augmentation structure and/or energy collector embodiments which enhance bioluminescence, chemo-luminescence, photoluminescence, fluorescence, and mechano-luminescence.

In one embodiment, the energy converter noted above includes for the one or more luminescent materials phosphorescent materials, fluorescent materials, electroluminescent materials, chemo-luminescent materials, bioluminescent materials, and mechano-luminescent materials used in conjunction with or not in conjunction with the energy augmentation structure noted above. When used in conjunction with the energy augmentation structure noted above, the emitted electromagnetic energy from the luminescent material is emitted with at least one augmented property compared to if the energy converter (e.g., the luminescent material) were remote from the at least one energy augmentation structure.

In one embodiment, the energy converter noted above includes for the one or more luminescing materials phosphorescent materials, fluorescent materials, electroluminescent materials, chemo-luminescent materials, bioluminescent materials, and mechano-luminescent materials used in conjunction with or not in conjunction with the energy augmentation structure noted above and which emit one of ultra-violet, visible, near infrared, and infrared light. In this embodiment, UV-emitting electroluminescent materials or mechano-luminescent devices and materials can be used. In this embodiment, UV-emitting bioluminescent materials can be used.

In one embodiment, there is provided a color enhancement structure having a) an energy collector comprising at least one energy augmentation structure, and b) an energy converter capable of converting a second wavelength of light into and emitting therefrom a third wavelength of light shifted in wavelength from the second wavelength of light. In one embodiment, the energy converter is disposed in a vicinity of the at least one energy augmentation structure such that the light shifted in wavelength is emitted with an intensity larger than if the converter were remote from the at least one energy augmentation structure.

In various embodiments, the color enhancement structures comprise a part of a paint, an ink, a fabric, a thread, a road sign, a highway marking, an automobile, a boat, a plane, a reflector, a building product, a concrete product, an epoxy product, a jewelry product, colored contact lens, a candle product, a rubber product, a plastic product, or other colored surface.

In another embodiment, there is provided a paint including a pigment and the color enhancement structure.

In another embodiment, there is provided an ink including a dye and the color enhancement structure.

In another embodiment, there is provided a display including a color filter or a color reflective surface and the color enhancement structure.

In additional embodiments, there are provided uses of the energy augmentation structure and energy collector embodiments in medical treatments, solar cells, adhesives/resins, sterilization, and other end uses.

In another embodiment, the energy converter noted above is disposed with an energy augmentation structure such that x-ray induced photoluminescence or fluorescence is higher compared to if the energy converter (e.g., x-ray induced photoluminescence or fluorescence materials) were remote from the at least one energy augmentation structure.

In another embodiment, the above noted distributed energy collector can deliver light to different positions within a medium inside a patient.

In another embodiment, the above noted distributed energy collector can collect or deliver light from or to different positions within a patient, including for example collecting or delivering light to different positions within an organ.

In another embodiment, a UV-emitting luciferase may be used alone or in conjunction with the above-noted energy augmentation structures to generate light inside a patient.

In another embodiment, there is provided a distributed energy collector having separate light collection components branched together for collecting solar light for conversion into electrical power.

In another embodiment, there is provided the above-noted distributed energy collector with separate light collection components collects solar light by directing the collected solar flux to a photovoltaic, thermoelectric, or thermionic emission cell.

In another embodiment, there is provided a distributed energy collector integrated with a photovoltaic at separate light collection components within the collector in order to convert solar light into electrical power at the light collection components.

In another embodiment, there is provided the above-noted distributed energy collector with separate light collection components and/or the above-noted energy augmentation structure having the region of the intensified electromagnetic field such that solar light heats a thermionic emission cell. When the region of the intensified electromagnetic field is disposed in a vicinity of the thermionic emission cell, the intensified electromagnetic field enhances thermionic emission.

In another embodiment, the above noted distributed energy collector can deliver light to different positions within an artificial medium for adhesive curing of the artificial medium.

In one embodiment, the above noted energy augmentation structure can be used alone to promote thermocuring of adhesives that are heated in a vicinity of the region of the intensified electromagnetic field.

In one embodiment, the above noted energy augmentation structure can be used in conjunction with the energy converters to promote curing of adhesives either in a vicinity of the region of the intensified electromagnetic field or outside of the energy augmentation structure by enhanced emissions from the energy converters because of their presence in the vicinity of the region of the intensified electromagnetic field. In the above two embodiments, excitation of the energy augmentation structure by an infrared laser generates the region of the intensified electromagnetic field. In the embodiment with energy converters, x-ray excitation or other high energy source (electrons, protons, gamma, or beta particles) can be used to stimulate luminescence from the energy converters for photocuring.

In another embodiment, the above noted distributed energy collector can deliver light to different positions within a medium for sterilization of the medium.

In one embodiment, the above noted energy augmentation structure can be used alone to promote localized heating in a vicinity of the region of the intensified electromagnetic field.

In one embodiment, the above noted energy augmentation structure can be used in conjunction with the energy converters to promote sterilization either in a vicinity of the region of the intensified electromagnetic field or outside of the energy augmentation structure by enhanced emissions from the energy converters because of their presence in the vicinity of the region of the intensified electromagnetic field. In the above two embodiments, excitation of the energy augmentation structure by an infrared laser generates the region of the intensified electromagnetic field. In the embodiment with energy converters, x-ray excitation or other high energy source (electrons, protons, gamma, or beta particles) can be used to stimulate luminescence from the energy converters for sterilization.

In another embodiment, there are provided uses of the energy augmentation structure and/or energy collector embodiments to generate signature light emissions from surfaces for security applications. In one embodiment, the above noted energy augmentation structure can be used in conjunction with the energy converters to produce different color and intensity pattern emissions to be read as a signature.

In another embodiment, there are provided uses of the energy augmentation structure and/or energy converters inside plasma (light-emitting) capsules to promote generation and maintenance of plasma state ions which light.

In another embodiment, there are provided uses of the energy augmentation structure and/or energy converters to enhance electron emission from surfaces in a vicinity of the energy augmentation structure.

In one embodiment, the energy converter noted above includes one or more electron emitting materials. The electron emitting materials may be photon-induced materials which photo-eject an electron under exposure to UV light, The electron emitting materials may be thermally heated materials which emit electrons from heated surfaces of the emitting materials.

In one embodiment, the energy converter noted above includes for the one or more electron emitting materials nanoscale field emission tips. When used in conjunction with the energy augmentation structure noted above, the emitted electron flux from the electron emitting materials is higher compared to if the energy converter (e.g., the nanoscale field emission tips) were remote from the at least one energy augmentation structure.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 4 is a schematic depicting a staggered antenna configuration as an illustrative energy augmentation structure of the invention;

FIG. 13 is a diagram showing a fractal antenna segment where the straight-line sides of the metal pads have locally intensified electric field;

FIG. 16 is a diagram showing a paired three-dimensional fractal structure with an intensified electric field in between;

FIG. 26 is a schematic illustrating various converter structures of the invention;

FIG. 28A is a schematic illustrating other various converter structures of the invention;

FIG. 28B is a further schematic illustrating other various converter structures of the invention;

FIG. 28C is a schematic illustrating various plasmonics-active converter structures of the invention;

FIG. 28D is a schematic illustration of photo-active molecules linked to plasmonics-active upconverter structures of the invention;

DETAILED DESCRIPTION OF THE INVENTION

Figure 1:
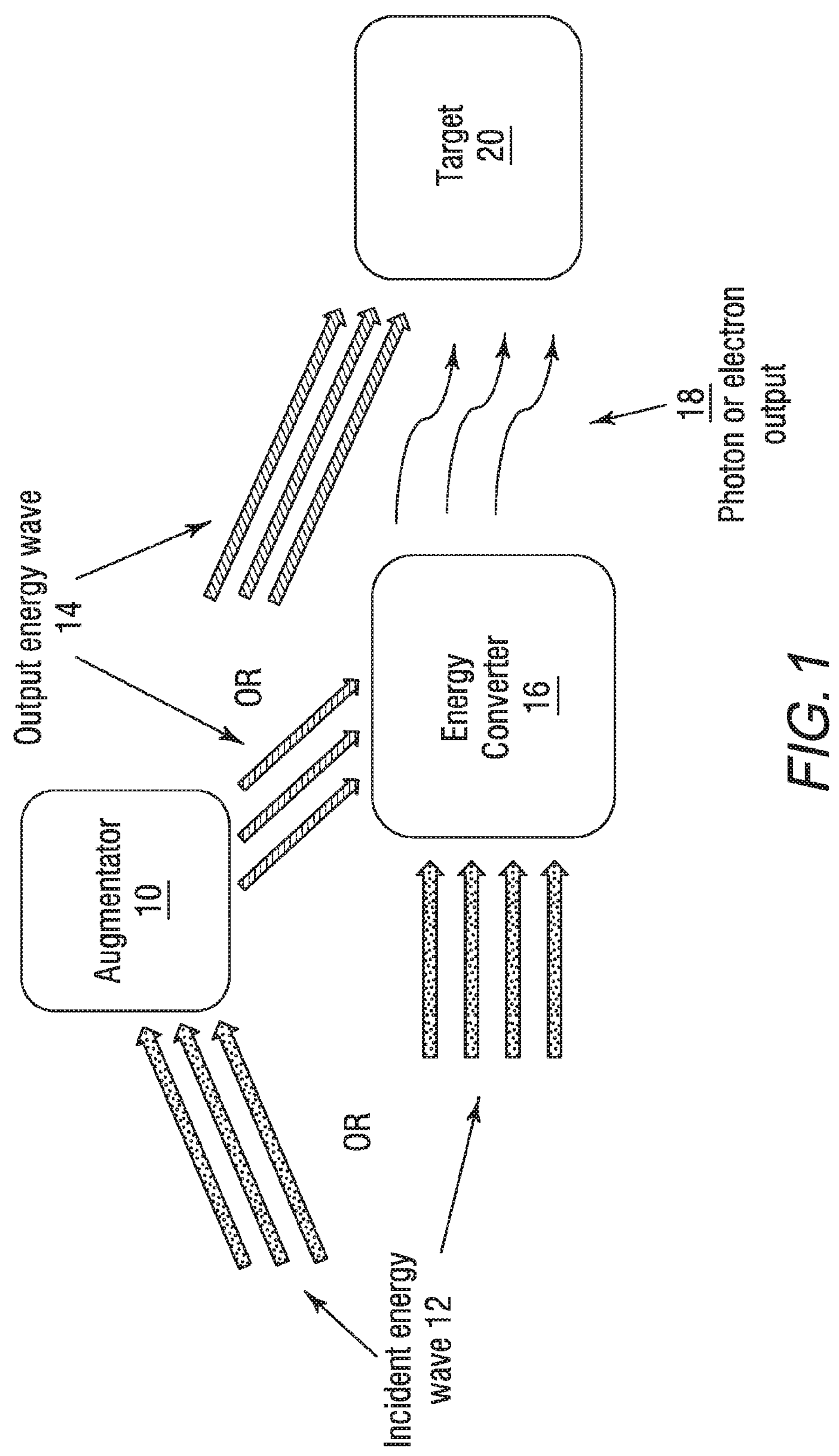
FIG. 1 is a schematic depicting an energy augmentator system of the invention with optional inclusion of an energy converter.

Reference will now be made in detail to a number of embodiments of the invention, examples of which are illustrated in the accompanying drawings, in which like reference characters refer to corresponding elements.

As noted above, energy converters such up conversion materials and down conversion materials have been used in a number of fields in effect to convert an incident wavelength of light to a different wavelength. Metallic structures have been placed on the phosphors or in a vicinity of the phosphors to generate a plasmonics effect which essentially is an amplification of the local field very nearby the outside of the metallic structures. In some applications, photonic band gap structures have been used in solar cell applications to prevent light of certain frequencies or wavelengths from propagating in one, two or any number of directions within the materials. Additionally, antireflection coatings and concentrators are well known in the literature.

The present inventors recognized that the shortcomings of these structures could be addressed by use of the energy augmentation structures described herein used separately or in conjunction with energy converters.

A. Energy Augmentation Structures

In the present invention, the term "energy augmentation" means effecting some change in one or more wavelengths of electromagnetic energy in at least one property, including, but not limited to, intensity, power, associated electrical field, associated magnetic field, wave amplitude, photonic flux, magnetic flux, phase, coherence, propagation direction, etc. The structure performing the energy augmentation can be termed an "energy augmentation structure" or an "energy augmentator". These terms are used interchangeably herein. Preferably the energy augmentation structure is a non-plasmonic structure (a structure that does not exhibit plasmonic properties).

The energy augmentator can take any desired form so long as it can perform the necessary function of augmenting the energy applied to it, causing a change in one or more wavelengths of electromagnetic energy in at least one property as noted above. Examples of such energy augmentators include, but are not limited to, at least one non-plasmonic member selected from the group consisting of resonators, fractal antennas, electrical grid patterns, antennas, cavities, etalons, nanoparticles, microparticles, nanostructures, and microstructures, just to name a few.

In one embodiment, as shown schematically in FIG. 1, an energy augmentator 10 is provided that is capable of receiving or capturing one or more wavelengths of electromagnetic energy representing an incident energy wave 12. Having received or captured the incident energy wave 12, the energy augmentator 10 is capable of augmenting the one or more wavelengths of received or captured energy wave flux 12 in at least one property. As shown in FIG. 1, in one embodiment, energy augmentator 10 then outputs an energy wave 14 with the at least one property augmented, with the augmented energy wave 14 incident on target 20. Details of the augmentation are described below.

In another embodiment, the output (augmented) energy wave 14 (i.e., one or more output wavelengths of electromagnetic energy) can be incident on an energy converter 16 (such as the up conversion materials and down conversion materials noted above). The energy converter 16 can output photons or electrons 18 which can be directed to target 20. In these embodiments, target 20 may receive the photons or electrons 18 or the output augmented energy wave 14 simultaneously or separately.

In one embodiment, the energy augmentator 10 may be one or more of an electromagnetic resonator structure, a folded resonator structure, and a fractal structure having a region of an intensified electromagnetic field within those structures.

Figure 2:
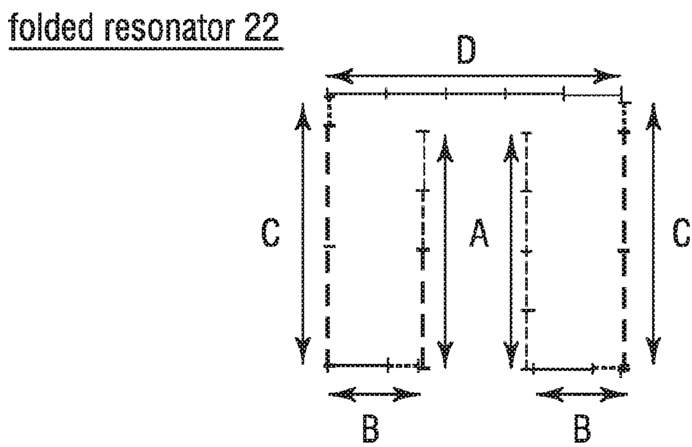
FIG. 2 is a schematic depicting a folded resonator as an illustrative energy augmentation structure of the invention.

FIG. 2 below is a diagram depicting a folded resonator structure 22 of this invention.

Figure 3:
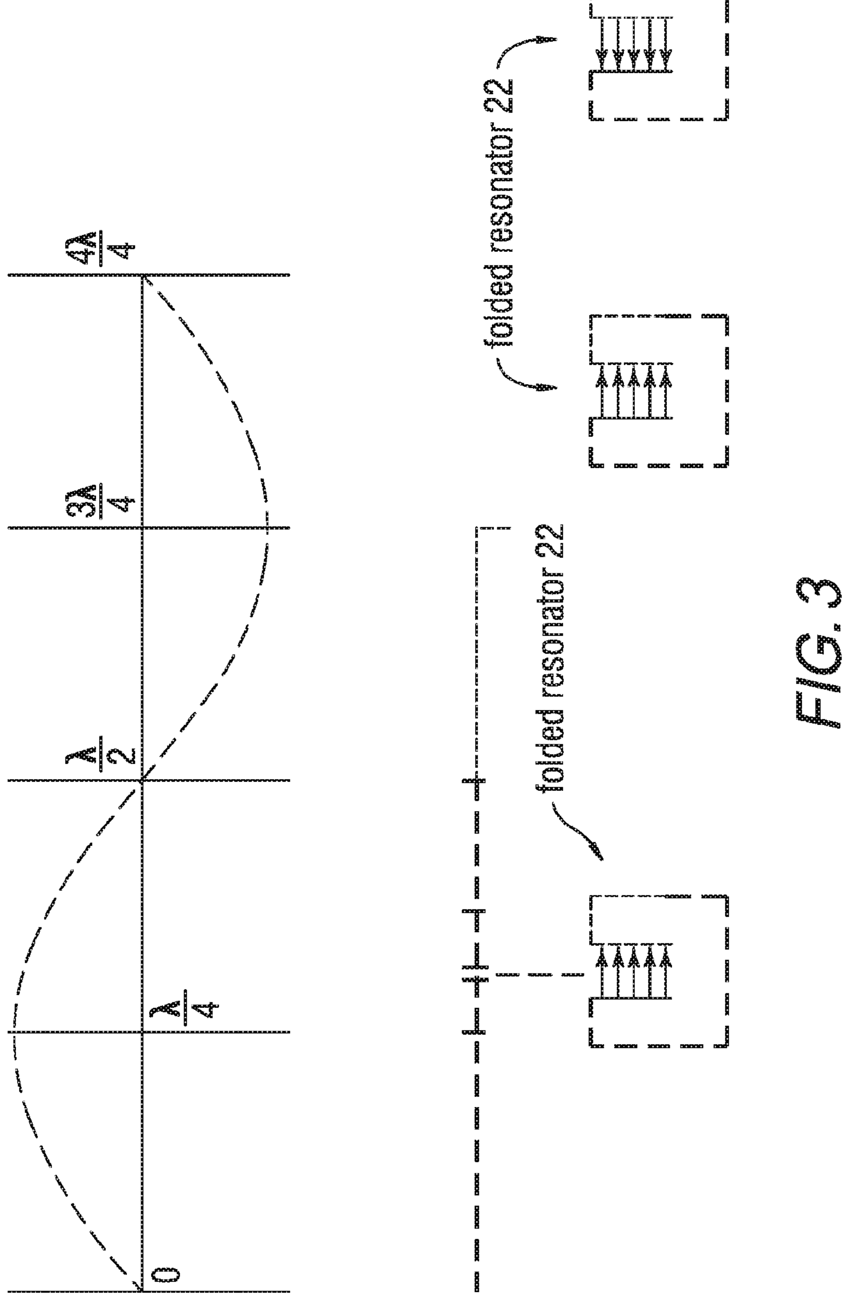
FIG. 3 is a diagram depicting the basic concepts underlying one of the energy augmentation structures of this invention.

The resonator in one embodiment of the present invention is a ¾λ metal structure bent, as shown in FIG. 2 having a "folded" structure making for opposing electrodes between which an intense electric field is developed. Exemplary characteristics of the "folded structure" antenna are listed in the following table:

FIG. 3 is a diagram depicting the basic concepts underlying one of the energy augmentation structures of this invention. In the depiction in FIG. 3 is a sinusoidal wave representing for example an instantaneous waveform of a light wave (an incident energy flux 12). The depiction shows the length of ¾ of the wavelength λ, and how in one embodiment a ¾ λ resonator is constructed with the open ends of the resonator "folded" together to form in this embodiment a ¾ λ folded resonator 22. As shown in FIG. 3, the folded ends form a region of an intensified, amplified electric field denoted by the horizontally directed arrows between the opposing open ends. When light nominally of a wavelength % (or harmonics thereof 2λ, 3λ, 4 λ, etc.) is incident on the folded antenna structure, a fraction—a of the light will be coupled into this structure establishing the amplified electric field. Since the light from sun comes continuously and at different rotational polarizations, subsequent light waves will continue to "pump" the electric fields in the resonant structure until some "loss" mechanism caps the strength of the electric fields. For resonators made of low loss materials, high Q-factors are obtained which, in this case, could mean that the electric field strength between the opposing electrodes may be for example 100 to 1000 times the peak amplitude of the electric field vector of the incident waveform.

In another embodiment, a resonating antenna could have the configuration below shown in FIG. 4. Here, the ¾ λ structures oppose and are interdigitated together without a "folded" structure. In the depiction in FIG. 4, the horizontal stubs are ¼ λ long, the vertical extending connectors are ¼ long, and the vertical spacing between the horizontal stubs and the extend of interdigitation varies as shown between configuration 1 and configuration 2. In one embodiment of the invention, an energy converter, a light or electron emitting material, or a color emitting or color converter material (i.e., emissive material 24) is placed inside or around the region of an intensified electric field, as shown in FIG. 4.

TABLE 1

| | Wavelength (nm) | | | | | | | | | | |
|---|---|---|---|---|---|---|---|---|---|---|---|
| Antenna Side | 1400 | 1300 | 1200 | 1100 | 1000 | 900 | 800 | 700 | 600 | 500 | 400 |
| A | 175.0 | 162.9 | 150.0 | 137.5 | 125.0 | 112.5 | 100.0 | 87.5 | 75.0 | 62.5 | 50.0 |
| B | 65.6 | 60.9 | 56.3 | 51.6 | 46.9 | 42.2 | 37.5 | 32.8 | 28.1 | 23.4 | 18.8 |
| C | 196.9 | 182.8 | 168.8 | 154.7 | 140.6 | 126.6 | 112.5 | 98.4 | 84.4 | 70.3 | 56.3 |
| D | 218.8 | 203.1 | 187.5 | 171.9 | 156.3 | 140.6 | 125.0 | 109.4 | 93.8 | 78.1 | 62.5 |
| Total | 1093.8 | 1015.6 | 937.5 | 859.4 | 782.3 | 703.1 | 625.0 | 546.9 | 468.8 | 390.6 | 312.5 |
| ¾ lambda | 1050 | 975 | 900 | 825 | 750 | 675 | 600 | 525 | 450 | 375 | 300 |

The calculations of a theoretical ¾ λ and the slightly oversized antenna to account for all the bending corners involved in making the antenna would result in this structure having a size between the theoretical 0.75*λ and the upper oversized limit 0.78*λ.

While the resonators shown in most of the drawings could be characterized as having a rectangular-shape loop connecting the opposing antenna sections or electrodes together, the invention is not so limited. Other "loop" shapes could be used, so long as the opposing electrodes are parallel and coplanar with one another, with the loop forming an electrical path having a length of ½ λ, with the opposing electrodes having a length of ⅛ λ each, thereby making the ¾ λ resonator.

Figure 5:
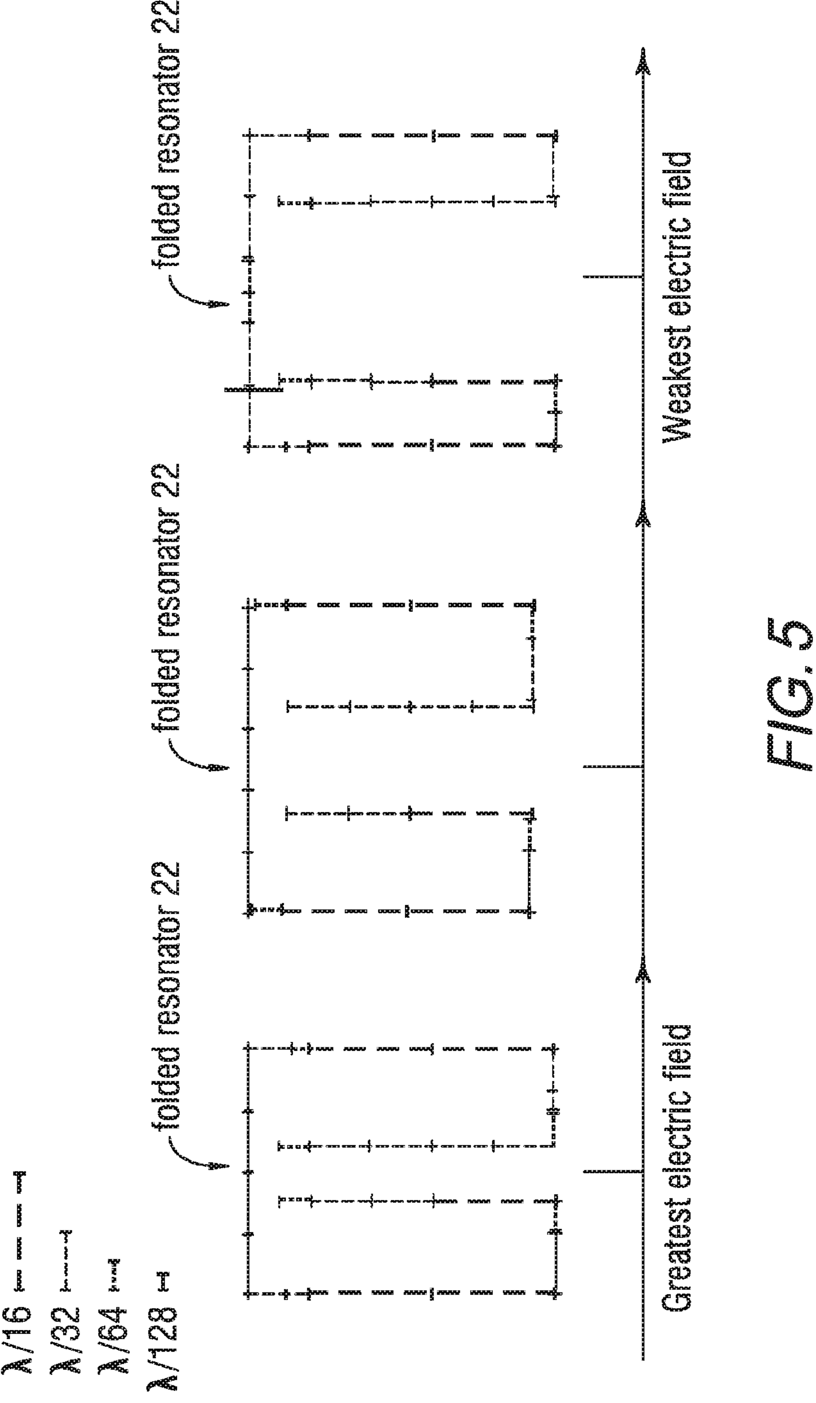
FIG. 5 is a schematic depicting the effect of electrode spacing in the folded resonator of the invention.

FIG. 5 shows that different ¾ λ folded resonators can be made having different distances between the opposing electrodes and thus different electric field strengths. In this way, the folded resonators of the invention can be adjusted such that the strength of the electric field between the opposing electrodes does not exceed the dielectric strength of any material in between. Exceeding the dielectric strength of any material in between could result in destruction of that material as intense current (e.g., a micro-arc) would flow during any time that the dielectric strength was exceeded, thus breaking the material down. As shown, here the opposing sides need not have an exact length of ⅛λ.

In one embodiment of the invention, an energy converter, a light or electron emitting material, or a color emitting or color converter material (i.e., an emissive material) 24 is placed inside or around the regions of intensified electric field near/between the opposing electrodes. In one embodiment of the invention, the color emitting or color converter material may itself be absorbing a color light such as for example blue light and emitting lower energy, down-shifted red light. In this case, a red phosphor could be the color emitting or color converter material.

While the ¾ λ folded resonator in one embodiment could be designed to resonate at blue light (λ=420 to 440 nm), the resonator is preferably designed to resonate from light at a different frequency than the blue light that is being absorbed by the red phosphor. In one embodiment, for color enhancement for objects under solar light, the ¾% folded resonator could be designed to be driven by infrared light from the solar spectrum (e.g. λ=700 to 1000 nm) to generate the intensified electric field, and the red phosphor disposed in the region of intensified electric field would have a brighter red emission than if the intensified electric field were not present.

Figure 6:
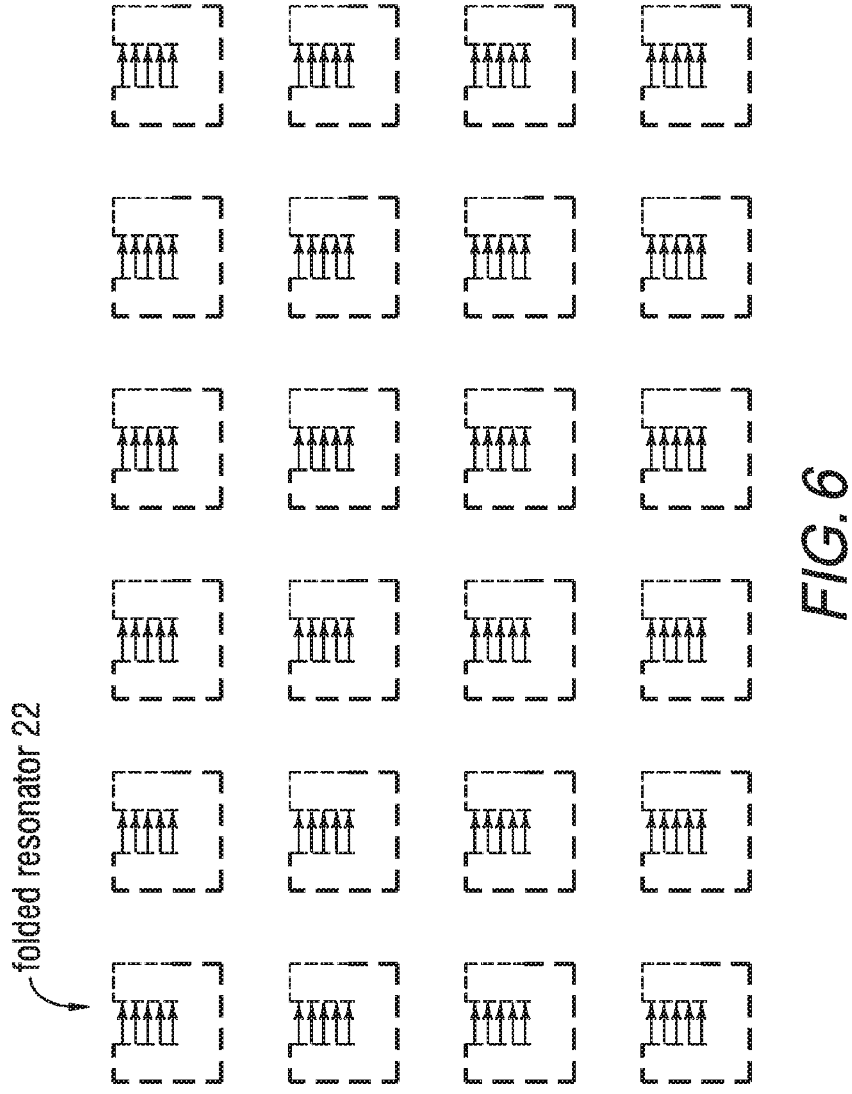
FIG. 6 is a diagram showing a pattern of ¾ λ folded resonators distributed in space.

FIG. 6 is diagram showing a pattern of ¾ λ folded resonators 22 distributed in space. As to be discussed in more detail later, there are numerous ways to distribute the ¾ λ folded resonators. The present invention is not limited to the regular, uniformly spaced and sized resonators shown in FIG. 6. There is no requirement that the distribution be regular, uniformly spaced, uniformly sized, or uniformly oriented. Differently sized, spaced, and oriented resonators may provide better utilization of the full spectrum of the sun or any other light source incident on the object.

Figure 7A:
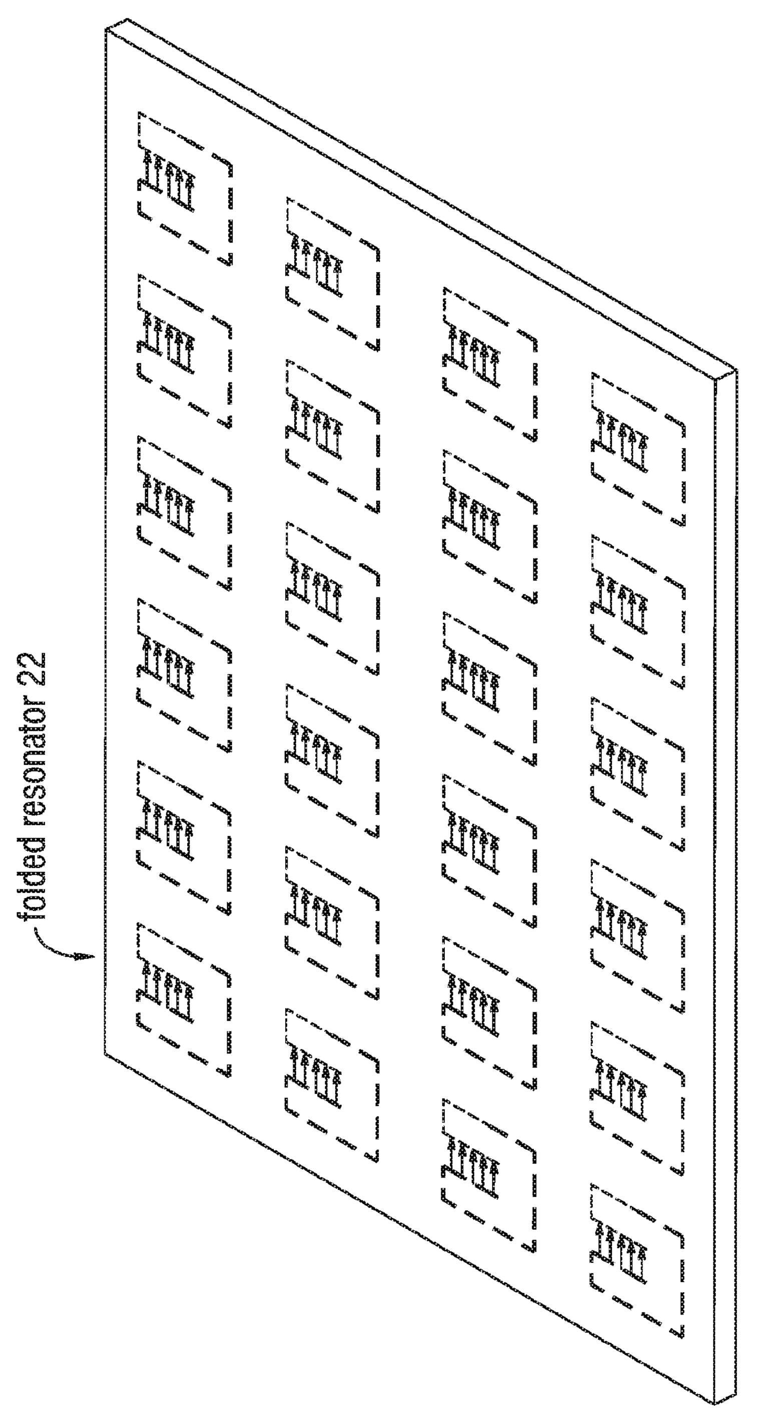
FIGS. 7A-7C are diagrams of several embodiments showing a pattern of ¾ λ folded resonators distributed in a plane or otherwise along a surface of an object.

FIG. 7A is a diagram showing a pattern of ¾ λ folded resonators 22 distributed in a plane or otherwise along a surface of an object. In one embodiment, this pattern could be formed by lithographic or stamping processes onto a planar surface such as a glass plate or onto a curved sheet type product. In one embodiment, the glass plate could itself be a phosphorescent plate or could have sections of different phosphorescent material deposited in a pattern that would align/match the respective positions of the opposing electrodes on each resonator. In one embodiment, the sheet product could be a laminate type of product applied to for example a nominally white object. Upon solar irradiation, the infrared part of the solar spectrum (normally only heating the surface) would generate the intensified electric field regions. In those regions, down converting phosphors converting deep blue and ultraviolet light to visible light would convert the deep blue and ultraviolet light of the solar spectrum to visible light, and the intensified electric field would enhance greater visible light emission.

Figure 7B:
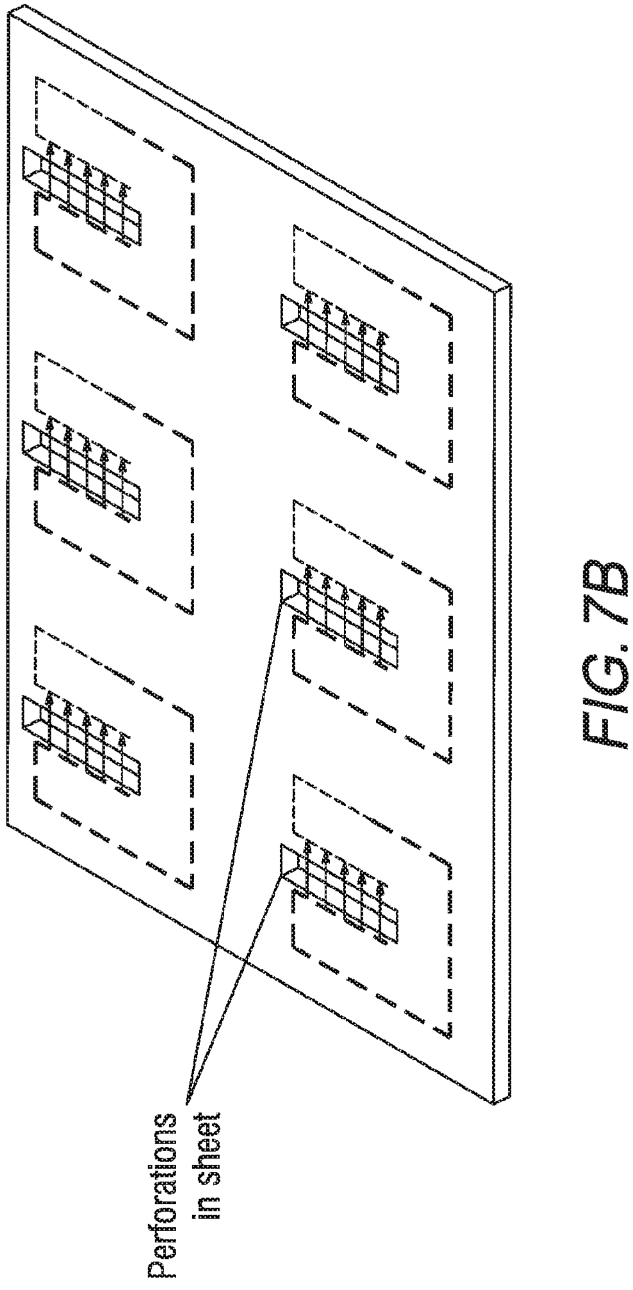

In one embodiment, the energy augmentators could be disposed on a perforated sheet, as shown in FIG. 7B. The perforations in one embodiment are in the regions of intensified electric field such that phosphors or other energy converting materials or devices could be disposed in the perforations.

In one embodiment (for color enhancement), the sheet product could be a laminate type of product applied to for example a nominally green object. Upon solar irradiation, the infrared part of the solar spectrum (normally only heating the surface) would generate the intensified electric field regions. In those regions, down converting phosphors converting blue, deep blue and ultraviolet light to green light would convert the blue, deep blue, and ultraviolet light of the solar spectrum to green light and the intensified electric field would enhance greater green light emission.

In one embodiment, the sheet product could be a laminate type of product applied to for example a nominally red object. Upon solar irradiation, the infrared part of the solar spectrum (normally only heating the surface) would generate the intensified electric field regions. In those regions, down converting phosphors converting green, blue, deep blue and ultraviolet light to red light would convert the green, blue, deep blue and ultraviolet light of the solar spectrum to red light and the intensified electric field would enhance greater red light emission.

Figure 7C:
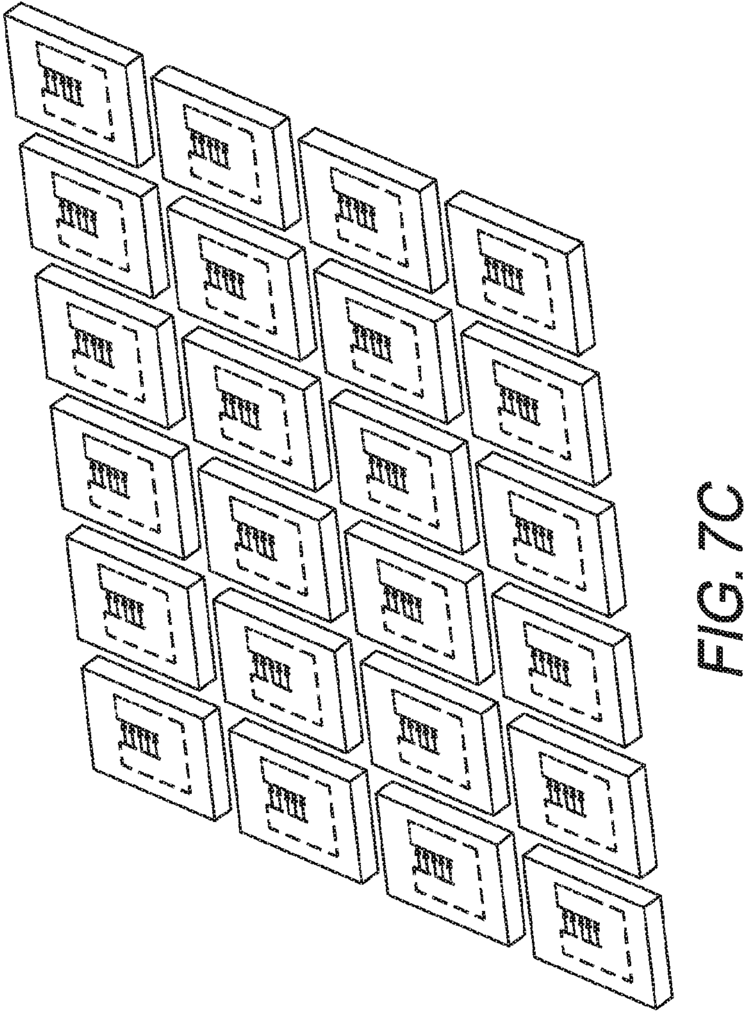

In one embodiment, the energy augmentators could be disposed on a sheet and then separated into distinct pieces, as shown in FIG. 7C, which could be readily added and mixed into a medium to be processed.

Figure 8:
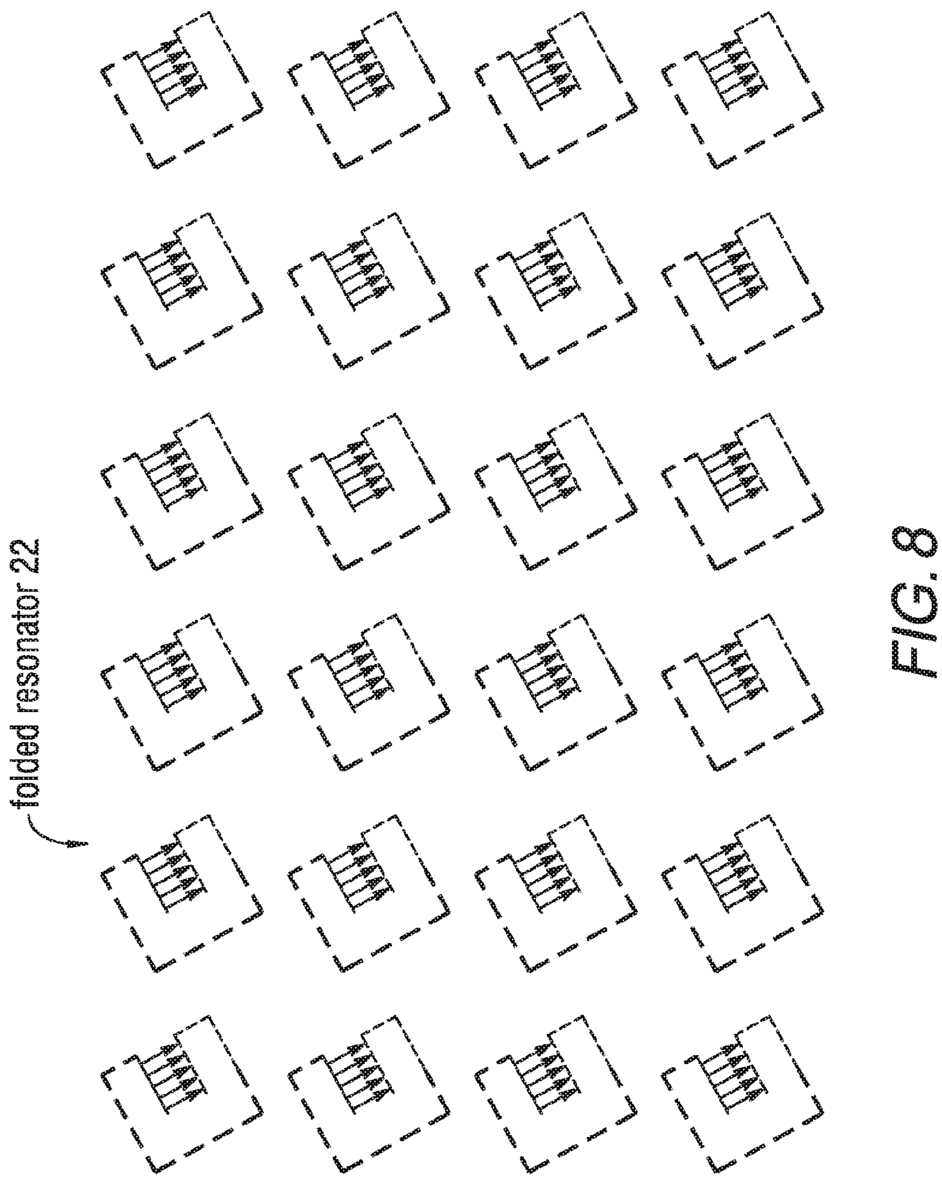
FIG. 8 is a diagram showing a pattern of ¾ λ folded resonators distributed in a plane or otherwise along a surface of an object and having a different orientation than in FIG. 1-D.

FIG. 8 is a diagram showing a pattern of ¾ λ folded resonators 22 distributed in a plane or otherwise along a surface of an object and having a different orientation than in FIG. 7. By having different orientations, the rotating polarized sun light waves which may at one instance not have an electric field alignment conducive to driving the ¾ λ folded resonators, would have their electric field alignment conducive to driving resonators of a different orientation and therefore better aligned. Accordingly, if the sheet type products were used, layers of differently oriented ¾ λ folded resonators could be stacked together.

Figure 9:
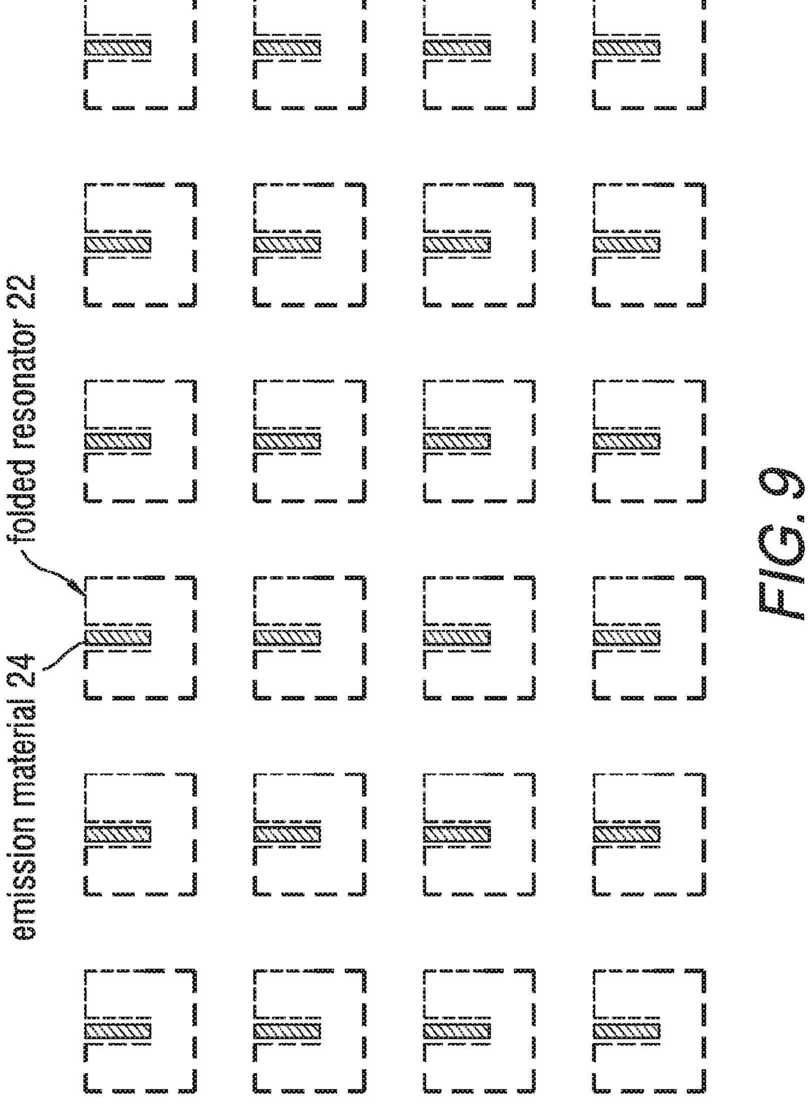
FIG. 9 is a diagram showing a pattern of ¾ λ folded resonators having a light or photon or electron emitting material deposited in the region of between the opposing electrodes.

FIG. 9 is a diagram showing a pattern of ¾ λ folded resonators 22 having an energy converter, a light or electron emitting material, or a color emitting or color converter material (i.e., emissive material 24) deposited in the region of between the opposing electrodes. Here, while shown in a plan view, the color converting or enhancing material deposited in the region of between the opposing electrodes may be deposited such that the color converting or enhancing material has an upper surface raised above the metal traces of the ¾ λ folded resonators. In this embodiment, the raised sections would intercept fringing fields of the intensified electric field between the opposing electrodes.

Figure 10:
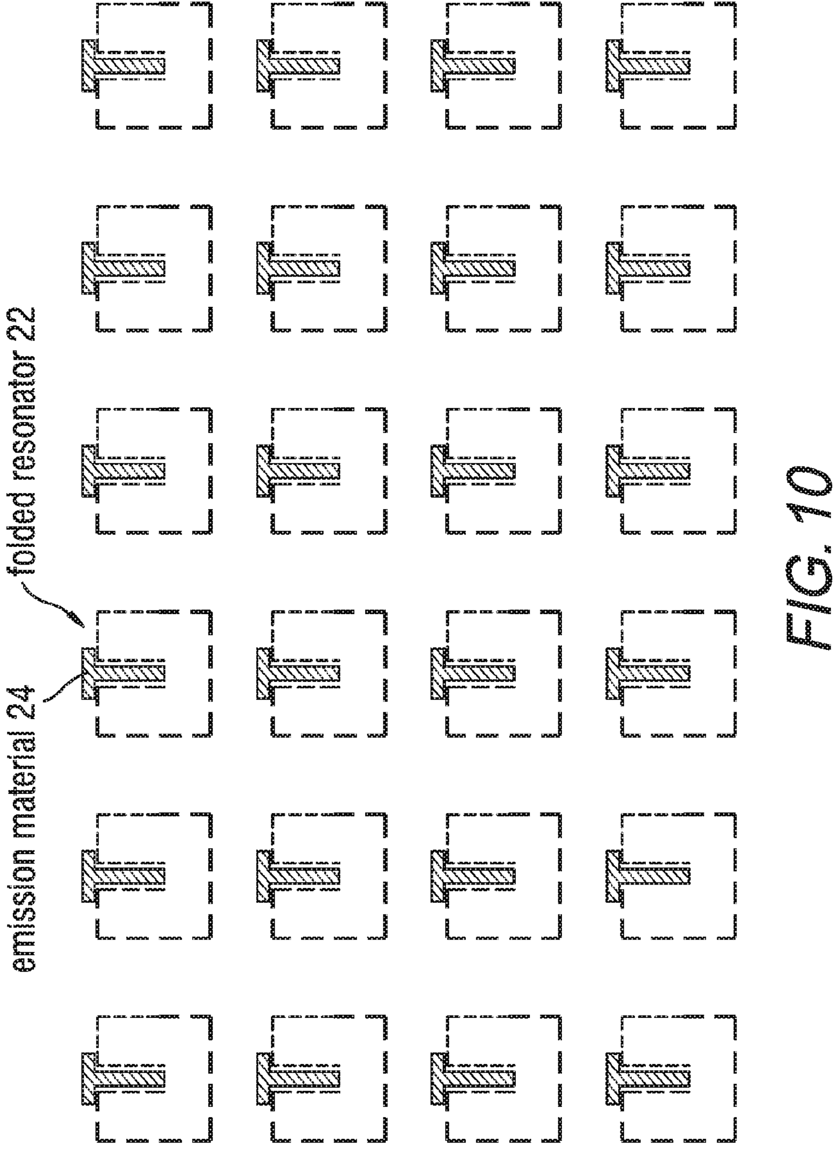
FIG. 10 is a diagram showing a pattern of ¾ λ folded resonators having a patterned deposit of a light or photon or electron emitting material in the region of between the opposing electrodes.

FIG. 10 is a diagram showing a pattern of ¾ λ folded resonators 22 having an energy converter, a light or electron emitting material, or a color emitting or color converter material (i.e., emissive material 24) deposited in the region of between the opposing electrodes. Here, as before, the color converting or enhancing material deposited in the region of between the opposing electrodes may be deposited such that the color converting or enhancing material has an upper surface raised above the metal traces of the ¾ λ folded resonators. In this embodiment, the raised sections would intercept fringing fields of the intensified electric field between the opposing electrodes. In this embodiment, the raised sections would extend around the corners where geometrically the corners would further intensify the electric field.

Figure 11:
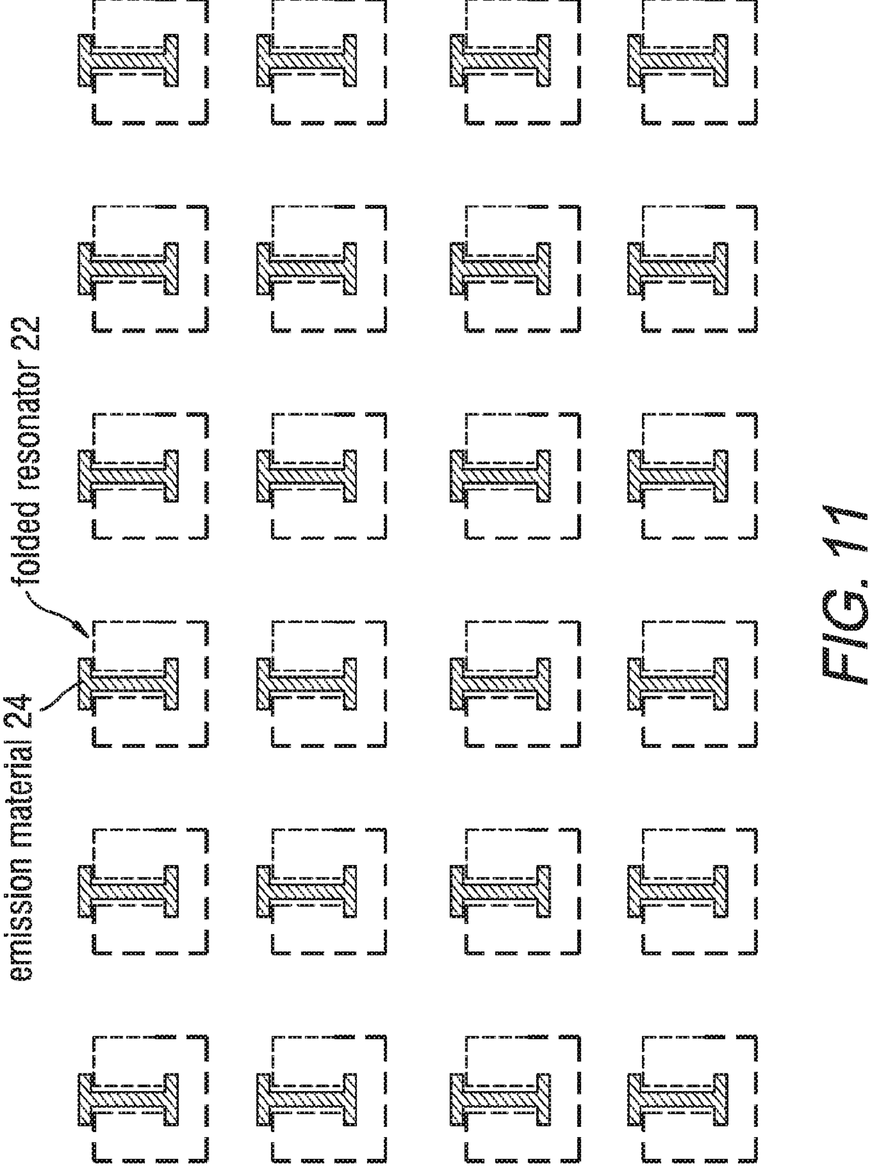
FIG. 11 is a diagram showing a pattern of ¾ λ folded resonators having a patterned deposit of a light or photon or electron emitting material in the region of between the opposing electrodes.

FIG. 11 is a diagram showing a pattern of ¾ λ folded resonators 22 having an energy converter, a light or electron emitting material, or a color emitting or color converter material (i.e., emissive material 24) deposited in the region of between the opposing electrodes. Here, as before, the color converting or enhancing material deposited in the region of between the opposing electrodes may be deposited such that the color converting or enhancing material has an upper surface raised above the metal traces of the ¾ λ folded resonators. In this embodiment, the raised sections would intercept fringing fields of the intensified electric field between the opposing electrodes. In this embodiment, the raised sections would extend around the corners where geometrically the corners would further intensify the electric field and would extend around the ends of the opposing electrodes.

In these embodiments shown in FIGS. 9, 10, and 11, the energy converters, or light or electron emitting materials, or color emitting or color converter materials (i.e., emissive materials 24) are disposed in a vicinity of one or more energy augmentation structures (i.e., the ¾ λ folded resonators). As such, the energy augmentation structures preferably are in a region of intensified electric field. The intensified electric field may represent a region of intensified energy especially if there is electrical current flow conductively coupling the energy converter to the one energy augmentation structures. In later embodiments, conductively coupling the energy converter to the one energy augmentation structures has advantages. Accordingly, the energy converters or color converting or enhancing materials disposed in a vicinity of one or more energy augmentation structures may have a physical conductive connection between the energy converter and the at least one energy augmentation structure. Alternatively, the coupling may be more that of radiatively or capacitively coupling the electric fields from the resonant structure into energy converters or color converting or enhancing materials disposed inside the energy augmentation structure, outside the energy augmentation structure, in a layer with the energy augmentation structure, or in a layer above or below the energy augmentation structure.

As used herein, in a vicinity of refers to the disposition of one thing inside the structure of another thing, outside and nearby or adjacent the structure of the other thing, and can include the disposition of one thing above or below the other thing in any three dimensional direction. Accordingly, in one embodiment of the present invention, the color converting or enhancing materials are disposed in a vicinity of the energy augmentation structures.

Figure 12:
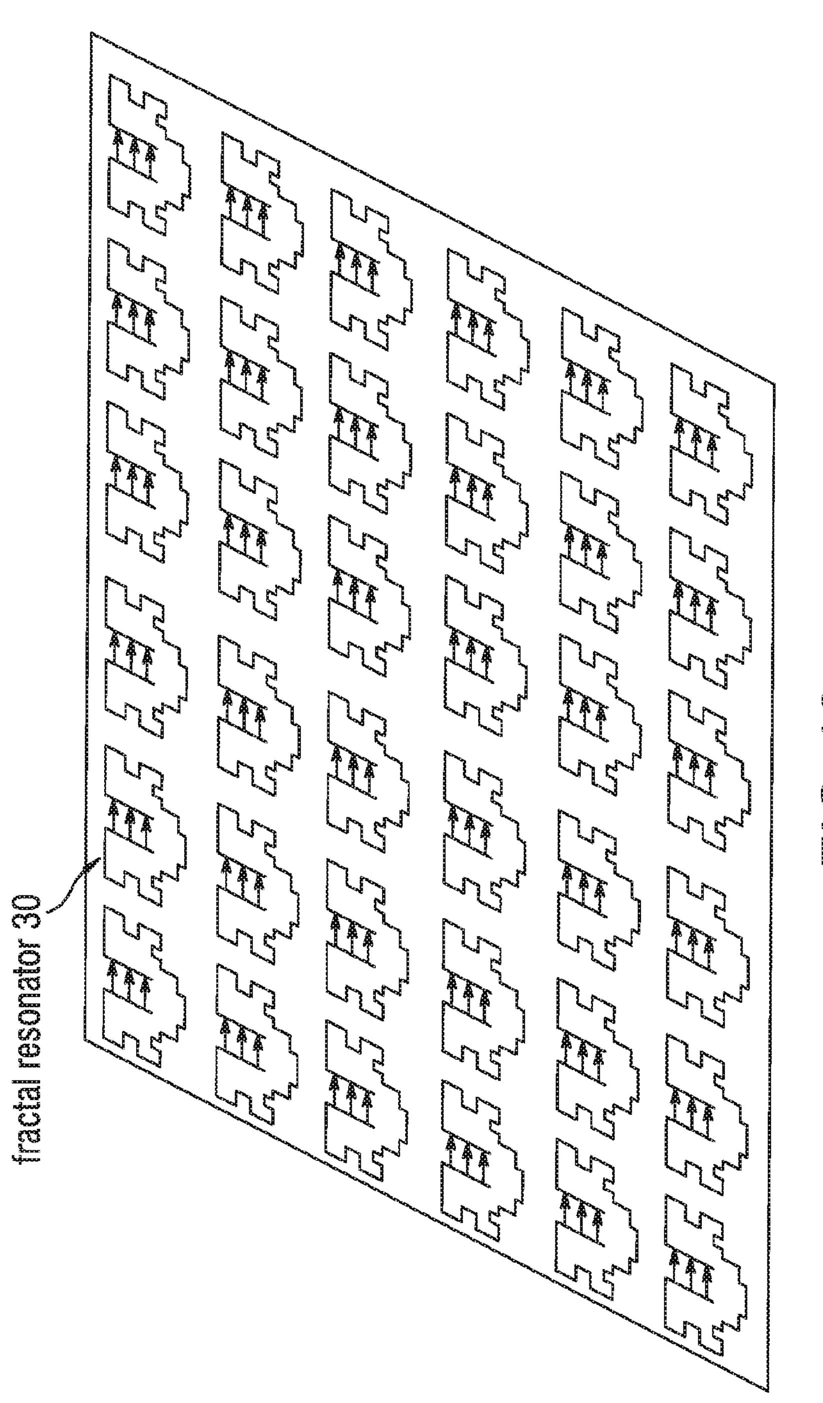
FIG. 12 is a diagram showing a pattern of ¾ λ folded resonators having for the metal traces a fractal pattern for the electrical path that loops around to connect the opposing electrodes.

FIG. 12 is a diagram showing a pattern of ¾ λ folded resonators 30 having for its metal traces a fractal pattern for the electrical path that loops around to connect the opposing electrodes. A fractal pattern for the electrical path with this pattern means that the metal trace can support various wavelengths resonating with the ¾ λ characteristics because of the multiplicity of possible loop paths available because the widths of each segment of the conductive path vary in width permitting electrical paths of different physical lengths to exist around the loop.

FIG. 13 is a diagram showing another fractal antenna segment 32 where the straight-line sides of the metal pads have regions 24 of locally intensified electric field. Here, in one embodiment, the fractal antenna segment is designed for resonance in the infrared range, with the intensifies electric field regions 34 (for example as shown toward the straight-line sides of the metal pads being the place where blue phosphors and red phosphors (or other emissive materials 24) would be deposited such that their emission, would be enhanced the intensified electric fields in those regions 34.

Figure 14:
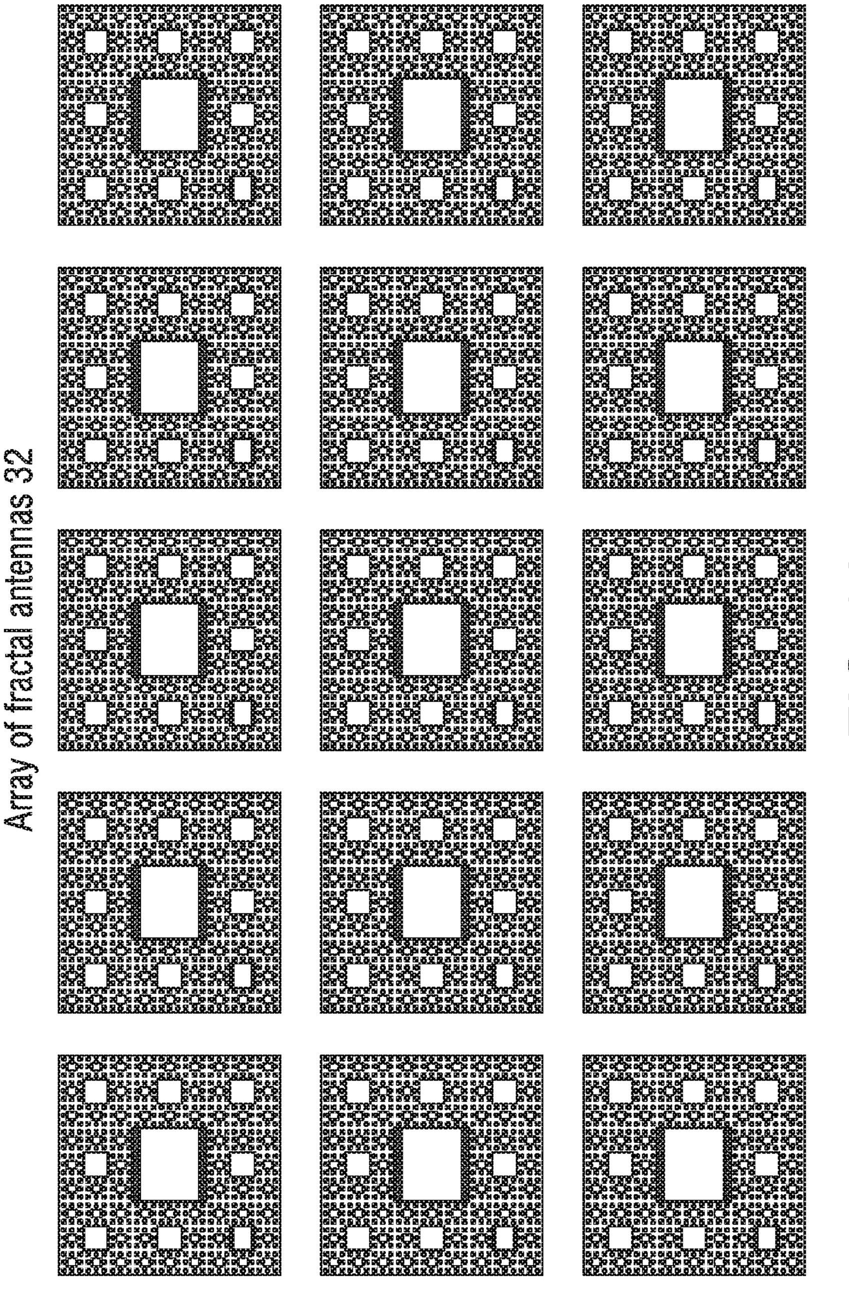
FIG. 14 is a diagram showing a repeated pattern of the fractal antenna segment of FIG. 13

FIG. 14 is a diagram showing a repeated pattern (array) of the fractal antenna segments 32 of FIG. 13.

Figure 15:
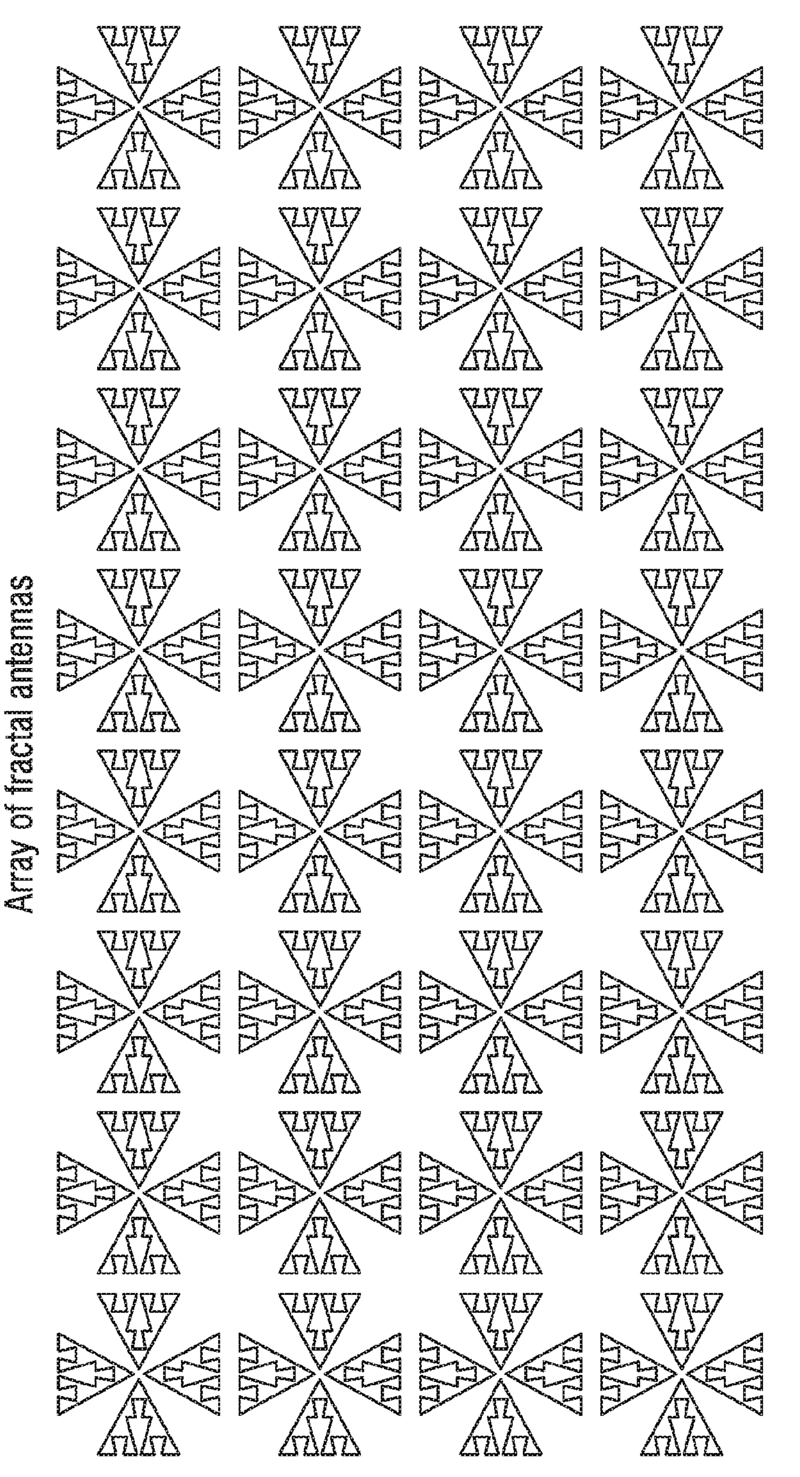
FIG. 15 is a diagram showing a pattern of bowtie fractal antenna segments.

FIG. 15 is a diagram showing a pattern (array) of bowtie fractal antenna segments, providing an alternative embodiment to the fractal antenna segments of FIG. 14.

In one embodiment of the invention, the resonant structures can comprise three-dimensional fractal patterns. Known in the art is the fabrication of three-dimensional fractal structures by nanoscale anisotropic etching of silicon such as described in Nanoscale etching of 3d fractal structures with many applications including 3d fractal antennas and structures for filters, by Brian Wang, Jun. 22, 2013, in the Journal of Micromechanics and Microengineering, (available at www.nextbigfuture.com/2013/06/nanoscale-etching-of-3d-fractal.html) the entire contents of which are incorporated herein by reference. In one embodiment of the invention, metal is deposited over a silicon three-dimensional fractal structure to form a multi-dimensional light collector.

Figure 16:
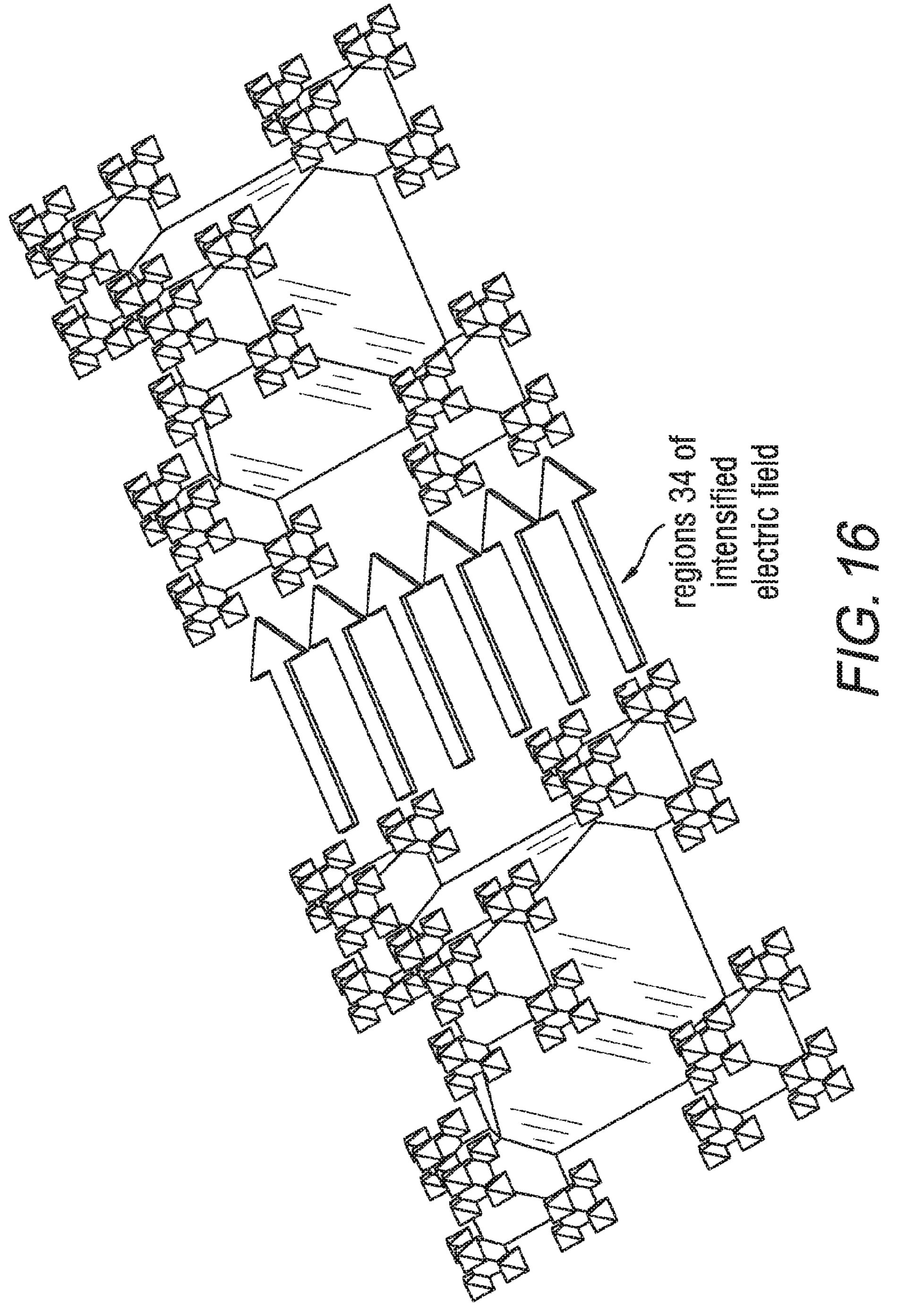

FIG. 16 is a diagram showing a paired three-dimensional fractal structure with regions 34 of an intensified electric field in between the pairs. The paired three-dimensional fractal structure is a color enhancement structure according to one embodiment of the invention. In one embodiment of the invention, these pyramidal type structures would be metallized with opposing faces metalized, a first loop conductor formed around the other sides of the first pyramid, then connecting across a region between the pair, and then a second loop formed around the sides of the second pyramid to the metallized opposing face of the second pyramid, to mimic (as seem from above) the ¾ λ folded resonators shown in FIG. 3.

In one embodiment, converter (emissive) materials 24 would be disposed nearby different sections of the pyramidal type structures and preferably between the opposing faces of the pair where the intensified electric field (depicted by the arrows) exists. With the three-dimensional aspect of this invention, red, yellow, green, and blue converters (or other designated emitters) could be disposed at different levels within this region of intensified electric field.

Figure 17:
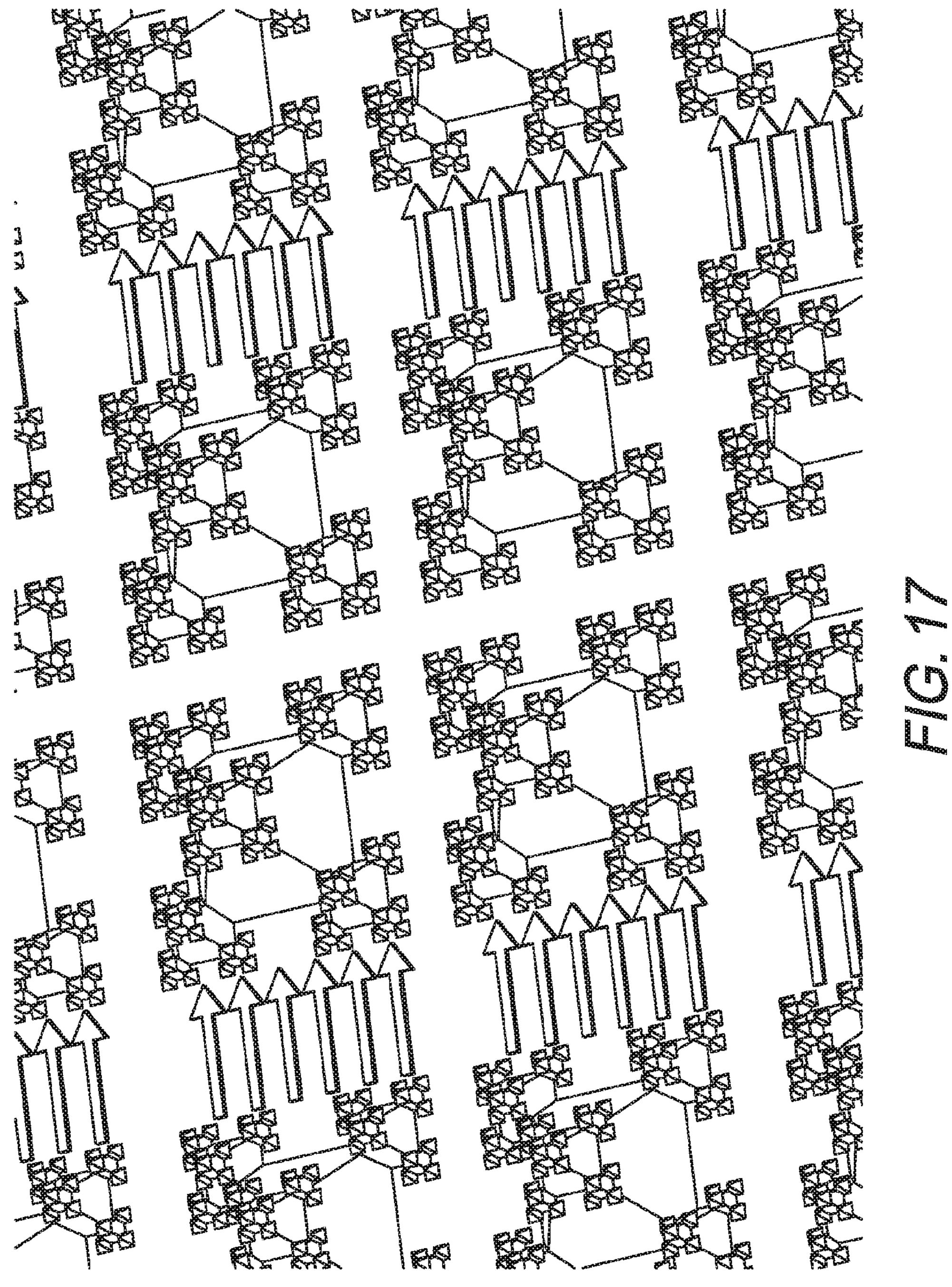
FIG. 17 is a diagram showing a pattern of the paired three-dimensional fractal structures.

FIG. 17 is a diagram showing a pattern (array) of the paired three-dimensional fractal structures of FIG. 16.

In these embodiments shown in FIGS. 12 to 17, the energy converters, or light or electron emitting materials, or color emitting or color converter materials (i.e., emissive materials 24) are disposed in a vicinity of one or more energy augmentation structures (i.e., the ¾ λ folded resonators). As such, the energy augmentation structures preferably are in a region of intensified electric field. The intensified electric field may represent a region of intensified energy especially if there is electrical current flow conductively coupling the energy converter to the one energy augmentation structures. In later embodiments, conductively coupling the energy converter to the one energy augmentation structures has advantages. Accordingly, the energy converters, or light or electron emitting materials, or color emitting or color converter materials disposed in a vicinity of one or more energy augmentation structures may have a physical conductive connection between the energy converter and the at least one energy augmentation structure. Alternatively, the coupling may be more that of radiatively coupling the electric fields from the resonant structure into energy converters or color converting or enhancing materials disposed inside the energy augmentation structure, outside the energy augmentation structure, in a layer with the energy augmentation structure, or in a layer above or below the energy augmentation structure.

Figures 18, 19:
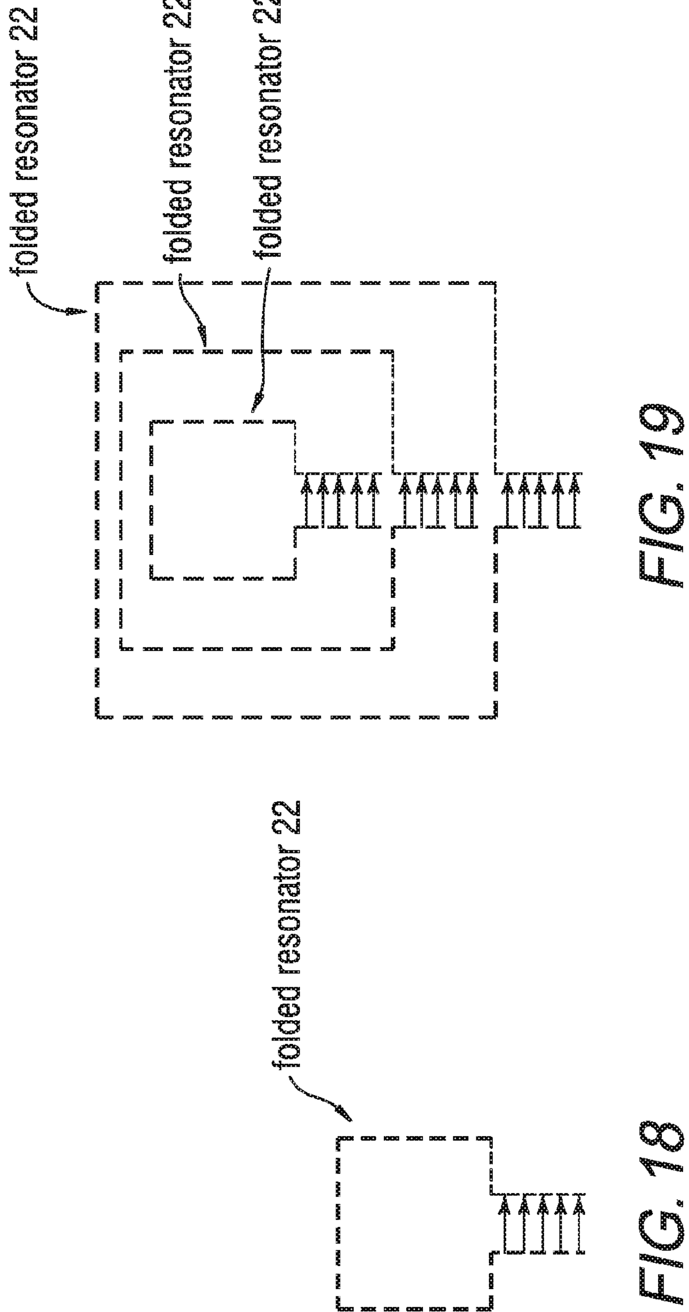
FIG. 18 is a diagram showing a ¾ wavelength resonator with the distal ends of the resonator antenna protruding outwardly while maintaining parallelism.
FIG. 19 is a diagram showing a packing configuration for three different ¾ wavelength resonators, that are maintained in plane with no overlapping distal ends.

The energy augmentation structures are not limited to those shown above. Other variants are possible. Moreover, in one embodiment of the invention, the ¾ λ folded resonators need not to have the "folded sections" which fold inwards as shown in FIG. 3. Instead, as shown in FIG. 18, the ¾ λ resonators of the invention can have folded sections which fold outward with the regions of intensified electric field being outside of the "loop" of the resonator. The distal ends of the antenna protrude outwardly while maintaining parallelism. Specifically, FIG. 8 is a schematic of a ¾ λ external-electrode folded resonator 22. This external, opposed electrode pair design follows the general apportioning, scaling aspects, converter material placement, etc., shown in FIGS. 5 through 11 but with the internal folded sections being replaced by the external-electrode pair.

In one embodiment of the invention, the ¾ λ external-electrode folded resonator 22 provides the capability to be packed in a concentric-type arrangement with progressively increasing or decreasing size resonators. These resonators are maintained in plane with no overlapping distal ends. FIG. 19 is a schematic of a plurality of concentric-type ¾ λ external-electrode folded resonators 22. Since each of the ¾ λ external-electrode folded resonators 22 has a different electrical length, the plurality of concentric-type ¾ λ external-electrode resonators will be "tuned" to the different wavelengths associated with the respective electrical lengths. Three different frequencies are therefore focused between the distal ends of the antennas.

Figures 20, 21:
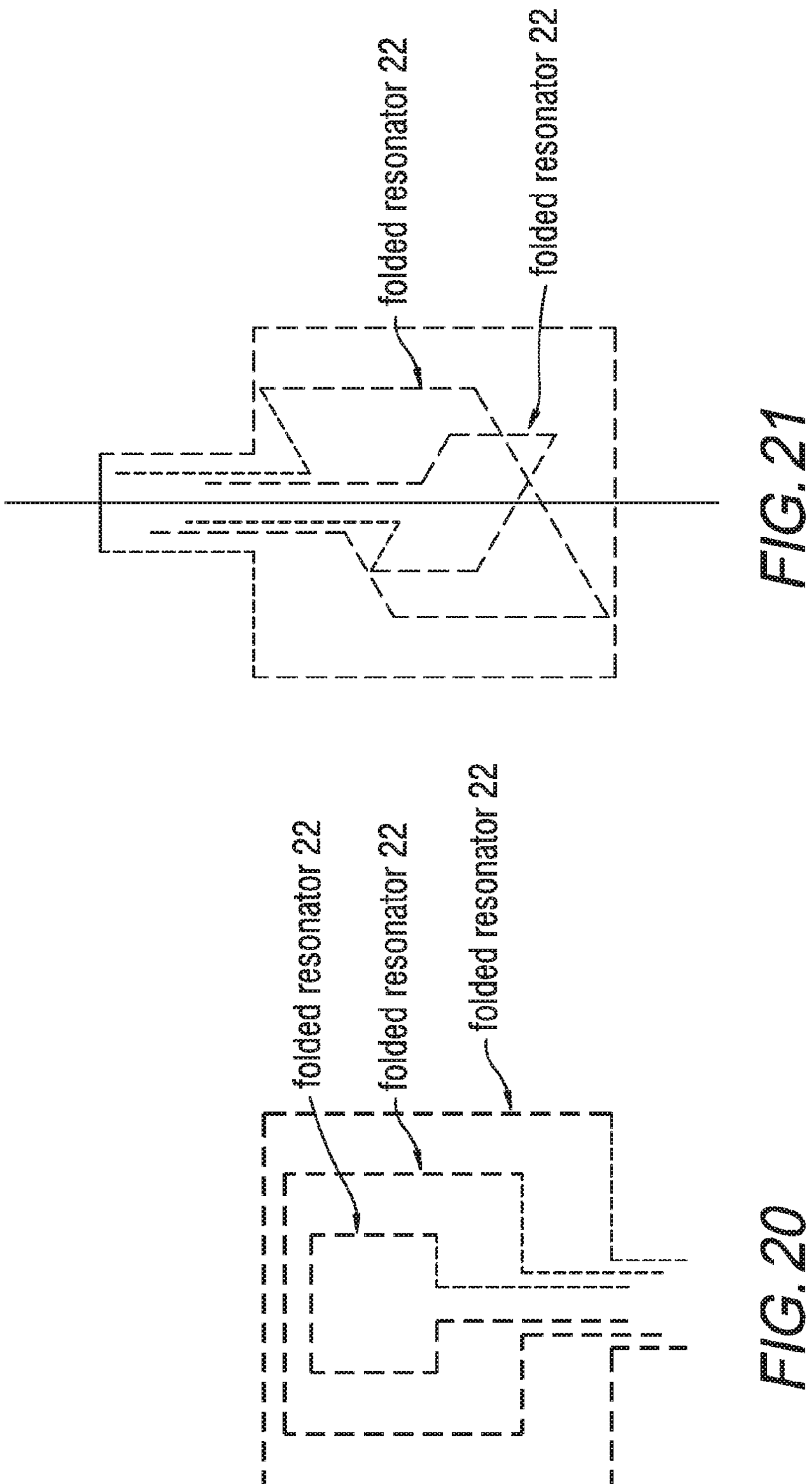
FIG. 20 is a diagram showing another packing configuration for three different ¾ wavelength resonators, that are maintained in plane with overlapping distal ends.
FIG. 21 is a diagram showing yet another packing configuration for the ¾ wavelength resonators, with an off (or out of) plane axial symmetry.

In another embodiment, FIG. 20 is a schematic of a plurality of concentric-type ¾ λ external-electrode folded resonators 22 with overlapping electrodes. In one embodiment, the overlapping provides a more concentrated/enhanced field region than in the non-overlapping arrangement of FIG. 19.

The present invention is not limited to planar concentric type packing arrangements as shown in FIG. 19 or 20. The three different ¾ wavelength resonators in FIG. 20 are maintained in plane with overlapping distal ends. These antennas are inductively coupled. In one embodiment, the present invention utilizes an off plane configuration with axial symmetry where the antennas are in an axially rotated, multiple frequency, interleaved ¾ wave resonator structure. FIG. 21 is a schematic of an axially rotated, multiple frequency, interleaved ¾ wave resonators 22 showing (in this example) three differently sized resonators for multiple frequency resonance disposed about/along a common axis but axially rotated. In one embodiment, in this configuration, the resultant electric field is concentrated without one electrode section perturbing the electric fields from another.

In a further embodiment, there is provided an energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

Figure 22:
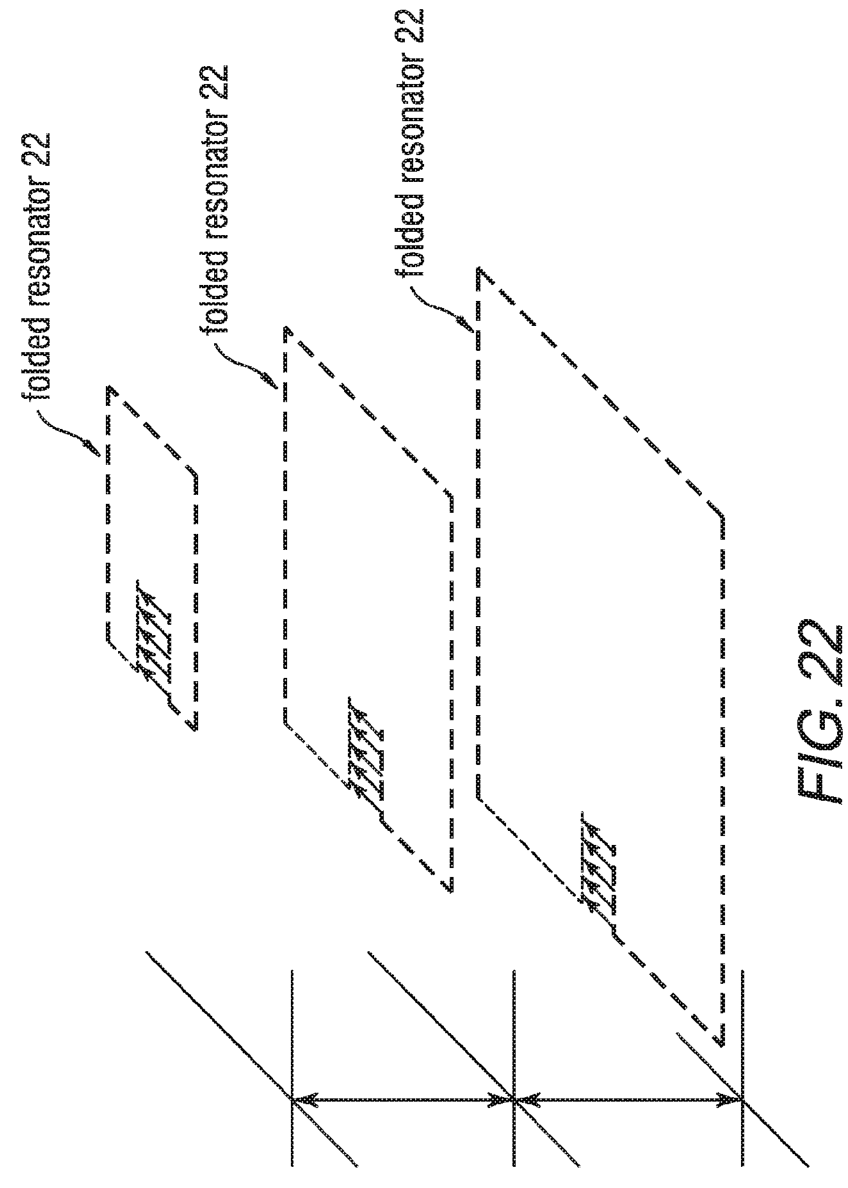
FIG. 22 is a diagram showing a multi-level packing configuration in parallel planes for the folded ¾ wavelength resonator shown.
Figure 23:
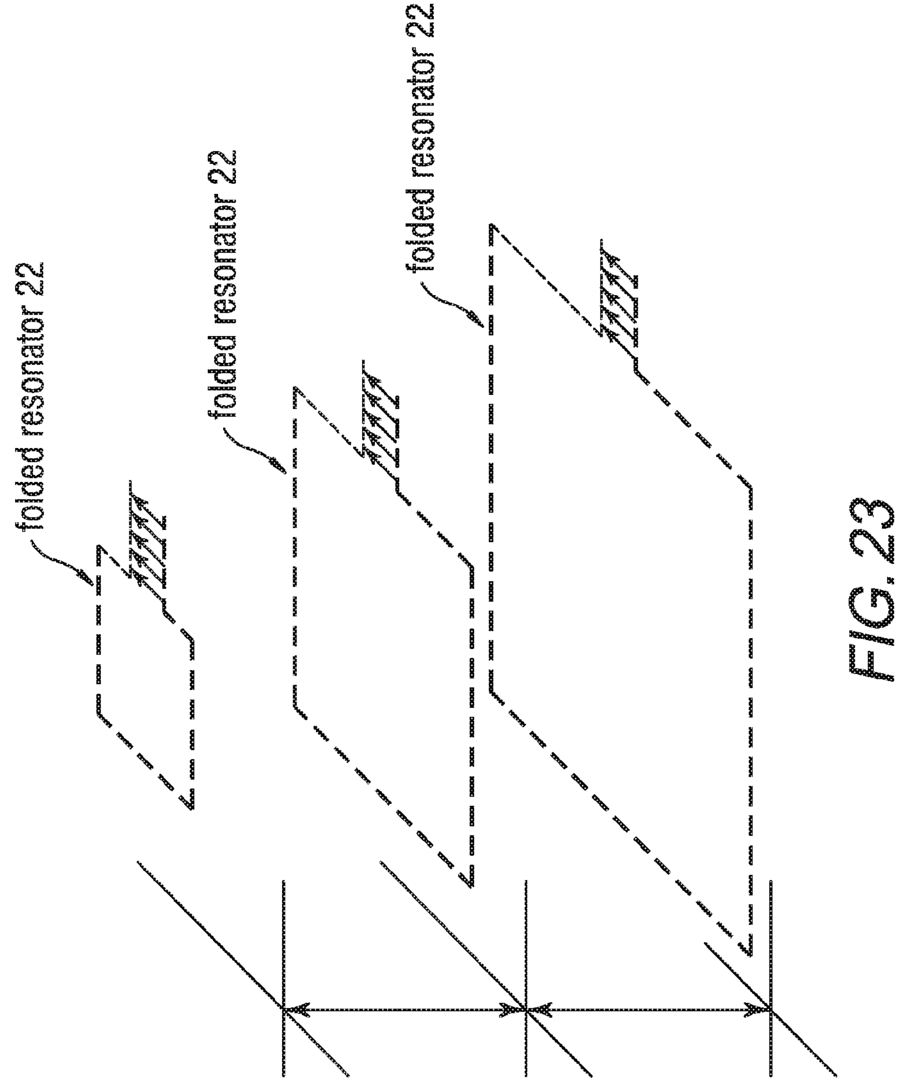
FIG. 23 is a diagram showing a multi-level packing configuration in parallel planes with distal ends protruding out for the ¾ wavelength resonator in FIG. 22.

In one embodiment, the present invention can use different levels for disposing ¾ λ resonators thereon regardless of the resonators being ¾ λ internally-folded resonators or ¾ λ external-electrode resonators. This packing is shown in FIGS. 22 and 23 for configuration in parallel planes with distal ends folded in or protruding out respectively.

Figure 24A:
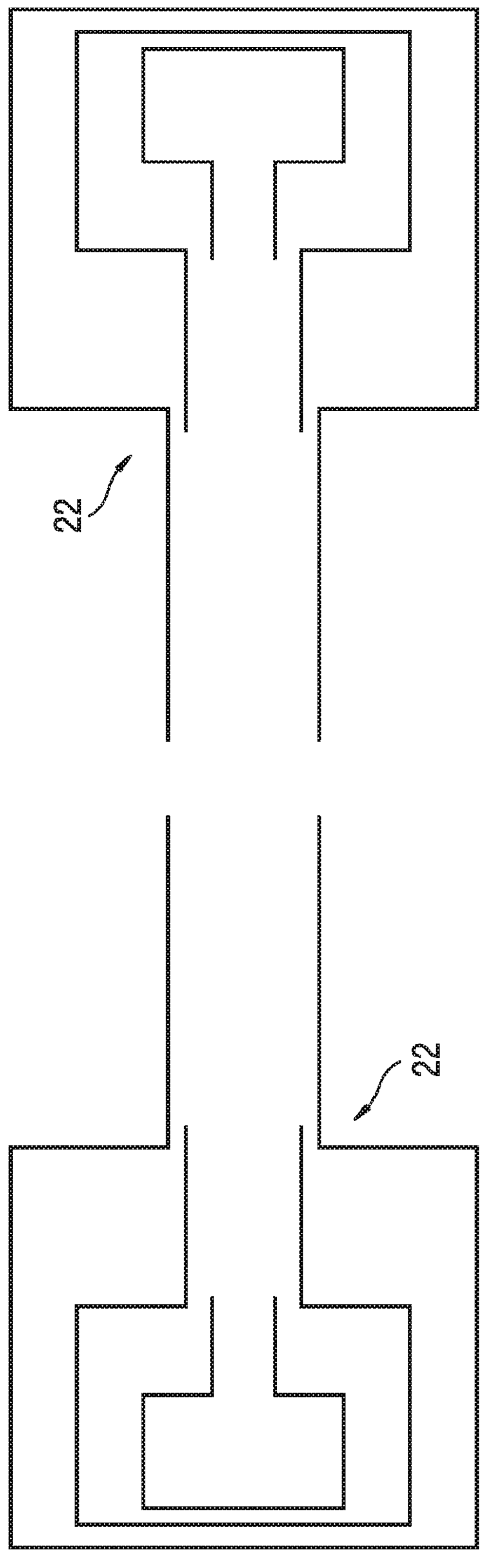
FIG. 24A is a diagram showing a different in-plane packing configuration.

In the embodiment of the invention depicted in FIG. 20 having a plurality of concentric-type ¾ λ external-electrode resonators 22, the antennas are inductively decoupled. This configuration allows the electric field to be focused from three different frequencies in a longer path. This configuration can be used to create a mirror image configuration to extend the length of focused electric field as is illustrated in FIG. 24A.

Figure 24B:
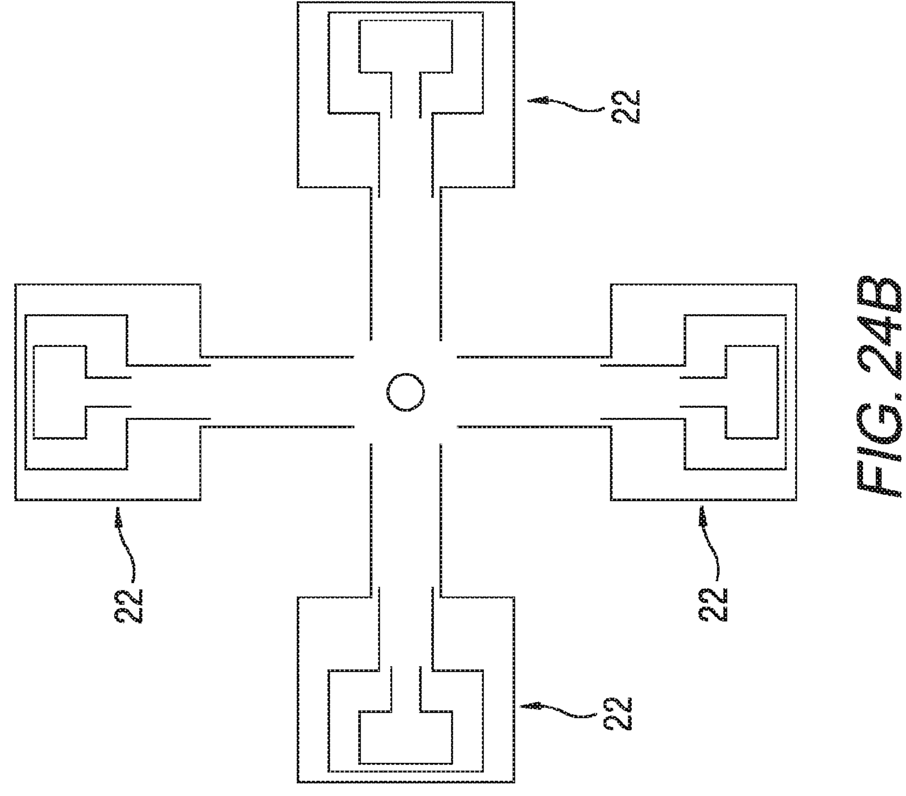
FIG. 24B is a diagram showing another different in-plane packing configuration.

The resonator configuration in this case is mirror imaged with another set of antennas (folded resonators 22) to create a longer path (doubled) of focused electric field. Furthermore, the resonator antenna configuration can be placed in more creative ways to enhance the electric field focusing around a target as is illustrated in the FIG. 24B.

The configuration in FIG. 25 allows the surrounding of a target within the plane of the resonator structure/antenna for the purpose of heating and focusing energy around the target. This prevents heat dissipation in silicon where the thermal conductivity is high. The silicon substrate in such an instance can be single crystalline, polycrystalline or amorphous.

In one embodiment of the present invention, an "energy augmentation structure" represents a structure whereby a spatial region of the energy collector contains a converter material (or other light or electron emitting material) exposed to energy which stimulates emission of light at a different energy (wavelength) from that to which it is exposed while being in a spatial area/volume (e.g., between or around or in a vicinity of the folded structures or the external-electrode pairs) where there is an artificially induced higher electrical field and/or a higher energy density. These artificial regions can be produced for example by use of structures including, but not limited to, multiple level collection optics, resonators, fractal antennas, and electrical grid (or electrode) patterns.

By having the light or electron emitting materials disposed in a vicinity of the energy augmentation structures of this invention, regardless of the whether the energy augmentation structure is in a region of intensified electric field or otherwise outside the region of intensified electric field, the energy augmentation structures of the invention are able to produce light which can be used for a variety of applications, in particular for photo-stimulation of biological, chemical, and physical reactions such as for example photoactivation of photoreactive drugs, photoactivation of photosensitive materials such as adhesives or lithographic photoresists, or for direct interaction with biological and chemical agents in the environment of the augmentation structures, as in sterilization.

In one embodiment, the light or electron emitting materials noted above are disposed with an energy augmentation structure comprising one or more of an electromagnetic resonator structure, a folded resonator structure, and a fractal resonating structure, any of which having a region of an intensified electromagnetic field within the resonating structures.

In one embodiment, the energy converter or light or electron emitting materials noted above includes one or more luminescing materials. As described herein, there are uses of the energy augmentation structure and/or energy collector embodiments which enhance bioluminescence, chemo-luminescence, photoluminescence, fluorescence, mechano-luminescence, and/or electron emission.

In one embodiment, the energy converter or light emitting materials noted above includes for the one or more luminescent materials phosphorescent materials, fluorescent materials, electroluminescent materials, chemo-luminescent materials, bioluminescent materials, and mechano-luminescent materials used in conjunction with or not in conjunction with the energy augmentation structure noted above. When used in conjunction with the energy augmentation structure noted above, the emitted electromagnetic energy from the luminescent material is emitted with at least one augmented property compared to if the energy converter (e.g., the luminescent material) were remote from the at least one energy augmentation structure.

In one embodiment, the bioluminescent materials are UV-emitting bioluminescent materials such as catalyzed luciferase and luminescent proteins.

In one embodiment, the energy converter or light emitting materials noted above includes for the one or more luminescing materials phosphorescent materials, fluorescent materials, electroluminescent materials, chemo-luminescent materials, bioluminescent materials, and mechano-luminescent materials used in conjunction with or not in conjunction with the energy augmentation structure noted above and which emit one of ultra-violet, visible, near infrared, and infrared light. In this embodiment, UV-emitting electroluminescent materials or mechano-luminescent devices and materials can be used. In this embodiment, UV-emitting bioluminescent materials can be used.

In some embodiments, metallic patterns form a folded resonator having opposing electrodes with electric fields directed in between, and a converter is positioned between the opposing electrodes or within fringing electric field of the opposing electrodes or otherwise in a vicinity of the opposing electrodes. In one example, the folded resonator is a $\frac{3}{4}\lambda$ folded resonator. In one example, metallic patterns comprise at least one of Au, Ag, Cu, Al, or transparent metal oxides. In another example, the metallic patterns can be formed with refractory metals such for example Ti, W, and Mo.

In some embodiments, the metallic patterns referenced above comprise an external external-electrode pair structure having opposing electrodes with electric fields directed in between, and a converter is positioned between the opposing electrodes or within fringing electric field of the opposing electrodes or otherwise in a vicinity of the opposing electrodes. In one example, the resonator is a $\frac{3}{4}\lambda$ external-electrode pair resonator. In one example, metallic patterns comprise at least one of Au, Ag, Cu, Al, or transparent metal oxides. In another example, the metallic patterns can be formed with refractory metals such for example Ti, W, and Mo.

In some embodiments, plural resonators and plural converters are disposed at multiple positions throughout a light collector. In one example, the plural converters are positioned to convert light being internally scattered within the light collector.

In some embodiments of the energy augmentation structures, a first level of metallic patterns (or a second level of metallic patterns) comprises a metal core cladded with a high-K dielectric and a subsequent cladding of a low-K dielectric. In some embodiments of the energy augmentation structures, the first level of metallic patterns noted above (or the second level of metallic patterns) comprises a radial pattern of conductors. In some embodiments of the energy augmentation structures, the first level of metallic patterns noted above (or the second level of metallic patterns) comprises a fractal pattern. In one example, the fractal pattern is embedded within a dielectric material.

In some embodiments of the energy augmentation structures, the first level of metallic patterns noted above (or the second level of metallic patterns) comprises a three-dimensional fractal structure.

In some embodiments of the energy augmentation structures, there is provided a panel with the first level of metallic patterns and the second level of metallic patterns and optionally multiple converters formed therein or thereon. In some embodiments of the augmentation structures, there is provided a sheet with the first level of metallic patterns and the second level of metallic patterns and optionally multiple converters formed therein or thereon.

In some embodiments of the energy augmentation structures, the first level of metallic patterns noted above (or the second level of metallic patterns) is of different sizes and/or orientations to each other of the first level of metallic patterns or with respect to the second level of metallic patterns.

In another embodiment, the energy augmentator can collect or distribute light.

Figure 25A:
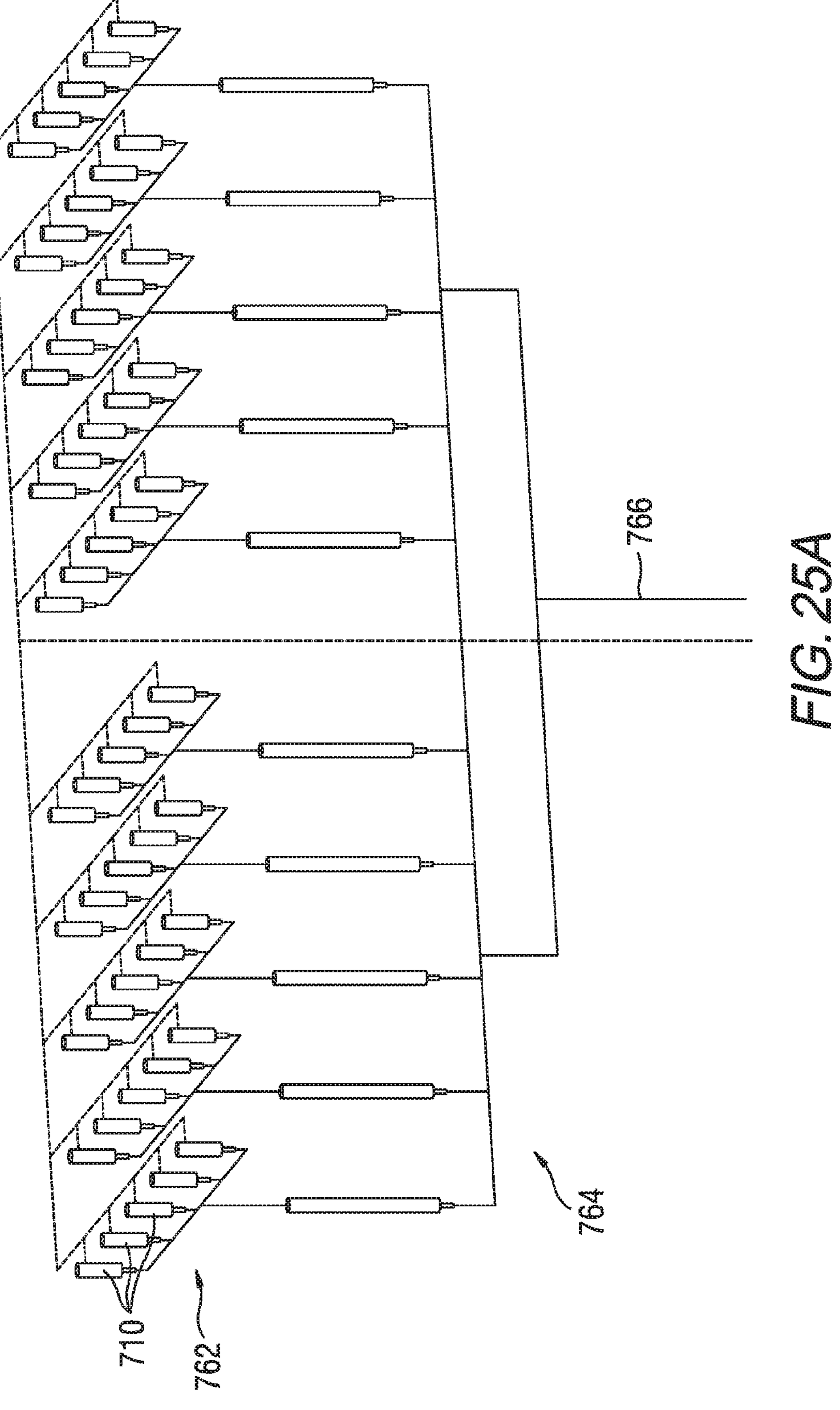
FIG. 25A is a schematic illustrating a distributed point light collector/transmitter of the invention.
Figure 25B:
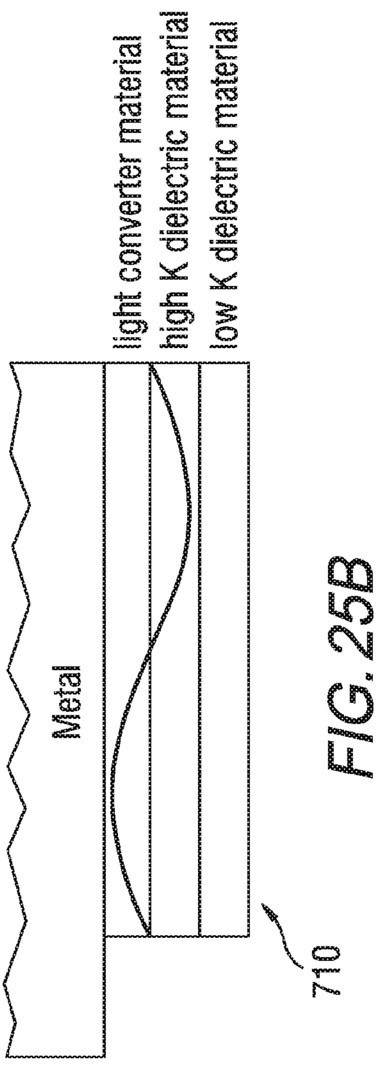
FIG. 25B is a schematic of a cross section of the collector/transmitter of FIG. 25A.

FIG. 25A is a schematic illustrating a distributed point light collector/transmitter of the invention showing a distribution of branches that can either collect light from distributed points 710 or conversely can distribute light from a central source 766 to the distributed points 710. The section of the collector/transmitter is shown in FIG. 25B showing a core metal, an optional light converter material, a high K dielectric, and a low K dielectric. In this arrangement, as shown, light is confined and not loss to scatter out of the collector/transmitter, except at the ends.

B. Energy Converters

In various embodiments of the invention, energy converters can be used with or without the energy augmentators described above. In some embodiments, the converters are for up conversion of light e.g., from the IR regime into visible electromagnetic radiation and for down conversion of light e.g., from the UV range into visible electromagnetic radiation. The invention in various embodiments up converts energy, preferably light in the visible spectrum. The invention encompasses a variety of applications where the up and down conversion materials with or without the energy augmentators are included to enhance electromagnetic energy emission, preferably light or photon emission. When an energy augmentator is present, it may be separate from or connected to the energy converter. In certain embodiments, the energy converter can have the energy augmentator formed on its surface through chemical vapor deposition ("CVD") or physical vapor deposition ("PVD") processes or other nanoscale "printing" methods. Such embodiments may be particularly useful in methods for treating human or animal patients, in which having such energy augmentators "imprinted" on a surface of the energy converter can guarantee proximity between the energy augmentator and the energy converter to maximize the interaction with the energy being applied. Alternatively, the energy augmentator can be formed on a surface of an inert non-energy converting particle, formed, for example, from silica or formed from a non-energy converting particle coated with an biologically and/or chemically inert coating (such as, for example, diamond, diamond-like carbon, or similar inert materials). Such an energy augmentator can then be co-administered with the energy converter to the human or animal patient.

Suitable energy modulation agents or energy converters (the two terms are used interchangeably herein) of the invention include, but are not limited to, a biocompatible fluorescing metal nanoparticle, fluorescing dye molecule, gold nanoparticle, a water soluble quantum dot encapsulated by polyamidoamine dendrimers, a luciferase (bioluminescence), a biocompatible phosphorescent molecule, a combined electromagnetic energy harvester molecule, and a lanthanide chelate capable of intense luminescence.

Alternatively, the energy modulation agent or energy converter can emit energy in a form suitable for absorption at a target site or receptor. For example, the initiation energy source may be acoustic energy and one energy converter may be capable of receiving acoustic energy and emitting photonic energy (e.g. sonoluminescent molecules) to be received by another energy converter that is capable of receiving photonic energy. Other examples include energy converters that receive energy at x-ray wavelength and emit energy at UV wavelength, preferably at UV-A wavelength.

A plurality of such energy converters may be used to form a cascade to transfer energy from initiation energy source via a series of energy converters.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a target site or a receptor such as a photoactivatable agent.

In a further embodiment, a biocompatible emitting source, such as a fluorescing metal nanoparticle or fluorescing dye molecule, is selected as an energy converter that emits in the UV-A band. In another embodiment, an energy converter comprising a UV-A emitting source can be a gold nanoparticle comprising for example a cluster of 5 gold atoms.

In another embodiment, an energy converter comprising a UV- or light-emitting luciferase is selected as the emitting source. A luciferase may be combined with ATP or another molecule, which may then be oxygenated with additional molecules to stimulate light emission at a desired wavelength. Alternatively, a phosphorescent emitting source may be used as the energy converter. One advantage of a phosphorescent emitting source is that the phosphorescent emitting molecules or other source may be electroactivated or photoactivated prior to insertion into the tumor either by systemic administration or direct insertion into the region of the tumor. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In one embodiment, the energy converters of the invention can include persistent after-glow phosphor materials emitting light in the visible to near ultraviolet and ultraviolet range. In one embodiment, Eu-doped strontium aluminate is used as an energy converter in which deep UV light or x-ray or electron beans "charge" the photoluminescence such that these phosphors can be charged outside for example a patient and then injected into target or diseased site where UV photons would be emitted. In another embodiment, gadolinium strontium magnesium aluminate is used as an energy converter in which deep UV light or x-ray or electron beans "charge" the photoluminescence such that these phosphors can be charged outside for example a patient and then injected into target or diseased site where UV photons would be emitted. U.S. Pat. Appl. Publ. No. 20070221883 (the entire contents of which are incorporated herein by reference) describes specifically gadolinium-activated strontium magnesium aluminate having an excitation maximum at about 172 nm, and which emits in a narrow-band UV emission at about 310 nm. The '883 publication also describes other useful energy converters for this invention, making note of emission spectra between 300 nm and 320 nm for a $Sr(Al,Mg)_{12}O_{19}$:Gd phosphor and two 312 nm line emitting phosphors, $YMgB_5O_{10}$:Gd, Ce and $YMgB_5O_{10}$: Gd. Ce, Pr. WO2016200349 (the entire contents of which are incorporated herein by reference) describes long lasting yellowish-green emitting phosphorescent pigments in the strontium aluminate (SrAl2O4) system, which could serve as energy converters in the present invention. WO 2016200348 (the entire contents of which are incorporated herein by reference) describes long lasting bluish-green emitting phosphorescent pigments in the strontium aluminate (Sr4Al14O25) system, which could serve as energy converters in the present invention. Xiong et al. in "Recent advances in ultraviolet persistent phosphors," Optical Materials X 2 (2019) (the entire contents of which are incorporated herein by reference) describes a number of ultraviolet persistent phosphors that could as energy converters in the present invention. The table below provides a listing of such persistent phosphors:

| | | |
|---|---|---|
| $SrO:Pb^{2+}$ | 390 | >1 h |
| $CaAl_2O_4:Ce^{3+}$ $Tb^{3+}$ | 400 | >10 h |
| $CaAl_2O_4:Ce^{3+}$ $Tb^{3+}$ | 413 | >10 h |
| $Sr_2Al_2SiO_7:Ce^{3+}$ | 400 | several minutes |
| $SrZrO_3$ | 395 | <1000 s |
| $BaZrO_3:Mg^{2+}$ | 400 | >2400 s |
| $SrZrO_3:Pr^{3+}$ | 356 | |
| $CdSiO_3:Bi^{3+}$ | 360 | |
| $CdSiO_3:Bi^{3+}$ $Dy^{3+}$ | 360 | |
| $CdSiO_3:Bi^{3+}$ $Gd^{3+}$ | 344 | >6 h |
| $Sr_2MgGe_2O_7:Pb^{2+}$ | 370 | >12 h |
| $NaLuGeO_4:Bi^{2+}$ $Eu^{3+}$ | 400 | >63 h |
| $CaZnGe_2O_6:Bi^{3+}$ | 300-700 | >12 h |
| $Cs_2NaYF_6:Pr^{3+}$ | 250 | >2 h |

In one embodiment, the phosphor described by Xiong et al. as $CaAl_2O_4:Ce^{3+}$ having an emission peak of 400 nm and a persistent time of more than 10 h could be used, where it would be charged by x-ray irradiation outside a patient and then injected at a diseased site to provide internally generated UV light.

In one embodiment, the persistent phosphors noted could be activated ex vivo and introduced along with psoralen (or other photoactivatable drug) into the patient by exchange of a bodily fluid or for example by supplying the persistent phosphors and the photoactivatable drug into a patient's blood stream.

In one embodiment, the persistent phosphors noted could be activated in vivo by injection of the phosphors into a diseased site and then exposure to x-rays.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. In another embodiment, a Stokes shift of an emitting source or a series of emitting sources arranged in a cascade is selected to convert a shorter wavelength energy, such as X-rays, to a longer wavelength fluorescence emission such an optical or UV-A.

In one embodiment, a lanthanide chelate capable of intense luminescence is used as an energy converter. In another embodiment, a biocompatible, endogenous fluorophore emitter is selected as an energy converter.

In one embodiment, the energy converters of the invention can include visible and UV-light emitting bioluminescent materials. In one embodiment, bioluminescent materials such as coelenterate-type luciferin analogues could be used including amide monoanion known to emit at 480 nm and oxyluciferin known to emit at 395 nm.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

This invention in various embodiments can use a wide variety of down conversion materials (or mixtures of down conversion materials) with or without the energy augmentators to enhance light or photon emission. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance light or photon emission can convert energy from one of ultraviolet light, x-rays, and high energy particles to visible light. The down conversion materials to enhance light or photon emission can convert energy from higher energy visible light to lower energy visible light.

In one embodiment of the invention, a quantum dot mixture with or without the energy augmentators can be used for the multiple nanoparticles. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted wavelength or energy emission. Quantum dots represent one way to down convert blue light of the spectrum to a targeted wavelength or energy emission.

As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSc), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm. Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 μm. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm. In practice, however, the excitation or pump radiation is at least about 50 nanometers shorter than the emitted radiation.

Specifically, in one embodiment of the invention, a quantum dot mixture (QDM) coating can be deposited using CVD and or sol-gel techniques using standard precipitation techniques. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. These and the other conversion materials described here can be used with or without energy augmentators. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, $ZnS{:}Mn^{2+}$, ferric oxide, titanium oxide, zinc oxide, zinc oxide containing small amounts of $Al_2O_3$, and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, BaFBr:$Eu^{2+}$ nanoparticles, Cesium Iodine, Bismuth Germanate, Cadmium Tungstate, and CsBr doped with divalent Eu.

In various embodiments of the invention, the following luminescent polymers with or without energy augmentators are also suitable as conversion materials: poly(phenylene ethynylene), poly(phenylene vinylene), poly(p-phenylene), poly(thiophene), poly(pyridyl vinylene), poly(pyrrole), poly (acetylene), poly(vinyl carbazole), poly(fluorenes), and the like, as well as copolymers and/or derivatives thereof.

In various embodiments of the invention, the following materials with or without energy augmentators can be used similar to that detailed in U.S. Pat. No. 7,090,355, the entire contents of which are incorporated herein by reference. For down-conversion, the following materials can be used. Inorganic or ceramic phosphors or nano-particles, including but not limited to metal oxides, metal halides, metal chalcogenides (e.g. metal sulfides), or their hybrids, such as metal oxo-halides, metal oxo-chalcogenides. Laser dyes and small organic molecules, and fluorescent organic polymers. Semiconductor nano-particles, such as II-VI or III-V compound semiconductors, e.g. fluorescent quantum dots. Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_mA_{1-m})_3(Al_nB_{1-n})_5O_{12}$, doped with Ce; where $0 \leq m, n \leq 1$, where A includes other rare earth elements, B includes B, Ga. In addition, phosphors containing metal silicates, metal borates, metal phosphates, and metal aluminates hosts can be used. In addition, nano-particulates phosphors containing common rare earth elements (e.g. Eu, Tb, Ce, Dy, Er, Pr, and Tm) and transitional or main group elements (e.g. Mn, Cr, Ti, Ag, Cu, Zn, Bi, Pb, Sn, and Tl) as the fluorescent activators, can be used. Materials such as Ca, Zn, Cd in tungstates, metal vanadates, ZnO, etc. can be used.

The commercial laser dye materials obtained from several laser dye vendors, including Lambda Physik, and Exciton, etc. can also be used with or without energy augmentators. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc. have been used in optoelectronic devices, such as polymer light emitting diodes (PLED). Such fluorescent polymers can be used directly as the fluorescent layer of the transparent 2-D display screen with and without energy augmentators.

As noted above, semiconductor nanoparticles (e.g., quantum dots) can be used with or without energy augmentators. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nanoparticle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion materials with or without energy augmentators. Such molecules include a metal center of rare earth elements including Eu, Tb, Er, Tm, Ce protected with organic chelating groups. The metal center may also include transitional elements such as Zn, Mn, Cr, Ir, etc. and main group elements such as B, Al, Ga. Such organometallic molecules can readily dissolve in liquid or transparent solid host media. Some examples of such fluorescent organometallic molecules include: 1. Tris(dibenzoylmethane)mono (phenanthroline)europium(III); 2. Tris(8-hydroxyquinoline) erbium; 3. Tris(1-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-conversion materials for red emission include those discussed above and europium complexes such as those described in JP Laid-open Patent Publication (Kokai) No. 2003-26969, constructed such that ß-diketone ligand is coordinated to europium forming an europium complex capable of emitting red fluorescence. Other specific examples of the rare earth element complexes include complexes include lanthanum (Ln), curopium (Eu), terbium (Tb), and gadolinium (Gd) and combinations thereof. An europium (Eu) complex is capable of emitting red fluorescence when irradiated with ultraviolet rays having a wavelength ranging from 365 nm to 410 nm. Terbium (Tb) is capable of emitting green fluorescence when irradiated with ultraviolet rays having a wavelength of 365 nm.

In other down-conversion embodiments, the down conversion materials which emit red light may include europium, light emitting particles which emit green light may include Terbium, and light emitting particles which emit blue or yellow light may include cerium (and/or thulium). In up-conversion embodiments, up conversion materials which emit red light may include praseodymium, light emitting particles which emit green light may include erbium, and light emitting particles which emit blue light may include thulium. In embodiments, the conversion materials can be light emitting particles made of fluorescent molecules that emit different colors (e.g. red, green, and blue), or different wavelengths or energies of light. In embodiments, the conversion materials can be light emitting particles made of pure organic or organo-metallic dyes with or without energy augmentators.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converter materials (which can be used with or without energy augmentators) include for example ZnS, PbS, $SbS_3$, $MoS_2$, PbTe, PbSe, BeO, MgO. $Li_2CO_3$, $Ca(OH)_2$, $MoO_3$, $SiO_2$, $Al_2O_3$, $TeO_2$, $SnO_2$, KBr, KCl, and NaCl. These materials can include dopants to tailor the emission properties, as noted above. Examples of doped (or alloyed) glass systems suitable for the include $Y_2O_3$:Gd, $Y_2O_3$:Dy, $Y_2O_3$:Tb, $Y_2O_3$:Ho, $Y_2O_3$:Er, $Y_2O_3$:Tm, $Gd_2O_3$:Eu, $Y_2O_2S$:Pr, $Y_2O_2S$:Sm, $Y_2O_2S$:Eu, $Y_2O_2S$:Tb, $Y_2O_2S$:Ho, $Y_2O_2S$:Er, $Y_2O_2S$:Dy, $Y_2O_2S$:Tm, ZnS:Ag:Cl (blue), ZnS:Cu:Al (green), $Y_2O_2S$:Eu (red), $Y_2O_3$:Eu (red), $YVO_4$:Eu (red), and $Zn_2SiO_4$:Mn (green).

With regard more specifically to down converter materials suitable for the invention, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention with or without energy augmentators. In one example, the infrared-triggered phosphors would be used in conjunction with the folded resonators, and the receipt of a microwave or IR signal would locally heat and trigger emission. (This application would be particularly well suited for color enhancement and/or security applications.)

In other embodiments of the invention, the down converter materials (or mixtures of down converters materials (which can be used with or without energy augmentators) can include $Y_2O_3$:Li. Sun et al. "Luminescent properties of Li+ doped nanosized $Y_2O_3$:Eu," Solid State Comm. 119 (2001) 393-396 (the entire contents of which are incorporated herein by reference) describe such materials. Hou et al. "Luminescent properties nano-sized $Y_2O_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria ($Y_2O_3$) powders have been successfully synthesized by a co-precipitation method. The powders were well crystallized, and the grains were almost spherical with good dispersibility. The quenching concentration of $Eu^{3+}$ ions is 9 mol % which is much higher than micro-scaled powders. The incorporation of Li+ ions greatly improved the luminescence intensity. The highest emission intensity was observed with 4 mol % Li+ doped $Y_2O_3$:Eu powder ($(Y_{0.87}Eu_{0.09}Li_{0.04})_2O_3$) and the fluorescence intensity was increased by as much as 79%. Yi et al. "Improved cathodoluminescent characteristics of $Y_2O_3$:$Eu^{3+}$ thin films by Li-doping," Appl. Phys. A 87, 667-671 (2007) (the entire contents of which are incorporated herein by reference) describe cathodoluminescent spectra for both $Y_2O_3$:$Eu^{3+}$ and Li-doped $Y_2O_3$:$Eu^{3+}$ films and methods for making these materials.

Specific downconverting materials may also include at least one or more of $Y_2O_3$, $Y_2O_3$:Gd, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS, ZnSe, MgS, CaS, $Zn_2SiO_4$:Mn, LaOBr:Tm and alkali lead silicate including compositions of $SiO_2$, $B_2O_3$, $Na_2O$, $K_2O$, PbO, MgO, or Ag, and combinations or alloys or layers thereof. Furthermore, the down-converting materials can be sulfur containing phosphors, which can help for example in the rubber vulcanization or other photoactivated processes. An example of such a sulfur containing phosphor is: (Sr,Ca)$Ga_2S_4$. Other examples wherein said phosphor particles comprise a thiogallate host material selected from the group consisting of $SrGa_2S_4$, $CaGa_2S_4BaGa_2S_4$, $MgGa_2S_4$ and solid solutions thereof. The particle size of such phosphor can be controlled from 25 nm to 300 microns in size as described in U.S. Pat. No. 6,153,123A. The downconverting materials can include a dopant including at least one of Er, Eu, Yb, Tm, Nd, Mn, Sb, Tb, Ce, Y, U, Pr, La, Gd and other rare-earth species or a combination thereof. The dopant can be included at a concentration of 0.01%-50% by mol concentration. At times it is preferable to have a combination of dopants rather than one dopant such is the case for a Mn and Sb in silicate matrices.

The invention in other embodiments can use a wide variety of up conversion materials (or mixtures of up converters) with or without the energy augmentators to enhance a particular wavelength or energy of light emitted from a material or surface. These up conversion materials can include similar materials as discussed above with regard to down conversion but typically included doped or impurity states in a host crystal that provide a mechanism for up conversion pumping. Accordingly, the up conversion materials to enhance wavelength or energy emission can convert energy from one of near infrared, infrared, and microwave irradiation. The upconversion materials to enhance color emission can convert energy from lower energy visible light to higher energy visible light.

In one example, a nanoparticle of a lanthanide doped oxide can be excited with near infrared light such as laser light at 980 nm and 808 nm to produce visible light in different parts of the red, green, blue spectrum (different wavelengths or energies) depending on the dopant trivalent rare earth ion(s) chosen, their concentration, and the host lattice.

The lanthanide doped oxides suitable for this invention differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the $NaYF_4$ such that the $Yb^{3+}$ ion has an energy state at $2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the $Yb^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention with or without the energy augmentators.

Further, materials specified for up conversion materials in the invention (with or without energy augmentation) include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\leq1$, and $0<y\leq1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and non-conducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn, Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . $0<z\leq1$, $o<q\leq1$).

Some nanoparticles such as ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn, $Er^{3+}$ are known in the art to function for both down-conversion luminescence and upconversion luminescence and would be suitable for the invention with or without energy augmentators. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size >0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative concentration in the host crystal. For the example of upconversion in a $Y_2O_3$ host crystal, to achieve a blue emission (~450-480 nm) one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)]. The concentrations of dopants relative to each other and the crystal matrix must be tuned for every combination, and there are multiple ways to achieve multiple wavelength or energy emissions from even the same dopants.

Up-conversion of red light with a wavelength of about 650 nm in $Tm^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a $Tm^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of $LuPO_4$:$Yb^{3+}$, $Tm^{3+}$, and $YbPO_4$:$Er^{3+}$ nanocrystals in chloroform. Excitation at 975 nm has been shown by others to produce visible emission in the blue, green, or red spectral regions.

Tellurium and germanium oxides (tellurites and germanates) are also suitable upconverters. These glasses can be doped with Tm, Yb, Ho, Er, Pr, for example.

$Yb^{3+}$ doped $BaZrO_3$ is also suitable for upconversion. $Er^{3+}$ and/or $Tm^{3+}$ doping are also suitable for tailoring the emission wavelengths.

In another embodiment, $Nd^{3+}$:$Cs_2NaGdCl_6$ and $Nd^{3+}$, $Yb^{3+}$:$Cs_2NaGdCl_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2→4I9/2), and (4G7/2→4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for the present invention. Among the up-conversion luminescences for the $ZrF_4$ fluoride glasses, the green emission was seen to be extremely strong and the blue and red emission intensities were very weak.

In another embodiment, $Tm^{3+}$/$Yb^{3+}$-codoped $TeO_2$—$Ga_2O_3$—$R_2O$ (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MLCT) transition in $[Ru(dmb);]^{2+}$ (dmb=4,4'-dimethyl-2,2'-bipyridine) in the presence of anthracene or 9,10-diphenylanthracene have been reported to be up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95) relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW peak power).

In certain embodiments, further energy converters include, but are not limited to, (not ranked by order of preference or utility):

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$, and $LuPO_4$:$Pr^{3+}$. Examples further include the alkali earth chalcogenide phosphors which are in turn exemplified by the following non-inclusive list: MgS:$Eu^{3+}$, CaS:$Mn^{2+}$, CaS:Cu, CaS:Sb, CaS:$Ce^{3+}$, CaS:$Eu^{2+}$, CaS:$Eu^{2+}Ce^{3+}$, CaS:$Sm^{3+}$, CaS:$Pb^{2+}$, CaO:$Mn^{2+}$, CaO:$Pb^{2+}$.

Further examples include the ZnS type phosphors that encompass various derivatives: ZnS:Cu,Al(Cl), ZnS:Cl(Al), ZnS:Cu,I(Cl), ZnS:Cu, ZnS:Cu,In.

Also included are the compound IIIb-Vb phosphors which include the group IIIb and Vb elements of the periodic table.

These semiconductors include BN, BP, BSb, AlN, AlP, AlAs, AlSb, GaN, GaP, GaAs, GaSb, InN, InP, InAs, InSb and these materials may include donors and acceptors that work together to induce light emission diodes. These donors include, but are not limited to, Li, Sn, Si, Li, Te, Se, S, O and acceptors include, but are not limited to, C, Be, Mg, Zn, Cd, Si, Ge. Further included are the major GaP light emitting diodes which include, but are not limited to, GaP:Zn,O, GaP:NN, Gap:N and GaP, which emit colors Red, Yellow, Green and Pure Green respectively.

The materials can further include such materials as GaAs with compositional variation of the following sort: $In_{1-y}(Ga_{1-x}Al_x)_yP$.

Also included is silicon carbide SiC, which has commercial relevancy as a luminescent platform in blue light emitting diodes. These include the polytypes 3C-SiC, 6H-SiC, 4H-SiC with donors such as N and Al and acceptors such as Ga and B.

Further examples include multiband luminescent materials include, but not limited to, the following compositions $(Sr, Ca, Ba)_5(PO_4)_3Cl:Eu^{2+}$, $BaMg_2Al_{16}O_{27}:Eu^{2+}$, $CeMgAl_{11}O_{19}:Ce^{3+}:Tb^{3+}$, $LaPO_4:Ce^{3+}:Tb^{3+}$, $GdMgB_5O_{10}:Ce_3:Tb^{3+}$, $Y_2O_3:Eu^{3+}$, $(Ba,Ca,Mg)_5(PO_4)_3Cl:Eu^{2+}$, $2SrO_{0.84}P2O50.16B2O3:Eu^{2+}$, $Sr_4Al_{14}O_{25}:Eu^{2+}$.

Materials typically used for fluorescent high pressure mercury discharge lamps are also included. These can be excited with X-Ray and are exemplified by way of family designation as follows: Phosphates $(Sr, M)(PO_4)_2:Sn^{2+}$, Mg or Zn activator, Germanate $4MgO\cdot GeO_2:Mn^{4+}$, $4(MgO, MgF_2)GeO_2:Mn^{4+}$, Yttrate $Y_2O_3:Eu^{3+}$, Vanadate $YVO_4:Eu^{3+}$, $Y(P,V)O_4:Eu^{3+}$, $Y(P,V)O_4:In^{+}$, Halo-Silicate $Sr_2Si_3O_{82}SrCl_2:Eu^{2+}$, Aluminate $(Ba,Mg)_2Al_{16}O_{24}:Eu^{2+}$, $(Ba, Mg)_2Al_{16}O_{24}:Eu^{2+},Mn^{2+}$, $Y_2O_3Al_2O_3:Tb^{3+}$.

Another grouping by host compound includes chemical compositions in the halophosphates phosphors, phosphate phosphors, silicate phosphors, aluminate phosphors, borate phosphors, tungstate phosphors, and other phosphors. The halophosphates include, but are not limited to: $3Ca_3(PO_4)_2\cdot Ca(F,Cl)_2:Sb^{3+}$, $3Ca_3(PO_4)_2\cdot Ca(F,Cl)_2:Sb^{3+}/Mn^{2+}$, $Sr_{10}(PO_4)_6Cl_2:Eu^{2+}$, $(Sr,Ca)_{10}(PO_4)_6Cl_2:Eu^{2+}$, $(Sr, Ca)_{10}(PO_4)_6\cdot nB_2O_3:Eu^{3+}$, $(Sr, Ca,Mg)_{10}(PO_4)_6Cl_2:Eu^{2+}$. The phosphate phosphors include, but are not limited to: $Sr_2P_2O_7:Sn^{2+}$, $(Sr,Mg)_3(PO_4)_2:Sn^{2+}$, $Ca_3(PO_4)_2\cdot Sn^{2+}$, $Ca_3(PO_4)_2:Tl^{+}$, $(Ca,Zn)_3(PO_4)_2:Tl^{+}$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3\cdot 0.2SiO_2\cdot 0.9P_2O_5:Ce^{3+}.Tb^{3+}$, $BaO\cdot TiO_2\cdot P_2O_5$. The silicate phosphors $Zn_2SiO_4:Mn^{2+}$, $CaSiO_3:Pb^{2+}/Mn^{2+}$, $(Ba, Sr, Mg)\cdot 3Si_2O_7:Pb^{2+}$, $BaSi_2O_5:Pb^{2+}$, $Sr_2Si_3O_8\cdot 2SrCl_2:Eu^{2+}$, $Ba_3MgSi_2O_8:Eu^{2+}$, $(Sr,Ba)Al_2Si_2O_8:Eu^{2+}$.

The aluminate phosphors include, but are not limited to: $LiAlO_2:Fe^{3+}$, $BaAl_8O_{13}:Eu^{2+}$, $BaMg_2Al_{16}O_{27}:Eu^{2+}$, $BaMg_2Al_{16}O_{27}:Eu^{2+}/Mn^{2+}$, $Sr_4Al_{14}O_{25}:Eu^{2+}$, $CeMgAl_{11}O_{19}:Ce^{3+}/Tb^{3+}$.

The borate phosphors include: $Cd_2B_2O_5:Mn^{2+}$, $SrB_4O_7F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include, but are not limited to: $CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO\cdot As_2O_5:Mn^{2}+$, $3.5MgO\cdot 0.5MgF_2\cdot GeO_2:Mn^{4+}$. The activators to the various doped phosphors include, but are not limited to: $Tl^{+}$, $Pb^{2+}$, $Ce^{3+}$, $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$. The luminescence center $Tl^{+}$ is used with a chemical composition such as: $(Ca,Zn)_3(PO_4)_2:Tl^{+}$, $Ca_3(PO_4)_2:Tl^{+}$. The luminescence center $Mn^{2+}$ is used with chemical compositions such as $MgGa_2O_4:Mn^{2+}$, $BaMg_2Al_6O_{27}:Eu^{2+}/Mn^{2+}$, $Zn_2SiO_4:Mn^{2+}$, $3Ca_3(PO_4)_2\cdot Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{10}:Ce^{3+}/Tb^{3+}/Mn^{2+}$. The luminescence center Sn2+ is used with chemical compositions such as: $Sr_2P_2O_7:Sn^{2+}$, $(Sr,Mg)_3(PO_4)_2:Sn^{2+}$. The luminescence center $Eu^{2+}$ is used with chemical compositions such as: $SrB_4O_7F:Eu^{2+}$, $(Sr,Ba)Al_2Si_2O_8:Eu^{2+}$, $Sr_3(PO_4)_2:Eu^{2+}$, $Sr_2P_2O_7:Eu^{2+}$, $Ba_3MgSi_2O_8:Eu^{2+}$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$. The luminescence center $Pb^{2+}$ is used with chemical compositions such as: $(Ba,Mg,Zn)_3Si_2O_7:Pb^{2+}$, $BaSi_2O_5:Pb^{2+}$, $(Ba,Sr)_3Si_2O_7:Pb^{2+}$.

The luminescence center $Sb^{2+}$ is used with chemical compositions such as: $3Ca_3(PO_4)_2\cdot Ca(F,Cl)_2:Sb^{3+}$, $3Ca_3(PO_4)_2\cdot Ca(F,Cl)_2:Sb^{3+}/Mn^{2+}$.

The luminescence center $Tb^{3+}$ is used with chemical compositions such as: $CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$. The luminescence center $Eu^{3+}$ is used with chemical compositions such as: $Y_2O_3:Eu^{3+}$, $Y(V,P)O_4:Eu^{3+}$. The luminescence center $Dy^{3+}$ is used with chemical compositions such as: $YVO_4:Dy^{3+}$. The luminescence center $Fe^{3+}$ is used with chemical compositions such as: $LiAlO_2:Fe^{3+}$. The luminescence center $Mn^{4+}$ is used with chemical compositions such as: $6MgO\cdot As_2O_5:Mn^{4+}$, $3.5MgO0.5MgF_2\cdot GeO_2:Mn^{4+}$. The luminescence center $Ce^{3+}$ is used with chemical compositions such as: $Ca_2MgSi_2O_7:Ce^{3+}$ and $Y_2SiO_5:Ce^{3+}$. The luminescence center $WO_4^{2-}$ is used with chemical compositions such as: $CaWO_4$, $(Ca,Pb)WO_4$, $MgWO_4$. The luminescence center $TiO_4^{4-}$ is used with chemical compositions such as: $BaO\cdot TiO_2\cdot P_2O_5$.

Additional phosphor chemistries of interest using X-Ray excitations include, but are not limited to, the k-edge of these phosphors. Low energy excitation can lead to intense luminescence in materials with low k-edge. Some of these chemistries and the corresponding k-edge are listed below:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| ZnS:Ag | 9.66 keV |
| (Zn, Cd)S:Ag | 9.66/26.7 keV |

These materials can be used alone or in combinations of two or more. A variety of compositions can be prepared to obtain the desired output wavelength or spectrum of wavelengths.

In the present invention, the phosphor selection could be chosen such that under x-ray or other high energy source irradiation, the light emitted from the phosphors could, for example, have exemplary characteristics including:

Emissions in 190-250 nm wavelength range;

Emissions in the 330-340 nm wavelength range.

Mechanoluminescent Materials (Organic and Inorganic):

In another embodiment of the invention, mechano-luminescent materials can be used as energy converters and optionally can be used with the energy augmentation structures described above.

Mechano-luminescent materials convert ultrasonic or mechanical energy (such as vibrations naturally existing on an article such as motor or vibrations from driven by transducers) into visible light. Here, for example, the mechano-luminescent materials would be placed in a vicinity (e.g., between or around or inside) the folded structures or the external-electrode pairs.

In one embodiment, an electromagnetic wave energy augmentator captures one or more wavelengths of electromagnetic energy, and augments the one or more wavelengths of electromagnetic energy in at least one property (such as electric field intensity in a vicinity of the mechano-luminescent materials), while at the same time the mechano-luminescent materials can be considered an energy converter converting the ultrasonic or mechanical energy into electromagnetic radiation (i.e., emitted light).

In one embodiment of the invention, the increased electric field in the folded structure or the external electrode pair increases the luminescence of the mechano-luminescent materials. The energy used to build the electric field in the folded structure or the external electrode pair being provided separately from the mechanical energy driving the mechano-luminescence.

Various mechano-luminescent materials suitable for the present invention with or without energy augmentators include $ZnS:Mn^{2+}$, $SrAl_2O_4:Eu^{2+}$, ZnS:Cu, $SrAMgSi_2O_7:Eu^{2+}$ (A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba_xAl_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, ZnS, ZnTe, $(ZnS)_{1-x}(MnTe)_x$ ($x<1/4$), CaZnOS, BaZnOS, $Ca_2MgSi_2O_7$, $Sr_2MgSi_2O_7$, $Ba_2MgSi_2O_7$, $SrCaMgSi_2O_7$, $SrBaMgSi_2O_7$, $Sr_nMgSi_2O_{5+n}$ ($1 \le n \le 2$), $Ca_2Al_2SiO_7$, $Sr_2Al_2SiO_7$, $CaYAl_3O_7$, $CaAl_2Si_2O_8$, $Ca_{1-x}Sr_xAl_2Si_2O_8$ (x<0.8), $SrMg_2(PO_4)_2$, $Ba_{1-x}Ca_xTiO_3$ (0.25<x<0.8), $Ba_{1-x}Ca_xTiO_3$, $LiNbO_3$, $Sr_2SnO_4$, $(Ca, Sr, Ba)_2SnO_4$, $Sr_3Sn_2O_7$, $Sr_3(Sn, Si)_2O_7$, $Sr_3(Sn, Ge)_2O_7$, $Ca_3Ti_2O_7$, $Ca_2Nb_2O_6$, $Ca_2Nb_2O_7$, $Ca_3Nb_2O_8$, $BaSi_2O_2N_2$, $SrSi_2O_2N_2$, $CaZr(PO_4)_2$, $ZrO_2$.

In one embodiment, a europium-holmium co-doped strontium aluminate can be used as a mechano-luminescent material (i.e., an energy converter) alone or in conjunction with the energy augmentators. The europium-holmium co-doped strontium aluminate and the other mechano-luminescent materials convert sonic or acoustic energy into photon emissions which may or may not be placed in a vicinity of the energy augmentators.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechanoluminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention with or without energy augmentators, such composites made of a piezoelectric material and an electroluminescent material, hereinafter "composite mechano-luminescent emitters," provides a structure that, upon stimulation with mechanical or vibrational energy such as from an acoustic or ultrasonic transducer, emit light.

Electroluminescent and phosphorescent materials (organic and inorganic): The present invention in various embodiments can utilize organic fluorescent molecules or inorganic particles capable or fluorescence and phosphorescence having crystalline, polycrystalline or amorphous micro-structures for the converters (optionally including the energy augmentation structures described above).

The list of inorganic molecules that can be used with or without energy augmentators for the electroluminescence and phosphorescent materials described below include but is not limited to the following inorganic electroluminescent phosphor materials:

$SrS:Ce^{3+}$
$CaGa_2S_4:Ce^{3+}$
$SrS:Cu^+$
$CaS:Pb^{2+}$
$BaAl_2S_4:Eu^{2+}$
$ZnS:Tb^{3+}$
$ZnMgS:Mn^{2+}$
$SrGa_2S_4:Eu^{2+}$
$CaAl_2S_4:Eu^{2+}$
$BaAl_2S_4:Eu^{2+}$
$ZnS:Mn^{2+}$
$MgGa_2O_4:Eu^{3+}$
$(Ca, Sr)Y_2S_4:Eu^{2+}$
$BaAl_2S_4:Eu^{2+}$

Organic molecules that can phosphoresce under the influence of an electric field are also of interest in the present application. The organic fluorescent compounds with high quantum yield include by way of illustration:

Naphthalene,
Pyrene,
Perylene,
Anthracene,
Phenanthrene,
p-Terphenyl,
p-Quartphenyl,
Trans-stilbene,
Tetraphenylbutadiene,
Distyrylbenzene,
2,5-Diphenyloxazole,
4-Methyl-7-diethylaminocoumarin,
2-Phenyl-5-(4-biphenyl)-1,3,4-oxadiazole,
3-Phenylcarbostyryl,
1,3,5-Triphenyl-2-pyrazoline,
1,8-Naphthoylene-1',2'-bezimidazole,
4-Amino-N-phenyl-naphthalimide.

The inorganic fluorescent and phosphorescent materials detailed here are numerous, and various examples are given by way of illustration rather than limitation and can be used with or without energy augmentators. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$.

Further included are alkali earth chalcogenide phosphors which are in turn exemplified by the following non-inclusive list:

$MgS:Eu^{3+}$, $CaS:Mn^{2+}$, CaS:Cu, CaS:Sb, $CaS:Ce^{3+}$, $CaS:Eu^{2+}$, $CaS:Eu^{2+}Ce^{3+}$, $CaS:Sm^{3+}$, $CaS:Pb^{2+}$, $CaO:Mn^{2+}$, $CaO:Pb^{2+}$.

The examples include the ZnS type phosphors that encompass various derivatives:

ZnS:Cu,Al(Cl), ZnS:Cl(Al), ZnS:Cu,I(Cl), ZnS:Cu, ZnS:Cu,In.

Compound IIIb-Vb phosphors which include the group IIIb and Vb elements of the periodic table are suitable for converter materials. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: In1-y(Ga1-xAlx)yP (provides a simple example).

Silicon Carbide SiC as a luminescent platform has commercial relevancy if the blue light emitting diodes. These include the polytypes 3C-SiC, 6H-SiC, 4H-SiC with donors such as N and Al and acceptors such as Ga and B.

Multiband luminescent materials suitable for converter materials include for example the following compositions:

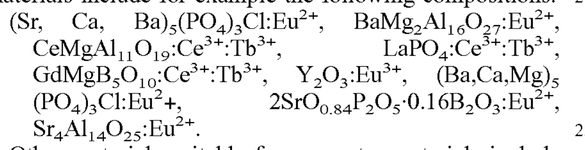
(Sr, Ca, Ba)$_5$(PO$_4$)$_3$Cl:Eu$^{2+}$, BaMg$_2$Al$_{16}$O$_{27}$:Eu$^{2+}$, CeMgAl$_{11}$O$_{19}$:Ce$^{3+}$:Tb$^{3+}$, LaPO$_4$:Ce$^{3+}$:Tb$^{3+}$, GdMgB$_5$O$_{10}$:Ce$^{3+}$:Tb$^{3+}$, Y$_2$O$_3$:Eu$^{3+}$, (Ba,Ca,Mg)$_5$(PO$_4$)$_3$Cl:Eu$^2$+, 2SrO$_{0.84}$P$_2$O$_5$·0.16B$_2$O$_3$:Eu$^{2+}$, Sr$_4$Al$_{14}$O$_{25}$:Eu$^{2+}$.

Other materials suitable for converter materials include those materials used for fluorescent high pressure mercury discharge lamps can be excited with X-Ray and are exemplified by way of family designation as follows:

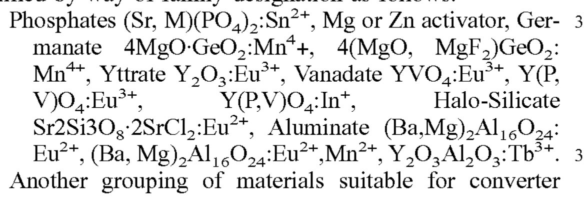
Phosphates (Sr, M)(PO$_4$)$_2$:Sn$^{2+}$, Mg or Zn activator, Germanate 4MgO·GeO$_2$:Mn$^4$+, 4(MgO, MgF$_2$)GeO$_2$:Mn$^{4+}$, Yttrate Y$_2$O$_3$:Eu$^{3+}$, Vanadate YVO$_4$:Eu$^{3+}$, Y(P,V)O$_4$:Eu$^{3+}$, Y(P,V)O$_4$:In$^+$, Halo-Silicate Sr2Si3O$_8$·2SrCl$_2$:Eu$^{2+}$, Aluminate (Ba,Mg)$_2$Al$_{16}$O$_{24}$:Eu$^{2+}$, (Ba, Mg)$_2$Al$_{16}$O$_{24}$:Eu$^{2+}$,Mn$^{2+}$, Y$_2$O$_3$Al$_2$O$_3$:Tb$^{3+}$.

Another grouping of materials suitable for converter materials by host compound include chemical compositions in the Halophosphates phosphors, Phosphate phosphors, Silicate phosphors, Aluminate phosphors, Borate phosphors, Tungstate phosphors, and other phosphors.

The halophosphates include by way of illustration:

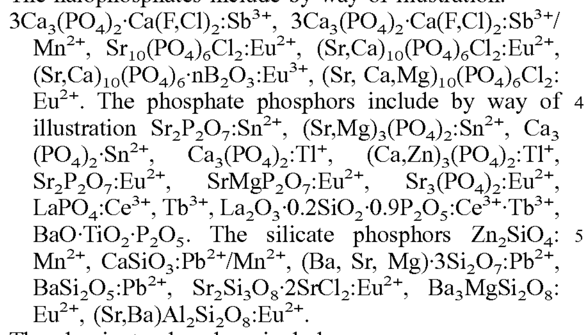
3Ca$_3$(PO$_4$)$_2$·Ca(F,Cl)$_2$:Sb$^{3+}$, 3Ca$_3$(PO$_4$)$_2$·Ca(F,Cl)$_2$:Sb$^{3+}$/Mn$^{2+}$, Sr$_{10}$(PO$_4$)$_6$Cl$_2$:Eu$^{2+}$, (Sr,Ca)$_{10}$(PO$_4$)$_6$Cl$_2$:Eu$^{2+}$, (Sr,Ca)$_{10}$(PO$_4$)$_6$·nB$_2$O$_3$:Eu$^{3+}$, (Sr, Ca,Mg)$_{10}$(PO$_4$)$_6$Cl$_2$:Eu$^{2+}$. The phosphate phosphors include by way of illustration Sr$_2$P$_2$O$_7$:Sn$^{2+}$, (Sr,Mg)$_3$(PO$_4$)$_2$:Sn$^{2+}$, Ca$_3$(PO$_4$)$_2$·Sn$^{2+}$, Ca$_3$(PO$_4$)$_2$:Tl$^+$, (Ca,Zn)$_3$(PO$_4$)$_2$:Tl$^+$, Sr$_2$P$_2$O$_7$:Eu$^{2+}$, SrMgP$_2$O$_7$:Eu$^{2+}$, Sr$_3$(PO$_4$)$_2$:Eu$^{2+}$, LaPO$_4$:Ce$^{3+}$, Tb$^{3+}$, La$_2$O$_3$·0.2SiO$_2$·0.9P$_2$O$_5$:Ce$^{3+}$·Tb$^{3+}$, BaO·TiO$_2$·P$_2$O$_5$. The silicate phosphors Zn$_2$SiO$_4$:Mn$^{2+}$, CaSiO$_3$:Pb$^{2+}$/Mn$^{2+}$, (Ba, Sr, Mg)·3Si$_2$O$_7$:Pb$^{2+}$, BaSi$_2$O$_5$:Pb$^{2+}$, Sr$_2$Si$_3$O$_8$·2SrCl$_2$:Eu$^{2+}$, Ba$_3$MgSi$_2$O$_8$:Eu$^{2+}$, (Sr,Ba)Al$_2$Si$_2$O$_8$:Eu$^{2+}$.

The aluminate phosphors include:

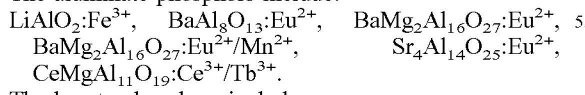
LiAlO$_2$:Fe$^{3+}$, BaAl$_8$O$_{13}$:Eu$^{2+}$, BaMg$_2$Al$_{16}$O$_{27}$:Eu$^{2+}$, BaMg$_2$Al$_{16}$O$_{27}$:Eu$^{2+}$/Mn$^{2+}$, Sr$_4$Al$_{14}$O$_{25}$:Eu$^{2+}$, CeMgAl$_{11}$O$_{19}$:Ce$^{3+}$/Tb$^{3+}$.

The borate phosphors include:

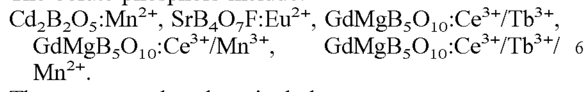
Cd$_2$B$_2$O$_5$:Mn$^{2+}$, SrB$_4$O$_7$F:Eu$^{2+}$, GdMgB$_5$O$_{10}$:Ce$^{3+}$/Tb$^{3+}$, GdMgB$_5$O$_{10}$:Ce$^{3+}$/Mn$^{3+}$, GdMgB$_5$O$_{10}$:Ce$^{3+}$/Tb$^{3+}$/Mn$^{2+}$.

The tungstate phosphors include:

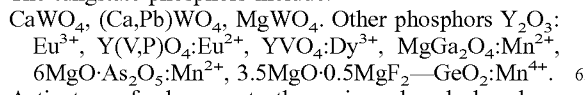
CaWO$_4$, (Ca,Pb)WO$_4$, MgWO$_4$. Other phosphors Y$_2$O$_3$:Eu$^{3+}$, Y(V,P)O$_4$:Eu$^{2+}$, YVO$_4$:Dy$^{3+}$, MgGa$_2$O$_4$:Mn$^{2+}$, 6MgO·As$_2$O$_5$:Mn$^{2+}$, 3.5MgO·0.5MgF$_2$—GeO$_2$:Mn$^{4+}$.

Activators of relevance to the various doped phosphors include the following list:

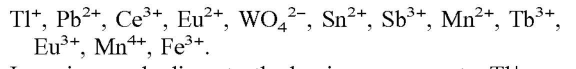
Tl$^+$, Pb$^{2+}$, Ce$^{3+}$, Eu$^{2+}$, WO$_4^{2-}$, Sn$^{2+}$, Sb$^{3+}$, Mn$^{2+}$, Tb$^{3+}$, Eu$^{3+}$, Mn$^{4+}$, Fe$^{3+}$.

In various embodiments, the luminescence center Tl$^+$ can be used with a chemical composition such as:

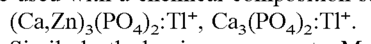
(Ca,Zn)$_3$(PO$_4$)$_2$:Tl$^+$, Ca$_3$(PO$_4$)$_2$:Tl$^+$.

Similarly, the luminescence center Mn2+ can be used with chemical compositions such as

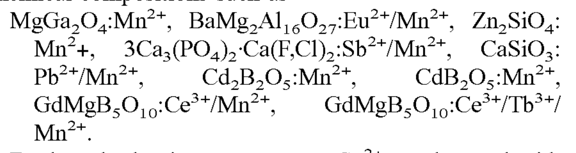
MgGa$_2$O$_4$:Mn$^{2+}$, BaMg$_2$Al$_{16}$O$_{27}$:Eu$^{2+}$/Mn$^{2+}$, Zn$_2$SiO$_4$:Mn$^2$+, 3Ca$_3$(PO$_4$)$_2$·Ca(F,Cl)$_2$:Sb$^{2+}$/Mn$^{2+}$, CaSiO$_3$:Pb$^{2+}$/Mn$^{2+}$, Cd$_2$B$_2$O$_5$:Mn$^{2+}$, CdB$_2$O$_5$:Mn$^{2+}$, GdMgB$_5$O$_{10}$:Ce$^{3+}$/Mn$^{2+}$, GdMgB$_5$O$_{10}$:Ce$^{3+}$/Tb$^{3+}$/Mn$^{2+}$.

Further, the luminescence center Sn$^{2+}$ can be used with chemical compositions such as:

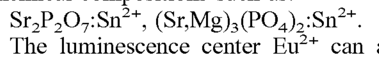
Sr$_2$P$_2$O$_7$:Sn$^{2+}$, (Sr,Mg)$_3$(PO$_4$)$_2$:Sn$^{2+}$.

The luminescence center Eu$^{2+}$ can also be used with chemical compositions such as:

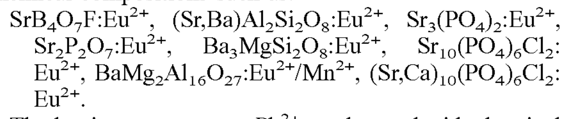
SrB$_4$O$_7$F:Eu$^{2+}$, (Sr,Ba)Al$_2$Si$_2$O$_8$:Eu$^{2+}$, Sr$_3$(PO$_4$)$_2$:Eu$^{2+}$, Sr$_2$P$_2$O$_7$:Eu$^{2+}$, Ba$_3$MgSi$_2$O$_8$:Eu$^{2+}$, Sr$_{10}$(PO$_4$)$_6$Cl$_2$:Eu$^{2+}$, BaMg$_2$Al$_{16}$O$_{27}$:Eu$^{2+}$/Mn$^{2+}$, (Sr,Ca)$_{10}$(PO$_4$)$_6$Cl$_2$:Eu$^{2+}$.

The luminescence center Pb$^{2+}$ can be used with chemical compositions such as:

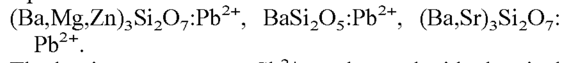
(Ba,Mg,Zn)$_3$Si$_2$O$_7$:Pb$^{2+}$, BaSi$_2$O$_5$:Pb$^{2+}$, (Ba,Sr)$_3$Si$_2$O$_7$:Pb$^{2+}$.

The luminescence center Sb$^{2+}$ can be used with chemical compositions such as:

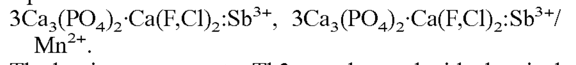
3Ca$_3$(PO$_4$)$_2$·Ca(F,Cl)$_2$:Sb$^{3+}$, 3Ca$_3$(PO$_4$)$_2$·Ca(F,Cl)$_2$:Sb$^{3+}$/Mn$^{2+}$.

The luminescence center Tb3+ can be used with chemical compositions such as:

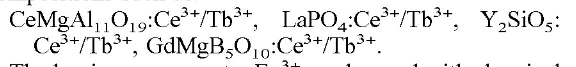
CeMgAl$_{11}$O$_{19}$:Ce$^{3+}$/Tb$^{3+}$, LaPO$_4$:Ce$^{3+}$/Tb$^{3+}$, Y$_2$SiO$_5$:Ce$^{3+}$/Tb$^{3+}$, GdMgB$_5$O$_{10}$:Ce$^{3+}$/Tb$^{3+}$.

The luminescence center Eu$^{3+}$ can be used with chemical compositions such as:

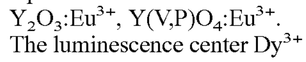
Y$_2$O$_3$:Eu$^{3+}$, Y(V,P)O$_4$:Eu$^{3+}$.

The luminescence center Dy$^{3+}$ can be used with chemical compositions such as:

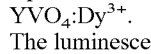
YVO$_4$:Dy$^{3+}$.

The luminescence center Fe$^{3+}$ can be used with chemical compositions such as:

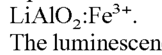
LiAlO$_2$:Fe$^{3+}$.

The luminescence center Mn$^{4+}$ can be used with chemical compositions such as:

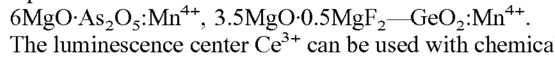
6MgO·As$_2$O$_5$:Mn$^{4+}$, 3.5MgO·0.5MgF$_2$—GeO$_2$:Mn$^{4+}$.

The luminescence center Ce$^{3+}$ can be used with chemical compositions such as:

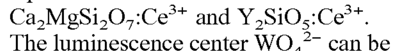
Ca$_2$MgSi$_2$O$_7$:Ce$^{3+}$ and Y$_2$SiO$_5$:Ce$^{3+}$.

The luminescence center WO$_4^{2-}$ can be used with chemical compositions such as:

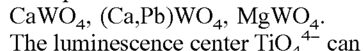
CaWO$_4$, (Ca,Pb)WO$_4$, MgWO$_4$.

The luminescence center TiO$_4^{4-}$ can be used with chemical compositions such as:

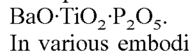
BaO·TiO$_2$·P$_2$O$_5$.

In various embodiments of this invention, the phosphor chemistry utilized in x-ray excitations can be used with or without energy augmentators. Of particular interest is the k-edge of these phosphors. Low energy excitation can lead to intense luminescence in materials with low k-edge. Some of these chemistries and the corresponding k-edge are included as follows:

| | |
|---|---|
| BaFCl:Eu$^{2+}$ | 37.38 keV |
| BaSO$_4$:Eu$^{2+}$ | 37.38 keV |
| CaWO$_4$ | 69.48 keV |

-continued

| | |
|---|---|
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| ZnS:Ag | 9.66 keV |
| (Zn, Cd)S:Ag | 9.66/26.7 keV |

In one embodiment of this invention, light from these materials (excited for example by high energy particles including x-rays, gamma rays, protons, and electrons) can have their emissions modulated by having those materials included in a vicinity of (including inside) the color enhancing structures described herein. For example, in medical treatments where x-ray excites phosphorescence to photo-stimulate reactions in a patient, simultaneous with irradiation by the high energy particles, there could be applied infrared irradiation to drive resonance in the energy augmentation structures described herein, where the x-ray phosphors would have enhanced light emissions when in the presence of the intensified electric fields. In another example, in medical or scientific instruments, for simultaneous with irradiation by the high energy particles, there could be applied electric fields to enhance emissions from these x-ray phosphors.

Electro Luminescent Materials: Various materials used for the electro-luminescence in the present invention with or without energy augmentators can include but are not limited to:

4,4',4"-Tris[phenyl(m-tolyl)amino]triphenylamine (m-MT-DATA)

N,N'-Bis(3-methylphenyl)-N,N'-diphenylbenzidine (TPD)

4,4',4"-Tris[phenyl(m-tolyl)amino]triphenylamine (m-MT-DATA)

N,N'-Bis(3-methylphenyl)-N,N'-diphenylbenzidine (TPD)

Tris-(8-hydroxyquinoline)aluminum 2,4,6-Tris(2-pyridyl)-s-triazine (TPT)

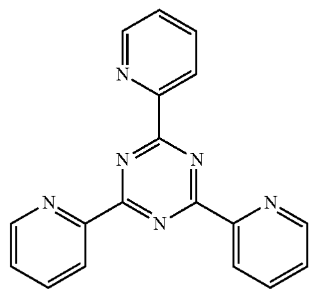 [SMILES: c1ccc(-c2nc(-c3ccccn3)nc(-c3ccccn3)n2)nc1]

2,2',2"-(1,3,5-Benzenetriyl)-tris(1-phenyl-1-H-benzimidazole) Alq

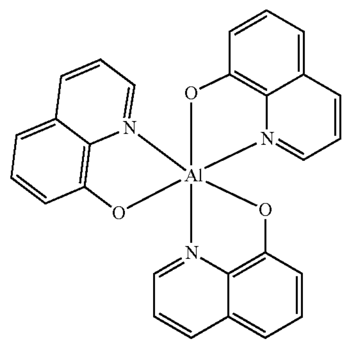

2,2',2"-(1,3,5-Benzenetriyl)-tris(1-phenyl-1-H-benzimidazole) TPBI

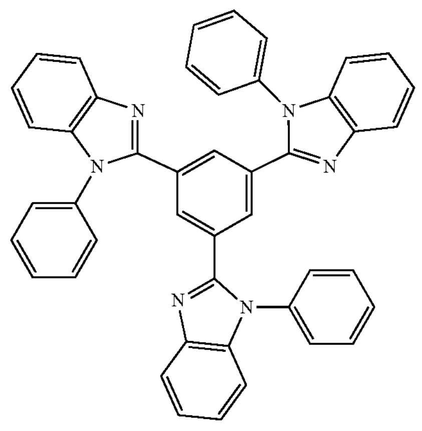 [SMILES: c1ccc(-n2c(-c3cc(-c4nc5ccccc5n4-c4ccccc4)cc(-c4nc5ccccc5n4-c4ccccc4)c3)nc3ccccc32)cc1]

2,9-Dimethyl-4,7-diphenyl-1,10-phenanthroline, BCP2,9-Dimethyl-4,7-diphenyl-1,10-phenanthroline, BCP

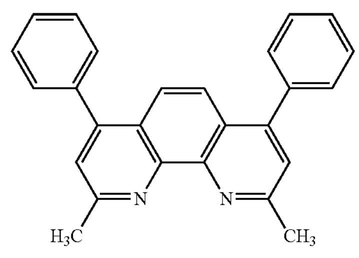 [SMILES: Cc1cc(-c2ccccc2)c2ccc3c(-c4ccccc4)cc(C)nc3c2n1]

Plasmonic enhancement structures: FIG. 26 is a schematic of a depiction of an upconverter or a down converter material (i.e., a photoactive material) according to one embodiment of the invention to be utilized in the color enhancement/augmentation structures noted herein with or without energy augmentators. FIG. 26 shows a number of structural configurations for placement of a dielectric core upconverter or a down converter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion may depend on the particular upconversion material and process being used in a particular application, for the purposes for discussion and illustration, the following explanation is offered.

In the context of FIG. 26, when a wavelength $\lambda_1$ interacts with a dielectric material core, three separate processes are well understood for the upconversion process involving trivalent rare earth ions. These three processes are:

1) excited state absorption whereby two photons are absorbed sequentially by the same ion to excite and populate one or more states;
2) energy transfer upconversion which is a transfer of excitation from one ion to another already in an excited state; and
3) a cooperative process of multiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion or down conversion process.

Therefore, the particular ion being activated (whether it be a dopant ion or a host ion of a lattice such as in the neodymium oxide) will be chosen based on the host material being processed, in order that the dopant ion or the host ion in the dielectric core provide ion states which are pumpable by a NIR source to generate the resultant emission $\lambda_2$.

Hence, the invention in one embodiment provides an upconversion or a down conversion material configured, upon exposure to a first wavelength $\lambda_1$ of radiation, to generate a second wavelength $\lambda_2$ of radiation having an energy higher or lower than the first wavelength $\lambda_1$. The system can include a metallic structure disposed in relation to the nanoparticle (e.g. a metallic shell covering a fraction of the nanoparticle). The system may include a receptor disposed in the medium in proximity to the nanoparticle. The receptor upon activation by the second wavelength $\lambda_2$ may itself fluoresce producing visible light. In one embodiment of the invention, a physical characteristic of metallic structure (such as those described above and below in the drawings) is set to a value where a surface plasmon resonance in the metallic structure resonates at a frequency which provides spectral overlap with either the first wavelength $\lambda_1$ or the second wavelength $\lambda_2$. This system with a metallic structure disposed in relation to an up-conversion or a down-conversion nanoparticle becomes the converter utilized in the color enhancement/augmentation structures noted herein.

Within the context of the invention, the term "physical characteristic" of the metallic shell or core can relate to any characteristic of the metal itself or the shell or core dimensions or shape which affects the surface plasmon resonance frequency. Such physical characteristics can include, but are not limited to, a conductivity, a radial dimension, a chemical composition or a crystalline state of the metal shell or core.

In various embodiments, the metallic structures can be a metallic shell encapsulating at least a fraction of the nanoparticle in the metallic shell wherein a conductivity, a radial dimension, or a crystalline state of the metallic shell sets the surface plasmon resonance in the metallic structure to resonate at a frequency which provides spectral overlap with either the first wavelength $\lambda_1$ or the second wavelength $\lambda_2$. In various embodiments, the metallic structures can be a multi-layer metallic shell encapsulating at least a fraction of the nanoparticle in the metallic shell wherein a conductivity, a radial dimension, or a crystalline state of the metallic shell sets the surface plasmon resonance in the metallic structure to resonate at the first wavelength $\lambda_1$ and the second wavelength $\lambda_2$. This capability permits radiation at $\lambda_1$ and $\lambda_2$ to be amplified.

In various embodiments, the metallic structures can be a metallic particle existing in one or more multiple structures. These multiple structures can have a variety of shapes including for example sphere, spheroid, rod, cube, triangle, pyramid, pillar, crescent, tetrahedral shape, star or combination thereof disposed adjacent the nanoparticle wherein a conductivity, a dimension (e.g. a lateral dimension or a thickness), or a crystalline state of the metallic structure sets the surface plasmon resonance in the metallic particle or rod to resonate at a frequency which provides spectral overlap with either the first wavelength $\lambda_1$ or the second wavelength $\lambda_2$. Such shapes are described in the present figures and in the figures in U.S. Ser. No. 12/401,478 which is incorporated by reference in its entirety. The shape choice can affect the frequency of the surface plasmon resonance. It is known that the plasmon band is changed by the shape of nanoparticles (e.g., prolate and obloid spheroids). The paper "Spectral bounds on plasmon resonances for Ag and Au prolate and oblate nanospheroids," in the Journal of Nanophotonics, Vol. 2, 029501 (26 Sep. 2008), the entire contents of which are incorporated by reference, shows plasmon resonance shifts for shaping of Ag and plasmon resonance shifts for shaping of Au of prolate and obloid spheroids. In one embodiment of the invention, with an increasing aspect ratio for a metallic structure of the invention, the prolate spheroid resonance is red shifted relative to a sphere with no lower limit (under the assumptions of a Drude dispersion model). On the other hand, the oblate resonances are "blue shifted" as the spheroid becomes increasingly flat, but up to a limit.

In various embodiments, the metallic structures disposed in relation to an up-conversion or a down-conversion nanoparticle can be a metallic structure disposed interior to the nanoparticle wherein a conductivity or a dimension (e.g. a lateral dimension or a thickness) of the metallic structure sets the surface plasmon resonance in the metallic structure to resonate at a frequency which provides spectral overlap with either the first wavelength $\lambda_1$ or the second wavelength $\lambda_2$. In various embodiments, the metallic structures can be a metallic multi-layer structure disposed interior to the nanoparticle wherein a conductivity or a dimension (e.g. a lateral dimension or a thickness) of the metallic structure sets the surface plasmon resonance in the metallic structure to resonate at the first wavelength $\lambda_1$ and the second wavelength $\lambda_2$. This capability once again permits radiation at $\lambda_1$ and $\lambda_2$ to be amplified.

In another embodiment, the invention provides a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structures to enhance upconversion of light from a first wavelength $\lambda_1$ to a second wavelength $\lambda_2$.

As described above, a shell (or other structure) is in particular designed with a layer thickness (or for example a lateral dimension) to enhance the photon upconversion process through plasmonic enhancement. The thickness of the shell (or other physical characteristic) is "tuned" in its thickness to the absorption process by having a dimension in which plasmons (i.e., electrons oscillations) in shell have a resonance in frequency which provides spectral overlap with the absorption band targeted. Thus, if the upconversion is to be stimulated by 980 nm NIR light, then the thickness of the shell is "tuned" in a thickness to where a plasmon resonance resonates at a frequency also of 980 nm (or in the neighborhood thereof as plasmon resonances are typically broad at these wavelengths).

Figure 27:
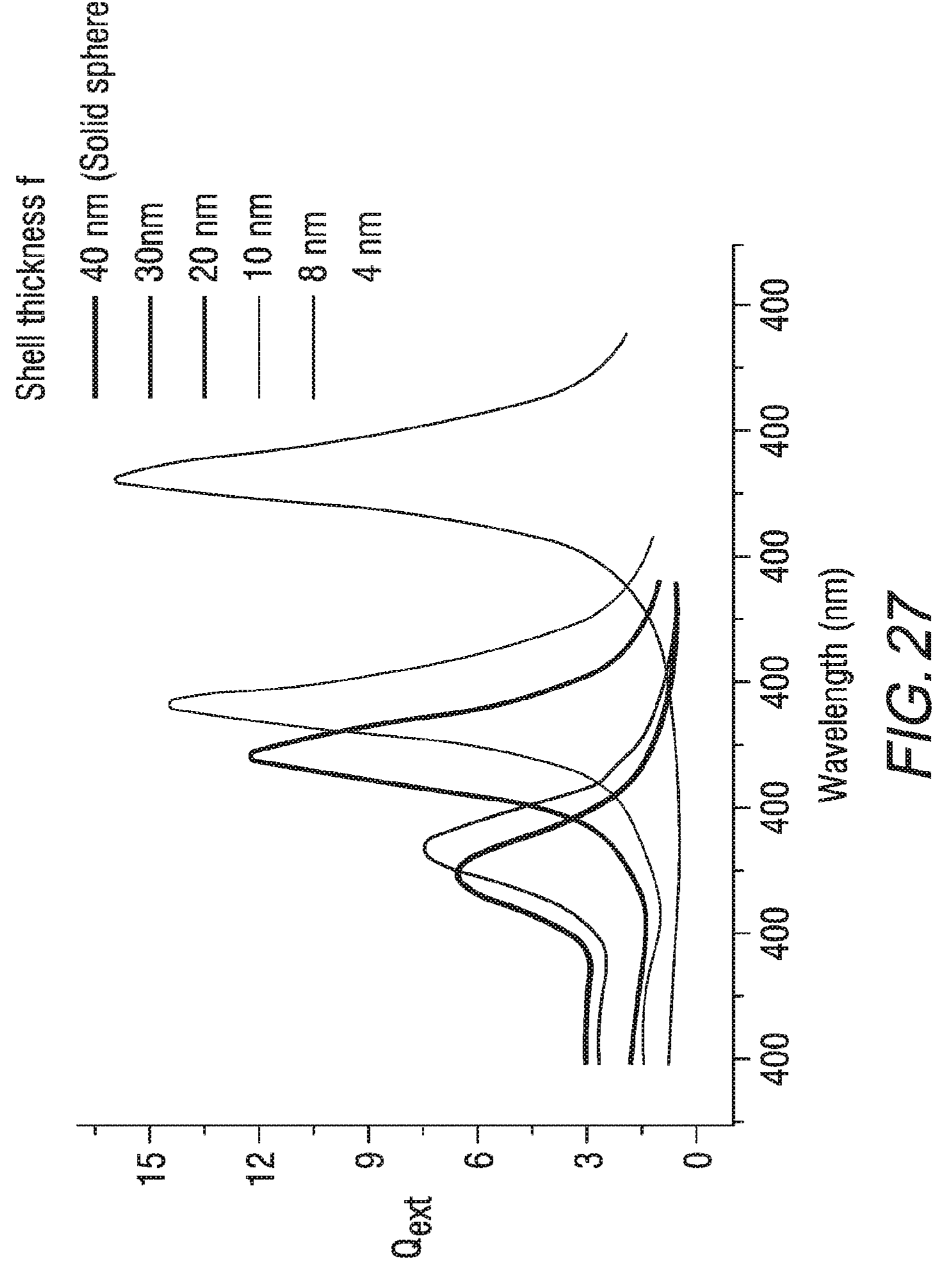
FIG. 27 is a schematic illustration of plasmon resonance as a function of shell thickness.

A plasmon resonating shell can be made of numerous transition metals, including though not limited to gold, silver, platinum, palladium, nickel, ruthenium, rhenium, copper, and cobalt or a combination or alloys or layers thereof. Such a plasmon resonating shell can be also made of a combination of metals and non-metals. When formed of a gold nanoshell, the recommended thickness to resonate with 980 nm light is approximately 3.5 nm surrounding an 80 nm upconverting core, as projected by extended Mie theory calculations. (See Jain et al., *Nanolett.* 2007, 7(9), 2854 the entire contents of which are incorporated herein by reference.) FIG. 27 is reproduced from Jain et al. and illustrates the capability in the invention to "tune" the metal shell to have a spectral overlap with the excitation and/or emission radiation wavelengths.

In one embodiment of the invention, the metallic structures disposed in relation to an up-conversion or a down-conversion nanoparticle can be an alloy such as for example an Au:Ag alloy. The alloy content can be set to adjust the frequency of the surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

In one embodiment of the invention, the converter nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a predetermined surface plasmon resonance. In one embodiment of the invention, the zinc sulfide and cadmium sulfide nanoparticle alloy can have an alloy content is set to provide a predetermined surface plasmon resonance.

Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of the invention, the thickness of the metal shell disposed in relation to an up-conversion or a down-conversion nanoparticle is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process.

Additionally, plasmon-phonon coupling may be used to reduce a resonance frequency through the tuning of the bands to a degree off resonance. This may be useful in optimizing resonance energy transfer processes for the purpose of shifting the outputted color to a color desirable for a painted, colored, or displayed surface. In one example, FIG. 27 shows an example of the plasmon resonance shift as a function of shell thickness.

Here, in one embodiment of the invention, the capability to produce stimulated emission at a targeted wavelength or color or energy is complemented by the ability to design nanoparticles that have designed absorption bands. Such absorption materials could for example further serve to improve the monochromaticity of light observed from a paint, ink, dye, or otherwise reflecting surface treated with the color enhancing compositions of the invention.

Details of the preparation of this nanoparticle system are included in U.S. Ser. No. 12/725,108, the entire contents of which are incorporated herein by reference. The absorption spectrum of $Y_2O_3$ alone (lower trace) is fairly featureless, showing absorption due to the tri-arginine near 200 nm and a gentle slope associated with scattering and absorption by the $Y_2O_3$ nanoparticles extending into the visible portion of the spectrum. The gold-coated $Y_2O_3$(upper trace), on the other hand, exhibit a strong absorption band at 546 nm, which is characteristic of the plasmonics resonance band due to the gold shell around the $Y_2O_3$ cores. The red-shifting of the plasmon absorption to 546 nm is consistent with the presence of a gold shell around a dielectric core.

In one embodiment of the invention, the converter materials for the upconverter dielectric core can include a wide variety of dielectric materials, as described above. In various embodiments of the invention, the upconverter dielectric core includes more specifically lanthanide doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence, suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) $4f^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above. Doping concentrations in the invention can range from 0.2% to 20% roughly per ion into the host lattice or in a weight or mol % variation. The efficiency of the upconversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide a rudimentary teaching of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg. 4865, the entire contents of which are incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of the invention, the dielectric core is coated, such as for example with a metallic shell, to enhance electron-phonon coupling and thereby increase up conversion or down conversion efficiency, as discussed above. In another embodiment of the invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. In another embodiment of the invention, the shell can include a $SiO_2$- and/or $TiO_2$-coating, and this coating is in one embodiment coated on doped $Y_2O_3$ down converting nanoparticles to thereby, in some instances, increase the down conversion efficiency relative to an uncoated nanocrystal. Further, in one embodiment of the invention, the coating can be a polymer. In one embodiment, this coating is provided on $NaYF_4$:Ln/$NaYF_4$ dielectric core. Such coatings can increase the upconversion efficiency relative to an uncoated upconverter.

In another embodiment of the invention, phonon modes of undoped host-lattice (e.g., $Y_2O_3$) nanocrystals are modulated, for example, by Au, Ag, Pt, and Pd shells of varying thicknesses. In various embodiments of the invention, the upconverter dielectric core and the shell system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure disposed in relation to an up-conversion or a down-conversion nanoparticle can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter.

In various embodiments of the invention, the upconverter or down converter dielectric core can be coated with thiol-terminated silanes to provide a coating of $SiO_2$ about the core of similar reactivity to $Y_2O_3$. In one embodiment of the invention, the above-described methodology is used to synthesize core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells where core and shell diameters varying from 2 to 20 nm. In these material systems, the tuned ratio of core-to-shell diameter may permit a plasmon-phonon resonance which should amplify absorption of NIR light and/or upconverted emission. In these material systems, control of the core and shell diameters is one factor determining the size dependent effect and subsequent tuning of plasmon-phonon resonance.

In one embodiment of the invention, the upconverter dielectric core can be mixed core-shell materials including for example semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and trioctylphosphine-oleic amine ($NaYF_4$ shell). All core-shell nanoparticles may further be solubilized into a colloidal suspension with the addition of triarginine peptide, polyethylene glycol, and polyethyleneimine surfactants.

FIG. 28A shows some of the various embodiments of the converter structures of the invention that can be designed: (a) a structure including upconverter (UC) molecules bound to a metal (gold) nanoparticle; (b) a structure including an UC-containing nanoparticle covered with metal nanoparticles, (c) a metal nanoparticle covered with an UC-containing nanocap; (d) an UC-containing nanoparticle covered with metal nanocap, (e) a metal nanoparticle covered with UC nanoshell, (f) an UC-containing nanoparticle covered with metal nanoshell, (g) an UC-containing nanoparticle covered with metal nanoshell with protective coating layer.

The configurations (while shown in the FIG. 28A with UC-containing materials) would be applicable for enhancement for down converting materials such as the quantum dots or phosphors described herein. Moreover, in one embodiment of the invention, dielectric spacers (for examples silicates as discussed below) can be used with the structure of FIG. 6A-b to space apart the particle type metallic structures. In another embodiment of the invention, dielectric spacers can be used with the structure of FIG. 28A to space apart the metal layers, whether or not these layers are partial metal layers or continuous metal layers.

See the schematics in FIG. 28B In various embodiments of the invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$. This feature also can be used in the down converting to enhance primarily the emission at wavelength $\lambda_2$ and potentially the excitation at wavelength $\lambda_1$.

Such metallic structures in various embodiments of the invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

Accordingly, FIG. 28A represents embodiments of the invention where the dielectric core is supplemented with a shell. The shell can include a metal layer of a prescribed thickness. The metal layer can include materials such as nickel, gold, iron, silver, palladium, platinum and copper and combinations thereof. The metal layer can be also made of a combination of metals and non-metals. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

As discussed below, the metallic shells in another embodiment of the invention serve as scattering centers for UV light where UV light which, even if absorbed in a paint or coating layer contributes at a minimum to localized heating of the paint or coating layer material, will be scattered from the paint or coated layer.

FIG. 28C shows still further embodiments of plasmonics-active nanostructures having upconverting (UC) materials that can be designed: (a) a metal nanoparticle, (b) an UC nanoparticle core covered with metal nanocap, (c) a spherical metal nanoshell covering an UC spheroid core, (d) an oblate metal nanoshell covering UC spheroid core, (e) a metal nanoparticle core covered with UC nanoshell, (f) a metal nanoshell with protective coating layer, (g) multi-layer metal nanoshells covering an UC spheroid core, (h) multi-nanoparticle structures, (i) a metal nanocube and nanotriangle/nanoprism, and (j) a metal cylinder.

FIG. 28D shows yet other embodiments of plasmonics-active nanostructures having upconverting materials with linked photo-active (PA) molecules that can be designed. For example, for the case of psoralen (as the PA molecule), the length of the linker between the PA molecule and the UC material or the metal surface is tailored such that it is sufficiently long to allow the PA molecules to be active (attach to DNA) and short enough to allow efficient excitation of light from the UC to efficiently excite the PA molecules. FIG. 28D shows (a) PA molecules bound to an UC nanoparticle, (b) an UC material-containing a nanoparticle covered with metal nanoparticles, (c) a metal nanoparticle covered with UC material nanocap, (D) an UC material-containing nanoparticle covered with metal nanocap, (e) a metal nanoparticle covered with an UC material nanoshell, (f) an UC material-containing nanoparticle covered with metal nanoshell, (g) an UC material-containing nanoparticle covered with metal nanoshell with protective coating layer.

With the upconverter and down converter structures of the invention, a plasmonics effect is advantageous. A plasmonics effect can increase the local intensity of the received light or the local intensity of the emitted light from the up and/or down converter structures of the invention. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively.

In various embodiments, nanoparticles of neodymium and ytterbium doped yttrium oxide, europium and ytterbium doped yttrium oxide, and any combination of rare earth trivalent ions doped into a neodymium oxide nanocrystal can be used. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nano-scale. There are advantages offered by these yttrium oxide nanostructures of the invention. The small scale synthetic methodology for creating nanoscale yttrium oxide is easier to control and produce in yttrium oxide than in YAG. The host structure of yttrium oxide scintillates by down conversion. These combinations of dopants in yttrium oxide for example can provide predetermined emission colors for the yttrium oxide nanocrystal for the color shifting of the invention.

In one embodiment of the invention, a dual dopant permits excitation of either ion in the host glass. For instance, excitation by 980 nm light excites an ytterbium ion, where through transfer of energy from one excited state of the ytterbium ion to another dopant provides a mechanism for upconversion emission of light in the visible and NIR spectral regions.

Up-conversion phosphors similar in chemical compositions to the down-conversion fluorescent materials discussed above can be used. The up-conversion phosphors can include laser dyes, e.g., the organic small molecules that can be excited by the absorption of at least two infrared photons with emission of visible light. The up-conversion phosphors can include fluorescent polymers, e.g., the class of polymers that can be excited by the absorption of at least two infrared photons with emission of visible light. The up-conversion phosphors can include inorganic or ceramic particles or nano-particles, including the conventional up-conversion phosphors (e.g. metal fluorides, metal oxides) that can be excited by the absorption of at least two infrared photons with emission of visible light. The up-conversion phosphors can include semiconductor particles, including nano-particles such as II-VI or III-V compound semiconductors, e.g. quantum dots, described in details in the "down-conversion" semiconductors above.

Fluorescent up-conversion inorganic phosphors can include but are not limited to metal oxides, metal halides, metal chalcogenides (e.g. sulfides), or their hybrids, such as metal oxo-halides, metal oxo-chalcogenides. Fluorescent up-conversion inorganic phosphors are usually doped with rare earth elements (e.g. $Yb^{3+}$, $Er^{3+}$, $Tm^{3+}$). Some host examples include, but are not limited to: $NaYF_4$, $YF_3$, $BaYF_5$, $LaF_3$, $La_2MoO_8$, $LaNbO_4$, $LnO_2S$; where Ln is the rare earth elements, such as Y, La, Gd).

These converters (and the other energy converters described herein which receive energy and generate light or electron emission) can optionally include any of the energy augmentation structures described above.

In various embodiments of the invention, energy converters can be used with the energy augmentators described above for color enhancement. In some embodiments, the converters are up conversion of light e.g., from the IR regime into visible electromagnetic radiation and for down conversion of light e.g., from the UV range into visible electromagnetic radiation. The invention in various embodiments up converts energy, preferably light in the visible spectrum. The invention encompasses a variety of applications where the up and down conversion materials with or without energy augmentators are included to enhance the color of the object being displayed. These application areas can include paints on signs, walls, cars, buildings, boats, airplanes. These application areas can include display monitors, computer monitors, telephone displays, watch dials, instrument dials to name but a few.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

This invention in various embodiments can use a wide variety of down conversion materials (or mixtures of down conversion materials) with or without the energy augmentators to enhance a particular color of light observable to an observer. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance color emission can convert energy from one of ultraviolet light, x-rays, and high energy particles to visible light. The down conversion materials to enhance color emission can convert energy from higher energy visible light to lower energy visible light with or without the energy augmentators.

In one embodiment of the invention, a quantum dot mixture with or without the energy augmentators can be used for color enhancement. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted color emission, such as for example a green light emission. Quantum dots represent one way to down convert blue light of the spectrum to a targeted color emission, such as for example a green light emission.

As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm. Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 μm. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm. In practice, however, the excitation or pump radiation is at least about 50 nanometers shorter than the emitted radiation.

Specifically, in one embodiment of the invention, a quantum dot mixture (QDM) coating can be deposited using CVD and or sol-gel techniques using standard precipitation techniques to be used with or without the energy augmentators. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. These and the other conversion materials here can be used with or without the energy augmentators. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, $ZnS:Mn^{2+}$, ferric oxide, titanium oxide, zinc oxide, zinc oxide containing small amounts of $Al_2O_3$, and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers are also suitable as conversion materials with or without the energy augmentators: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

In various embodiments of the invention, the following materials can be used similar to that detailed in U.S. Pat. No. 7,090,355, the entire contents of which are incorporated herein by reference. For down-conversion, the following materials can be used with or without the energy augmentators. Inorganic or ceramic phosphors or nano-particles, including but not limited to metal oxides, metal halides, metal chalcogenides (e.g. metal sulfides), or their hybrids, such as metal oxo-halides, metal oxo-chalcogenides. Laser dyes and small organic molecules, and fluorescent organic polymers. Semiconductor nano-particles, such as II-VI or III-V compound semiconductors, e.g. fluorescent quantum dots.

Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_mA_{1-m})_3(Al_nB_{1-n})_5O_{12}$, doped with Ce; where $0 \le m, n \le 1$, where A includes other rare earth elements, B includes B, Ga. In addition, phosphors containing metal silicates, metal borates, metal phosphates, and metal aluminates hosts can be used. In addition, nano-particulates phosphors containing common rare earth elements (e.g. Eu, Tb, Ce, Dy, Er, Pr, Tm) and transitional or main group elements (e.g. Mn, Cr, Ti, Ag, Cu, Zn, Bi, Pb, Sn, TI) as the fluorescent activators, can be used. Materials such as Ca, Zn, Cd in tungstates, metal vanadates, ZnO, etc. can be used with or without the energy augmentators.

The commercial laser dye materials obtained from several laser dye vendors, including Lambda Physik, and Exciton, etc. can also be used with or without the energy augmentators. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc. have been used in opto-electronic devices, such as polymer light emitting diodes (PLED). Such fluorescent polymers can be used directly as the fluorescent layer of the transparent 2-D display screen.

As noted above, semiconductor nanoparticles (e.g., quantum dots) can be used with or without the energy augmentators. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nano-particle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion materials with or without the energy augmentators. Such molecules include a metal center of rare earth elements including Eu, Tb, Er, Tm, Ce protected with organic chelating groups. The metal center may also include transitional elements such as Zn, Mn, Cr, Ir, etc. and main group elements such as B, Al, Ga. Such organometallic molecules can readily dissolve in liquid or transparent solid host media. Some examples of such fluorescent organometallic molecules include: 1. Tris(dibenzoylmethane)mono(phenanthroline)europium(III); 2. Tris(8-hydroxyquinoline)erbium; 3. Tris(1-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-conversion materials for red emission include those discussed above and europium complexes such as those described in JP Laid-open Patent Publication (Kokai) No. 2003-26969, constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. A europium (Eu) complex is capable of emitting red fluorescence when irradiated with ultraviolet rays having a wavelength ranging from 365 nm to 410 nm. Terbium (Tb) is capable of emitting green fluorescence when irradiated with ultraviolet rays having a wavelength of 365 nm.

In other down-conversion embodiments with or without the energy augmentators, the down conversion materials which emit red light may include europium, light emitting particles which emit green light may include Terbium, and light emitting particles which emit blue or yellow light may include cerium (and/or thulium). In up-conversion embodiments, up conversion materials which emit red light may include praseodymium, light emitting particles which emit green light may include erbium, and light emitting particles which emit blue light may include thulium. In embodiments, the conversion materials can be light emitting particles made of fluorescent molecules that emit different colors (e.g. red, green, and blue). In embodiments, the conversion materials can be light emitting particles made of pure organic or organo-metallic dyes with or without the energy augmentators.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converter materials with or without the energy augmentators include for example ZnS, PbS, $SbS_3$, $MoS_2$, PbTe, PbSe, BeO, MgO. $Li_2CO_3$, $Ca(OH)_2$, $MoO_3$, $SiO_2$, $Al_2O_3$, $TeO_2$, $SnO_2$, KBr, KCl, and NaCl. These materials can include dopants to tailor the emission properties, as noted above. Examples of doped (or alloyed) glass systems suitable for the include $Y_2O_3$:Gd, $Y_2O_3$:Dy, $Y_2O_3$:Tb, $Y_2O_3$:Ho, $Y_2O_3$:Er, $Y_2O_3$:Tm, $Gd_2O_3$:Eu, $Y_2O_2S$:Pr, $Y_2O_2S$:Sm, $Y_2O_2S$:Eu, $Y_2O_2S$:Tb, $Y_2O_2S$:Ho, $Y_2O_2S$:Er, $Y_2O_2S$:Dy, $Y_2O_2S$:Tm, ZnS:Ag:Cl (blue), ZnS:Cu:Al (green), $Y_2O_2S$:Eu (red), $Y_2O_3$:Eu (red), $YVO_4$:Eu (red), and $Zn_2SiO_4$:Mn (green).

With regard more specifically to down converter materials suitable for the invention with or without the energy augmentators, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention with or without the energy augmentators.

In other embodiments of the invention, the down converter materials (or mixtures of down converters materials can include $Y_2O_3$: Li. Sun et al. "Luminescent properties of Li+ doped nanosized $Y_2O_3$:Eu," Solid State Comm. 119 (2001) 393-396 (the entire contents of which are incorporated herein by reference) describe such materials. Hou et al. "Luminescent properties nano-sized $Y_2O_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria ($Y_2O_3$) powders have been successfully synthesized by a co-precipitation method. The powders were well crystallized, and the grains were almost spherical with good dispersibility. The quenching concentration of $Eu^{3+}$ ions is 9 mol % which is much higher than micro-scaled powders. The incorporation of Li+ ions greatly improved the luminescence intensity. The highest emission intensity was observed with 4 mol % Li+ doped $Y_2O_3$:Eu powder ($(Y_{0.87}Eu_{0.09}Li_{0.04})_2O_3$) and the fluorescence intensity was increased by as much as 79%. Yi et al. "Improved cathodoluminescent characteristics of $Y_2O_3$:$Eu^{3+}$ thin films by Li-doping," Appl. Phys. A 87, 667-671 (2007) (the entire contents of which are incorporated herein by reference) describe cathodoluminescent spectra for both $Y_2O_3$:$Eu^{3+}$ and Li-doped $Y_2O_3$:$Eu^{3+}$ films and methods for making these materials.

The invention in other embodiments can use a wide variety of up conversion materials (or mixtures of up converters) with or without the energy augmentators to enhance a particular color of light observable from reflective material or surface. These up conversion materials can include similar materials as discussed above with regard to down conversion but typically included doped or impurity states in a host crystal that provide a mechanism for up conversion pumping. Accordingly, the up conversion materials to enhance color emission can convert energy from one of near infrared, infrared, and microwave irradiation. The upconversion materials to enhance color emission can convert energy from lower energy visible light to higher energy visible light.

Upconversion materials with or without the energy augmentators can be used in various ways to enhance visible light emission by way of conversion of infrared light from a solar spectrum (as in daylight exposure) or a black body spectrum (as in an incandescent lamp). In one example, a nanoparticle of a lanthanide doped oxide can be excited with near infrared light such as laser light at 980 nm and 808 nm to produce visible light in different parts of the red, green, blue spectrum depending on the dopant trivalent rare earth ion(s) chosen, their concentration, and the host lattice.

The lanthanide doped oxides suitable for this invention differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the $NaYF_4$ such that the $Yb^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the $Yb^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention with or without the energy augmentators.

Further, materials specified for up conversion materials in the invention with or without the energy augmentators include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}Mn_xS_y$, $Ca_{1-x}Mn_xS_y$, $Ba_{1-x}Mn_xS_y$ and $Sr_{1-x}$, etc. (wherein, $0<x\leq1$, and $0<y\leq1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0\ .\ .\ .\ 1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, 0; B=S, . . . $0<z\leq1$, $o<q\leq1$).

Some nanoparticles such as ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$ are known in the art to function for both down-conversion luminescence and upconversion luminescence and would be suitable for the invention with or without the energy augmentators. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size >0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative concentration in the host crystal. For the example of upconversion in a $Y_2O_3$ host crystal, to achieve a blue emission (~450-480 nm) one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)]. The concentrations of dopants relative to each other and the crystal matrix must be tuned for every combination, and there are multiple ways to achieve multiple colors from even the same dopants with or without the energy augmentators.

Up-conversion of red light with a wavelength of about 650 nm in $Tm^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a $Tm^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of $LuPO_4$:$Yb^{3+}$, $Tm^{3+}$, and $YbPO_4$:$Er^{3+}$ nanocrystals in chloroform. Excitation at 975 nm has been shown by others to produce visible luminescence in the blue, green, or red spectral regions.

Tellurium and germanium oxides (tellurites and germinates) are also suitable upconverters. These glasses can be doped with Tm, Yb, Ho, Er, Pr, for example.

$Yb^{3+}$ doped $BaZrO_3$ is also suitable for upconversion. $Er^{3+}$ and/or $Tm^{3+}$ doping are also suitable for tailoring the emission wavelengths.

In another embodiment, $Nd^{3+}$:$Cs_2NaGdCl_6$ and $Nd^{3+}$, $Yb^{3+}$:$Cs_2NaGdCl_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2→4I9/2), and (4G7/2→4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for the present invention. Among the up-conversion luminescences for the $ZrF_4$ fluoride glasses, the green emission was seen to be extremely strong and the blue and red emission intensities were very weak.

In another embodiment, $Tm^{3+}$/$Yb^{3+}$-codoped $TeO_2$—$Ga_2O_3$—$R_2O$ (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MLCT) transition in $[Ru(dmb)_3]^{2+}$ (dmb=4,4'-dimethyl-2,2'-bipyridine) in the presence of anthracene or 9,10-diphenylanthracene have been reported converters and are suitable for the present invention. Upconverted to be up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95) relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW peak power).

The structures described herein for color enhancement with the energy augmentation structures are denoted as color enhancing/energy augmentation structures or as energy enhancing/augmentation structures.

By having the energy converters or color converting or enhancing materials disposed in a vicinity of the energy augmentation structures of this invention, regardless of the whether the energy augmentation structure is in a region of intensified electric field or otherwise outside the region of intensified electric field, the color enhancing/energy augmentation structures or the energy enhancing/augmentation structures of the invention are able to produce light which can be used for a variety of applications, in particular for photo-stimulation of biological, chemical, and physical reactions such as for example photoactivation of photoreactive drugs, photoactivation of photosensitive materials such as adhesives or lithographic photoresists, or for direct interaction with biological and chemical agents in the environment of the augmentation structures, as in sterilization.

Accordingly, in one embodiment of the invention, the color enhancement structures described herein can receive polychromatic light from a variety of sources such as sunlight, incandescent bulbs, fluorescent tube, and LED light sources with each having different wavelengths or wavelength bands. For these wavelength different bands, the resonators are "matched" or "tuned" to those wavelengths such that an intense electric field is established especially between the external-electrode pairs, or the folded resonator electrode pairs if used. In those regions of intense electric field can be disposed color converters (up and/or down phosphors) which can take light from one of the different wavelengths or wavelength bands, and have light of another wavelength or of different wavelength bands be emitted therefrom. In one embodiment, the intense electric field increases the intensity of the emitted light from the phosphors. Moreover, unlike the above-noted plasmonics where the electric field enhancement is restricted to regions within 100 to 200 nm of the metal, the resonators establish an increased electric field within the volume of the external-electrode pair, or the folded resonator electrode pairs if used, such that the phosphor material in a vicinity and within the external-electrode pair (or the folded resonator electrode pairs) exhibits an intensity larger than if the converter were remote from the resonator.

In view of the above, this invention is directed in general to methods and systems for color enhancement utilizing a color enhancement structure having a) an energy collector comprising at least one energy augmentation structure, and b) an energy converter capable of converting a second wavelength/quantum of electromagnetic energy into and emitting therefrom a third wavelength of light shifted in wavelength/energy from the second wavelength/quantum of electromagnetic energy. In one embodiment, the energy converter is disposed in a vicinity of the at least one energy augmentation structure such that the light shifted in wavelength is emitted with an intensity larger than if the converter were remote from the at least one energy augmentation structure. For ease of understanding, the term "wavelength" will be used to describe the electromagnetic energy entering into the energy converter, even though that electromagnetic energy may be better described in certain embodiments based upon its energy level or strength.

By having the energy converters or color converting or enhancing materials disposed in a vicinity of the energy augmentation structures of this invention, regardless of the whether the energy augmentation structure is in a region of intensified electric field or otherwise outside the region of intensified electric field, the color enhancing/augmentation structures or the energy enhancing/augmentation structures of the invention are able to enhance the conversion of one form of energy to another, as a conversion from one or more wavelengths of light to other wavelengths of light, or as a conversion from the one or more wavelengths of light to electrical energy, or as a conversion from the one or more wavelengths of light to heat.

Conversion from the one or more wavelengths of light to other wavelengths of light is useful for color shifting and color enhancement applications. Conversion from the one or more wavelengths of light to electrical energy is useful for harvesting solar energy using for example photovoltaic cells. Conversion from the one or more wavelengths of light to heat is useful also for harvesting solar energy using for example thermoelectric cells or other heat-to-electrical energy devices such as thermoelectric generators.

In some embodiments of the color enhancing/energy augmentation structures, the color enhancing structure includes a multi-dimensional light collector comprising a first level of metallic patterns and a second level of metallic patterns offset in at least one of a lateral or axial direction from the first level of metallic patterns. At least one of the metallic patterns optionally comprises a first resonator dimensioned to be resonant with a first wavelength of light. The first resonator can be one of a folded structure or an external-electrode pair structure as noted above. The color enhancement structure has a converter capable of converting a second wavelength of light into and emitting therefrom a third wavelength of light shifted in wavelength from the second wavelength of light. The converter is disposed with the first resonator such that the light shifted in wavelength is emitted with an intensity larger than if the converter were remote from the first resonator.

In some embodiments, the energy converter being disposed in a vicinity of the at least one energy augmentation structure is conductively coupled the energy converter to the at least one energy augmentation structure.

For example, in some embodiments, the energy converter being disposed in a vicinity of the at least one energy augmentation structure comprises a physical conductive connection between the energy converter and the at least one energy augmentation structure.

In some embodiments of the color enhancing/energy augmentation structures, the color enhancing structure, the energy converter comprises a down converter converting ultraviolet or blue light into red, yellow, or green light. In some embodiments of the color enhancing/augmentation structures, the energy converter comprises an up converter converting infrared or red light into yellow, green light, or blue light.

In some embodiments of the color enhancing/energy augmentation structures, the metallic patterns referenced above comprises a folded resonator having opposing electrodes with electric fields directed in between, and the converter is positioned between the opposing electrodes or within fringing electric field of the opposing electrodes or otherwise in a vicinity of the opposing electrodes. In one example, the folded resonator is a $3/4\lambda$ folded resonator. In one example, metallic patterns comprise at least one of Au, Ag, Cu, Al, or transparent metal oxides. In another example, the metallic patterns can be formed with refractory metals such for example Ti, W, and Mo.

In some embodiments of the color enhancing/energy augmentation structures, the metallic patterns referenced above comprises an external external-electrode pair structure having opposing electrodes with electric fields directed in between, and the converter is positioned between the opposing electrodes or within fringing electric field of the opposing electrodes or otherwise in a vicinity of the opposing electrodes. In one example, the resonator is a $3/4\lambda$ external-electrode pair resonator. In one example, metallic patterns comprise at least one of Au, Ag, Cu, Al, or transparent metal oxides. In another example, the metallic patterns can be formed with refractory metals such for example Ti, W, and Mo.

In some embodiments of the color enhancing/energy augmentation structures, the color enhancing structure, there is an antireflection film disposed on at least one of the metallic patterns or on the converter.

In some embodiments of the color enhancing/energy augmentation structures, the color enhancing structure, the first resonator noted above comprises plural resonators, the converter noted above comprises plural converters, and the plural converters are disposed at multiple positions throughout the light collector. In one example, the plural converters are positioned to convert light being internally scattered within the light collector.

In some embodiments of the color enhancing/energy augmentation structures, the first level of metallic patterns noted above (or the second level of metallic patterns) comprises a metal core cladded with a high-K dielectric and a subsequent cladding of a low-K dielectric. In some embodiments of the color enhancing/energy augmentation structures, the first level of metallic patterns noted above (or the second level of metallic patterns) comprises a radial pattern of conductors. In some embodiments of the color enhancing/energy augmentation structures, the first level of metallic patterns noted above (or the second level of metallic patterns) comprises a fractal pattern. In one example, the fractal pattern is embedded within a dielectric material.

In some embodiments of the color enhancing/energy augmentation structures, the first level of metallic patterns noted above (or the second level of metallic patterns) comprises a three-dimensional fractal structure.

In some embodiments of the color enhancing/energy augmentation structures, the light collector comprises a transparent panel with the first level of metallic patterns and the second level of metallic patterns and optionally multiple converters formed therein. In some embodiments of the color enhancing/augmentation structures, the light collector comprises a transparent sheet with the first level of metallic patterns and the second level of metallic patterns and optionally multiple converters formed therein.

In some embodiments of the color enhancing/energy augmentation structures, the first level of metallic patterns noted above (or the second level of metallic patterns) are of different sizes and/or orientations to each other of the first level of metallic patterns or with respect to the second level of metallic patterns.

Figure 29:
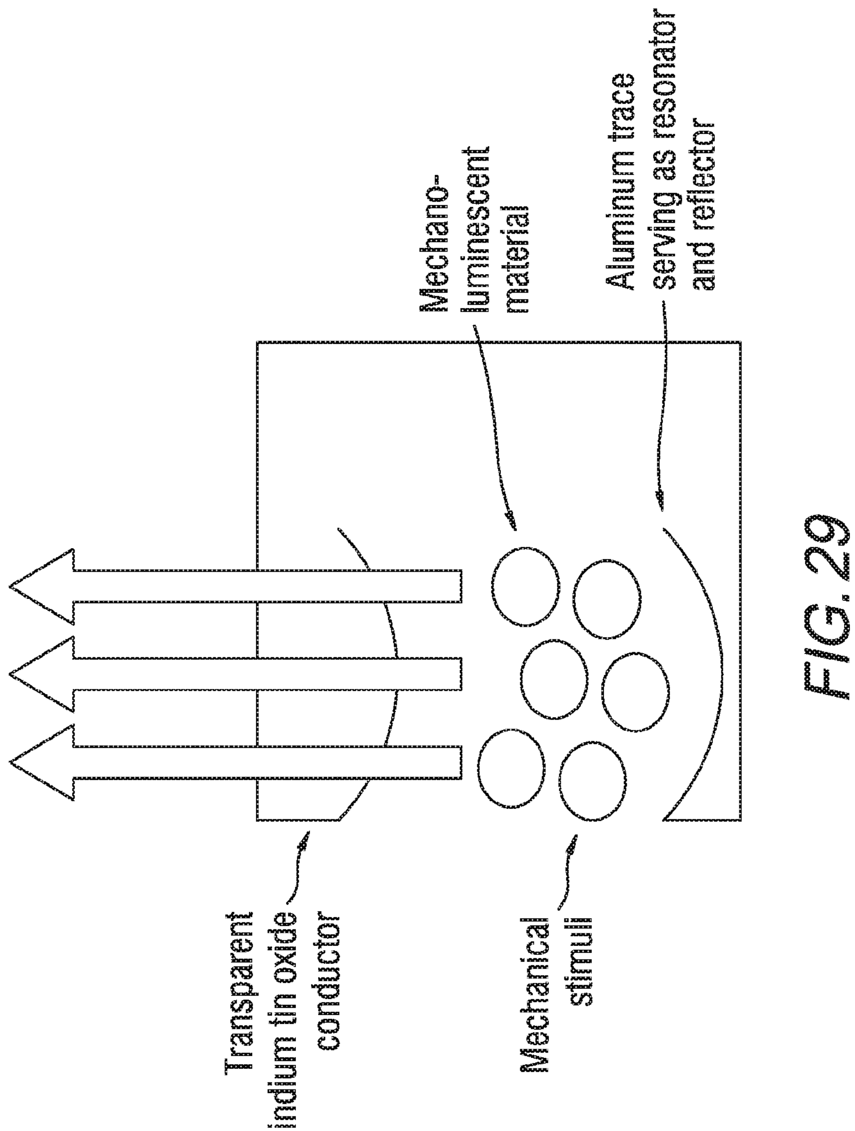
FIG. 29 is a diagram showing a mechanoluminescent emitter of the present invention.

Indeed, FIG. 29 is a schematic of a reflective resonator of this invention including mechano-luminescent materials, in this example the mechano-luminescent materials being placed between a folded resonator structure, although mechano-luminescent materials could be placed between an external electrode pair resonator structure. Thus, in one embodiment, an electromagnetic wave energy augmentator captures one or more wavelengths of electromagnetic energy, and augments the one or more wavelengths of electromagnetic energy in at least one property (such as electric field intensity in a vicinity of the mechano-luminescent materials), while at the same time the mechano-luminescent materials can be considered an energy converter converting the ultrasonic or mechanical energy into electromagnetic radiation (i.e., emitted light).

In one embodiment of the invention, the increased electric field in the folded structure or the external electrode pair increases the luminescence of the mechano-luminescent materials. The energy used to build the electric field in the folded structure or the external electrode pair being provided separately from the mechanical energy driving the mechano-luminescence.

For example, the reflective resonator of FIG. 29 could be placed adjacent an exhaust stack of an engine or other waste heat dissipating machine. In one embodiment, the reflective resonator of FIG. 29 would be mounted on a stainless steel arm connected to the heat stack. The stainless steel would couple mechanical vibrations to the reflective resonator while thermally isolating the reflective resonator from the exhaust stack, thereby permitting even inorganic mechano-luminescent materials to be used.

When the engine began to show higher levels of vibration or vibrations at different frequencies, the intensity of the light emitted would change providing a visible light signal that the engine or machine was under stress from power loads or wear or mechanical failure.

In one embodiment of the invention, the reflective structure shown in FIG. 29 need not include the resonator and its resonating elements. In one embodiment of the invention, the reflective structure shown in FIG. 29 could be placed directly on a machine operating at a relatively cold temperature around 100° C. In this embodiment, the reflective structure need not include the resonator and its resonating elements. However, if the resonator and its resonating elements were present, a laser such as 656 nm laser could "probe" the resonator and intensify "on demand" the mechano-luminescence. In this way, early detection of developing mechanical problems could be detected.

Various mechano-luminescent materials suitable for the present invention include $ZnS{:}Mn^{2+}$, $SrAl_2O_4{:}Eu^{2+}$, ZnS:Cu, $SrAMgSi_2O_7{:}Eu^{2+}$ (A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba_xAl_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, ZnS, ZnTe, $(ZnS)_{1-x}(MnTe)_x$(x<¼), CaZnOS, BaZnOS, $Ca_2MgSi_2O_7$, $Sr_2MgSi_2O_7$, $Ba_2MgSi_2O_7$, $SrCaMgSi_2O_7$, $SrBaMgSi_2O_7$, $Sr_nMgSi_2O_{5+n}$ (1≤n≤2), $Ca_2Al_2SiO_7$, $Sr_2Al_2SiO_7$, $CaYAl_3O_7$, $CaAl_2Si_2O_8$, $Ca_{1-x}Sr_xAl_2Si_2O_8$ (x<0.8), $SrMg_2(PO_4)_2$, $Ba_{1-x}Ca_xTiO_3$ (0.25<x<0.8), $Ba_{1-x}Ca_xTiO_3$, $LiNbO_3$, $Sr_2SnO_4$, $(Ca, Sr, Ba)_2SnO_4$, $Sr_3Sn_2O_7$, $Sr_3(Sn, Si)_2O_7$, $Sr_3(Sn, Ge)_2O_7$, $Ca_3Ti_2O_7$, $CaNb_2O_6$, $Ca_2Nb_2O_7$, $Ca_3Nb_2O_8$, $BaSi_2O_2N_2$, $SrSi_2O_2N_2$, $CaZr(PO_4)_2$, $ZrO_2$.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechanoluminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention, such composites made of a piezoelectric material and an electroluminescent material, hereinafter "composite mechano-luminescent emitters," provides a structure that, upon stimulation with mechanical or vibrational energy such as from an acoustic or ultrasonic transducer, emit light. Details of various electroluminescent materials that can be used for the composite mechano-luminescent emitters are provided in the next section where electroluminescent materials alone are placed in vicinity of the opposing resonator electrodes.

Figure 30:
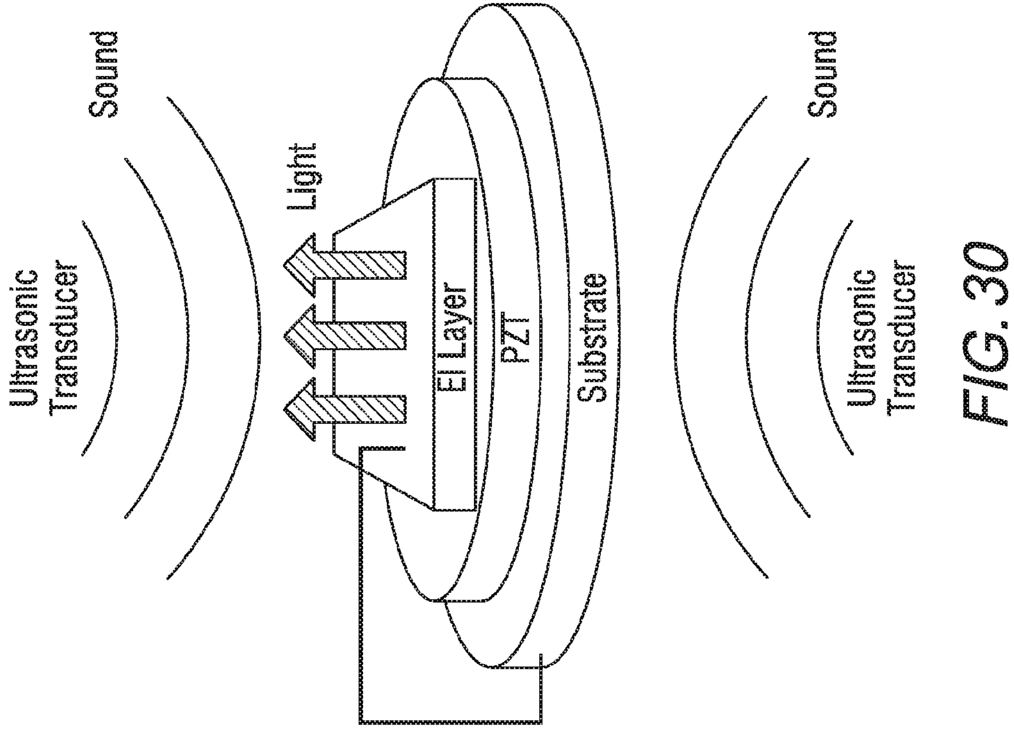
FIG. 30 is a diagram showing a composite piezoelectric/electroluminescent emitter of the present invention.

FIG. 30 is a schematic of composite mechano-luminescent emitter composed of a piezoelectric material and an electroluminescent material which, in one embodiment, could be mechano-luminescent light emitters in FIG. 29.

Figure 31:
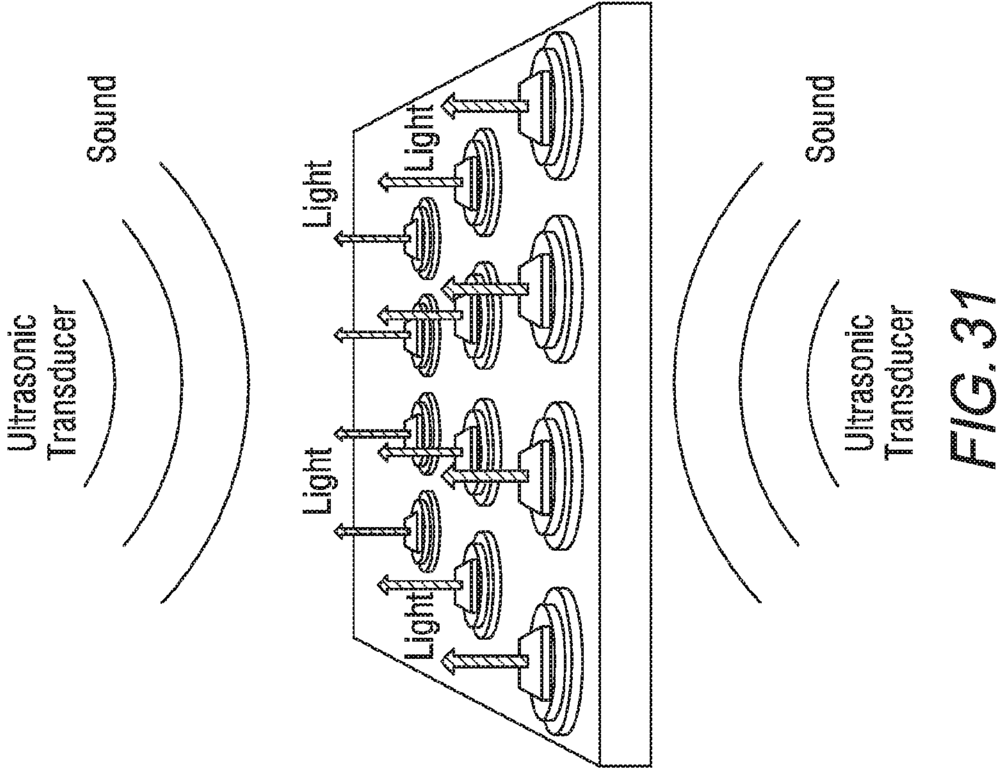
FIG. 31 is a diagram showing a distribution of the composite emitters of FIG. 30 across a surface for light emission.

In another embodiment, the composite mechano-luminescent emitters could be used without need for any resonator structure. FIG. 31 is schematic showing the composite mechano-luminescent emitters distributed across a sector of interest for generation of light therefrom. FIG. 31 shows that an ultrasonic transducer can be used for stimulation/activation of these composite mechano-luminescent emitters.

In color enhancement applications, application of ultrasonic energy could change the color emission from a surface. Such applications could be for security systems where an item would contain a pattern of the composite mechano-luminescent emitters. The pattern would not be apparent until it was activated with ultrasonic or acoustic energy upon which time light of a predetermined wavelength would be emitted. The light emitted might be visible or infrared light depending on the type of detector used to detect the emitted light.

Figure 32:
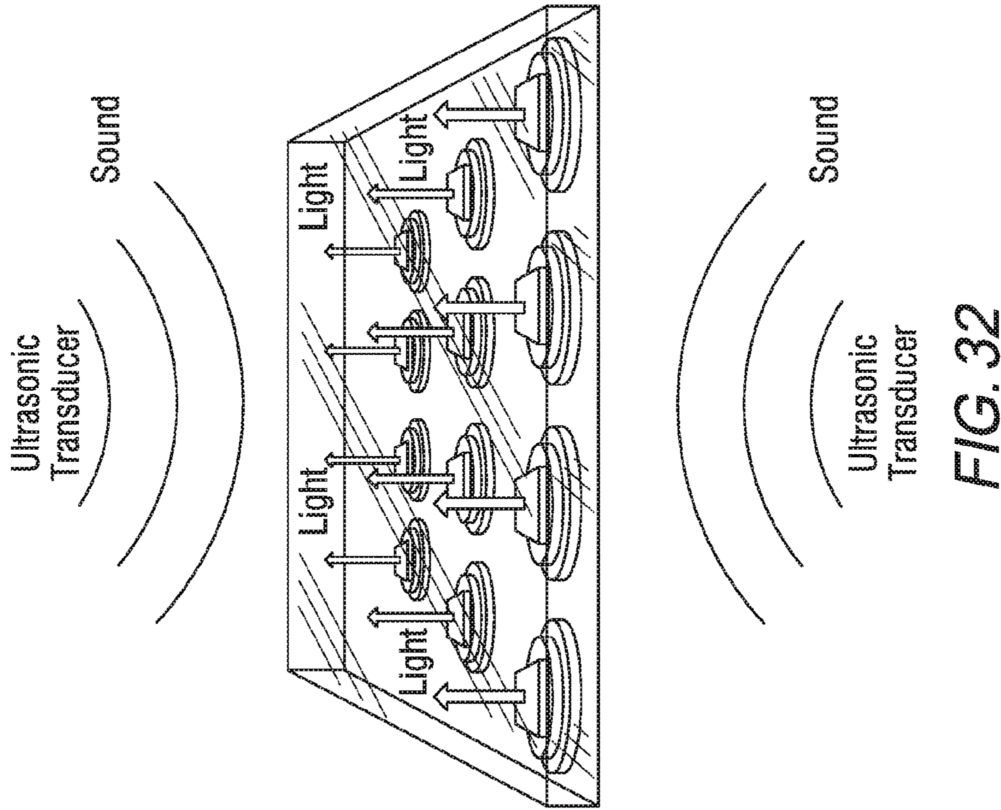
FIG. 32 is a diagram showing a distribution of the composite emitters of FIG. 30 within a target region for light emission.

In a related application of these composite mechano-luminescent emitters, FIG. 32 is schematic showing the composite mechano-luminescent emitters distributed inside a medium of interest for generation of light therein or therefrom. With the present invention, light can be turned on and off with the on/off status of an ultrasonic transducer and the intensity of the light can be varied. There are no power leads to run into the medium of interest. There is no space taken up by batteries or control elements to turn power on and off. The composite mechano-luminescent emitters can be miniaturized. The composite mechano-luminescent emitters could be agglomerated in a container. In some embodiments, the container would not be completely packed permitting the tilting of the container to relocate the composite mechano-luminescent emitters within the container.

Electroluminescent and phosphorescent materials (organic and inorganic): The present invention in various embodiments with or without energy augmentators can utilize in organic fluorescent molecules or inorganic particles capable or fluorescence and phosphorescence having crystalline, polycrystalline or amorphous micro-structures for the converters (optionally including the energy augmentation structures described above).

The list of inorganic molecules that can be used in the resonating structures to enhance the color emission include but is not limited to the following inorganic electroluminescent phosphor materials:

$SrS:Ce^{3+}$ $CaGa_2S_4:Ce^{3+}$ $SrS:Cu^{+}$ $CaS:Pb^{2+}$ $BaAl_2S_4:Eu^{2+}$ $ZnS:Tb^{3+}$ $ZnMgS:Mn^{2+}$ $SrGa_2S_4:Eu^{2+}$ $CaAl_2S_4:Eu^{2+}$ $BaAl_2S_4:Eu^{2+}$ $ZnS:Mn^{2+}$ $MgGa_2O_4:Eu^{3+}$ $(Ca, Sr)Y_2S_4:Eu^{2+}$ $BaAl_2S_4:Eu^{2+}$

The organic molecules that can phosphoresce under the influence of an electric field are also of interest in the present application. The organic fluorescent compounds with high quantum yield include by way of illustration:

Naphthalene,

Pyrene,

Perylene,

Anthracene,

Phenanthrene, p-Terphenyl, p-Quartphenyl,

Trans-stilbene,

Tetraphenylbutadiene,

Distyrylbenzene, 2,5-Diphenyloxazole,

4-Methyl-7-diethylaminocoumarin,

2-Phenyl-5-(4-biphenyl)-1,3,4-oxadiazole,

3-Phenylcarbostyryl, 1,3,5-Triphenyl-2-pyrazoline, 1,8-Naphthoylene-1',2'-bezimidazole, 4-Amino-N-phenyl-naphthalimide.

The inorganic fluorescent and phosphorescent materials detailed here are numerous, and various examples are given by way of illustration rather than limitation. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$.

Further included are alkali earth chalcogenide phosphors which are in turn exemplified by the following non-inclusive list:

$MgS:Eu^{3+}$, $CaS:Mn^{2+}$, CaS:Cu, CaS:Sb, $CaS:Ce^{3+}$, $CaS:Eu^{2+}$, $CaS:Eu^{2+}Ce^{3+}$, $CaS:Sm^{3+}$, $CaS:Pb^{2+}$, $CaO:Mn^{2+}$, $CaO:Pb^{2+}$.

The examples include the ZnS type phosphors that encompass various derivatives:

ZnS:Cu,Al(Cl), ZnS:Cl(Al), ZnS:Cu,I(Cl), ZnS:Cu, ZnS:Cu,In.

Compound IIIb-Vb phosphors which include the group IIIb and Vb elements of the periodic table are suitable for converter materials. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: In1-y(Ga1-xAlx)yP (provides a simple example). Silicon Carbide SiC as a luminescent platform has commercial relevancy if the blue light emitting diodes. These include the polytypes 3C-SiC, 6H-SiC, 4H-SiC with donors such as N and Al and acceptors such as Ga and B.

Multiband luminescent materials suitable for converter materials include for example the following compositions:

$(Sr, Ca, Ba)_5(PO_4)_3Cl:Eu^{2+}$, $BaMg_2Al_6O_{27}:Eu^{2+}$, $CeMgAl_{11}O_{19}:Ce^{3+}:Tb^{3+}$, $LaPO_4:Ce^{3+}:Tb^{3+}$, $GdMgB_5O_{10}:Ce^{3+}:Tb^{3+}$, $Y_2O_3:Eu^{3+}$, $(Ba,Ca,Mg)_5(PO_4)_3Cl:Eu^{2+}$, $2SrO_{0.84}P_2O_5\cdot 0.16B_2O_3:Eu^{2+}$, $Sr_4Al_{14}O_{25}:Eu^{2+}$.

Other materials suitable for converter materials include those materials used for fluorescent high pressure mercury discharge lamps can be excited with X-Ray and are exemplified by way of family designation as follows:

Phosphates $(Sr, M)(PO_4)_2:Sn^{2+}$, Mg or Zn activator, Germanate $4MgO\cdot GeO_2:Mn^{4}+$, $4(MgO, MgF_2)GeO_2:Mn^{4+}$, Yttrate $Y_2O_3:Eu^{3+}$, Vanadate $YVO_4:Eu^{3+}$, $Y(P,V)O_4:Eu^{3+}$, $Y(P,V)O_4:In^{+}$, Halo-Silicate $Sr2Si3O_8\cdot 2SrCl_2:Eu^{2+}$, Aluminate $(Ba,Mg)_2Al_{16}O_{24}:Eu^{2+}$, $(Ba, Mg)_2Al_{16}O_{24}:Eu^{2+},Mn^{2+}$, $Y_2O_3Al_2O_3:Tb^{3+}$.

Another grouping of materials suitable for converter materials by host compound include chemical compositions in the Halophosphates phosphors, Phosphate phosphors, Silicate phosphors, Aluminate phosphors, Borate phosphors, Tungstate phosphors, and other phosphors.

The halophosphates include by way of illustration:

$3Ca_3(PO_4)_2 \cdot Ca(F,Cl)_2:Sb^{3+}$, $3Ca_3(PO_4)_2 \cdot Ca(F,Cl)_2:Sb^{3+}/Mn^{2+}$, $Sr_{10}(PO_4)_6Cl_2:Eu^{2+}$, $(Sr,Ca)_{10}(PO_4)_6Cl_2:Eu^{2+}$, $(Sr,Ca)_{10}(PO_4)_6 \cdot nB_2O_3:Eu^{3+}$, $(Sr, Ca,Mg)_{10}(PO_4)_6Cl_2:Eu^{2+}$. The phosphate phosphors include by way of illustration $Sr_2P_2O_7:Sn^{2+}$, $(Sr,Mg)_3(PO_4)_2:Sn^{2+}$, $Ca_3(PO_4)_2 \cdot Sn^{2+}$, $Ca_3(PO_4)_2:Tl^{+}$, $(Ca,Zn)_3(PO_4)_2:Tl^{+}$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3 \cdot 0.2SiO_2 \cdot 0.9P_2O_5:Ce^{3+} \cdot Tb^{3+}$, $BaO \cdot TiO_2 \cdot P_2O_5$. The silicate phosphors $Zn_2SiO_4:Mn^{2+}$, $CaSiO_3:Pb^{2+}/Mn^{2+}$, $(Ba, Sr, Mg) \cdot 3Si_2O_7:Pb^{2+}$, $BaSi_2O_5:Pb^{2+}$, $Sr_2Si_3O_8 \cdot 2SrCl_2:Eu^{2+}$, $Ba_3MgSi_2O_8:Eu^{2+}$, $(Sr,Ba)Al_2Si_2O_8:Eu^{2+}$.

The aluminate phosphors include:

$LiAlO_2:Fe^{3+}$, $BaAl_8O_{13}:Eu^{2+}$, $BaMg_2Al_{16}O_{27}:Eu^{2+}$, $BaMg_2Al_6O_{27}:Eu^{2+}/Mn^{2+}$, $Sr_4Al_{14}O_{25}:Eu^{2+}$, $CeMgAl_{11}O_{19}:Ce^{3+}/Tb^{3+}$.

The borate phosphors include:

$Cd_2B_2O_5:Mn^{2+}$, $SrB_4O_7F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include:

$CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO \cdot As_2O_5:Mn^{2+}$, $3.5MgO \cdot 0.5MgF_2—GeO_2:Mn^{4+}$.

Activators of relevance to the various doped phosphors include the following list:

$Tl^{+}$, $Pb^{2+}$, $Ce^{3+}$, $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$.

In various embodiments, the luminescence center $Tl^{+}$ can be used with a chemical composition such as:

$(Ca,Zn)_3(PO_4)_2:Tl^{+}$, $Ca_3(PO_4)_2:Tl^{+}$.

Similarly, the luminescence center Mn2+ can be used with chemical compositions such as $MgGa_2O_4:Mn^{2+}$, $BaMg_2Al_{16}O_{27}:Eu^{2+}/Mn^{2+}$, $Zn_2SiO_4:Mn^2$+, $3Ca_3(PO_4)_2 \cdot Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{10}:Ce^{3+}/Tb^{3+}/Mn^{2+}$.

Further, the luminescence center $Sn^{2+}$ can be used with chemical compositions such as:

$Sr_2P_2O_7:Sn^{2+}$, $(Sr,Mg)_3(PO_4)_2:Sn^{2+}$.

The luminescence center $Eu^{2+}$ can also be used with chemical compositions such as:

$SrB_4O_7F:Eu^{2+}$, $(Sr,Ba)Al_2Si_2O_8:Eu^{2+}$, $Sr_3(PO_4)_2:Eu^{2+}$, $Sr_2P_2O_7:Eu^{2+}$, $Ba_3MgSi_2O_8:Eu^{2+}$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$.

The luminescence center $Pb^{2+}$ can be used with chemical compositions such as:

$(Ba,Mg,Zn)_3Si_2O_7:Pb^{2+}$, $BaSi_2O_5:Pb^{2+}$, $(Ba,Sr)_3Si_2O_7:Pb^{2+}$.

The luminescence center $Sb^{2+}$ can be used with chemical compositions such as:

$3Ca_3(PO_4)_2Ca(F,Cl)_2:Sb^{3+}$, $3Ca_3(PO_4)_2Ca(F,Cl)_2:Sb^{3+}/Mn^{2+}$.

The luminescence center Tb3+ can be used with chemical compositions such as:

$CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$.

The luminescence center $Eu^{3+}$ can be used with chemical compositions such as:

$Y_2O_3:Eu^{3+}$, $Y(V,P)O_4:Eu^{3+}$.

The luminescence center $Dy^{3+}$ can be used with chemical compositions such as:

$YVO_4:Dy^{3+}$.

The luminescence center $Fe^{3+}$ can be used with chemical compositions such as:

$LiAlO_2:Fe^{3+}$.

The luminescence center $Mn^{4+}$ can be used with chemical compositions such as:

$6MgO \cdot As_2O_5:Mn^4$+, $3.5MgO \cdot 0.5MgF_2 \cdot GeO_2:Mn^{4+}$.

The luminescence center $Ce^{3+}$ can be used with chemical compositions such as:

$Ca_2MgSi_2O_7:Ce^{3+}$ and $Y_2SiO_5:Ce^{3+}$.

The luminescence center $WO_4^{2-}$ can be used with chemical compositions such as:

$CaWO_4$, $(Ca,Pb)WO_4$, $MgWO_4$.

The luminescence center $TiO_4^{4-}$ can be used with chemical compositions such as:

$BaO \cdot TiO_2 \cdot P_2O_5$.

In various embodiments of this invention, the phosphor chemistry utilized in X-Ray excitations can be used. Of particular interest is the k-edge of these phosphors. Low energy excitation can lead to intense luminescence in materials with low k-edge. Some of these chemistries and the corresponding k-edge are included as follows:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| ZnS:Ag | 9.66 keV |
| (Zn, Cd)S:Ag | 9.66/26.7 keV |

In one embodiment of this invention, light from these materials (excited for example by high energy particles including x-rays, gamma rays, protons, and electrons) can have their emissions modulated by having those materials included in a vicinity of (including inside) the color enhancing structures described herein. For example, in medical treatments where x-ray excites phosphorescence to photostimulate reactions in a patient, simultaneous with irradiation by the high energy particles there could be applied infrared irradiation to drive resonance in the color enhancing structures/energy augmentation structures described herein, where the x-ray phosphors would have enhanced emissions when in the presence of the intensified electric fields. In another example, in medical or scientific instruments, simultaneous with irradiation by the high energy particles there could be applied electric fields to enhance emissions from these x-ray phosphors.

C. Color Enhancement Structures

This invention provides methods, systems and devices which use phosphorescing fluorescing and scintillating materials or other of the energy conversion materials and devices described herein, with and without the energy augmentation structures described above for increasing the effectiveness and/or the efficiency of light emission from a medium. With the energy augmentation structures, this invention can generate local regions of intense electric fields to enhance or accelerate light, or photon, or electron emission of materials in proximity to those local regions.

Figure 33:
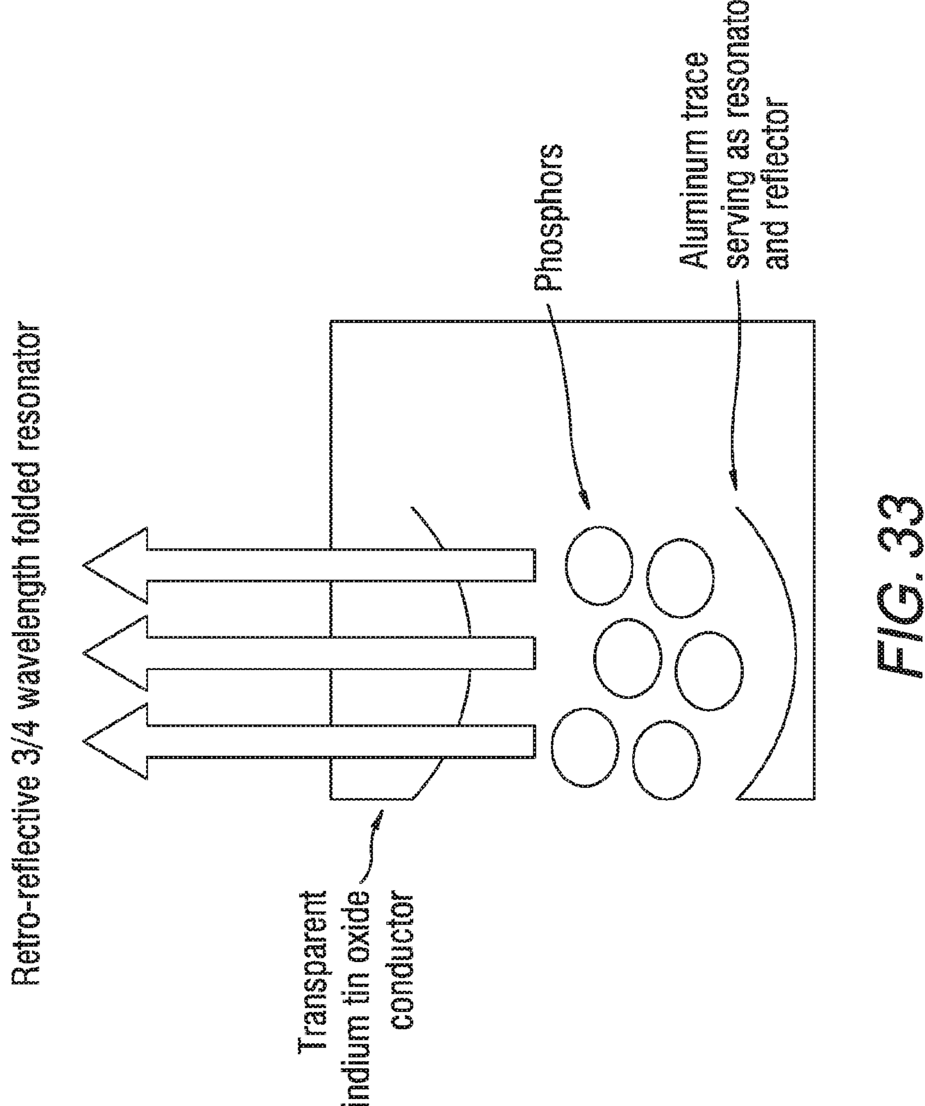
FIG. 33 is a schematic of a reflective resonator of this invention.

Phosphorescent Devices: Having now described numerous converter materials that can be used in this invention for color enhancement, FIG. 33 is a schematic of a reflective resonator of this invention where converter materials (such as the phosphors and other luminescent materials described above) are used inside a ¾ λ folded resonator having one side of the metal trace made with transparent indium tin oxide and the other side made of a reflective metal such Au, Ag, Al, or Cu. Alternatively, the resonator could have an external-electrode pair structure (instead of the folded structure shown), and the converter materials would reside within the electrode pair.

Figure 34:
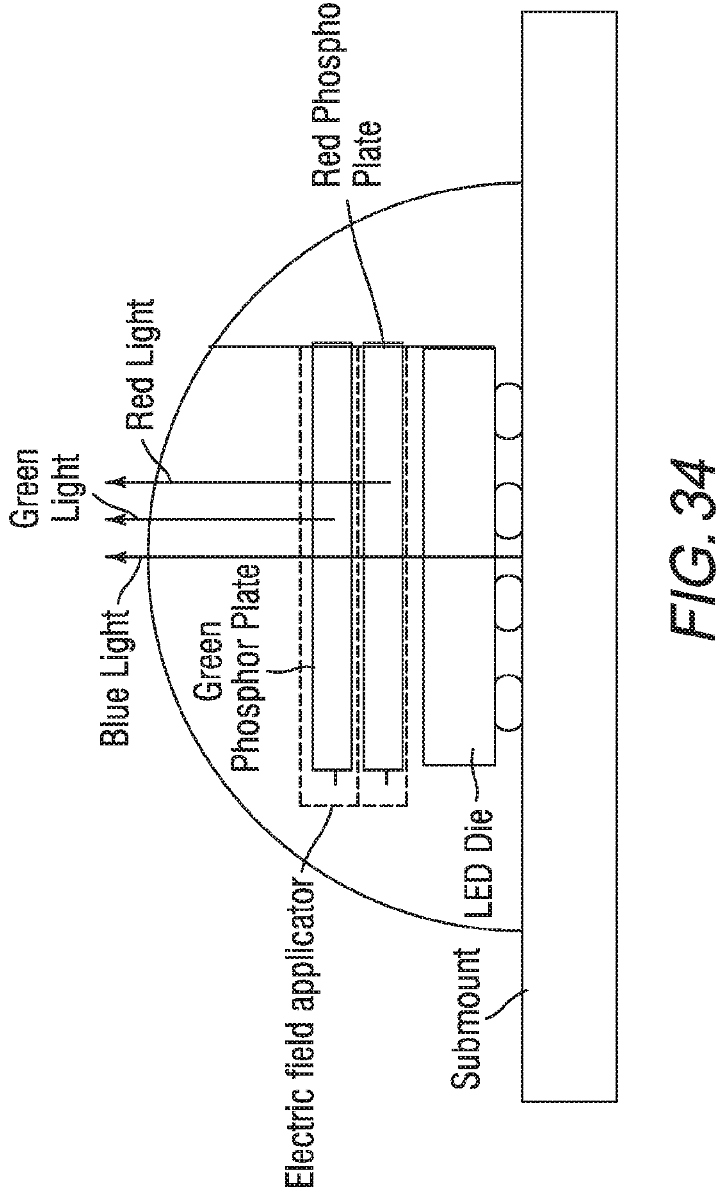
FIG. 34 is a schematic of a LED white light source with variable color temperature control.

FIG. 34 is a schematic of a LED white light source with variable color temperature control. This structure follows closely that described in US Pat. Appl. Publ. No. 2007/0215890 (the entire contents of which are incorporated herein by reference).

As shown above, in this embodiment, a conventional blue light LED is attached to a submount using solder bumps or other means. The submount has metal contact pads on its surface to which the LED is electrically connected. The contact pads lead to other conductors formed on the periphery or underside of the submount for connection to a power supply such as a current source. Here, in one embodiment of the present color enhancing invention, the submount is electrically connected to the electric field applicator. The electric field applicator can be simple grid elements as shown having a controllable voltage different established at each of the depicted levels such the electric fields inside the red phosphor plate and the green phosphor plate can be adjusted. By increasing or decreasing the electric field inside the red phosphor plate or the electric field inside the green phosphor plate, the intensity of the red light and the green light can be adjusted on demand and continuously, if needed.

Here, in one embodiment of the present color enhancing invention, the submount is not electrically connected to the electric field applicator, and the electric field applicator can be a folded resonator such as the ¾ λ folded resonator described above or can be a ¾ λ resonator with the external-electrode pair structure. Here, especially for high power LED operation where waste heat is generated, the wavelength of the ¾ λ folded resonator or the ¾ λ external-electrode pair resonator. Here, especially for high power LED operation where waste heat is generated, would be approximately 5-10 microns.

As in the '890 publication, the LED may be formed using AlInGaN materials and preferable emits blue light that has a peak wavelength of about 460-470 nm to match the spectral distribution of a conventional blue filter in an LCD. Other emission wavelengths, also considered blue, may also be suitable, such as 440-480 nm. The top surface of the blue LED may be any size, with typical sizes being equal to or less than 1 $mm^2$.

Placed over the LED are a red phosphor plate and a green phosphor plate. The size of each plate may match the size of the LED or may be slightly larger or smaller depending on the emission pattern of the LED, tolerances, and the characteristics of the phosphor plates. The plates may extend beyond the LED surface by as much as 25%. In one embodiment, the plates are smaller than the LED (e.g., up to 50% smaller) to create a larger blue component in the white light or to allow green and red phosphor plates to be placed side by side. With a thin LED, there will be insignificant side emission. Any side emission will be mixed in the backlight box with the white light.

As in the '890 publication, the thickness of each phosphor plate can be between 50-300 microns, depending on the type of phosphor used, the type of blue LED used (e.g., higher power LEDs may need thicker plates), the density of the phosphor, and other factors which would be understood by those in the art.

Figure 35:
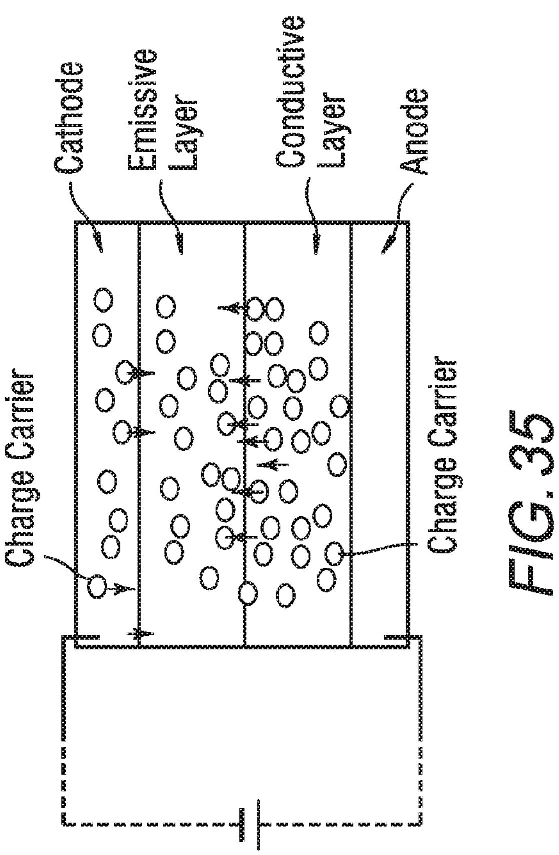
FIG. 35 is a schematic of an electroluminescent light source.

Electro Luminescent Devices: FIG. 35 is a schematic of an electroluminescent light source. Typical modern electroluminescent (EL) devices have two co-layered organic materials. The EL devices are composed of a transparent Indium-Tin-Oxide (ITO) anode, a hole transport layer (HTL), and electron transport layer (ETL), and a metal cathode made of alloyed metals and numerous examples are possible. Electron current flow (charge carrier flow) provides electrons to the emissive layer. Hole creation and flow (charge carrier) in the emissive layer can recombine with the electron in the emissive layer and output light.

Figure 36:
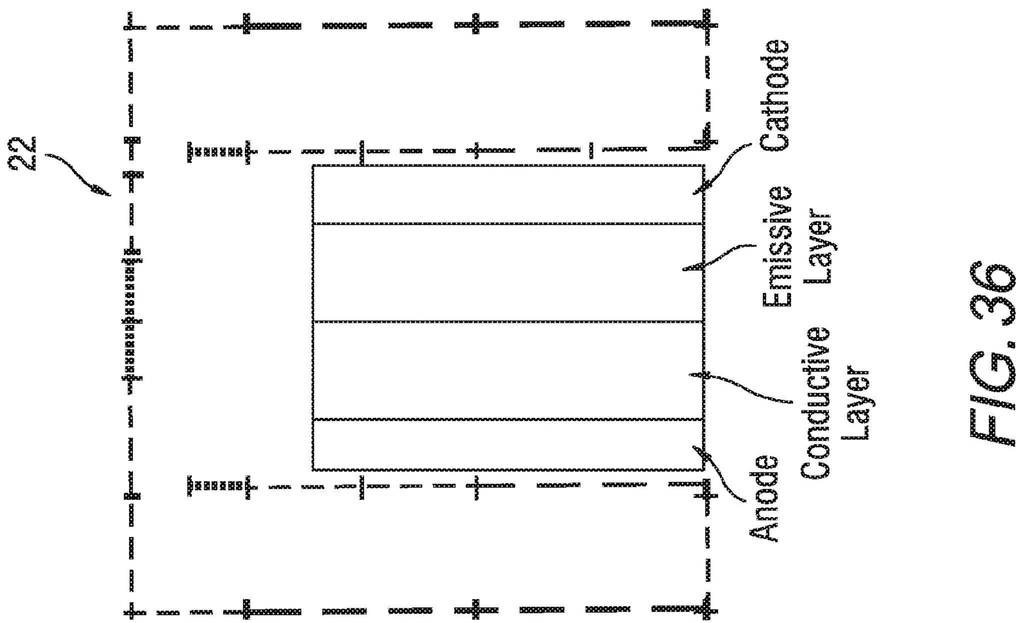
FIG. 36 is a schematic of an electroluminescent light source of this invention.

FIG. 36 is a schematic of an electroluminescent light source of this invention with the electroluminescent medium within the folded resonant electrodes.

Various materials used for the coating in the emissive layer of the present invention can include but are not limited to:

4,4',4"-Tris[phenyl(m-tolyl)amino]triphenylamine (m-MTDATA)

N,N'-Bis(3-methylphenyl)-N,N'-diphenylbenzidine (TPD)

4,4',4"-Tris[phenyl(m-tolyl)amino]triphenylamine (m-MTDATA)

N,N'-Bis(3-methylphenyl)-N,N'-diphenylbenzidine (TPD)

Tris-(8-hydroxyquinoline)aluminum 2,4,6-Tris(2-pyridyl)-s-triazine (TPT)

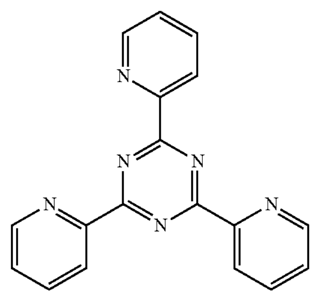 [SMILES: c1ccc(-c2nc(-c3ccccn3)nc(-c3ccccn3)n2)nc1]

2,2',2"-(1,3,5-Benzenetriyl)-tris(1-phenyl-1-H-benzimidazole) Alq

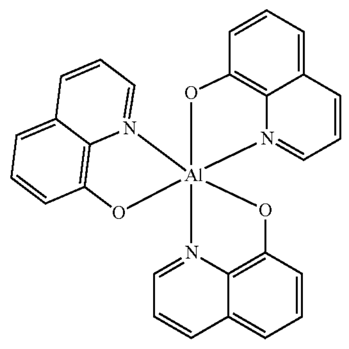

2,2',2"-(1,3,5-Benzenetriyl)-tris(1-phenyl-1-H-benzimidazole) TPBI

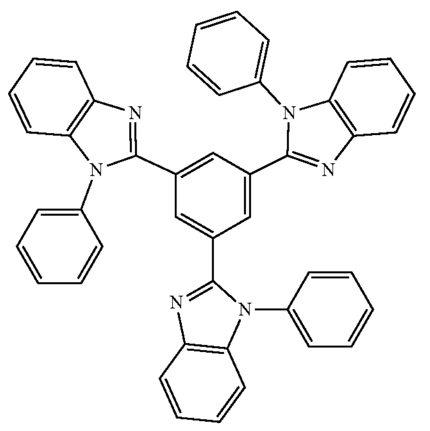 [SMILES: c1ccc(-n2c(-c3cc(-c4nc5ccccc5n4-c4ccccc4)cc(-c4nc5ccccc5n4-c4ccccc4)c3)nc3ccccc32)cc1]

2,9-Dimethyl-4,7-diphenyl-1,10-phenanthroline, BCP2,9-Dimethyl-4,7-diphenyl-1,10-phenanthroline, BCP

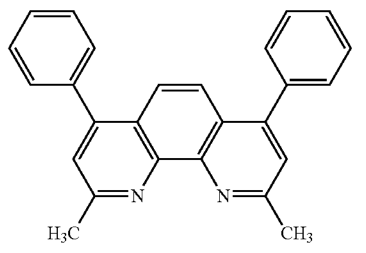 [SMILES: Cc1cc(-c2ccccc2)c2ccc3c(-c4ccccc4)cc(C)nc3c2n1]

In another embodiment, an optically transparent anode such as indium tin oxide ITO is used. The converter materials are placed in the capacitive portion of the bent antenna which exposes the organic layers composed of the hole transport layer (HTL), and electron transport layer (ETL), and a metal cathode. The electromagnetic energy that couples to the antenna in this example can operate from the RF and microwave regimes to the IR and the UV regimes.

In the embodiments of FIG. 3-2, the energy converter or color converting or enhancing materials is disposed in a vicinity of an energy augmentation structures (i.e., the ¾ $\lambda$ folded resonator). As such, the energy augmentation structure preferably is in the region of intensified electric field between the folded opposing electrodes. In one embodiment of the invention, the intensified electric field is a region of intensified energy because there is current flow conductively coupling the energy converter (the electroluminescent material) to the one energy augmentation structure (the ¾ $\lambda$ folded resonator).

Plasmonic Enhancement Structures for the Color Enhancement Devices:

The color enhancement devices noted above can utilize the plasmonic enhancement structures noted above. As noted above, FIG. 26 is a schematic of a depiction of an upconverter or a down converter material (i.e., a photoactive material) according to one embodiment of the invention to be utilized in the color enhancement/augmentation structures noted herein with or without energy augmentators. FIG. 26 shows a number of structural configurations for placement of a dielectric core upconverter or a down converter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion may depend on the particular upconversion material and process being used in a particular application, for the purposes for discussion and illustration, the following explanation is offered.

In the context of FIG. 26, when a wavelength $\lambda_1$ interacts with a dielectric material core, three separate processes are well understood for the upconversion process involving trivalent rare earth ions. These three processes are:

1) excited state absorption whereby two photons are absorbed sequentially by the same ion to excite and populate one or more states;
2) energy transfer upconversion which is a transfer of excitation from one ion to another already in an excited state; and
3) a cooperative process of multiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion or down conversion process.

Therefore, the particular ion being activated (whether it be a dopant ion or a host ion of a lattice such as in the neodymium oxide) will be chosen based on the host material being processed, in order that the dopant ion or the host ion in the dielectric core provide ion states which are pumpable by a NIR source to generate the resultant emission $\lambda_2$.

Hence, the invention in one embodiment provides an upconversion or a down conversion material configured, upon exposure to a first wavelength $\lambda_1$ of radiation, to generate a second wavelength $\lambda_2$ of radiation having an energy higher or lower than the first wavelength $\lambda_1$. The system can include a metallic structure disposed in relation to the nanoparticle (e.g. a metallic shell covering a fraction of the nanoparticle). The system may include a receptor disposed in the medium in proximity to the nanoparticle. The receptor upon activation by the second wavelength $\lambda_2$ may itself fluoresce producing visible light. In one embodiment of the invention, a physical characteristic of metallic structure (such as those described above and below in the drawings) is set to a value where a surface plasmon resonance in the metallic structure resonates at a frequency which provides spectral overlap with either the first wavelength $\lambda_1$ or the second wavelength $\lambda_2$. This system with a metallic structure disposed in relation to an up-conversion or a down-conversion nanoparticle becomes the converter utilized in the color enhancement/augmentation structures noted herein.

Within the context of the invention, the term "physical characteristic" of the metallic shell or core can relate to any characteristic of the metal itself or the shell or core dimensions or shape which affects the surface plasmon resonance frequency. Such physical characteristics can include, but are not limited to, a conductivity, a radial dimension, a chemical composition or a crystalline state of the metal shell or core.

In various embodiments, the metallic structures can be a metallic shell encapsulating at least a fraction of the nanoparticle in the metallic shell wherein a conductivity, a radial dimension, or a crystalline state of the metallic shell sets the surface plasmon resonance in the metallic structure to resonate at a frequency which provides spectral overlap with either the first wavelength $\lambda_1$ or the second wavelength $\lambda_2$. In various embodiments, the metallic structures can be a multi-layer metallic shell encapsulating at least a fraction of the nanoparticle in the metallic shell wherein a conductivity, a radial dimension, or a crystalline state of the metallic shell sets the surface plasmon resonance in the metallic structure to resonate at the first wavelength $\lambda_1$ and the second wavelength $\lambda_2$. This capability permits radiation at $\lambda_1$ and $\lambda_2$ to be amplified.

In various embodiments, the metallic structures can be a metallic particle existing in one or more multiple structures. These multiple structures can have a variety of shapes including for example sphere, spheroid, rod, cube, triangle, pyramid, pillar, crescent, tetrahedral shape, star or combination thereof disposed adjacent the nanoparticle wherein a conductivity, a dimension (e.g. a lateral dimension or a thickness), or a crystalline state of the metallic structure sets the surface plasmon resonance in the metallic particle or rod to resonate at a frequency which provides spectral overlap with either the first wavelength $\lambda_1$ or the second wavelength $\lambda_2$. Such shapes are described in the present figures and in the figures in U.S. Ser. No. 12/401,478 which is incorporated by reference in its entirety. The shape choice can affect the frequency of the surface plasmon resonance. It is known that the plasmon band is changed by the shape of nanoparticles (e.g., prolate and obloid spheroids). The paper "Spectral bounds on plasmon resonances for Ag and Au prolate and oblate nanospheroids," in the Journal of Nanophotonics, Vol. 2, 029501 (26 Sep. 2008), the entire contents of which are incorporated by reference, shows plasmon resonance shifts for shaping of Ag and plasmon resonance shifts for shaping of Au of prolate and obloid spheroids. In one embodiment of the invention, with an increasing aspect ratio for a metallic structure of the invention, the prolate spheroid resonance is red shifted relative to a sphere with no lower limit (under the assumptions of a Drude dispersion model). On the other hand, the oblate resonances are "blue shifted" as the spheroid becomes increasingly flat, but up to a limit.

In various embodiments, the metallic structures disposed in relation to an up-conversion or a down-conversion nanoparticle can be a metallic structure disposed interior to the nanoparticle wherein a conductivity or a dimension (e.g. a lateral dimension or a thickness) of the metallic structure sets the surface plasmon resonance in the metallic structure to resonate at a frequency which provides spectral overlap with either the first wavelength $\lambda_1$ or the second wavelength $\lambda_2$. In various embodiments, the metallic structures can be a metallic multi-layer structure disposed interior to the nanoparticle wherein a conductivity or a dimension (e.g. a lateral dimension or a thickness) of the metallic structure sets the surface plasmon resonance in the metallic structure to resonate at the first wavelength $\lambda_1$ and the second wavelength $\lambda_2$. This capability once again permits radiation at $\lambda_1$ and $\lambda_2$ to be amplified.

In another embodiment, the invention provides a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structures to enhance upconversion of light from a first wavelength $\lambda_1$ to a second wavelength $\lambda_2$.

As described above, a shell (or other structure) is in particular designed with a layer thickness (or for example a lateral dimension) to enhance the photon upconversion process through plasmonic enhancement. The thickness of the shell (or other physical characteristic) is "tuned" in its thickness to the absorption process by having a dimension in which plasmons (i.e., electrons oscillations) in shell have a resonance in frequency which provides spectral overlap with the absorption band targeted. Thus, if the upconversion is to be stimulated by 980 nm NIR light, then the thickness of the shell is "tuned" in a thickness to where a plasmon resonance resonates at a frequency also of 980 nm (or in the neighborhood thereof as plasmon resonances are typically broad at these wavelengths).

A plasmon resonating shell can be made of numerous transition metals, including though not limited to gold, silver, platinum, palladium, nickel, ruthenium, rhenium, copper, and cobalt or a combination or alloys or layers thereof. Such a plasmon resonating shell can be also made of a combination of metals and non-metals. When formed of a gold nanoshell, the recommended thickness to resonate with 980 nm light is approximately 3.5 nm surrounding an 80 nm upconverting core, as projected by extended Mie theory calculations. (See Jain et al., *Nanolett.* 2007, 7(9), 2854 the entire contents of which are incorporated herein by reference.) FIG. 27 is reproduced from Jain et al. and illustrates the capability in the invention to "tune" the metal shell to have a spectral overlap with the excitation and/or emission radiation wavelengths.

In one embodiment of the invention, the metallic structures disposed in relation to an up-conversion or a down-conversion nanoparticle can be an alloy such as for example an Au:Ag alloy. The alloy content can be set to adjust the frequency of the surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

In one embodiment of the invention, the converter nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a predetermined surface plasmon resonance. In one embodiment of the invention, the zinc sulfide and cadmium sulfide nanoparticle alloy can have an alloy content is set to provide a predetermined surface plasmon resonance.

Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of the invention, the thickness of the metal shell disposed in relation to an up-conversion or a down-conversion nanoparticle is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process.

Additionally, plasmon-phonon coupling may be used to reduce a resonance frequency through the tuning of the bands to a degree off resonance. This may be useful in optimizing resonance energy transfer processes for the purpose of shifting the outputted color to a color desirable for a painted, colored, or displayed surface. In one example, FIG. 27 shows an example of the plasmon resonance shift as a function of shell thickness.

Here, in one embodiment of the invention, the capability to produce stimulated emission at a targeted wavelength or color or energy is complemented by the ability to design nanoparticles that have designed absorption bands. Such absorption materials could for example further serve to improve the monochromaticity of light observed from a paint, ink, dye, or otherwise reflecting surface treated with the color enhancing compositions of the invention.

Details of the preparation of this nanoparticle system are included in U.S. Ser. No. 12/725,108, the entire contents of which are incorporated herein by reference. The absorption spectrum of $Y_2O_3$ alone (lower trace) is fairly featureless, showing absorption due to the tri-arginine near 200 nm and a gentle slope associated with scattering and absorption by the $Y_2O_3$ nanoparticles extending into the visible portion of the spectrum. The gold-coated $Y_2O_3$(upper trace), on the other hand, exhibit a strong absorption band at 546 nm, which is characteristic of the plasmonics resonance band due to the gold shell around the $Y_2O_3$ cores. The red-shifting of the plasmon absorption to 546 nm is consistent with the presence of a gold shell around a dielectric core.

In one embodiment of the invention, the converter materials for the upconverter dielectric core can include a wide variety of dielectric materials, as described above. In various embodiments of the invention, the upconverter dielectric core includes more specifically lanthanide doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence, suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) $4f^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above. Doping concentrations in the invention can range from 0.2% to 20% roughly per ion into the host lattice or in a weight or mol % variation. The efficiency of the upconversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide a rudimentary teaching of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg. 4865, the entire contents of which are incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of the invention, the dielectric core is coated, such as for example with a metallic shell, to enhance electron-phonon coupling and thereby increase up conversion or down conversion efficiency, as discussed above. In another embodiment of the invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. In another embodiment of the invention, the shell can include a $SiO_2$- and/or $TiO_2$-coating, and this coating is in one embodiment coated on doped $Y_2O_3$ down converting nanoparticles to thereby, in some instances, increase the down conversion efficiency relative to an uncoated nanocrystal. Further, in one embodiment of the invention, the coating can be a polymer. In one embodiment, this coating is provided on $NaYF_4$:Ln/$NaYF_4$ dielectric core. Such coatings can increase the upconversion efficiency relative to an uncoated upconverter.

In another embodiment of the invention, phonon modes of undoped host-lattice (e.g., $Y_2O_3$) nanocrystals are modulated, for example, by Au, Ag, Pt, and Pd shells of varying thicknesses. In various embodiments of the invention, the upconverter dielectric core and the shell system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure disposed in relation to an up-conversion or a down-conversion nanoparticle can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter.

In various embodiments of the invention, the upconverter or down converter dielectric core can be coated with thiol-terminated silanes to provide a coating of $SiO_2$ about the core of similar reactivity to $Y_2O_3$. In one embodiment of the invention, the above-described methodology is used to synthesize core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells where core and shell diameters varying from 2 to 20 nm. In these material systems, the tuned ratio of core-to-shell diameter may permit a plasmon-phonon resonance which should amplify absorption of NIR light and/or upconverted emission. In these material systems, control of the core and shell diameters is one factor determining the size dependent effect and subsequent tuning of plasmon-phonon resonance.

In one embodiment of the invention, the upconverter dielectric core can be mixed core-shell materials including for example semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and trioctylphosphine-oleic amine ($NaYF_4$ shell). All core-shell nanoparticles may further be solubilized into a colloidal suspension with the addition of triarginine peptide, polyethylene glycol, and polyethyleneimine surfactants.

FIG. 28A shows some of the various embodiments of the converter structures of the invention that can be designed: (a) a structure including upconverter (UC) molecules bound to a metal (gold) nanoparticle; (b) a structure including an UC-containing nanoparticle covered with metal nanoparticles, (c) a metal nanoparticle covered with an UC-containing nanocap; (d) an UC-containing nanoparticle covered with metal nanocap, (e) a metal nanoparticle covered with UC nanoshell, (f) an UC-containing nanoparticle covered with metal nanoshell, (g) an UC-containing nanoparticle covered with metal nanoshell with protective coating layer.

The configurations (while shown in the FIG. 28A with UC-containing materials) would be applicable for enhancement for down converting materials such as the quantum dots or phosphors described herein. Moreover, in one embodiment of the invention, dielectric spacers (for examples silicates as discussed below) can be used with the structure of FIG. 6A-b to space apart the particle type metallic structures. In another embodiment of the invention, dielectric spacers can be used with the structure of FIG. 28A to space apart the metal layers, whether or not these layers are partial metal layers or continuous metal layers. See the schematics in FIG. 28B.

In various embodiments of the invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$. This feature also can be used in the down converting to enhance primarily the emission at wavelength $\lambda_2$ and potentially the excitation at wavelength $\lambda_1$.

Such metallic structures in various embodiments of the invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

Accordingly, FIG. 28A represents embodiments of the invention where the dielectric core is supplemented with a shell. The shell can include a metal layer of a prescribed thickness. The metal layer can include materials such as nickel, gold, iron, silver, palladium, platinum and copper and combinations thereof. The metal layer can be also made of a combination of metals and non-metals. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

As discussed below, the metallic shells in another embodiment of the invention serve as scattering centers for UV light where UV light which, even if absorbed in a paint or coating layer contributes at a minimum to localized heating of the paint or coating layer material, will be scattered from the paint or coated layer.

FIG. 28C shows still further embodiments of plasmonics-active nanostructures having upconverting (UC) materials that can be designed: (a) a metal nanoparticle, (b) an UC nanoparticle core covered with metal nanocap, (c) a spherical metal nanoshell covering an UC spheroid core, (d) an oblate metal nanoshell covering UC spheroid core, (e) a metal nanoparticle core covered with UC nanoshell, (f) a metal nanoshell with protective coating layer, (g) multi-layer metal nanoshells covering an UC spheroid core, (h) multi-nanoparticle structures, (i) a metal nanocube and nanotriangle/nanoprism, and (j) a metal cylinder.

FIG. 28D shows yet other embodiments of plasmonics-active nanostructures having upconverting materials with linked photo-active (PA) molecules that can be designed. For example, for the case of psoralen (as the PA molecule), the length of the linker between the PA molecule and the UC material or the metal surface is tailored such that it is sufficiently long to allow the PA molecules to be active (attach to DNA) and short enough to allow efficient excitation of light from the UC to efficiently excite the PA molecules. FIG. 28D shows (a) PA molecules bound to an UC nanoparticle, (b) an UC material-containing a nanoparticle covered with metal nanoparticles, (c) a metal nanoparticle covered with UC material nanocap, (D) an UC material-containing nanoparticle covered with metal nanocap, (e) a metal nanoparticle covered with an UC material nanoshell, (f) an UC material-containing nanoparticle covered with metal nanoshell, (g) an UC material-containing nanoparticle covered with metal nanoshell with protective coating layer.

With the upconverter and down converter structures of the invention, a plasmonics effect is advantageous. A plasmonics effect can increase the local intensity of the received light or the local intensity of the emitted light from the up and/or down converter structures of the invention. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively.

In various embodiments, nanoparticles of neodymium and ytterbium doped yttrium oxide, europium and ytterbium doped yttrium oxide, and any combination of rare earth trivalent ions doped into a neodymium oxide nanocrystal can be used. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nano-scale. There are advantages offered by these yttrium oxide nanostructures of the invention. The small scale synthetic methodology for creating nanoscale yttrium oxide is easier to control and produce in yttrium oxide than in YAG. The host structure of yttrium oxide scintillates by down conversion. These combinations of dopants in yttrium oxide for example can provide predetermined emission colors for the yttrium oxide nanocrystal for the color shifting of the invention.

In one embodiment of the invention, a dual dopant permits excitation of either ion in the host glass. For instance, excitation by 980 nm light excites an ytterbium ion, where through transfer of energy from one excited state of the ytterbium ion to another dopant provides a mechanism for upconversion emission of light in the visible and NIR spectral regions.

Up-conversion phosphors similar in chemical compositions to the down-conversion fluorescent materials discussed above can be used. The up-conversion phosphors can include laser dyes, e.g., the organic small molecules that can be excited by the absorption of at least two infrared photons with emission of visible light. The up-conversion phosphors can include fluorescent polymers, e.g., the class of polymers that can be excited by the absorption of at least two infrared photons with emission of visible light. The up-conversion phosphors can include inorganic or ceramic particles or nano-particles, including the conventional up-conversion phosphors (e.g. metal fluorides, metal oxides) that can be excited by the absorption of at least two infrared photons with emission of visible light. The up-conversion phosphors can include semiconductor particles, including nano-particles such as II-VI or III-V compound semiconductors, e.g. quantum dots, described in details in the "down-conversion" semiconductors above.

Fluorescent up-conversion inorganic phosphors can include but are not limited to metal oxides, metal halides, metal chalcogenides (e.g. sulfides), or their hybrids, such as metal oxo-halides, metal oxo-chalcogenides. Fluorescent up-conversion inorganic phosphors are usually doped with rare earth elements (e.g. $Yb^{3+}$, $Er^{3+}$, $Tm^{3+}$). Some host examples include, but are not limited to: $NaYF_4$, $YF_3$, $BaYF_5$, $LaF_3$, $La_2MoO_8$, $LaNbO_4$, $LnO_2S$; where Ln is the rare earth elements, such as Y, La, Gd).

These up conversion and down conversion materials, according to the invention, are a mixture of color emitters configured to emit, upon exposure to a light source, visible light at a first wavelength $\lambda_1$ in response to absorption of light or energy across a band of wavelengths inside and outside the visible spectrum. The visible light emission is enhanced relative to an amount of light which would be emitted only by reflection of the first wavelength $\lambda_1$.

The color emitter particles can have a diameter less than about 1000 nanometers. The light emitting particles (up or down) can include a metallic structure disposed in relation to the particle. A physical characteristic of the metallic structure maybe set to a value where a surface plasmon resonance in the metallic structure resonates at a frequency which provides spectral overlap with either the first wavelength $\lambda_1$. The physical characteristic of the metallic structure is set to a value where a surface plasmon resonance in the metallic structure resonates at a frequency which provides enhanced emission at the first wavelength $\lambda_1$.

Other Applications of the Color Enhancing/Augmentation Structures: As detailed below, a mixture of color-emitters and the color enhancing structures noted above (optionally including the energy augmentators noted above) can be used in a display. The mixture of color-emitters and the color enhancing structures noted above can be a color emitting pixel display element. The mixture of color-emitters and the color enhancing structures noted above can be a component of a color filter. The mixture of color-emitter and the color enhancing structures noted above s can be a component of a color filter for a display. The mixture of color-emitters and the color enhancing structures noted above can be a component of a colored surface. The mixture of color-emitters and the color enhancing structures noted above can be a component of a colored reflective surface. The mixture of color-emitters and the color enhancing structures noted above can be a component of a colored reflective surface in a pixel for a display. The mixture of color-emitters and the color enhancing structures noted above can be a component of a white-light emitting pixel display element. The mixture of color-emitters can be a paint component. The mixture of color-emitters and the color enhancing structures noted above can be a component disposed on glass beads in a retroreflective paint. The mixture of color-emitters and the color enhancing structures noted above can be a component of a binder layer securing glass beads in a retroreflective paint to a base paint. The mixture of color-emitters can be an ink component.

The mixture of color-emitters and the color enhancing structures noted above can be at least one of red, blue, and green emitters configured to produce red, blue, and green emissions from an up conversion process. The mixture of color-emitters and the color enhancing structures noted above can be at least one of red, blue, and green emitters configured to produce red, blue, and green emissions from a down conversion process. The mixture of color-emitters and the color enhancing structures noted above can be at least one of red, blue, and green emitters configured to produce red, blue, and green emissions from a mixture of up converters and down converters.

The mixture of color-emitters included with the color enhancing structures noted above can be fluorescent emitters including at least one of europium, terbium, cerium, and erbium or combinations thereof. The mixture of color-emitters and the color enhancing structures noted above can include a first material configured to emit a first visible color in response to absorption of ultraviolet light and a second material configured to emit a second visible color in response to absorption of infrared light, wherein the second visible color is different from the first visible color. The mixture of color-emitters and the color enhancing structures noted above can include a third material configured to emit a third visible color in response to absorption of the ultraviolet light, wherein the third visible color is different from the first visible color and the second visible color. The first visible color, the second visible color, and the third visible color can be the primary colors or a mixture of the primary colors. Alternatively or in addition, the mixture of color-emitters and the color enhancing structures noted above can include a third material configured to emit a third visible color in response to absorption of the infrared light. The third visible color can be different from the first visible color and the second visible color.

The mixture of color-emitters and the color enhancing structures noted above can include a first material configured to emit a first visible color in response to absorption of ultraviolet light and a second material configured to emit a second visible color in response to absorption of infrared light. The second visible color can be substantially the same color as the first visible color. The mixture of color-emitters and the color enhancing structures noted above can include a third material configured to emit a third visible color in response to absorption of the ultraviolet light. The third visible color can be different from the first visible color and the second visible color. Alternatively or in addition, the mixture of color-emitters and the color enhancing structures noted above can include a third material configured to emit a third visible color in response to absorption of the infrared light. The third visible color can be different from the first visible color and the second visible color. The first visible color, the second visible color, and the third visible color can be the primary colors or a mixture of the primary colors.

The mixture of color-emitters and the color enhancing structures noted above can include a metallic structure disposed in relation to a nanoparticle emitter. The metallic structure can be a metallic shell including at least one of a spherical shell, an oblate shell, a crescent shell, or a multilayer shell. The metallic structure can be at least one of Au, Ag, Cu, Ni, Pt, Pd, Co, Ru, Rh, Al, Ga, or a combination or alloys or layers thereof. The nanoparticle emitter can be at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof. The nanoparticle emitter can include a dopant including at least one of Er, Eu, Yb, Tm, Nd, Tb, Ce, Y, U, Pr, La, Gd and other rare-earth species or a combination thereof. The dopant can have a concentration of 0.01%-50% by mol concentration.

The color-emitters can be a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$, alkali lead silicate including compositions of $SiO_2$, $B_2O_3$, $Na_2O$, $K_2O$, PbO, MgO, or Ag, and combinations or alloys or layers thereof. The color-emitters can be a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof. The dielectric up converter can have a particle diameter ranging from at least one of 2-1000 nm, 2-100 nm, 2-50 nm, 2-20 nm, or 2-10 nm. The dielectric up converter can include a dopant of at least one of Er, Eu, Yb, Tm, Nd, Tb, Ce, Y, U, Pr, La, Gd and other rare-earth species or a combination thereof. The dopant can have a concentration of 0.01%-50% by mol concentration. A metallic structure can be disposed in relation to the dielectric up converter, and the metallic structure includes at least one of Au, Ag, Cu, Ni, Pt, Pd, Co, Ru, Rh, Al, Ga, or alloys or layers thereof. The dielectric up converter can be configured to exhibit visible emission upon interaction with NIR light.

Method of applying antennas to particulates used as pigments and dyes for color enhancements: The present invention in various embodiments provides color enhancements of various paint pigments and dyes. Fabrication of these "micro-color enhancement augmentation devices" is described below.

In one embodiment, a glass substrate is used as a carrier in this case. The glass substrate can be made of various compositions including soda-lime-silicate, borosilicate and sodium-aluminosilicate.

Figures 37, 38:
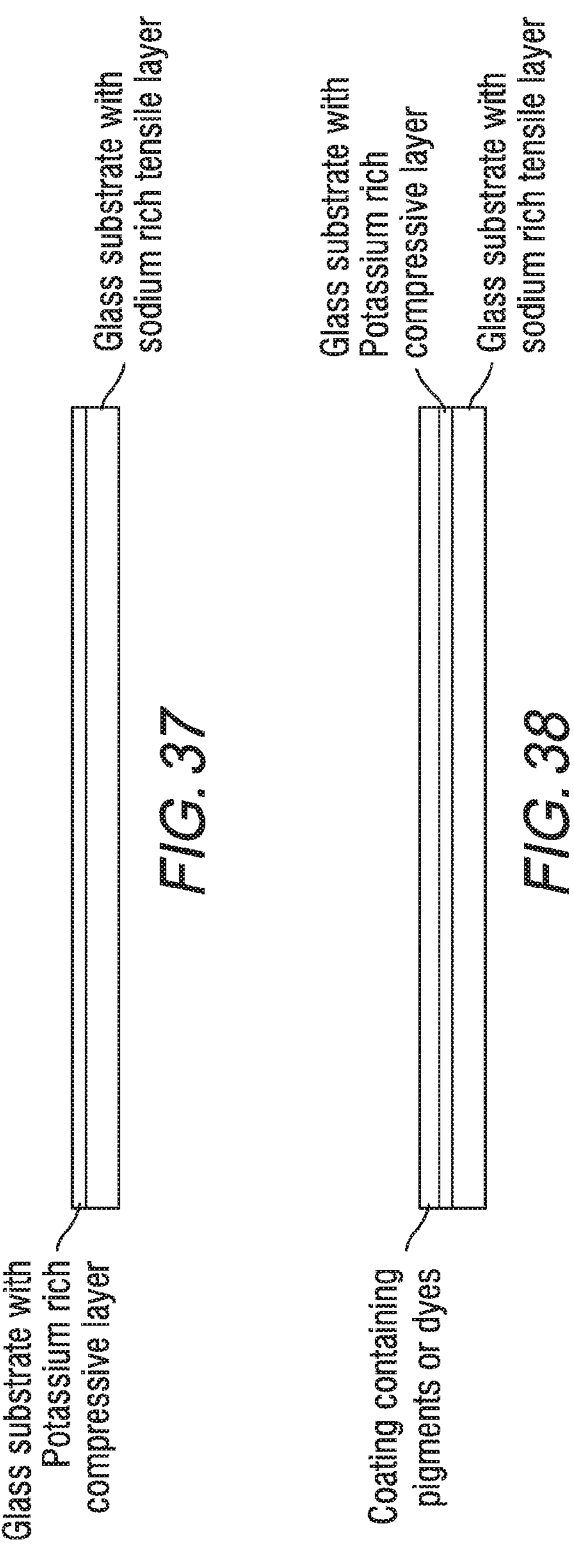
FIG. 37 is a schematic of a compression layer substrate configuration according to one embodiment of this invention.
FIG. 38 is a schematic of a coating layer formed on the compression layer substrate configuration of FIG. 37.

The glass substrate in this embodiment is subjected to a potassium salt KNb3 in molten form to exchange the sodium in the glass for the potassium in the molten bath. During this ion exchange, the outer most layers enter in compression state since potassium ions are larger than sodium ions. The compression layer is characterized by its depth of penetration and the concentration of potassium. In the case of sodium aluminosilicates with a high gamma ratio Γ above 1, provide a glass vehicle where the depth of penetration of potassium is shallow, and the concentration is high. Gamma ratio Γ in this case refers to the ratio of the number of moles of $Al_2O_3$ to $NaO_2$ in the glass chemistry. As such, a potassium rich thin layer under high compression is formed over a sodium rich glass layer under tension. FIG. 37 is a schematic of a compression layer substrate configuration according to one embodiment of this invention.

The glass substrate is then coated using a slurry containing the paint pigment or the dye dissolved into or mixed with a solvent (as appropriate). The slurry can be applied using different techniques including but not limited to spin coating, a draw bar, a Mayer bar, screen printing or simply printing using an ink jet printer equipped to handle solvents. The substrate is dried at low temperatures to remove the solvent. The "painted" layer is ready to receive the antenna at this stage.

FIG. 38 is a schematic of a coating layer formed on the compression layer substrate configuration of FIG. 37. At this stage, the glass substrate may have a paint pigment or dye coating or phosphor layer applied as a coating. The present invention can have for the coating layer any of the converters described herein. In this example, the compression layer thickness may be around 5 microns in thickness. The coating containing pigment or dyes or phosphors or other converters may be in the range of 3 microns thick.

The antenna (or resonator) structure is prepared on a different substrate (preferably a silicon wafer coated with a thin glass chemistry). The wafer upon which the antenna is developed undergoes the various steps of photo definable, lithographic type steps such as chemistries, etching and metallization to layout the antenna structure of interest. Once the antenna is ready, a laser can drill though the glass layer that is adhered to the silicon wafer. The laser drilling can be performed in columns and rows to single out each antenna structure.

Figure 39:
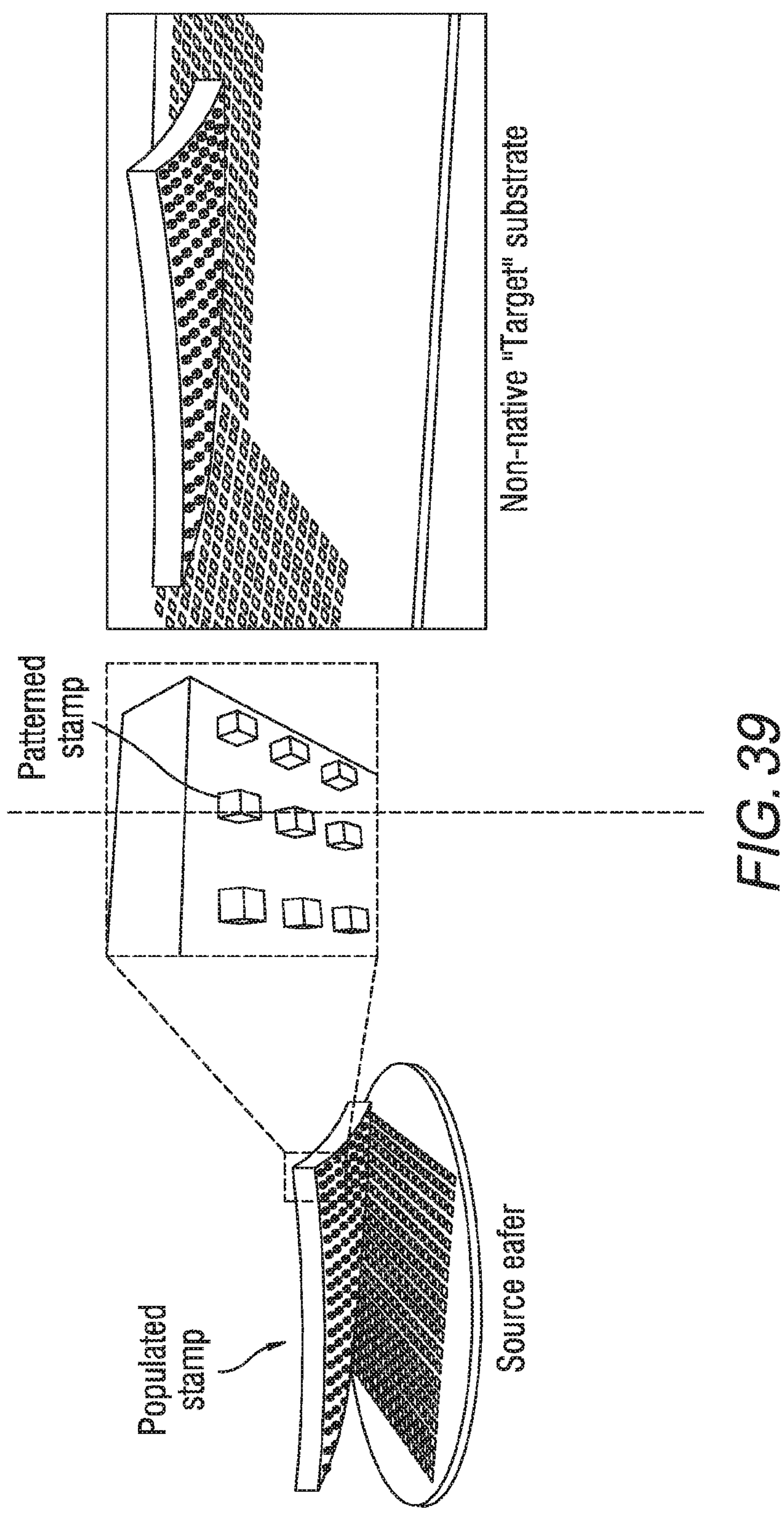
FIG. 39 is a schematic of a micro-transfer-printing technique of the present invention.

The antenna structure is now ready to be transferred using for example a micro-transfer-printing technique as depicted by the process shown in FIG. 39. The source wafer has the antenna pattern of interest. The patterned stamp picks up a number of antennas and transfers them to the target substrate (the coated glass substrate coated with paint pigments in this case).

Figure 40:
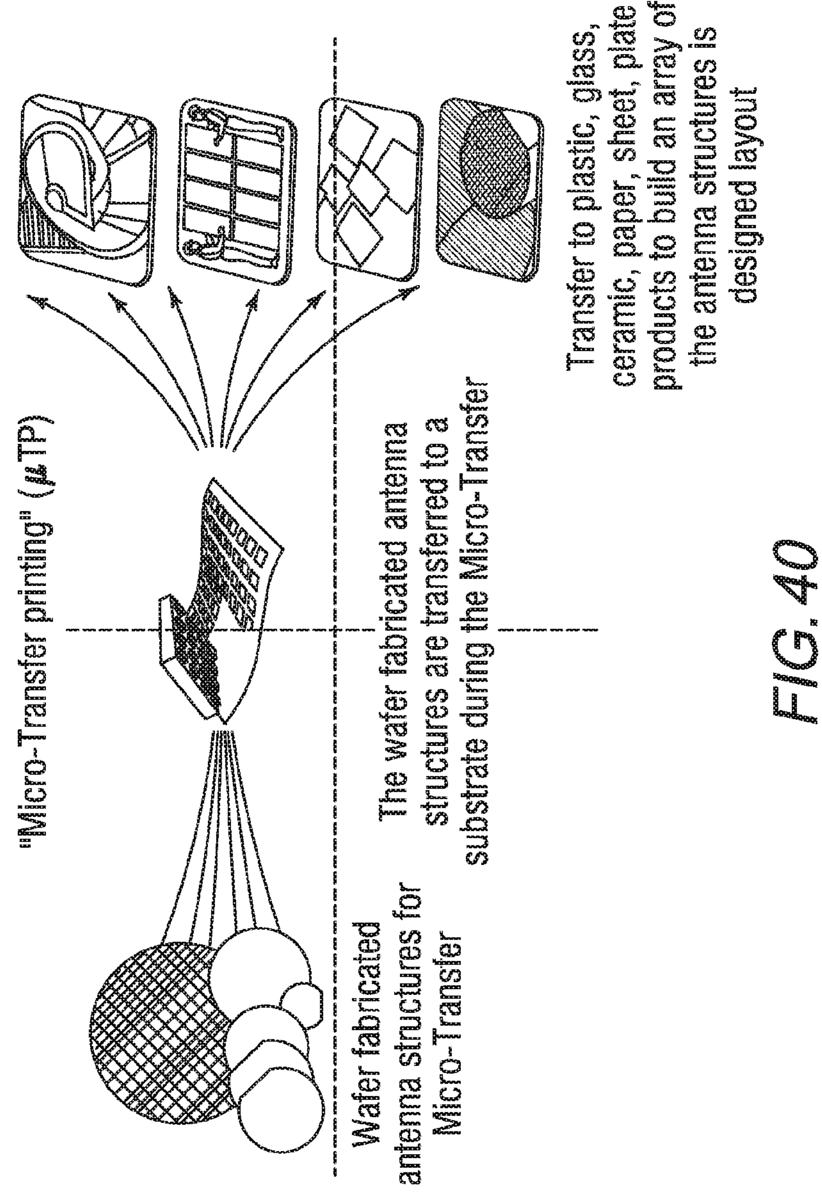
FIG. 40 is an overall depiction of the micro-transfer-printing process of FIG. 6G.

This process is known as process that can be used for transferring small features as small nano and micro sized features from a source to a target substrate. The source substrate can be a wafer upon which various devices have been finely produces including Integrated circuits, LED, or antenna in this case. The target wafer can be different kinds of other substrates including plastic, glass, ceramic and paper. FIG. 40 is an overall depiction of this process.

Figure 41:
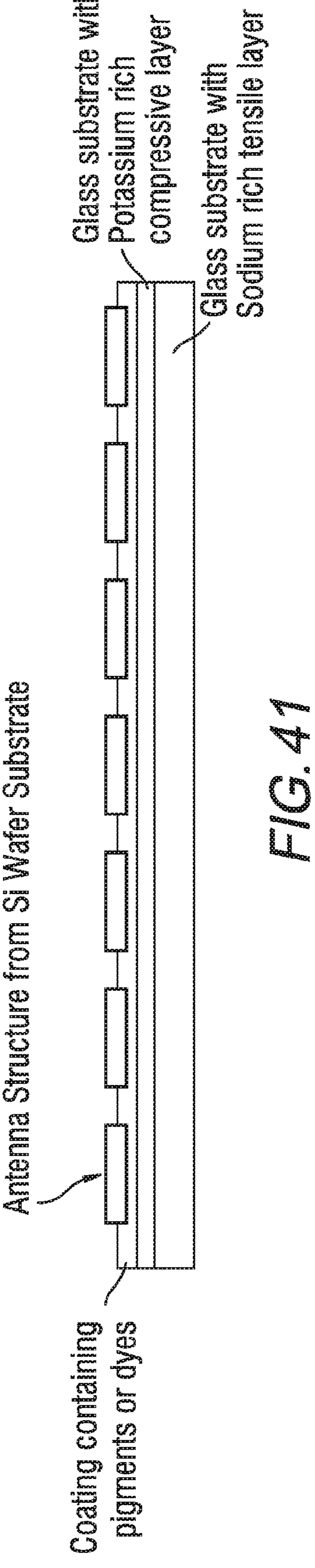
FIG. 41 is a schematic of the micro-transferred antennas on a precoated compression-stressed glass substrate.

In one embodiment of the invention, the antenna structures are transferred from the Si wafer containing the lithographically defined antennas to the glass substrate which had been precoated with the pigment or dyes or phosphors or other converters. FIG. 41 is a schematic of the micro-transferred antennas on a precoated compression-stressed glass substrate.

Figure 42:
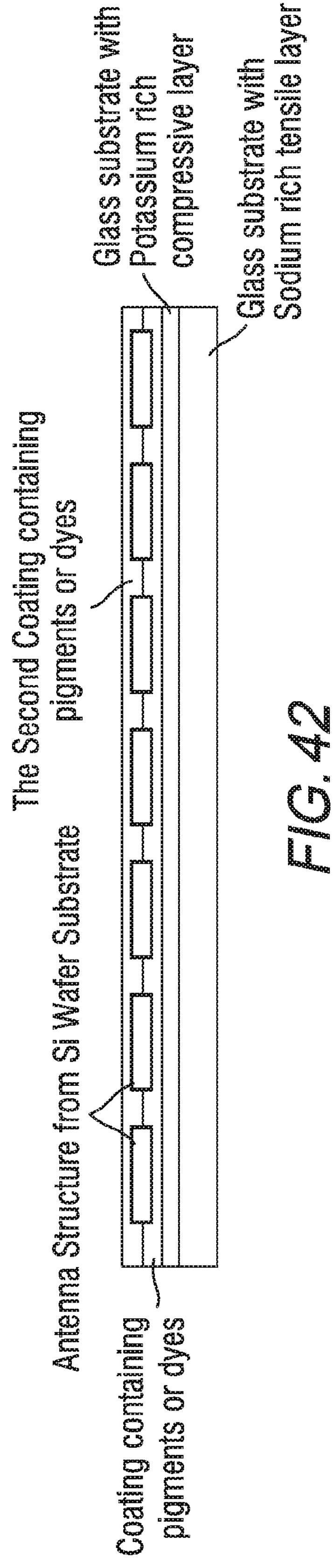
FIG. 42 is a schematic depicting a multilayered structure of this invention with the antennas (resonators) of the present invention embedded therein.

Once the antenna is arrayed onto the glass substrate an optional coating is applied to the glass layer. Preferably, this optional coating is similar to the previously applied coating of paint pigment, dye, or phosphor coating. The glass substrate has a multilayered structure with the antennas (resonators) of the present invention embedded in the pigment or organic dye as depicted in the schematic. FIG. 42 is a schematic depicting a multilayered structure of this invention with the antennas (resonators) of the present invention embedded therein.

In order to promote the release of the embedded antenna in paint pigments, a diamond scribe is used to crack through and bridge the compressive layer all the way to the tensile region. Once this is achieved, an instantaneous fragmentation of the glass into small pieces occurs. The glass shatters in million pieces and the missile if freed from the glass dome.

Figure 43:
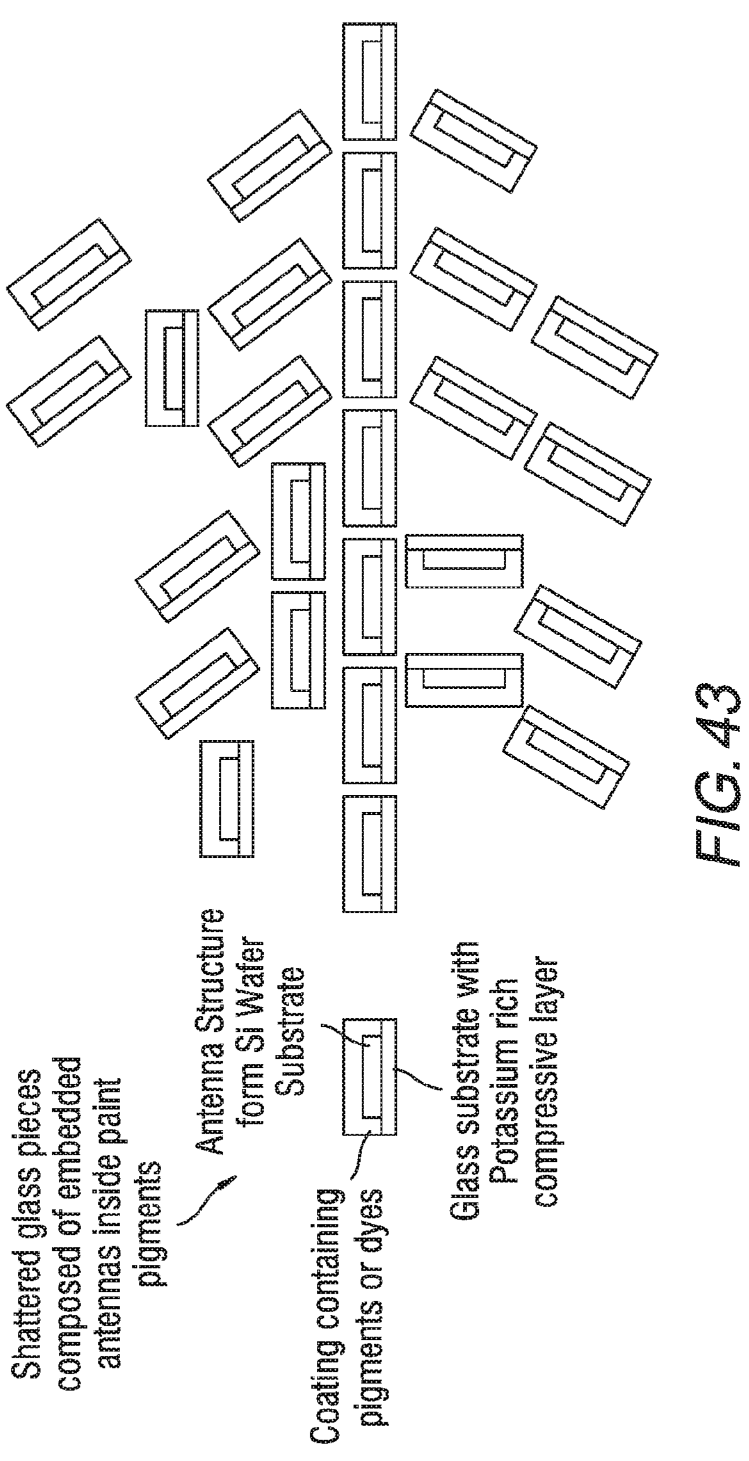
FIG. 43 is a schematic depicting the formation of discrete micro color augmentators of the present invention.

FIG. 43 is a schematic depicting the formation of discrete micro color energy augmentators of the present invention. Once the glass is shattered, the pieces obtained have a glass portion on top of which reside coating with embedded antennas.

Stainless steel, aluminum, and copper are a few examples of materials that do not necessarily require a coated, painted, stained, or sealed protective layer. The coated surfaces are almost always of a particular color chosen to improve the attractiveness of the object.

As described at http://www.howeverythingworks.org/supplements/paint.pdf, pigment particles in paint are responsible for the opacity or color of the paint. Pure white paint has pigment that absorbs no light but rather scatters light in random directions. White pigment particles are clear and have relatively high refractive indices. The pigment particles are embedded in a polymer layer. As light tries to pass through the paint, part of the light is reflected at every boundary between polymer and pigment, and almost none of the light reaches the back of the layer. Because the pigment particles in the paint are typically rough and randomly oriented, the pigment particles scatter the light in every direction making the paint appear to be white. This high reflectivity gives paint its hiding power-its ability to prevent light from reaching the material beneath the paint and then returning to paint's surface.

Paints with very high refractive index pigments are best at hiding the surfaces they cover. Absorption of light in the pigments will give the paint. For example, a pigment which absorbs blue light will give the paint a yellow tint. The reflected light has a color characteristic of the non-absorbed colors of the spectrum. In other words, colored pigments give paints their colors by selectively absorbing some of the spectrum of light striking the paint.

U.S. Pat. No. 4,283,320 (the entire contents of which are incorporated herein by reference) describes an opacified latex paint having small particle film-forming latex binders in combination with minor amounts of opacifying pigment, and substantial amounts of non-film-forming polymeric particles (plastic pigment) provides a semi-gloss latex paint composition having excellent hard enamel surfaces along with desirable film integrity properties. The plastic pigment particles in U.S. Pat. No. 4,283,320 are between about 0.1 and 0.5 microns and contain 0.2 to 2% copolymerized monomers containing carboxylic acid groups. The semi-gloss plastic pigment latex paint of U.S. Pat. No. 4,283,320 is compounded at pigment-volume-content (PVC) between about 30% and 45% and considerably higher than conventional high quality enamel latex paints. Into the latex paint of U.S. Pat. No. 4,283,320 or onto painted surface of U.S. Pat. No. 4,283,320, in one embodiment of the invention, the color enhancing mixtures described herein are applied.

U.S. Pat. No. 5,134,186 (the entire contents of which are incorporated herein by reference) describes a paint having a film former and polymeric composition. The polymeric composition comprises about 30 to about 50 weight percent of a substantially non-self-polymerizable monomer and about 50 to about 70 weight percent of a copolymerizable monomer having a water-soluble homopolymer. Into the latex paint of U.S. Pat. No. 5,134,186 or onto painted surface of U.S. Pat. No. 5,134,186, in one embodiment of the invention, the color enhancing mixtures described herein are applied.

U.S. Pat. No. 4,789,694 (the entire contents of which are incorporated herein by reference) describes a paint coating composition having a cationic free, functional emulsion polymer mixture adapted to be coreacted at room temperature with glycoluril to provide a cured thermoset paint film. The curing copolymerizes ethylenically unsaturated monomers, including functional monomers, but excluding amine monomers, in an aqueous polymerization medium, followed by ion exchange of the resulting reactive emulsion polymer. The glycoluril can be processed through an ion exchange step separately or in conjunction with the reactive emulsion polymer. Into the latex paint of U.S. Pat. No. 4,789,694 or onto painted surface of U.S. Pat. No. 4,789,694, in one embodiment of the invention, the color enhancing mixtures described herein are applied.

U.S. Pat. No. 4,613,633 (the entire contents of which are incorporated herein by reference) describes a copolymer latex having heterogeneous polymer particles which is particularly suitable for paper coating, and to a paper coating composition comprising this latex which gives coated paper having improved adaptability to blister packaging and printing. Into the latex paint of U.S. Pat. No. 4,613,633 or onto painted surface of U.S. Pat. No. 4,613,633, in one embodiment of the invention, the color enhancing mixtures described herein are applied.

U.S. Pat. No. 7,682,435 (the entire contents of which are incorporated herein by reference) describes an oil-based pigmented ink composition containing at least a pigment, a polymer compound and an organic solvent, which contains, as the organic solvent, methoxybutyl acetate in an amount of 20 to 90% by weight based on the entire ink composition; and particularly to the above oil-based pigmented ink composition, which contains, as the other organic solvent, a nitrogen-containing and/or oxygen-containing heterocyclic compound in an amount of 1 to 50% by weight based on the entire ink composition and/or a (poly)alkylene glycol derivative in an amount of 1 to 50% by weight based on the entire ink composition; and to the above oil-based pigmented ink composition, which has a flash point of 61° C. or higher, a viscosity of 2.0 to 6.5 cp at 25° C., and a surface tension of 20 to 40 mN/m at 25° C. Into the oil based pigmented ink of U.S. Pat. No. 7,682,435 or onto painted surface of U.S. Pat. No. 7,682,435, in one embodiment of the invention, the color enhancing mixtures described herein are applied.

U.S. Pat. Application Publ. No. 20090088500 (the entire contents of which are incorporated herein by reference) describes an oil-based ink composition having a colorant, an organic solvent and a polymeric compound, and optionally an alkylamine ethylene oxide derivative as a pH adjusting agent, in which the pH of an aqueous phase is from 5.5 to 10, when ions in the ink composition are transferred to water. This oil-based ink composition prevents corrosion of a nozzle plate and is improved in storage stability, and thus can ensure printer reliability such as ink-jet stability obtainable even after long storage thereof, and can withstand outdoor service environments. Into the oil-based ink composition of Pat. Application Publ. No. 20090088500, in one embodiment of the invention, the color enhancing mixtures described herein are applied.

In general, the color enhancing mixtures and the color enhancing/augmentation structures noted above described herein are applicable to other paints or inks to enhance the color perceived by an observer.

Human eyes are not instruments which measure precise wavelengths of light. Instead, a human eye looks for three different ranges of wavelengths. Within the retina of the human eye, there are specialized cells that only detect light of certain wavelengths. Some of these cells detect reddish light, others detect greenish light, and still others detect bluish light. These three types of color sensitive cells are called cone cells. Cone cells are most abundant in the fovea—the regions of high visual acuity near the center of the retina. Retinal cells are more light-sensitive than cone cells but can not distinguish color. Rod cells sense light and dark. It might seem as through these three types of color sensors will only allow one to see three colors. Yet, a wide variety of colors are perceived when two or more of the color sensors are stimulated at once. Each sensor informs the brain about how much light it sees and the brain interprets the mixture of responses as a particular color.

In general, visible light of a particular wavelength stimulates all three types of cone cells to some extent. However, the cells do not respond equally to each wavelength of light. When exposed 680 nm (680 nanometer) light, the cone cells specialized for reddish light respond much more strongly than those specialized for greenish or bluish light. Because of this strong response by the red sensors, the light appears to be red. Yellow light at 580 nm is in between red and green light. Both the red sensitive cone cells and the green sensitive cone cells respond moderately when exposed to yellow light. The brain interprets this balanced response as yellow light.

But the same response can be invoked from your retina by exposing it to an equal mixture of pure red and green lights. Again, both the red sensitive and green sensitive cone cells respond moderately, and it appears to the brain as yellow light, even though there is no pure yellow light at 580 nm reaching your retina. Likewise, a mixture of pure red, green, and blue lights can make one see virtually any color. The only problem comes in choosing the pure red, green, and blue wavelengths. This is the technique used by a television. It creates relatively pure red, green, and blue lights with phosphor dots and "tricks" the eyes into seeing any color across the visible spectrum.

Accordingly, in a red paint, this paint absorbs light that would stimulate green or blue sensors of your eyes. All that is left is reflected light that stimulates red sensors, so the eye perceives the paint as red. Most paint pigments are based on specific molecules that absorb light in a particular range of wavelengths. Many metal compounds, including those of copper, chromium, iron, antimony, nickel, and lead absorb certain wavelengths of light and appear brightly colored. If one starts with white light and removes various amounts of the three primary colors of light, one can create any color of paint. If you remove all light, the paint appears to be black. A yellow pigment absorbs some blue light, and a cyan pigment absorbs some red light. What is left is mostly green light. The more of each primary pigment added to the paint, the more completely the paint will absorb its color of light, and the deeper the color the paint will become.

Inks are similar to paints except that inks contain dissolved dyes rather than solid pigment particles. Inks do not contain any reflective white pigments. Inks themselves tend to be transparent but colored. Inks rely on the underlying paper to reflect light. Paper consists mainly of cellulose, a clear natural polymer. Because this cellulose is finely divided in paper, it reflects light at each surface and the paper appears white. Often white paint pigments are applied to paper during manufacture to make the paper even whiter.

In one aspect of the invention, the conventional dynamic of the absorption of light in a paint normally resulting only in the heating of the paint is changed to a dynamic of the absorbed light (normally lost from the absorption) being emitted a color of light of intended paint color. Thus, the brightness of the paint or ink or coating is enhanced over that which would normally be lost to absorption, especially with the paint or ink including the color enhancing structures noted above. Furthermore, "color shifting" from bands of light outside the visible in the ultraviolet or infrared which normally contribute nothing to the perceived light reflected to the eye provides an additional source of color enhancement.

Conventionally, in the production of the fluorescent ink, fluorescent pigments were employed in place of organic or inorganic color pigments exhibiting absorption in a visible light region and being used in the ordinary printing inks. In order to identify fluorescent images formed on an image-printed article, it is required to irradiate the image-printed article with ultraviolet rays employed as an exciting light. When the image-printed article was irradiated with ultraviolet rays, the ultraviolet rays are absorbed by the fluorescent substance of fluorescent images, thereby causing the emission of fluorescence in the visible region. This fluorescence was recognized through visual observation or using a camera, and represents a limited demonstration of the concept utilized and yet extended by the present invention. In one aspect of the invention here, a mixture of down-converting particles tuned to a specific excitation and emission are used instead of a fixed fluorescent particle and used with the color enhancing structures noted above. In one aspect of the invention here, a mixture of down-converting particles tuned to a specific excitation and emission are used instead of or in complement to the mixture of down-converting particles and used with the color enhancing structures noted above.

As described in U.S. Pat. No. 6,744,960 (the entire contents of which are incorporated herein by reference) and applicable to this invention, pump radiation may comprise natural light, i.e., sunlight, or artificial light such as from UV or blue light emitting diodes (LED) or fluorescent lights. The light incident on the fluorescent structure need only comprise radiation having wavelengths within the absorption spectrum of the quantum dots. Since the absorption spectrum of the quantum dots comprises wavelengths shorter than the wavelength of emission from the quantum dots, the pump radiation includes wavelengths shorter than the emitted wavelengths. For example, sunlight can be employed to pump a fluorescent structure 10 having a layer of quantum dots comprising CdSe particles 5.0 nm in diameter, which emit at an optical wavelength of 625 nm, since the sun radiates light across a broad spectrum including light having wavelengths at least 50 nm shorter than 625 nm. Alternatively, such a fluorescent structure can be pumped with one or more light emitting diodes (LEDs) that provide light of, for example, 550 nm. Incandescent lights as well as ultraviolet light sources such as UV LEDs would also be capable of exciting the layer of quantum dots.

The fluorescent structures described in U.S. Pat. No. 6,744,960 and applicable to this invention can be employed in various applications requiring bright, narrowband illumination. For example, light sources of colored illumination are useful in constructing signs, in creating artistic or architectural designs, and in producing bright regions of color, including outlines, bands and borders on products including but not limited to furniture, automobiles, appliances, electronics, clothes or any other object where bright color is useful for aesthetic or functional purposes. These fluorescent structures are advantageously capable of producing intense colored light illumination during daytime when exposed to daylight. Since, quantum dots do not degrade with exposure to UV rays such as produced by the sun, the structure has a long lifetime and can be incorporated in architectural features, such as a border to highlight a rooftop of a building during the daytime.

Yet, unlike that in U.S. Pat. No. 6,744,960, in this invention, upconverting particles stimulated by IR light from natural or artificial sources complement the fluorescence and yield even brighter structures. Moreover, mixtures of the down converters and the color enhancing/augmentation structures noted above permit a wider spectrum of the "out-of-band" color region from the natural or artificial radiation source to be utilized and tuned for example to a specific color emission or to a mixture of primary color emissions.

In still another embodiment of the invention, there is provided a light emitting composition including first color emitters configured to emit, upon exposure to an energy source, visible light at a target color in response to absorption of energy at a first band of wavelengths and second color emitters configured to emit, upon exposure to the energy source, visible light offset from the target color in response to absorption of energy at the first band of wavelengths, Light intensity observable at the target color is enhanced relative to reflected white light without emission from the first and second color emitters, especially when the color enhancing/augmentation structures noted above are included in the composition. Further, by offsetting the emissions about the target color, the resulting color would appear to the human eye to be richer in color. The offset can be an offset of 5, 10, 15, 20, 25, and 30 nm or more. The offset can be a positive or negative offset from the target color. More specifically, a color purity or chromaticity can be changed by the offset defined above.

In another embodiment, the offset values can produce a saturation quality where the target color will appear different under different lighting conditions. For instance, a room painted to a specific target color by the mixtures of different color emitters will appear different at night (under artificial lighting conditions) than in daylight. The offset can be an offset of 50, 100, 150, 200, 250, and 300 nm or more. The offset can be a positive or negative offset from the target color.

Moreover, a target color can vary from its original color by adding white pigment to make a lighter version or by adding black pigment to make a darker version.

Table 2 included below includes the recognized wavelength intervals for the major visible color bands.

TABLE 2

| color | wavelength interval |
|---|---|
| red | ~700-635 nm |
| orange | ~635-590 nm |
| yellow | ~590-560 nm |
| green | ~560-490 nm |
| blue | ~490-450 nm |
| violet | ~450-400 nm |

Figure 44:
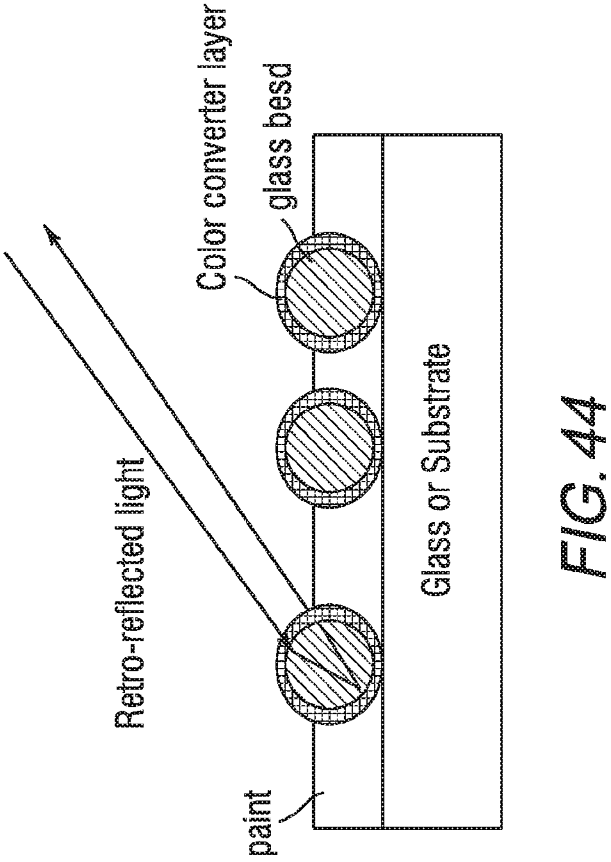
FIG. 44 is a schematic representation of the retro-reflective paint geometry using the color enhancing structures of this invention.

One area of particular application for the color shifting particle mixtures would be their use as coatings on glass beads for use in retro-reflective paints. FIG. 7 shows a schematic representation of the retro-reflective paint geometry. The glass bead serves as an optical element directing incident light along a path of reflection back to the observer that is nearly, if not perfectly, aligned with the incident ray. Instead of diffuse scatter, the light is directed back and appears brighter than "normal." In this invention, the color shifting particle mixtures and the color enhancing/augmentation structures noted above would be applied to the paint binder or, as shown in FIG. 44 as a color converter layer on the glass bead so that light (not of the color of the painted surface) would be converted to that color of the painted surface (or of a combination of primary color emissions simulating the color of the painted surface) so that additional light enhancement is realizable.

In conventional retroreflective road paint applications, there exist two classes of retroreflective beads: IGB-I and IGB-II. IGB-I is used to be mixed with the paint prior to stripping the road. As the paint layers wear, the beads are exposed giving the enhanced visibility of road markings IGB-II is used to be dropped on the freshly stripped paint surface on the road to give immediate enhanced visibility to night drivers. Table 3 (reproduced below from http://www.indoglassbeads.com/road-marking-glass-beading.htm) provides recognized specifications for these materials.

TABLE 3

| Chemical & Physical Properties | |
|---|---|
| Basic material | SiO2 69-71% |
| Shape | Spherical |
| Color | Clear |

TABLE 3-continued

| Chemical & Physical Properties | | |
|---|---|---|
| Specify gravity g/cm3 | 2.5 | |
| Hardness (Moh's) | 6.0 | |
| Refractive Index | 1.5-1.55 | |
| Type | Sieve Size um | Retained by % |
| IGB-I | 1180 | 0-3 |
| (Intermix) | 850 | 5-20 |
| | 425 | 65-95 |
| | <425 | 0-10 |
| | Roundness | >70% |
| IGB-II | 850 | 0-5 |
| (Drop On) | 600 | 5-20 |
| | 300 | 30-75 |
| | 180 | 10-30 |
| | <180 | 0-15 |
| | Roundness | >80% |

U.S. Pat. No. 5,650,213 (the entire contents of which are incorporated herein by reference) describe retroreflective compositions having a non-volatile matrix material, a volatile constituent, and a plurality of retroreflective microsphere beads where the ratio of the volume of matrix material to the volume of retroreflective microsphere beads is in the range of 75% to 185%. The retroreflective microsphere beads in U.S. Pat. No. 5,650,213 had a diameter of 20 to 200 microns, were constructed of glass, and had an index of refraction ranging from 1.7 to 2.5. In one embodiment of the invention, these and other retroreflective compositions include the color enhancing mixtures (optionally including the color enhancing/augmentation structures noted above) of the present invention coated thereon or in the paint composition itself.

Accordingly, in this invention, a glass bead in for example a blue paint would have down converters and up converters in the color converter layer and include the color enhancing/augmentation structures noted above on the glass bead so that white light (for example as from a head light on a car) would have its UV and IR light converted more to blue light thereby producing more blue light to be reflected from the blue painted surface. Alternatively, for a green painted surface, white light would have its UV and IR light converted more to green thereby producing more green light to be reflected from the glass bead in the painted surface.

Figure 45:
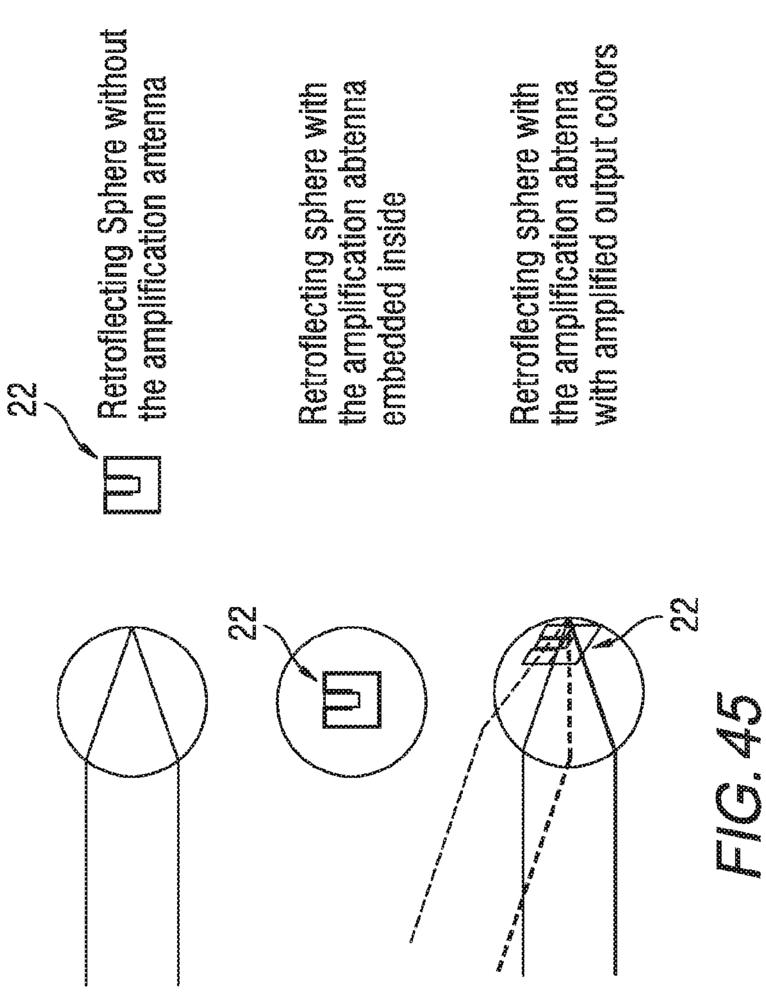
FIG. 45 is a schematic illustrating the effect of the amplification/resonator antenna of this invention in a coating.

In one embodiment of the present invention, retroreflection bounces light rays around a 3D reflective surface in order to send the rays back in the direction of the source. The micro color augmentators of the present invention (with the resonator/antenna structures) are added to the glass beads to form in one embodiment a paint additive such as for coating highway panels. FIG. 45 is a schematic illustrating the effect of the amplification/resonator antenna of this invention in a coating.

Besides for use on traffic signs and other coating applications, these retroflection/resonator structures are applicable to many applications where light is used to scan an object and the reflected light "read" and in barcode applications.

Figure 46:
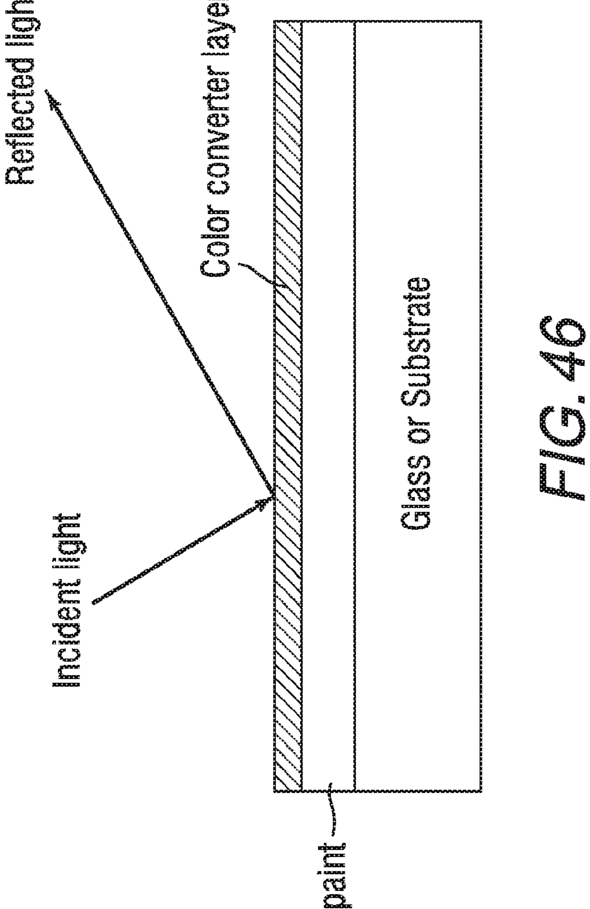
FIG. 46 is a schematic representation of a top coat on a painted surface which includes the color enhancing structures of this invention.

FIG. 46 shows a schematic representation of a painted surface in which a color shifting layer in disposed as a topcoat. Similar to above before, a blue paint with the color enhancing/augmentation structures noted above would have down converters and/or up converters in the color converter layer applied at a topcoat so that white light (for example as from a head light on a car) would have its UV and IR light converted more to blue light thereby producing more blue light to be reflected from the blue painted surface. Alternatively, for a green painted surface, white light would have its UV and IR light converted more to green light thereby producing more green light to be reflected from the glass bead in the painted surface.

In another embodiment, the colors in the visible part of the spectrum are also color shifted. A blue paint with the color enhancing/augmentation structures noted above would have down converters and/or up converters in the color converter layer applied at a topcoat so that white light (for example as from a head light on a car) would have its deep blue and red-green light converted more to blue light thereby producing more blue light to be reflected from the blue painted surface. Alternatively, for a green painted surface, white light would have its blue and red light converted more to green light thereby producing more green light to be reflected from the glass bead in the painted surface.

Stated differently, with the color shifting particles of the invention in the color converter layer along with the color enhancing/augmentation structures noted above, the red paint or ink has color shifting particles which down convert the spectrum of light of a higher energy than red (e.g., a blue light) and/or up convert the spectrum of light of a lower energy than red (e.g., near IR and IR light). Similarly, the green paint or ink has color shifting particles which down convert the spectrum of light of a higher energy than green (e.g., a blue light) and/or up convert the spectrum of light of a lower energy than green (e.g., red, near IR, and IR light). Similarly, the blue paint or ink has color shifting particles which down convert the spectrum of light of a higher energy than blue (e.g., a UV light) and/or up convert the spectrum of light of a lower energy than blue (e.g., green, red, near IR, and IR light).

Cosmetic products: Cosmetics are substances used to enhance the appearance or odor of the human body. Cosmetics include but are not limited to skin-care creams, lotions, powders, perfumes, lipsticks, fingernail and toe nail polish, eye and facial makeup, permanent waves, colored contact lenses, hair colors, hair sprays and gels, deodorants, baby products, bath oils, bubble baths, bath salts, butters and many other types of products. A subset of cosmetics is called "make-up," which refers primarily to colored products intended to alter the user's appearance. Many manufacturers distinguish between decorative cosmetics and care cosmetics.

In one aspect of the invention, the color mixtures described above with the color enhancing/augmentation structures noted above are included in those cosmetics that are intended to alter the user's appearance. In one aspect of the invention, the color mixtures described above are included in those cosmetics that are used to protect the body from the harmful UV aging effects.

Accordingly, those products where the color mixtures described above with the color enhancing/augmentation structures noted above would be suitable for inclusion include but are not limited to lipstick, lip gloss, lip liner, lip plumper, lip balm, lip conditioner, lip primer, and lip boosters. Those products further include foundation, used to smooth out the face and cover spots or uneven skin coloration, usually a liquid, cream, or powder. Those products could further include powders, used to give a matte finish, and also to conceal small flaws or blemishes. Those products could further include rouge, blush or blusher, cheek coloring used to bring out the color in the cheeks and make the cheekbones appear more defined. Those products could further include bronzers, used to give skin a bit of color by adding a golden or bronze glow. Those products could further include mascara used to darken, lengthen, and thicken the eyelashes (available in natural colors such as brown and black, but also comes in bolder colors such as blue, pink, or purple). Those products could further include eye liners, eye shadows, eye shimmers, and glitter eye pencils as well as different color pencils used to color and emphasize the eyelids, eyebrow pencils, creams, waxes, gels and powders used to color and define the brows. Those products could further include nail polish, used to color the fingernails and toenails. Those products could further include concealers and makeup used to cover any imperfections of the skin.

Also included in the general category of cosmetics are skin care products. These include creams and lotions to moisturize the face and body, sunscreens to protect the skin from damaging UV radiation, and treatment products to repair or hide skin imperfections (acne, wrinkles, dark circles under eyes, etc.). Cosmetics can be liquid or cream emulsions; powders, both pressed and loose; dispersions; and anhydrous creams or sticks.

In this application area, the color mixtures of the invention with the color enhancing/augmentation structures noted above can both provide color shifting capability (as detailed above), but can also moderate UV light damage to skin or hair exposed to UV light irradiation. The cosmetics in this way can additionally or optionally provide a protective coating which has a mixture of light scattering and light emitting particles configured, upon exposure to UV light, to convert a first part of the UV light into visible light, emit from the mixture a fraction of the visible light, and reflect from the mixture a second part of the UV light such that the second part of the UV light is not absorbed by the skin or hair.

For example, while not limited to the details described below, UV light from the sun incident on the protective coating could have 50% or more of the UV light reflected due to the index of refraction change between air and the protective coating. That part of the UV light entering the interior layers of the protective coating converted into visible light. Other parts of the UV light would be scattered from protective coating and not incident on the underlying surface.

Regardless, the color shifting mixtures of the invention can include a cosmetically acceptable medium compatible with all skin, lip, or hair materials with which it comes into contact with. When these composition with the color enhancing/augmentation structures noted above are to be applied in the form of an emulsion, the composition may optionally additionally include a surfactant, preferably in a quantity of 0 to 30% by weight, preferably from 0.01 to 30% by weight based on the total weight of the composition. The emulsion may be a single emulsion or multiple emulsions. The color shifting mixtures of the invention may be present in any one or more of these phases.

According to the application envisaged, the composition with the color enhancing/augmentation structures noted above may also additionally include at least one film-forming polymer, in particular for mascaras, eyeliner or hair compositions of the lacquer type. The polymer may be dissolved or dispersed in a cosmetically acceptable medium and possibly associated with at least one coalescing agent and/or at least one plasticizer. The composition with the color enhancing/augmentation structures noted above according to the invention may also include a fat phase that contains in particular at least one liquid fat and/or at least one fat that is solid at ambient temperature and atmospheric pressure. Liquid fats, often called oils, may constitute 0 to 90%, preferably 0.01 to 85% by weight based on the total weight of the fat phase. Solid or pasty fats may be chosen in particular from waxes, gums and mixtures thereof. The composition may contain 0 to 50%, preferably 0.01 to 40%, and in particular 0.1 to 30% by weight of solid or pasty fats based on the total weight of the composition.

The composition with the color enhancing/augmentation structures noted above according to the invention may additionally include 0 to 30%, preferably 0.01 to 35% by weight of other particles based on the total weight of the composition. These particles may in particular be a pigment other than the color mixtures of the invention, a pearl pigment or a filler. The presence of these other particles makes it possible in particular to make the composition opaque.

In addition, the composition with the color enhancing/augmentation structures noted above according to the invention may include ingredients conventionally present in such compositions, such as preservatives, antioxidants, thickeners, perfumes, moisturizing agents, sun filters, essential oils, vegetable extracts and vitamins.

In one embodiment of the invention, the color shifting mixtures of the invention can be used in shampoos, conditioners, gels, styling compounds, sprays, and other beauty products. In one embodiment of the invention, the color shifting mixtures of the invention with the color enhancing/augmentation structures noted above are added to these hair and beauty products to increase the sheen of one's hair for example. The sheen in one's hair is a property of the surface finish of the hair and the scattering of the light at the top surfaces. Standard hair treatments "repair" i.e., fill the surfaces torn in the hair by aging, excessive washing, etc. In this embodiment of the invention the color converters in the hair treatments also fill into the broken surfaces. The effect would be to provide a surface of the hair which reflects more visible light and also has less diffusive scatter, by the filing and smoothing of the surfaces.

The color shifting mixtures of the invention with the color enhancing/augmentation structures noted above can include (in addition to the up converters and down converters described herein) a number of other emulsions and conditioning agents such as described in U.S. Pat. Appl. No. 2005/0136258, U.S. Pat. Appl. No. 2005/0265935, U.S. Pat. Appl. No. 2006/0083762, U.S. Pat. Appl. No. 2006/0165621, U.S. Pat. Appl. No. 2007/0274938, and U.S. Pat. No. 7,608,237, the entire contents of each of these patent documents are incorporated herein by reference.

Displays: In a conventional electronic ink display, i.e. an electrophoretic display, titanium dioxide particles approximately one micrometer in diameter are dispersed in a hydrocarbon oil. A dark-colored dye is also added to the oil, along with surfactants and charging agents that cause the particles to take on an electric charge. This mixture is placed between two parallel, conductive plates are typically separated by a gap of 10 to 100 Φm. Upon applying a voltage the two plates, the particles will migrate electrophoretically to the plate bearing the opposite charge from that on the particles. When the particles are located at the front (viewing) side of the display, it appears white, because light is scattered back to the viewer by the high-index "white" titanium dioxide particles. When the particles are located at the rear side of the display, the display appears dark, because the incident light is absorbed by the colored dye. If the rear electrode is divided into a number of small picture elements (pixels), then an image can be formed by applying the appropriate voltage to each region of the display to create a pattern of reflecting and absorbing regions.

U.S. Pat. Appl. Publ. No. 20040257330 (the entire contents of which are incorporated herein by reference) describes details of formation of a conventional electronic ink display that would be applicable to the base components depicted in the displays of this invention. U.S. Pat. Appl. Publ. No. 20040257330 describes for example that it is possible to use a liquid filling the pixel cells, which is high insulative and colorless and transparent, including: aromatic hydrocarbons, such as toluene, xylene, ethylbenzene and dodecylbenzene; aliphatic hydrocarbons, such as hexane, cyclohexane, kerosene, normal paraffin and isoparaffin; halogenated hydrocarbons, such as chloroform, dichloromethane, pentachloromethane, tetrachloroethylene, trifluoroethylene and tetrafluoroethylene, various natural or synthetic oils, etc. These may be used singly or in mixture of two or more species.

A dispersion liquid can be used which may be colored with oil soluble dye having a color of R (red), G (green), B (blue), C (cyan), M (magenta), Y (yellow), etc. Examples of the dye may preferably include azo dyes, anthraquinone dyes, quinoline dyes, nitro dyes, nitroso dyes, penoline dyes, phthalocyanine dyes, metal complex salt dyes, naphthol dyes, benzoquinone dyes, cyanine dyes, indigo dyes, quinoimine dyes, etc. These may be used in combination. Examples of the oil soluble dye may include Vari Fast Yellow (1101, 1105, 3108, 4120), Oil Yellow (105, 107, 129, 3G, GGS), Vari Fast Red (1306, 1355, 2303, 3304, 3306, 3320), Oil Pink 312, Oil Scarlet 308, Oil Violet 730, Vari Fast Blue (1501, 1603, 1605, 1607, 2606, 2610, 3405). Oil Blue (2N, BOS, 613), Macrolex Blue RR, Sumiplast Gren G, Oil Green (502, BG), etc. A concentration of these dyes may preferably be 0.1-3.5 wt. %.

At the particle surface of the electrophoretic particles in the pixels, at least an amphipathic residual group derived from a reactive surfactant is fixed. Particles used for reaction may include organic or inorganic particles, pigment particles coated with a polymer, and polymer particles coated with a dye. An average particle size of these particles may be 10 nm to 5 μm, preferably 15 nm to 2 μm.

Examples of organic pigments which can be used in the pixel cells include azo pigments, phthalocyanine pigments, quinacridone pigments, isoindolinone pigments isoindoline pigments, dioazine pigments, perylene pigments, perinone pigments, thioindigo pigments, quinophthalone pigments, anthraquinone pigments, nitro pigments, and nitroso pigments. Specific examples thereof may include: rod pigments, such as Quinacridone Red, Lake Red, Brilliant Carmine, Perylene Red, Permanent Red, Toluidine Red and Madder Lake; green pigments, such as Diamond Green Lake, Phthalocyanine Green, and Pigment Green; blue pigments, such as Victoria Blue Lake, Phthalocyanine Blue, and Fast Sky Blue; yellow pigments, such as Hansa Yellow, Fast Yellow, Disazo Yellow, Isoindolinone Yellow, an Quinophthalone Yellow; and black pigments, such as Aniline Block and Diamond Black.

Examples of the inorganic pigments which can be used in the pixel cells include: white pigments, such as titanium oxide, aluminum oxide, zinc oxide, lead oxide, and zinc sulfide; black pigments, such as carbon black, manganese ferrite block, cobalt ferrite black, and titanium black; red pigments, such as cadmium red, red iron oxide, and molybdenum red; green pigments, such as chromium oxide, viridian, titanium cobalt green, cobalt green, and Victoria green; blue pigments, such as ultramarine blue, Prussian blue, and cobalt blue; and yellow pigments, such as cadmium yellow, titanium yellow, yellow iron oxide, chrome yellow, and antimony yellow.

As the pigment particles coated with a polymer, it is possible to use particles of the above described pigments coated with a polymer, such as polystyrene, polyethylene, polymethylacrylate, and polymethylmethacrylate. Coating of the pigment particles with the polymer may be performed by using a known method such as a polymer precipitation method or suspension polymerization.

As the polymer particles colored with a dye, it is possible to use particles of preliminarily synthesized crosslinkable polymer fine particles colored with a dye, particles obtained through suspension polymerization or emulsion polymerization of a polymerizable monomer containing a dye, etc.

In the electrophoretic particles to which surface at least the reactive surfactant-derived amphipathic residual group can be fixed, when the reactive surfactant is adsorbed by the particle surface and co-polymerized, a comonomer to be co-polymerized with the reactive surfactant is solubilized in the adsorption layer and polymerized or co-polymerized with the use of a polymerization initiator. As a result, the reactive surfactant-derived amphipathic residual group can be fixed at the particle surface.

Specific formulation procedures described in U.S. Pat. Appl. Publ. No. 20040257330 are suitable for this invention. Accordingly, in this invention, white electrophoretic particles and a dispersion medium colored with a blue dye can be filled in a pixel cell. The electrophoretic particles can be positively charged by fixing an amphipathic residual group derived from a reactive surfactant having a cationic functional group. When an electric field E is applied to the electrophoretic liquid, the positively charged electrophoretic particles are moved toward the upper side of the cell and distributed over the upper display surface. As a result, when the cell is observed from above, the cell looks white due to distribution of the white electrophoretic display. On the other hand, when the electric field E is applied to the electrophoretic liquid in an opposite direction, white electrophoretic particles are moved toward the bottom of the cell and distributed thereover, so that the cell looks blue when observed from above.

Accordingly, in this invention, a colorless dispersion medium with the color enhancing/augmentation structures noted above and two types (white and black) of electrophoretic particles can be included in a pixel cell. The white electrophoretic particles are positively charged by fixing an amphipathic residual group derived from a reactive surfactant having a cationic functional group, and the black electrophoretic particles are negatively charged by fixing an amphipathic residual group derived from an anionic functional group. When an electric field E is applied to the electrophoretic liquid, the positively charged white electrophoretic particles are moved toward the upper side of the cell and the negatively charged black electrophoretic particles 1 e are moved toward the lower (bottom) side of the cell. As a result, when the cell is observed from above, the cell looks white due to distribution of the white electrophoretic display. On the other hand, when the electric field E is applied to the electrophoretic liquid in the opposite direction, the black electrophoretic particles are moved toward the upper side of the cell, and the white electrophoretic particles are moved toward the bottom of the cell, so that the cell looks black when observed from above.

U.S. Pat. Appl. Publ. No. 20040257330 describes for example a surfactant synthesis example where 4.8 g (41 mmol) of chlorosulfuric acid was gradually added dropwise to 35 ml of pyridine cooled at 0° C., followed by stirring for 30 minutes. To the reactive mixture, 9 ml of a pyridine solution containing 7.0 g (41 mmol) of 10-undecene alcohol was gradually added dropwise, followed by stirring for 1 hour at 0° C. and further stirring for 20 hours at 55° C. The reaction mixture was poured into a saturated sodium hydrogen-carbonate aqueous solution cooled at 0° C., and stirred for 1 hour and further stirred of 20 hours at room temperature. After the reaction, the solvent of the reaction mixture was distilled off under reduced pressure. To the residue, acetone was added to precipitate a crystal. The crystal was dissolved in methanol and thereafter, a methanol insoluble content was removed, followed by removal of the solvent under reduced pressure to obtain a crystal. The crystal was recrystallized from a mixture solvent (methanol/acetone=⅓) to obtain a reactive surfactant having an anionic functional group represented by the following formula (Yield: 80%).

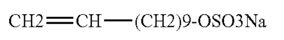

As a result of 1H-NMR (400 MHz, CD 3, OD) of the resultant reactive surfactant, measured values (δ/ppm) including 1.33 (12H), 1.68 (2H), 2.02 (2H), 4.00 (2H), 4.95 (2H) and 5.83 (1H) were obtained, thus identifying synthesis of the objective reactive surfactant (33).

U.S. Pat. Appl. Publ. No. 20040257330 describes thereafter the process for making a pixel solution, 5 wt. parts of titanium oxide and 3 wt. parts of the reactive surfactant prepared in the synthesis example above were added in 100 wt. parts of water, followed by irradiation of ultrasonic wave to form a bimolecular adsorption layer of the reactive surfactant at the surface of titanium oxide particles.

To the above treated particles, 2 wt. parts of di-n-butyl fumarate and 0.05 wt. part of potassium persulfate were added, followed by polymerization reaction for 48 hours at 60° C. in a nitrogen atmosphere. After coarse particles contained in the reaction mixture were removed with a filter, objective particles contained in the removed with a filter, objective particles contained in the reaction mixture were separated by centrifugation. The resultant precipitate was repeatedly recovered by filtration and washed, followed by drying to obtain particles to which the reactive surfactant-derived amphipathic residual group was fixed at the particle surface.

The obtained particles were subjected to salt exchange reaction by using a methanol solution o of n-hexadecyltrimethylammonium hydride (C16H33 (CH 3) 3 NOH), followed by washing of excessive ions with acetonitrile to obtain objective electrophoretic particles.

An electrophoretic liquid was prepared by dispersing 5 wt. parts of the electrophoretic particles in 50 wt. parts of isoparaffin ("Isopar H", mfd. by Exxon Corp.) colored blue by the addition of 0.1 wt. part of a dye ("Oil Blue N", mfd. by Aldrich Corp.). The prepared electrophoretic liquid was filled and sealed in a plurality of cells In this invention, the particles in U.S. Pat. Appl. Publ. No. 20040257330 (e.g., the titanium oxide) would be replaced with a mixture of color emitting particles or larger microscopic particle of the titanium oxide would be coated with nano-meter size mixtures of the color emitters of the invention including the color enhancing/augmentation structures noted above.

Figure 47:
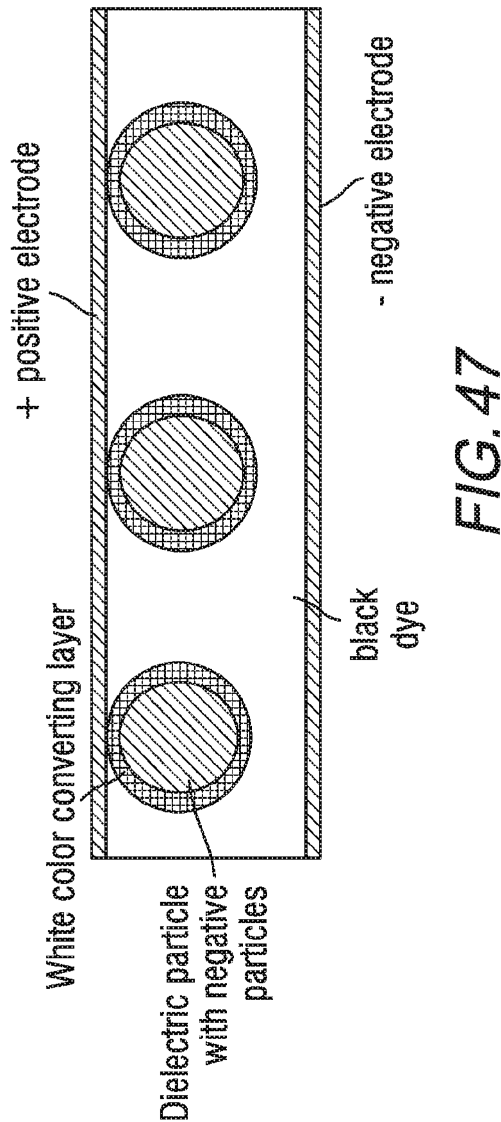
FIG. 47 is a schematic representation of an electronic ink display using the color enhancing structures of this invention.

FIG. 47 shows one example of an electronic ink display where a white color converting layer is applied for example to dielectric (e.g., titanium dioxide) particles. Here, depending on the voltage state of a pixel, the "white particles" in the black or dark dye are either drawn up to the near surface of the top electrode where white light is reflected or are repelled face the top electrode where the black dye, not at the near surface of the top electrode, absorbs incident light. The contrast then depends on the amount of light reflected from the "white particles" as opposed to the light not reflected from the blue dye. Here, in this embodiment, the dielectric particles include the color shifting particles of this invention with the color enhancing/augmentation structures noted above to produce more white light by up converting of the infrared part of the spectrum and down converting of the UV part of the spectrum.

Upon reversing the charge on the top electrode, the dielectric particles are attracted to the bottom electrode, and little if any light is reflected. Thus, the voltage state of each pixel thus determines whether that pixel appears white or black to the observer on the top side.

The excitation light for the display shown in FIG. 9 may be an ultraviolet light source or a black body or solar source (having wavelengths in the ultraviolet), in accordance with various embodiments of the invention. If the excitation light is ultraviolet light, then when the light emitting material emits visible light in response to the ultraviolet light, a down-conversion physical phenomenon occurs. Specifically, ultraviolet light has a shorter wavelength and higher energy than visible light. Accordingly, when the light emitting material absorbs the ultraviolet light and emits lower energy visible light, the ultraviolet light is down-converted to visible light because the ultraviolet light's energy level decreases when it is converted into visible light. In embodiments, the light emitting material is fluorescent material including the color enhancing/augmentation structures noted above.

The excitation light for the display shown in FIG. 47 may be infrared light source or a black body or solar source (having wavelengths in the infrared), in accordance with various embodiments of the invention. If the excitation light is infrared light, then when the light emitting material emits visible light in response to the infrared light, an up-conversion physical phenomenon occurs. Specifically, infrared light has a longer wavelength and lower energy than visible light. Accordingly, when the light emitting material absorbs the infrared light and emits higher energy visible light, the infrared light is up-converted to visible light because the infrared light's energy level increases when it is converted into visible light. Accordingly, in down-conversion embodiments, when ultraviolet light is absorbed by light emitting particles on the blue dye, visible light is emitted from the light emitting particles. Likewise, in up-conversion embodiments, when infrared light is absorbed by light emitting particles, visible light is emitted from the light emitting particles.

The size of the particles in the white light converting layer may be smaller than the wavelength of visible light, which may reduce or eliminate visible light scattering by the particles. Examples of particles that are smaller than the wavelength of visible light are nanoparticles or molecules. According to these embodiments, each of the light emitting particles could have a diameter that is less than about 500 nanometers. According to these embodiments, each of the light emitting particles could have a diameter that is less than about 400 nanometers. According to embodiments, each of the light emitting particles could have s a diameter that is less than about 300 nanometers. According to these embodiments, each of the light emitting particles could have a diameter that is less than about 200 nanometers. According to these embodiments, each of the light emitting particles could have a diameter that is less than about 100 nanometers. The light emitting particles may be individual molecules.

Figure 48:
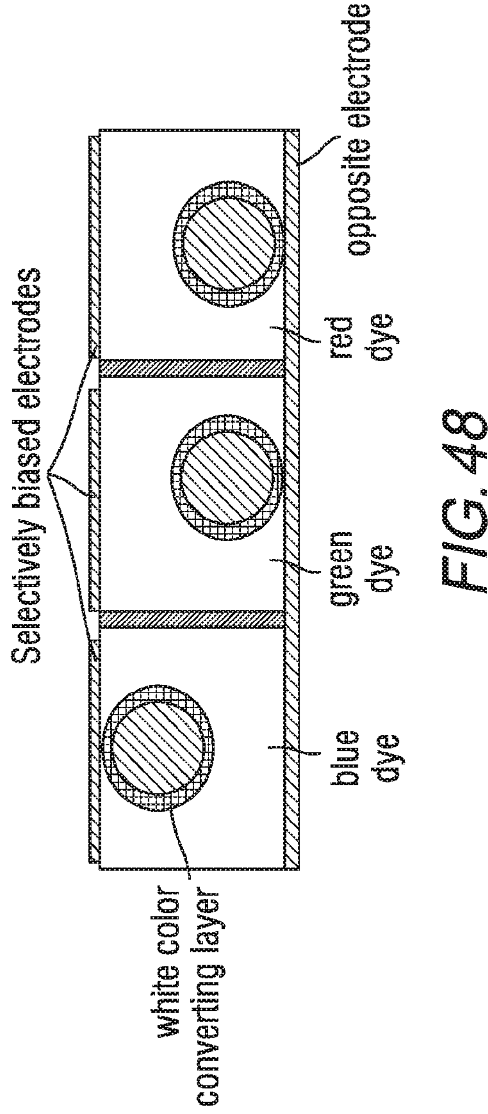
FIG. 48 is another schematic representation of an electronic ink display using the color enhancing structures of this invention.

Different types of light emitting particles may be used together that have different physical characteristics. For example, in order to emit color images from selected pixels of the display of FIG. 48, for example, different types of dyes may be utilized in pixels associated with different colors. FIG. 48 shows three pixels including respectively, red, green and blue dyes. When the top electrode attracts the dielectric particles with the white color enhancing layers to the top surface, the dye molecules in those pixels are displaced, turning that particular pixel the color of the dye. In one embodiment of the invention, the dyes (similar to the inks described below) contain nanoparticles of the color-shifting mixtures with the color enhancing/augmentation structures noted above.

For example, a first type of light emitting particles may be associated with the color red, a second type of light emitting particles may be associated with the color green, and a third type of light emitting particles may be associated with the color blue. Although the example first type, second type, and third type of light emitting particles are primary colors, other combinations of colors (e.g. types of colors and number of colors) can be used to facilitate a color display.

Figure 49:
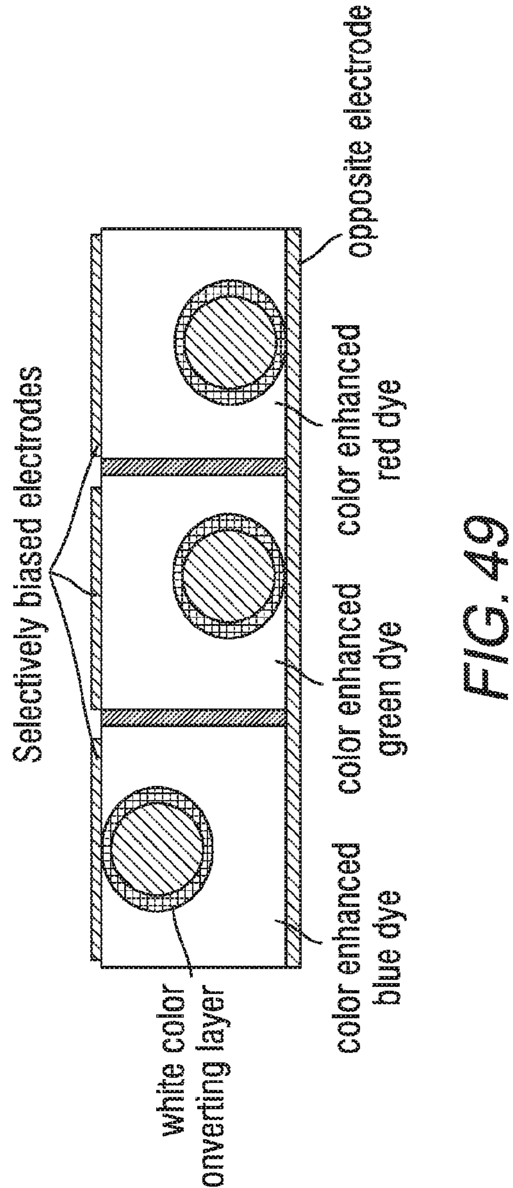
FIG. 49 is another schematic representation of an electronic ink display using the color enhancing structures of this invention.

FIG. 49 shows another embodiment in which three pixels include respectively, red, green and blue dyes where the dyes themselves have contain the color-shifting (and thus color enhancing) mixtures. When the top electrode attracts the dielectric particles with the white color enhancing layers to the top surface, the dye molecules in those pixels are displaced, turning that particular pixel the color of the color-enhanced dye. In one embodiment of the invention, the dyes (similar to the inks described below) contain nanoparticles of the color-shifting mixtures with the color enhancing/augmentation structures noted above.

Figure 50:
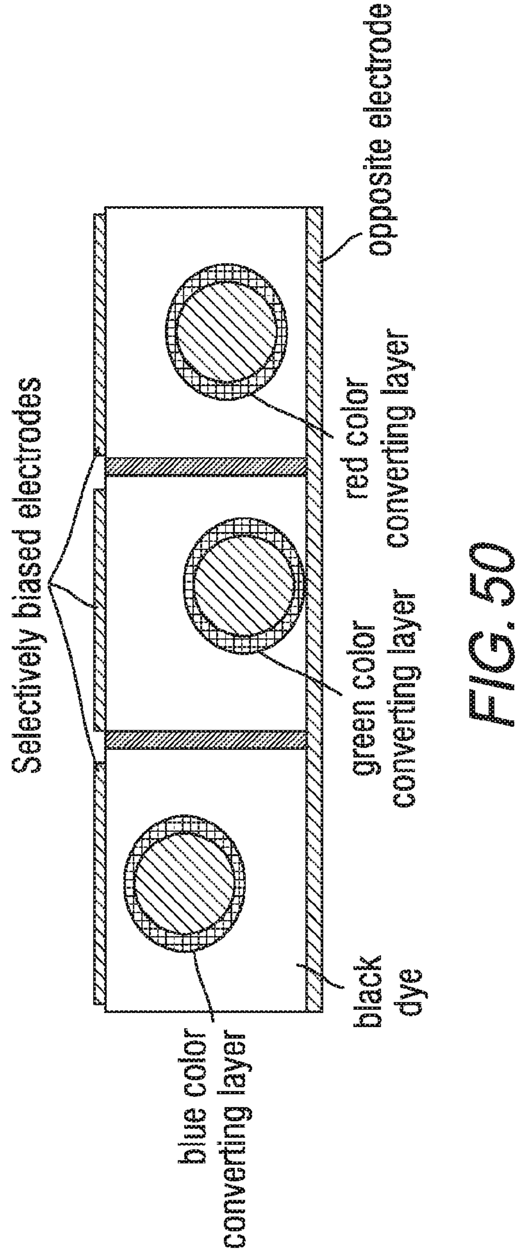
FIG. 50 is another schematic representation of an electronic ink display using the color enhancing structures of this invention.

FIG. 50 shows another embodiment in which three pixels include dielectric particles with respectively, red, green and blue color enhancing layers. When the top electrode attracts the dielectric particles with the distinct color enhancing layers to the top surface, the dye molecules in those pixels are displaced, turning that particular pixel the color of the dielectric particle's converting layer.

Figure 51:
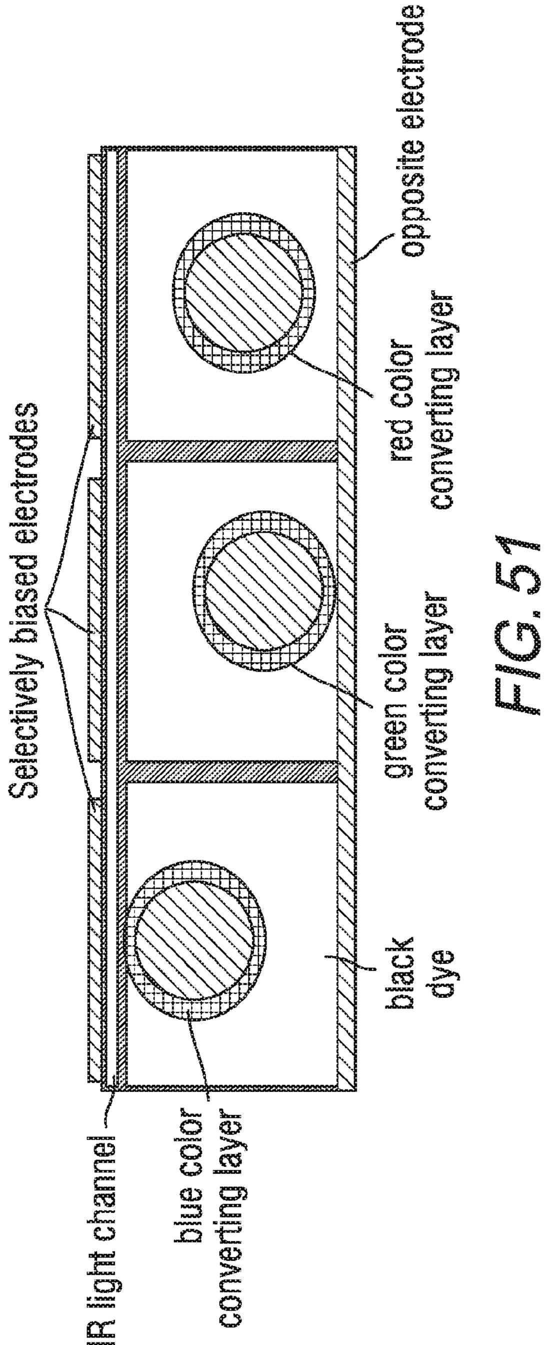
FIG. 51 is schematic representations of IR light activated displays using the color enhancing structures of this invention.

FIG. 51 shows one example of an IR light activated display of the invention. Accordingly, in this embodiment, a display can be produced utilizing color shifting particles of different upconversion color emission characteristics segregated into different display pixels.

In this embodiment, an IR laser illuminates a near surface of a pixilated surface having the color shifting particles attracted thereto (by selectively biasing separate pixels). In one embodiment, IR light is emitted so as to undergo total internal reflection along the interior surface of the IR light channel plate. For the IR light channel plate, typically crystalline materials are transparent in the 980 nm (NIR) light range; quartz, glass, $Y_2O_3$, etc. Also, small polymers (length/molecular weight) can also be transmissive but transmission in the range of IR is dependent on type and length etc.

In one embodiment, the IR light channel plate contains within itself scattering centers which scatter light off axis so as to illuminate a portion of the pixel region close to the IR light channel plate. In the example shown in FIG. 51, an IR light channel provides IR light propagation across the pixilated surface. The IR light in this example only stimulates the blue color converting layer with the color enhancing/augmentation structures noted above, as the bias electrode above the blue pixel has attracted the blue color converting layer (e.g., with negative particles) to the near surface, while the red and green color converting layers are repelled.

Different types of light emitting particles may absorb different ranges of excitation light to emit the different colors. Accordingly, the wavelength range of the excitation light may be modulated in order to control the visible color emitted from the light emitting particles. In embodiments, different types of light emitting particles may be mixed together and integrated into/onto a substrate or in the dyes or inks of the pixel (and include optionally the color enhancing/augmentation structures noted above). $B_y$ modulating the wavelength of the excitation light, along with spatial modulation and intensity modulation of the excitation light, visible light with specific color characteristics can be created in substrate. For example, by selectively exciting specific combinations of different types of light emitting particles associated with primary colors, virtually any visible color can be emitted.

Figure 52:
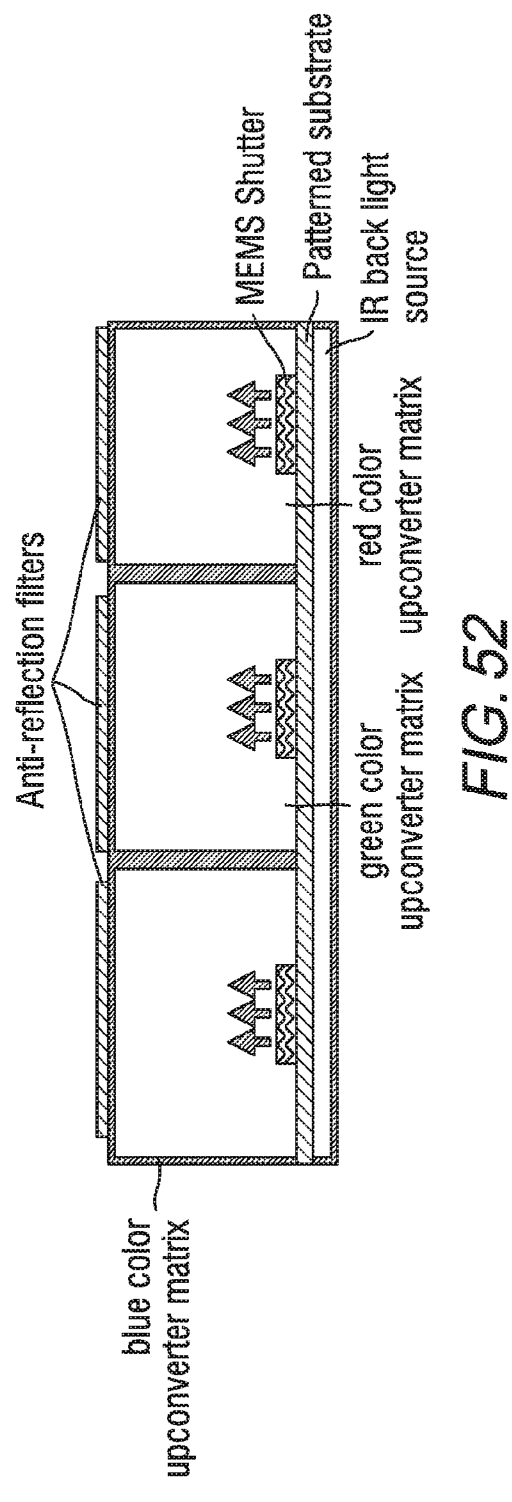
FIG. 52 is another schematic representation of IR light activated displays using the color enhancing structures of this invention.

FIG. 52 shows another example of an IR light activated display of the invention. In this embodiment, infrared light emitting diodes are patterned on a substrate. The pattern of diodes is registered with a pattern of pixels. Each of the pixels contains a specific color emitter, for example a blue color upconverter matrix containing the color shifting mixtures and the color enhancing/augmentation structures noted above of the invention.

In one embodiment, anti-reflective coatings or filters can be applied. For example, a reflective layer may be employed on surface opposite the LED light sources to reflect unconverted light back through the color shifting particle mixture. Indeed, as in laser cavity designs, this color pass filer would reflect light of the "wrong" unconverted wavelength back through the color shifting particle mixture for increased conversion.

U.S. Pat. No. 6,054,724 (the entire contents of which are incorporated herein by reference) describes ways to produce arrays of infrared light emitting diodes. The techniques described in that patent would be applicable for forming the patterned substrate containing the infrared light emitting LEDs shown in FIG. 10B. Alternatively, bonding technologies can be used to take diced laser diodes and mount laser diodes into the red, blue, and green pixel elements shown in FIG. 10B.

U.S. Pat. No. 6,104,740 (the entire contents of which are incorporated herein by reference) describes ways to produce arrays of infrared light emitting diodes and blue light emitting diodes on the same chip. The techniques described in that patent would be applicable for forming the patterned substrate containing the infrared light emitting LEDs shown in FIG. 10B. In this case, some of the light emitting LEDs would be blue light emitters, whose light could be either directly passed through the display or itself down converted.

Figure 53:
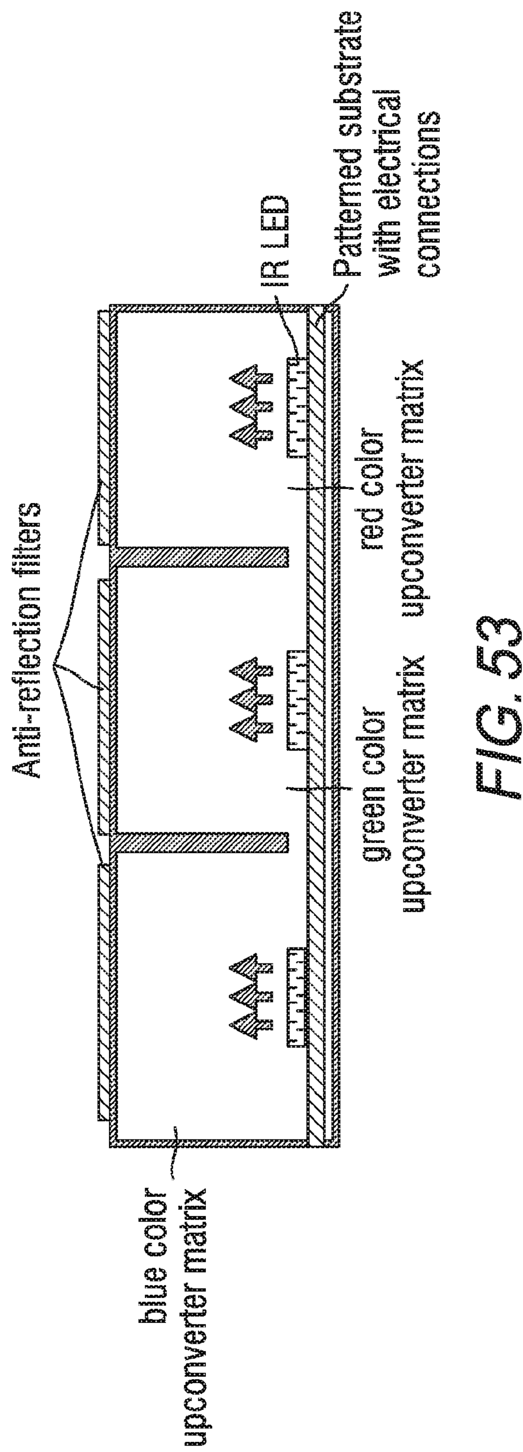
FIG. 53 is another schematic representation of IR light activated displays using the color enhancing structures of this invention.

FIG. 53 shows another example of an IR light activated display of the invention. In this embodiment, microelectrical mechanical systems (MEMS) are patterned on a substrate. The MEMS devices contain shutters which when open allow IR light from a back light source to pass through holes in the substrate and illuminate respective pixels. Each of the pixels contains a specific color emitter, for example a blue color upconverter matrix containing the color shifting mixtures (and optionally the color enhancing/augmentation structures noted above) are included in the composition of the invention. The IR back light source may be an infrared glow bar with appropriate filters or could be light diffused from an IR LED or IR laser source.

Figure 54:
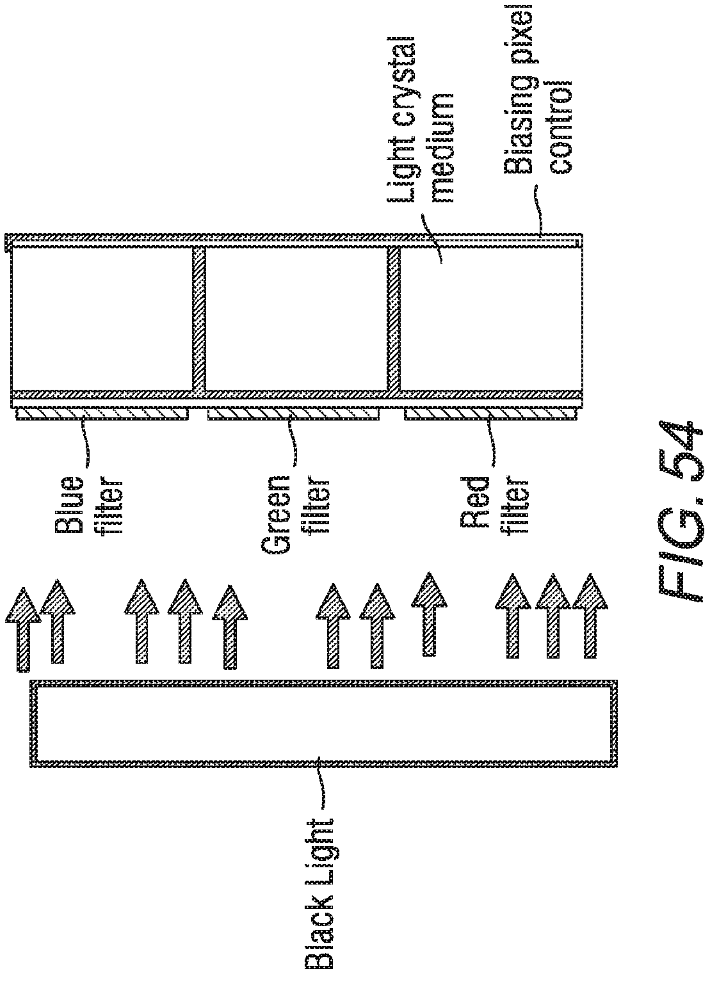
FIG. 54 is a schematic representation of a LCD light activated display in which the color filters have the color enhancing structures of this invention.

FIG. 54 shows one example of a liquid crystal (LC) light activated display in which the color filters have the color shifting particles of this invention. In one embodiment of this invention, the color shifting particles with the color enhancing/augmentation structures noted above can be employed in the color filter elements associated with conventional liquid crystal display technology. In this embodiment, light from a back light source passes through red, blue, and green color filters disposed in front of respective pixels of the liquid crystal display. Normally, light of the "wrong" color from the white back light would be merely absorbed making no contribution to the front side luminance of the display. With the color shifting particles and the color enhancing/augmentation structures noted above of the invention, the white light for the red filter has color shifting particles which down convert the spectrum of light of a higher energy than red (e.g., a blue light) and/or up convert the spectrum of light of a lower energy than red (e.g., near IR and IR light). Similarly, the white light for the green filter has color shifting particles which down convert the spectrum of light of a higher energy than green (e.g., a blue light) and up convert the spectrum of light of a lower energy than green (e.g., red, near IR, and IR light). Similarly, the white light for the blue filter has color shifting particles which down convert the spectrum of light of a higher energy than blue (e.g., a UV light) and up convert the spectrum of light of a lower energy than blue (e.g., green, red, near IR, and IR light).

Similar principles would apply to reflective LCD structures where ambient light is passed through LC elements and reflected from colored surfaces back through the LC elements to be viewed. Here, the colored surfaces with the color enhancing/augmentation structures noted above would have their respective reflected light luminance increased by color shifting particles which down convert the spectrum of light of a higher energy than red (e.g., a blue light) and up convert the spectrum of light of a lower energy than red (e.g., near IR and IR light) to reflect a higher luminance of red. Similarly, the white light for the green filter has color shifting particles which down convert the spectrum of light of a higher energy than green (e.g., a blue light) and up convert the spectrum of light of a lower energy than green (e.g., red, near IR, and IR light) to reflect a higher luminance of green. Similarly, the white light for the blue filter has color shifting particles which down convert the spectrum of light of a higher energy than blue (e.g., a UV light) and up convert the spectrum of light of a lower energy than blue (e.g., green, red, near IR, and IR light) to reflect a higher luminance of blue.

In various embodiments, reflective layers with the color enhancing/augmentation structures noted above can be used at respective color pixels, and these reflective layers can be selective waveband reflective layers to compensate for varying emission efficiencies of different light emitting materials. For example, if light emitting materials that emit red light from the red pixel emit light at a higher intensity than light emitting materials from a blue pixel emit blue light, a selective waveband reflective layer may compensate for these differences in emission efficiencies. For example, a "blue" reflective layer may reflect blue light with a higher intensity than a "red" reflective layer reflects red light.

Aging Resistance: Chalking, blistering, and cracking are common signs of the aging of latex and oil based paints. UV light exposure plays a significant role in the deterioration of paint pigments leading to these visual discrepancies. In one embodiment of the invention, UV light (and thus the energy contained in the UV light) is converted and/or scattered back away from a coated or painted or stained surface.

In this embodiment, a protective coating for moderating UV light damage to an object exposed to UV light irradiation is provided with the color enhancing/augmentation structures noted above. The protective coating has a mixture of light scattering and light emitting particles configured, upon exposure to UV light, to convert a first part of the UV light into visible light, emit from the mixture a fraction of the visible light, and reflect from the mixture a second part of the UV light such that the second part of the UV light is not absorbed by said object.

For example, while not limited to the details described below, UV light from the sun incident on the protective coating could have 50% or more of the UV light reflected due to the index of refraction change between air and the protective coating. That part of the UV light entering the interior layers of the protective coating converted into visible light. Other parts of the UV light would be scattered from protective coating and would not be incident on the underlying surface.

Industrial applications: The color enhancing mixtures and the color enhancing/energy augmentation structures noted above of the invention described above are applicable across a broad variety of artificially colored products. These products included (in addition to those products listed above) the following non-exhaustive list of products. For example, the color enhancing mixtures of the invention described above with the color enhancing/energy augmentation structures noted above can be included in or on the surface of building products such as concrete products, asphalt, pavement, bathroom and kitchen tiles, structural tiles, pavers, bricks (e.g., as a glazing bricks) and other glazing or glazed products.

In one illustrative example, the color contrast of tennis court lines in day light or artificial light could be enhanced by the color mixtures of the present invention including the color enhancing/augmentation structures noted above. Moreover, depending on the mixture additives which could include down converters targeted to for example a primary emission line in a plasma or arc discharge lamp, under artificial lighting (such as night-time lighting), the tennis pavement and the lines could exhibit a significant color change at nighttime, adding attraction to tennis as a night time sport.

Other products where the color enhancing mixtures with the color enhancing/energy augmentation structures noted above would have value would be jewelry, rings, earrings, necklaces, bracelets, mood rings, candles, epoxies, contact lens, rubber products, plastic products. Of particular example, contact lenses permit one to change their eye color. Besides adding the color enhancing mixtures of the invention to the typical colorants used in this product, the colorants can be added as the retroreflective glass spheres described above in order to produce a "cat-eyed" effect of reflecting light from a source more directionally to an observer.

U.S. Pat. No. 6,896,369 (the entire contents of which are incorporated herein by reference) describes the construction of colored contact lenses. In one embodiment of this invention, the color enhancing mixtures of the invention (with or without a retroreflective component) and optionally the color enhancing/augmentation structures noted above would be added to the multicolored pattern region having an epithelial region, a pupillary margin region, a collarette region, crypts of Fuchs elements, and a dilator pupillae region. These regions would have a plurality of colored elements or a combination of colored and non-colored elements. A colored element would be a colorant sufficiently opaque to mask the underlying region of the wearer's iris. An uncolored element would preferably clear, but may be slightly colored by a colorant which is sufficiently non-opaque so as not to mask the underlying region of the wearer's iris. To the colorants of U.S. Pat. No. 6,896,369, the color enhancing mixtures of the invention would be added with the color enhancing/energy augmentation structures noted above.

Tagging and Labeling Applications: U.S. Pat. No. 8,389,958 (the entire contents of which are incorporated by reference herein) describes nanotechnology for security and tagging operations. Besides the applications presented above, the color enhancing/augmentation structures noted above are useful on security and tagging operations where a primary light source, for example a NIR beam is focused and directed onto a target object. Applications of the color enhancing/augmentation structures noted above for security and tagging include: (i) detecting and removing of counterfeit currency from circulation, (ii) detecting and removing of counterfeit adulterated products (e.g., fake drugs), (iii) tracing the origin of products (e.g., alcohol, tobacco, firearms) and commodities (e.g., oil/gas tag and trace), (iv) tagging controlled substances (e.g. military explosives) or restricted technology (e.g. nuclear and communications technologies), (v) marking single source, high value commodities (e.g., specialty fibers), and (vi) brand protection, and (vii) verifying the authenticity of documents, financial instruments (e.g. bearer bonds), and various forms of identification. With the NIR beam incident on nanoparticles of yttrium oxide for example, the yttrium oxide nanoparticles will emit in the visible wavelength range which can then be detected by a hand-held reader, a CCD camera, or a person's eyes. For example, 100 to 1,000 milliwatt power of NIR light at wavelength λt 980 nanometers, the color enhancing/energy augmentation structures noted above including upconverters of the types described in this application would show bright green emission, blue emission, or red emission to the naked eye.

Alternatively or complementarily, the color enhancing/energy augmentation structures noted above could have applications in security and tagging operations where the primary light source is X-ray excitation and UV/VIS/NIR readout is used for the viewing.

In conventional bar coding operations, a scanner is used to essentially read a series of black and white lines with the density and spacings being indicative of a particular coded item. In this invention, these printed bar codes could make use of the nanocore emitters described above which offer the possibility of a multicolor emission from either singular or multiple infrared laser sources. Thus, the amount of information that can be encoded into a traditional bar code area may be greatly increased. For example, specific color categorization could introduce completely different encodings for what would normally be the same series of black and white lines. Further, combinations of differing color lines would permit further encoding of information even on top of the existing bar code lines which could be read by existing black and white imagers, adding information that would be indicative of the classes of product, class of distributers, class of manufacturers, classes of retailers, etc., in the product distribution chain. In this way, bar codes applied at the manufacture or food packager could be used for example in food product tracking safety and monitoring.

In these tagging and labeling applications, the color enhancing/energy augmentation structures of this invention provide a system for identification of an object. The system would include a readable medium (e.g., a paper product, a plastic product, and a glass product which may be a part of a security tag or a bar code on any product), a nanoparticle included in or on the surface of the readable medium. The nanoparticle, upon exposure to a first wavelength λ1 of radiation, is configured to emit a second wavelength λ2 of radiation having a higher energy than the first wavelength λ1. The second wavelength λ2 is in at least one of infrared, visible, and ultraviolet light to permit identification of the object by detecting the second wavelength λ2.

A metallic shell can encapsulate at least a fraction of the nanoparticle. As explained above, a radial dimension of the metallic shell can be set to a value where a surface plasmon resonance in the metallic shell resonates at a frequency which provides spectral overlap with either the first wavelength λ1 or the second wavelength λ2. The nanoparticle can more generally include a plurality of nanoparticles.

As such, the nanoparticles can be divided into multiple groups or categories of different light-emitting nanoparticles. A first group can for example exhibit visible emission upon interaction with the first wavelength λ1, while a second group can exhibit infrared emission upon interaction with the first wavelength λ1. In this embodiment, the first group can be a part of a visible tag on the object, and the second group can be a part of an invisible tag on the object. Alternatively, the first group can exhibit visible emission upon interaction with the first wavelength λ1, while the second group can exhibit ultraviolet emission upon interaction with the first wavelength λ1. In this embodiment also, the first group can be a part of a visible tag on the object, and the second group can be a part of an invisible tag on the object.

In one embodiment, the upconverter structures of the invention are complexed with the X-ray down converting particles or other energy converters permitting for example X-ray irradiation to also assist in this process. In one embodiment, the X-ray down converting particles or other energy converters or metallic structures described herein permit X-ray irradiation to be used alone or in combination with the up converting particles.

In one embodiment, the color enhancing/energy augmentation structures noted above are integrally included with the up converting or down converting particles. In one embodiment, the color enhancing/energy augmentation structures noted above are attached as a sheet or cover over or under the up converting or down converting particles. In one embodiment, the color enhancing/energy augmentation structures noted above are attached as a sheet the up converting or down converting materials deposited in a vicinity of the intensified electric fields.

In another embodiment, noted above, the color enhancing/energy augmentation structures could include mechano-luminescent structures, and application of ultrasonic energy to the mechano-luminescent structures would change the color emission from a surface. Such applications could be used in security systems where an item would contain a pattern of the composite mechano-luminescent emitters. The pattern would not be apparent until it was activated with ultrasonic or acoustic energy upon which time light of a predetermined wavelength would be emitted. The light emitted might be visible or infrared light depending on the type of detector used to detect the emitted light.

Accordingly, the energy augmentation structures of the present invention can be used in conjunction with the energy converters described herein in a wide variety of applications, including but not limited to, medical treatments using energy generated in situ within a subject being treated (whether using an energy converter or not), solar cells, adhesives and other resins, sterilization treatment for various materials (such as wastewater, beverages, etc.). The use of energy converters in such applications has been described in the following: US Published Application No. 2008/0248001; US Published Application No. 2009/0104212; US Published Application No. 2009/0294692; US Published Application No. 2010/0003316; US Published Application No. 2010/0016783; US Published Application No. 2010/0261263; US Published Application No. 2010/0266621; US Published Application No. 2011/0021970; US Published Application No. 2011/0117202; US Published Application No. 2011/0126889; US Published Application No. 2011/0129537; US Published Application No. 2011/0263920; US Published Application No. 2012/0064134; US Published Application No. 2012/0089180; US Published Application No. 2013/0102054; US Published Application No. 2013/0129757; US Published Application No. 2013/0131429; US Published Application No. 2013/0156905; US Published Application No. 2013/0171060; US Published Application No. 2013/0240758; US Published Application No. 2014/0134307; US Published Application No. 2014/0163303; US Published Application No. 2014/0166202; US Published Application No. 2014/0222117; US Published Application No. 2014/0242035; US Published Application No. 2014/0243934; US Published Application No. 2014/0272030; US Published Application No. 2014/0323946; US Published Application No. 2014/0341845; US Published Application No. 2014/0343479; US Published Application No. 2015/0182934; US Published Application No. 2015/0202294; US Published Application No. 2015/0246521; US Published Application No. 2015/0251016; US Published Application No. 2015/0265706; US Published Application No. 2015/0283392; US Published Application No. 2015/0290614; US Published Application No. 2016/0005503; US Published Application No. 2016/0067524; US Published Application No. 2016/0159065; US Published Application No. 2016/0243235; US Published Application No. 2016/0263393; US Published Application No. 2016/0325111; US Published Application No. 2016/0331731; US Published Application No. 2016/0354467; US Published Application No. 2016/0362534; US Published Application No. 2017/0027197; US Published Application No. 2017/0043178; US Published Application No. 2017/0050046; US Published Application No. 2017/0096585; US Published Application No. 2017/0113061; US Published Application No. 2017/0121472; US Published Application No. 2017/0154866; US Published Application No. 2017/0157418; US Published Application No. 2017/0162537; US Published Application No. 2017/0173350; US Published Application No. 2017/0186720; US Published Application No. 2017/0190166; US Published Application No. 2017/0196977; US Published Application No. 2017/0239489; US Published Application No. 2017/0239637; US Published Application No. 2017/0240717; US Published Application No. 2017/0258908; US Published Application No. 2017/0319868; US Published Application No. 2017/0319869; US Published Application No. 2018/0036408; US Published Application No. 2018/0154171; US Published Application No. 2018/0154178; US Published Application No. 2018/0169433; US Published Application No. 2018/0170028; US Published Application No. 2018/0269174; US Published Application No. 2018/0271121; US Published Application No. 2018/0304225; US Published Application No. 2018/0311355; US Published Application No. 2018/0317307; US Published Application No. 2018/0344850; US Published Application No. 2018/0358327; US Published Application No. 2019/0016869; US Published Application No. 2019/0022221; US Published Application No. 2019/0100680; US Published Application No. 2019/0134419; US Published Application No. 2019/0134595; US Published Application No. 2019/0134596; US Published Application No. 2019/0157234; US Published Application No. 2019/0168015; US Published Application No. 2019/0184190; US Published Application No. 2019/308030; US Published Application No. 2019/0336605; US Published Application No. 2019/0336785; US Published Application No. 2019/0336786; US Published Application No. 2019/0341364; U.S. application Ser. No. 16/074,707, filed Aug. 1, 2018; U.S. application Ser. No. 16/516,463, filed Jul. 19, 2019; U.S. application Ser. No. 16/554,831, filed Aug. 29, 2019 U.S. application Ser. No. 16/599,732, filed Oct. 11, 2019; U.S. application Ser. No. 16/674,435, filed Nov. 5, 2019; and U.S. application Ser. No. 16/728,803, filed Dec. 27, 2019; the contents of each of which are hereby incorporated by reference in their entireties. The energy augmentation structures and/or energy converters described herein have uses with the subject matter in the above noted published and unpublished US patent applications.

The following are exemplary embodiments of the present invention:

Embodiment 1. An energy emitter comprising:

at least one energy augmentation structure; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present.

Embodiment 2. The emitter of Embodiment 1, wherein the at least one energy augmentation structure comprises a structure in which a locally intensified electric field exists in one part of the structure when the structure receives electromagnetic energy.

Embodiment 3. The emitter of one of Embodiments 1 or 2, wherein the at least one energy augmentation structure comprises at least one resonator dimensioned to be resonant with the applied electromagnetic energy.

Embodiment 4. The emitter of Embodiment 3, wherein the resonator comprises a folded resonator.

Embodiment 5. The emitter of Embodiment 4, wherein the folded resonator comprises electrical conductors configured as a fractal pattern.

Embodiment 6. The emitter of one of Embodiments 3 or 4, wherein the folded resonator comprises a ¾ wavelength resonator having opposing ends folded inwards from a center of the folded resonator with a gap in between the opposing ends.

Embodiment 7. The emitter of Embodiment 6, wherein the locally intensified electric field exists in a vicinity of the opposing ends.

Embodiment 8. The emitter of Embodiment 4, wherein the folded resonator comprises a ¾ wavelength resonator having opposing ends folded outwards from a center of the folded resonator with a gap in between the opposing ends.

Embodiment 9. The emitter of Embodiment 8, wherein the locally intensified electric field exists in a vicinity of the opposing ends.

Embodiment 10. The emitter of Embodiment 3, wherein the resonator comprises a fractal pattern.

Embodiment 11. The emitter of Embodiment 10, wherein fractal pattern comprises a three-dimensional fractal pattern.

Embodiment 12. The emitter of Embodiment 3, wherein the at least one resonator comprises a plurality of resonators.

Embodiment 13. The emitter of Embodiment 12, wherein the resonators are disposed on a sheet.

Embodiment 14. The emitter of Embodiment 13, wherein the sheet comprises a sheet for disposal within a medium to be treated.

Embodiment 15. The emitter of Embodiment 13, wherein the sheet comprises a flexible sheet for disposal within a medium to be treated.

Embodiment 16. The emitter of Embodiment 13, wherein the sheet comprises a rigid sheet for disposal within a medium to be treated.

Embodiment 17. The emitter of Embodiment 13, wherein the plurality of resonators comprises an array of the resonators disposed on a sheet.

Embodiment 18. The emitter of Embodiment 12, wherein each of the resonators comprises a free-standing resonator.

Embodiment 19. The emitter of Embodiment 18, wherein the free-standing resonator is disposed within a medium to be treated.

Embodiment 20. The emitter of Embodiment 1, wherein the at least one energy augmentation structure comprises a first level of metallic patterns and a second level of metallic patterns offset in in at least one of a lateral or axial direction from the first level of metallic patterns.

Embodiment 21. The emitter of Embodiment 20, wherein at least one of the metallic patterns comprises a first resonator dimensioned to be resonant with an applied electromagnetic energy.

Embodiment 22. The emitter of Embodiment 21, wherein the at least one of the metallic patterns comprises a folded resonator having opposing electrodes with electric fields directed in between, and the energy converter is positioned between the opposing electrodes or within fringing electric field of the opposing electrodes.

Embodiment 23. The emitter of Embodiment 22, wherein the opposing electrodes are directed external to the folded resonator and parallel to one another.

Embodiment 24. The emitter of Embodiment 22, wherein the opposing electrodes are directed internal to the folded resonator and parallel to one another.

Embodiment 25. The emitter of any one of Embodiments 22-24, wherein the folded resonator comprises a ¾ $\lambda$ folded resonator.

Embodiment 26. The emitter of Embodiment 20, wherein the at least one of the metallic patterns comprises a plurality of the folded resonators concentrically arranged and optionally co-planar to one another, such that the external opposing electrodes of each folded resonator do not overlap spatially with the external opposing electrodes of the other of the plurality of folded resonators.

Embodiment 27. The emitter of Embodiment 20, wherein the at least one of the metallic patterns comprises a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 28. The emitter of Embodiment 1, wherein the at least one energy augmentation structure comprises at least one of Au, Ag, Cu, Al, transparent metal oxides or refractory metals.

Embodiment 29. The emitter of Embodiment 1, further comprising an antireflection film disposed on the at least one energy augmentation structure or the energy converter.

Embodiment 30. The emitter of Embodiment 1, wherein the at least one energy augmentation structure is disposed in vicinity of a down conversion material comprising the energy converter.

Embodiment 31. The emitter of Embodiment 1, wherein the at least one energy augmentation structure is disposed in vicinity of an up-conversion material comprising the energy converter.

Embodiment 32. The emitter of Embodiment 1, wherein the at least one energy augmentation structure is disposed in vicinity of a phosphor comprising the energy converter.

Embodiment 33. The emitter of Embodiment 1, wherein the at least one energy augmentation structure is disposed in vicinity of a piezoelectric device comprising the energy converter.

Embodiment 34. The emitter of Embodiment 33, wherein the piezoelectric device is configured to receive sonic or acoustic energy and emit at least one of ultraviolet or visible light in response to absorbing the sonic or acoustic energy.

Embodiment 35. The emitter of Embodiment 1, wherein the at least one energy augmentation structure is disposed in vicinity of a mechanoluminescent device comprising the energy converter.

Embodiment 36. The emitter of Embodiment 35, wherein the mechanoluminescent device is configured to receive sonic or acoustic energy and emit at least one of ultraviolet or visible light in response to absorbing the sonic or acoustic energy.

Embodiment 37. The emitter of Embodiment 1, wherein the at least one energy augmentation structure is disposed inside a plasma capsule device comprising the energy converter.

Embodiment 38. The emitter of Embodiment 37, wherein the plasma capsule device is configured to receive radio frequency or microwave energy and emit at least one of ultraviolet or visible light in response to absorbing the radio frequency or microwave energy.

Embodiment 39. The emitter of Embodiment 1, wherein the at least one energy augmentation structure is disposed in vicinity of an x-ray stimulated phosphor comprising the energy converter.

Embodiment 40. The emitter of Embodiment 39, wherein the x-ray stimulated phosphor emits one of ultraviolet or visible light in response to absorbing x-rays.

Embodiment 41. The emitter of Embodiment 40, wherein the x-ray stimulated phosphor emits the one of ultraviolet or visible light for at least a time of 1 minute after x-ray stimulation.

Embodiment 42. The emitter of Embodiment 40, wherein the x-ray stimulated phosphor emits the one of ultraviolet or visible light for at least a time of 10 minutes after x-ray stimulation.

Embodiment 43. The emitter of Embodiment 40, wherein the x-ray stimulated phosphor emits the one of ultraviolet or visible light for at least a time of 60 minutes after x-ray stimulation.

Embodiment 44. The emitter of Embodiment 39, wherein the x-ray stimulated phosphor emits lower energy x-rays in response to absorbing higher energy x-rays.

Embodiment 45. The emitter of Embodiment 1, wherein the energy received from the energy source is one or more selected from acoustic waves, sound waves, radio waves, microwaves, far infrared, near infrared, visible light, UV, x-rays, gamma rays, electron beams, and proton beams.

Embodiment 46. The emitter of any one of Embodiments 1 to 45, wherein the energy converter being disposed in a vicinity of the at least one energy augmentation structure comprises a conductive coupling of the energy converter to the at least one energy augmentation structure.

Embodiment 47. The emitter of Embodiment 46, wherein the conductive coupling comprises a physical conductive connection between the energy converter and the at least one energy augmentation structure.

Embodiment 48. The emitter of Embodiment 1, wherein the energy converter comprises either one or both of (i) a down converter converting ultraviolet or blue light into red, yellow, or green light, or (ii) an up converter converting infrared or red light into yellow, green light, or blue light.

Embodiment 49. The emitter of any one of Embodiments 1 to 48, wherein the at least one energy augmentation structure comprises a plurality of energy collectors.

Embodiment 50. The emitter of Embodiment 49, wherein the energy converters are positioned to convert energy being internally scattered within the energy collectors.

Embodiment 51. The emitter of Embodiment 49, wherein the energy collectors comprise a metal core cladded with a high-K dielectric and a subsequent cladding of a low-K dielectric.

Embodiment 52. The emitter of Embodiment 49, wherein the energy collectors comprise a radial pattern of collectors.

Embodiment 53. The emitter of Embodiment 7, wherein the energy collectors comprise a fractal pattern.

Embodiment 54. The emitter of Embodiment 53, wherein the fractal pattern is embedded within a dielectric material.

Embodiment 55. The emitter of any one of Embodiments 1-54, wherein the at least one energy augmentation structure comprises a component of at least one of a paint, an ink, a fabric, a thread, a road sign, a highway marking, an automobile, a boat, a plane, a reflector, a building product, a concrete product, an epoxy product, a jewelry product, colored contact lens, a candle product, a rubber product, a plastic product, a colored surface, a solar cell, a plasma capsule, an x-ray detector, or a sterilizer.

Embodiment 56. The emitter of any one of Embodiments 1-54, wherein the energy converter comprises a component of at least one of a paint, an ink, a fabric, a thread, a road sign, a highway marking, an automobile, a boat, a plane, a reflector, a building product, a concrete product, an epoxy product, a jewelry product, colored contact lens, a candle product, a rubber product, a plastic product, a colored surface, a solar cell, a plasma capsule, an x-ray detector, or a sterilizer.

Embodiment 57. The emitter of any one of Embodiments 1 to 54, wherein the energy converter comprises a component of a colored reflective surface.

Embodiment 58. The emitter of any one of Embodiments 1 to 54, wherein the energy converter comprises a component of a colored reflective surface in a pixel for a display.

Embodiment 59. The emitter of any one of Embodiments 1 to 54, wherein the energy converter comprises a component of a white-light emitting pixel display element.

Embodiment 60. The emitter of any one of Embodiments 1 to 54, wherein the energy converter comprises a component disposed in a retroreflective paint.

Embodiment 61. The emitter of any one of Embodiments 1 to 54, wherein the energy converter comprises an ink component.

Embodiment 62. The emitter of Embodiment 1, wherein the energy converter comprises at least one of red, blue, and green emitters configured to produce red, blue, and green emissions from an up conversion process.

Embodiment 63. The emitter of Embodiment 3, wherein the energy converter comprises at least one of red, blue, and green emitters configured to produce red, blue, and green emissions from an up conversion process.

Embodiment 64. The emitter of Embodiment 1, wherein the energy converter comprises at least one of red, blue, and green emitters configured to produce red, blue, and green emissions from a down conversion process.

Embodiment 65. The emitter of Embodiment 3, wherein the energy converter comprises at least one of red, blue, and green emitters configured to produce red, blue, and green emissions from a down conversion process.

Embodiment 66. The emitter of Embodiment 1, wherein the energy converter comprises at least one of red, blue, and green emitters configured to produce red, blue, and green emissions from a mixture of up converters and down converters.

Embodiment 67. The emitter of Embodiment 3, wherein the energy converter comprises at least one of red, blue, and green emitters configured to produce red, blue, and green emissions from mixtures of up converters and down converters.

Embodiment 68. The emitter of Embodiment 1, wherein the energy converter comprises a mixture of fluorescent emitters including at least one of europium, terbium, cerium, and erbium or combinations thereof.

Embodiment 69. The emitter of Embodiment 3, wherein the energy converter comprises mixtures of fluorescent emitters including at least one of europium, terbium, cerium, and erbium or combinations thereof.

Embodiment 70. The emitter of any one of Embodiments 1 to 54, wherein the energy converter comprises:

a first material configured to emit a first visible color in response to absorption of ultraviolet light; and a second material configured to emit a second visible color in response to absorption of infrared light, wherein the second visible color is different from the first visible color.

Embodiment 71. The emitter of Embodiment 70, wherein the energy converter further comprises a third material configured to emit a third visible color in response to absorption of the ultraviolet light, wherein the third visible color is different from the first visible color and the second visible color.

Embodiment 72. The emitter of Embodiment 71, wherein the first visible color, the second visible color, and the third visible color are primary colors.

Embodiment 73. The emitter of Embodiment 70, wherein the energy converter further comprises a third material configured to emit a third visible color in response to absorption of the infrared light, wherein the third visible color is different from the first visible color and the second visible color.

Embodiment 74. The emitter of Embodiment 1, wherein the energy converter comprises:

a first material configured to emit a first visible color in response to absorption of ultraviolet light; and a second material configured to emit a second visible color in response to absorption of infrared light, wherein the second visible color is substantially the same color as the first visible color.

Embodiment 75. The emitter of Embodiment 74, wherein the energy converter further comprises a third material configured to emit a third visible color in response to absorption of the ultraviolet light, wherein the third visible color is different from the first visible color and the second visible color.

Embodiment 76. The emitter of Embodiment 74, wherein the energy converter further comprises a third material configured to emit a third visible color in response to absorption of the infrared light, wherein the third visible color is different from the first visible color and the second visible color.

Embodiment 77. The emitter of Embodiment 76, wherein the first visible color, the second visible color, and the third visible color are at least two of the primary colors.

Embodiment 78. The emitter of any one of Embodiments 1 to 54, wherein the energy converter comprises a component of a colored reflective surface.

Embodiment 79. The emitter of any one of Embodiments 1 to 54, wherein the energy converter comprises a component of a colored reflective surface in a pixel for a display.

Embodiment 80. The emitter of any one of Embodiments 1 to 54, wherein the energy converter comprises a component of a white-light emitting pixel display element.

Embodiment 81. The emitter of any one of Embodiments 1 to 54, wherein the energy converter comprises a component disposed in a retroreflective paint.

Embodiment 82. The emitter of any one of Embodiments 1 to 54, wherein the energy converter comprises an ink component.

Embodiment 83. The emitter of any one of Embodiments 78-82, wherein the energy converter comprises at least one of red, blue, and green emitters configured to produce red, blue, and green emissions from an up conversion process.

Embodiment 84. The emitter of any one of Embodiments 1 to 54, wherein the energy converter comprises at least one of red, blue, and green emitters configured to produce red, blue, and green emissions from an up conversion process.

Embodiment 85. The emitter of any one of Embodiments 78-82, wherein the energy converter comprises at least one of red, blue, and green emitters configured to produce red, blue, and green emissions from a down conversion process.

Embodiment 86. The emitter of any one of Embodiments 1 to 54, wherein the energy converter comprises at least one of red, blue, and green emitters configured to produce red, blue, and green emissions from a down conversion process.

Embodiment 87. The emitter of any one of Embodiments 78-82, wherein the energy converter comprises at least one of red, blue, and green emitters configured to produce red, blue, and green emissions from a mixture of up converters and down converters.

Embodiment 88. The emitter of any one of Embodiments 1 to 54, wherein the energy converter comprises at least one of red, blue, and green emitters configured to produce red, blue, and green emissions from mixtures of up converters and down converters.

Embodiment 89. The emitter of any one of Embodiments 78-82, wherein the energy converter comprises a mixture of fluorescent emitters including at least one of europium, terbium, cerium, and erbium or combinations thereof.

Embodiment 90. The emitter of any one of Embodiments 1 to 54, wherein the energy converter comprises mixtures of fluorescent emitters including at least one of europium, terbium, cerium, and erbium or combinations thereof.

Embodiment 91. The emitter of any one of Embodiments 78-82, wherein the energy converter comprises:

- a first material configured to emit a first visible color in response to absorption of ultraviolet light; and
- a second material configured to emit a second visible color in response to absorption of infrared light, wherein the second visible color is different from the first visible color.

Embodiment 92. The emitter of Embodiment 91, wherein the energy converter further comprises a third material configured to emit a third visible color in response to absorption of the ultraviolet light, wherein the third visible color is different from the first visible color and the second visible color.

Embodiment 93. The emitter of Embodiment 92, wherein the first visible color, the second visible color, and the third visible color are primary colors.

Embodiment 94. The emitter of Embodiment 91, wherein the energy converter further comprises a third material configured to emit a third visible color in response to absorption of the infrared light, wherein the third visible color is different from the first visible color and the second visible color.

Embodiment 95. The emitter of any one of Embodiments 78-82, wherein the energy converter comprises:

- a first material configured to emit a first visible color in response to absorption of ultraviolet light; and
- a second material configured to emit a second visible color in response to absorption of infrared light, wherein the second visible color is substantially the same color as the first visible color.

Embodiment 96. The emitter of Embodiment 95, wherein the energy converter further comprises a third material configured to emit a third visible color in response to absorption of the ultraviolet light, wherein the third visible color is different from the first visible color and the second visible color.

Embodiment 97. The emitter of Embodiment 95, wherein the energy converter further comprises a third material configured to emit a third visible color in response to absorption of the infrared light, wherein the third visible color is different from the first visible color and the second visible color.

Embodiment 98. The emitter of Embodiment 97, wherein the first visible color, the second visible color, and the third visible color are at least two of the primary colors.

Embodiment 99. The emitter of Embodiment 1, wherein the at least one energy augmentation structure comprises metallic conductors including at least one of Au, Ag, Cu, Ni, Pt, Pd, Co, Ru, Rh, Al, Ga, or a combination or alloys or layers thereof.

Embodiment 100. The emitter of Embodiment 1, wherein the energy converter comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

Embodiment 101. The emitter of Embodiment 100, wherein the energy converter further comprises a dopant including at least one of Er, Eu, Yb, Tm, Nd, Tb, Ce, Y, U, Pr, La, Gd and other rare-earth species or a combination thereof.

Embodiment 102. The emitter of Embodiment 101, wherein the dopant is included at a concentration of 0.01%-50% by mol concentration.

Embodiment 103. The emitter of Embodiment 1, wherein the energy converter comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn, $Er^{3+}$.

Embodiment 104. The emitter of Embodiment 1, wherein the energy converter comprises an up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

Embodiment 105. The emitter of Embodiment 1, wherein the energy converter comprises an up converter including at least one of $Tm^{3+}$ doped flourozirconate glasses, $LuPO_4$: $Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 106. A paint comprising:
- a pigment; and
- the emitters of any one of Embodiments 1-105.

Embodiment 107. An ink comprising:
- a dye; and
- the emitters of any one of Embodiments 1-105.

Embodiment 108. A light display comprising:
- at least one of a color filter or a color reflective surface;
- the emitters of any one of Embodiments 1-105 included in the color filter or as part of the color reflective surface.

Embodiment 109. A protective coating for moderating UV light damage to an object exposed to UV light irradiation, comprising:
- a mixture of light scattering particles and the emitters of any one of Embodiments 1-105; and
- the mixture configured, upon exposure to UV light, to convert a first part of the UV light into visible light,
- emit from the mixture a fraction of the visible light, and
- reflect from the mixture a second part of the UV light such that said second part of the UV light is not absorbed by said object.

Embodiment 110. A light emitting composition comprising:
- first color emitters configured to emit, upon exposure to an energy source at an energy higher than or lower than the visible light spectrum, visible light at a first target color;
- second color emitters configured to emit, upon exposure to the energy source, visible light at a second target color; and
- the emitters of any one of Embodiments 1-105.

Embodiment 111. A cosmetic product comprising: color emitters including,
- first color emitters configured to emit, upon exposure to an energy source, visible light at a first target color in response to absorption of energy across a first band of wavelengths;
- second color emitters configured to emit, upon exposure to the energy source, visible light at a second target color in response to absorption of energy across a second band of wavelengths; and
- the emitters of any one of Embodiments 1-105.

Embodiment 112. The product of Embodiment 111, wherein the cosmetic product is
a skin cream.

Embodiment 113. The product of Embodiment 111, wherein the cosmetic product is
a mascara.

Embodiment 114. The product of Embodiment 111, wherein the cosmetic product is at least one member selected from the group consisting of a shampoo, hair conditioner, hair gel, hair styling compound, hair spray, and hair cream.

Embodiment 115. The product of Embodiment 111, wherein the cosmetic product is a lip balm.

Embodiment 116. The product of Embodiment 111, wherein the cosmetic product is a blush.

Embodiment 117. A method for enhancing visible light emission from a surface, comprising:
- providing on the surface at least one of the emitters of any one of Embodiments 1-105;
- exposing the surface and the at least one color enhancement structure to an applied energy from an energy source; and
- emitting visible light at at least one target color by conversion of a part of said applied energy into said visible light.

Embodiment 118. A method for enhancing visible light emission from a paint, comprising:
- providing in the paint or in a vicinity of a surface of the paint at least one of the structures of any one of Embodiments 1-105;
- exposing the surface and the at least one structure to an applied energy from an energy source; and
- emitting said visible light at at least one target color by conversion of a part of said applied energy into said visible light.

Embodiment 119. A method for enhancing visible light emission from an ink, comprising:
- providing in the ink at least one of the structures of any one of Embodiments 1-105;
- exposing the ink and the at least one color enhancement structure to an applied energy from an energy source; and
- emitting said visible light at at least one target color by conversion of a part of said applied energy into said visible light.

Embodiment 120. A method for enhancing visible light emission from a display, comprising:
- providing on a color filter or a color reflective surface of the display at least one of the structures of any one of Embodiments 1-105;
- exposing the color filter or color reflective surface, and the at least one color enhancement structure to an applied energy from an energy source; and
- emitting said visible light at at least one target color by conversion of a part of said applied energy into said visible light.

Embodiment 121. An energy or color enhancement device comprising:
- an energy collector comprising at least one energy augmentation structure; and
- an energy converter capable of receiving an applied electromagnetic energy, converting the applied electromagnetic energy and emitting therefrom a wavelength of emitted energy shifted in wavelength/energy from the applied electromagnetic energy, and the energy converter being disposed in a vicinity of the energy augmentation structure,
- wherein the energy augmentation structure is configured to provide an electric field between opposing elements of the structure.

Embodiment 122. An energy or color enhancement device comprising:
- an energy collector comprising at least one energy augmentation structure; and
- an energy converter capable of receiving an applied electromagnetic energy, converting the applied electromagnetic energy and emitting therefrom a wavelength of emitted energy shifted in wavelength/energy from the applied electromagnetic energy, and the energy converter being disposed in a vicinity of the energy augmentation structure, wherein the energy collector collects energy from a branched antenna.

Embodiment 123. The device of Embodiment 122, wherein each array element of the branched antenna comprising a metallic core and a dielectric clad.

Embodiment 124. An energy or color enhancement device comprising:

an energy collector comprising optionally at least one energy augmentation structure; and an energy converter comprising a mechanoluminescent emitter capable of receiving at least one acoustic, vibrational, and ultrasonic energy, converting the received energy and emitting therefrom a wavelength of light from the energy converter.

Embodiment 125. The device of Embodiment 124, wherein the mechanoluminescent emitter comprises a piezoelectric material connected to an electroluminescent material to thereby form a composite emitter.

Embodiment 126. An energy augmentation structure capable of capturing one or more wavelengths of electromagnetic energy, and augmenting the one or more wavelengths of electromagnetic energy in at least one property.

Embodiment 127. The energy augmentation emitter of Embodiment 126, wherein the energy augmentation structure is at least one non-plasmonic member selected from the group consisting of resonators, fractal antennas, electrical grid patterns, antennas, cavities, etalons, nanoparticles, microparticles, nanostructures, and microstructures.

Embodiment 128. The energy augmentation structure of Embodiment 126, comprising a folded resonator having opposing electrodes with electric fields directed in between.

Embodiment 129. The energy augmentation structure of Embodiment 128, wherein the opposing electrodes are directed external to the folded resonator and parallel to one another.

Embodiment 130. The energy augmentation structure of Embodiment 128, wherein the opposing electrodes are directed internal to the folded resonator and parallel to one another.

Embodiment 131. The energy augmentation structure of any one of Embodiments 128-130, wherein the folded resonator comprises a ¾ $\lambda$ folded resonator.

Embodiment 132. The energy augmentation structure of Embodiment 128, wherein the folded resonator is a plurality of the folded resonators concentrically arranged and optionally co-planar to one another, such that the external opposing electrodes of each folded resonator do not overlap spatially with the external opposing electrodes of the other of the plurality of folded resonators.

Embodiment 133. The energy augmentation structure of Embodiment 128, wherein the folded resonator is a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 134. An energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

Embodiment 135. The energy collector of Embodiment 134, wherein the at least one energy converter is at least one member selected from the group consisting of phosphors, lumiphors, electroluminescent particles, up-converters, down-converters, and scintillators.

Embodiment 136. The energy collector of Embodiment 134, wherein the energy augmentation structure is at least one non-plasmonic member selected from the group consisting of resonators, fractal antennas, electrical grid patterns, antennas, cavities, etalons, nanoparticles, microparticles, nanostructures, and microstructures.

Embodiment 137. The energy collector of Embodiment 134, wherein having the energy converter disposed in a vicinity of the at least one energy augmentation structure comprises conductively coupling the at least one energy converter to the at least one energy augmentation structure.

Embodiment 138. The energy collector of Embodiment 137, wherein conductively coupling comprises having the at least one energy converter be proximate the at least one energy augmentation structure, physically located within the at least one energy augmentation structure, or located within a generated electric field of the at least one energy augmentation structure.

Embodiment 139. The energy collector of Embodiment 137, wherein conductively coupling comprises a physical conductive connection between the at least one energy converter and the at least one energy augmentation structure.

Embodiment 140. The energy collector of Embodiment 134, wherein the applied electromagnetic energy is selected from radio waves, microwaves, far infrared, near infrared, visible light, UV, x-rays, gamma rays, electron beams, and proton beams.

Embodiment 141. The energy collector of Embodiment 134, wherein the at least one energy augmentation structure comprises a first resonator dimensioned to be resonant with the applied electromagnetic energy, said first resonator optionally comprising a fractal pattern.

Embodiment 142. The energy collector of Embodiment 134, wherein the energy augmentation structure comprises a folded resonator having opposing electrodes with electric fields directed in between.

Embodiment 143. The energy collector of Embodiment 140, wherein the opposing electrodes are directed external to the folded resonator and parallel to one another.

Embodiment 144. The energy collector of Embodiment 140, wherein the opposing electrodes are directed internal to the folded resonator and parallel to one another.

Embodiment 145. The energy collector of any one of Embodiments 142-144, wherein the folded resonator comprises a ¾ $\lambda$ folded resonator.

Embodiment 146. The energy collector of Embodiment 142, wherein the folded resonator is a plurality of the folded resonators concentrically arranged and optionally co-planar to one another, such that the external opposing electrodes of each folded resonator do not overlap spatially with the external opposing electrodes of the other of the plurality of folded resonators.

Embodiment 147. The energy collector of Embodiment 142, wherein the folded resonator is a plurality of the folded resonators concentrically arranged and optionally co-planar to one another, such that the external opposing electrodes of each folded resonator overlap spatially with the external opposing electrodes of one or more of the other of the plurality of folded resonators.

Numerous modifications and variations of the invention are possible in light of the above teachings. It is therefore to be understood that within the scope of the appended claims, the invention may be practiced otherwise than as specifically described herein.

The invention claimed is:

1. An energy augmentation structure capable of capturing one or more wavelengths of electromagnetic energy, and augmenting the one or more wavelengths of electromagnetic energy in at least one property, wherein the energy augmentation structure comprises a ¾ $\lambda$ folded resonator.

2. An energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure, wherein the energy augmentation structure is capable of capturing one or more wavelengths of electromagnetic energy, and augmenting the one or more wavelengths of electromagnetic energy in at least one property, and wherein the energy augmentation structure comprises either (i) a non-plasmonic fractal antenna or (ii) a folded resonator having opposing electrodes with electric fields directed in between.

3. The energy collector of claim 2, wherein the at least one energy converter is at least one member selected from the group consisting of phosphors, lumiphores, electroluminescent particles, up-converters, down-converters, and scintillators.

4. The energy collector of claim 2, wherein having the energy converter disposed in a vicinity of the at least one energy augmentation structure comprises conductively coupling the at least one energy converter to the at least one energy augmentation structure.

5. The energy collector of claim 4, wherein conductively coupling comprises:

(i) having the at least one energy converter be proximate the at least one energy augmentation structure, physically located within the at least one energy augmentation structure, or located within a generated electric field of the at least one energy augmentation structure, or (ii) a physical conductive connection between the at least one energy converter and the at least one energy augmentation structure.

6. An energy emitter comprising:

at least one energy augmentation structure; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present, wherein the energy augmentation structure is capable of capturing one or more wavelengths of electromagnetic energy, and augmenting the one or more wavelengths of electromagnetic energy in at least one property, and wherein the energy augmentation structure comprises either (i) a non-plasmonic fractal antenna or (ii) a folded resonator having opposing electrodes with electric fields directed in between.

7. The energy emitter of claim 6, wherein the at least one energy augmentation structure comprises a structure in which a locally intensified electric field exists in one part of the structure when the structure receives electromagnetic energy.

8. The energy emitter of claim 6, wherein the at least one energy augmentation structure comprises the folded resonator having opposing electrodes with electric fields directed in between.

9. The energy emitter of claim 8, wherein the folded resonator comprises:

(i) electrical conductors configured as a fractal pattern, or (ii) a ¾ wavelength resonator having opposing ends folded inwards from a center of the folded resonator with a gap in between the opposing ends, or (iii) a ¾ wavelength resonator having opposing ends folded outwards from a center of the folded resonator with a gap in between the opposing ends.

10. The energy emitter of claim 7, wherein the at least one energy augmentation structure comprises at least one folded resonator having opposing electrodes with electric fields directed in between and dimensioned to be resonant with the applied electromagnetic energy, wherein the at least one folded resonator comprises a fractal pattern.

11. The energy emitter of claim 10, wherein the fractal pattern comprises a three-dimensional fractal pattern.

12. The energy emitter of claim 6, wherein the at least one energy augmentation structure comprises at least one of Au, Ag, Cu, Al, transparent metal oxides or refractory metals.

13. The energy emitter of claim 6, further comprising an antireflection film disposed on the at least one energy augmentation structure or the energy converter.

14. The energy emitter of claim 6, wherein the at least one energy augmentation structure is disposed:

(i) in vicinity of a down conversion material comprising the energy converter; or (ii) in vicinity of an up-conversion material comprising the energy converter; or (iii) in vicinity of a phosphor comprising the energy converter; or (iv) in vicinity of a piezoelectric device comprising the energy converter; or (v) in vicinity of a mechanoluminescent device comprising the energy converter; or (vi) inside a plasma capsule device comprising the energy converter; or (vii) in vicinity of an x-ray stimulated phosphor comprising the energy converter.

15. The energy emitter of claim 6, wherein the at least one energy augmentation structure comprises a plurality of energy collectors, wherein:

(i) the energy converters are positioned to convert energy being internally scattered within the energy collectors; or (ii) the energy collectors comprise a metal core cladded with a high-K dielectric and a subsequent cladding of a low-K dielectric; or (iii) the energy collectors comprise a radial pattern of collectors.

16. The energy emitter of claim 6, wherein the energy converter:

(i) is a component of at least one of a paint, an ink, a fabric, a thread, a road sign, a highway marking, an automobile, a boat, a plane, a reflector, a building product, a concrete product, an epoxy product, a jewelry product, colored contact lens, a candle product, a rubber product, a plastic product, a colored surface, a solar cell, a plasma capsule, an x-ray detector, or a sterilizer; or (ii) is a component of a colored reflective surface; or (iii) is a component of a colored reflective surface in a pixel for a display; or (iv) is a component of a white-light emitting pixel display element; or (v) is a component disposed in a retroreflective paint; or (vi) is an ink component; or (vii) comprises at least one of red, blue, and green emitters configured to produce red, blue, and green emissions from an up conversion process; or (viii) comprises at least one of red, blue, and green emitters configured to produce red, blue, and green emissions from a down conversion process.

17. The energy emitter of claim 6, wherein the energy converter comprises:

(i) at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof, or (ii) a down converter including at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$; or (iii) an up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof; or (iv) an up converter including at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$-$Ga_2O_3$-$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

18. An energy emitter comprising:

at least one energy augmentation structure capable of capturing one or more wavelengths of electromagnetic energy, and augmenting the one or more wavelengths of electromagnetic energy in at least one property, wherein the energy augmentation structure comprises either (i) a non-plasmonic fractal antenna or (ii) a folded resonator having opposing electrodes with electric fields directed in between; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

wherein the energy converter comprises:

(i) at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof; or (ii) a down converter including at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn, $Er^{3+}$; or (iii) an up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof; or (iv) an up converter including at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$-$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine); and wherein the energy converter further comprises a dopant including at least one of Er, Eu, Yb, Tm, Nd, Tb, Ce, Y, U, Pr, La, Gd and other rare-earth species or a combination thereof.

19. The energy emitter of claim 18, wherein the dopant is included at a concentration of 0.01%-50% by mol concentration.

* * * * *